(12) United States Patent
Moskowitz et al.

(10) Patent No.: US 11,000,311 B2
(45) Date of Patent: *May 11, 2021

(54) TACTILE SENSING AND NEEDLE GUIDANCE DEVICE

(71) Applicant: IntuiTap Medical, Inc., Houston, TX (US)

(72) Inventors: Nicole C. Moskowitz, Monsey, NY (US); Jessica Traver, Sierra Madre, CA (US); Xavier Garcia-Rojas, The Woodlands, TX (US); Yashar Ganjeh, Chicago, IL (US); Matthew Cruz, Chicago, IL (US); Jonathan Rae Plumb, Halstead (GB); Jack Alexander Lowe, Leeds (GB); Alexander Keith Gomer Pratten Jones, Cambridge (GB)

(73) Assignee: INTUITAP MEDICAL, INC., Houston, TX (US)

( * ) Notice: Subject to any disclaimer, the term of this patent is extended or adjusted under 35 U.S.C. 154(b) by 95 days.

This patent is subject to a terminal disclaimer.

(21) Appl. No.: 16/379,695

(22) Filed: Apr. 9, 2019

(65) Prior Publication Data

US 2019/0231332 A1  Aug. 1, 2019

Related U.S. Application Data

(63) Continuation of application No. 16/230,566, filed on Dec. 21, 2018, now Pat. No. 10,383,610, which is a (Continued)

(51) Int. Cl.
*A61B 17/34* (2006.01)

(52) U.S. Cl.
CPC ...... *A61B 17/3403* (2013.01); *A61B 17/3401* (2013.01); *A61B 2017/3405* (2013.01); *A61B 2017/3413* (2013.01)

(58) Field of Classification Search
CPC ........... A61B 17/3401; A61B 17/3403; A61B 2017/3405; A61B 2017/3413
See application file for complete search history.

(56) References Cited

U.S. PATENT DOCUMENTS

| 4,919,653 A | 4/1990 | Martinez et al. |
| 5,097,842 A | 3/1992 | Bonn |

(Continued)

FOREIGN PATENT DOCUMENTS

| CN | 101877192 A | 11/2010 |
| CN | 102133096 A | 7/2011 |

(Continued)

OTHER PUBLICATIONS

European Patent Application No. 17793167.2 Extended European Search Report dated Oct. 31, 2019.

(Continued)

*Primary Examiner* — Melanie R Tyson
(74) *Attorney, Agent, or Firm* — Wilson Sonsini Goodrich & Rosati

(57) ABSTRACT

Tactile sensing devices, systems, and methods to image a target tissue location are disclosed. When force is applied onto a tissue surface using the tactile sensing device, sensors of a sensor array output voltage signals to a computing device and display screen operatively connected to the sensor array. The sensor array relays its output voltage signals to the computing device, the computing device processes the output voltage signals, and an image of the output voltage signals is visualized on the display screen to help identify a target tissue insertion site.

20 Claims, 29 Drawing Sheets

Related U.S. Application Data continuation of application No. PCT/US2018/057860, filed on Oct. 26, 2018.

(60) Provisional application No. 62/700,505, filed on Jul. 19, 2018, provisional application No. 62/578,147, filed on Oct. 27, 2017.

(56) References Cited

U.S. PATENT DOCUMENTS

| | | |
|---|---|---|
| 5,163,901 A | 11/1992 | Eldor |
| 5,706,815 A | 1/1998 | Sarvazyan et al. |
| 5,785,663 A | 7/1998 | Sarvazyan |
| 5,795,307 A | 8/1998 | Krueger |
| 5,833,633 A | 11/1998 | Sarvazyan |
| 5,833,634 A | 11/1998 | Laird et al. |
| 6,063,031 A | 5/2000 | Cundari et al. |
| 6,142,959 A | 11/2000 | Sarvazyan et al. |
| 6,251,686 B1 | 6/2001 | Studer et al. |
| 6,468,215 B1 | 10/2002 | Sarvazyan et al. |
| 6,468,231 B2 | 10/2002 | Sarvazyan et al. |
| 6,500,119 B1 | 12/2002 | West et al. |
| 6,569,108 B2 | 5/2003 | Sarvazyan et al. |
| 6,595,933 B2 | 7/2003 | Sarvazyan et al. |
| 6,620,115 B2 | 9/2003 | Sarvazyan et al. |
| 7,291,109 B1 | 11/2007 | Sarvazyan |
| 7,819,824 B2 | 10/2010 | Sarvazyan et al. |
| 7,922,674 B2 | 4/2011 | Sarvazyan et al. |
| 7,955,278 B1 | 6/2011 | Sarvazyan |
| 8,016,777 B1 | 9/2011 | Egorov et al. |
| 8,052,622 B2 | 11/2011 | Egorov et al. |
| 8,069,735 B1 | 12/2011 | Egorov et al. |
| 8,142,368 B2 | 3/2012 | Egorov et al. |
| 8,187,208 B2 | 5/2012 | Egorov et al. |
| 8,419,659 B2 | 4/2013 | Egorov et al. |
| 8,480,404 B2 | 7/2013 | Savitsky |
| 8,814,807 B2 | 8/2014 | Hulvershorn et al. |
| 8,840,571 B2 | 9/2014 | Egorov et al. |
| 9,179,875 B2 | 11/2015 | Hua |
| 10,004,450 B2 | 6/2018 | Moskowitz et al. |
| 10,383,610 B2 * | 8/2019 | Moskowitz ........ A61B 17/3401 |
| 2004/0010204 A1 | 1/2004 | Weber et al. |
| 2004/0254503 A1 | 12/2004 | Sarvazyan et al. |
| 2004/0267121 A1 | 12/2004 | Sarvazyan et al. |
| 2004/0267165 A1 | 12/2004 | Sarvazyan et al. |
| 2005/0075665 A1 | 4/2005 | Brenzel et al. |
| 2006/0122555 A1 | 6/2006 | Hochman |
| 2006/0195043 A1 | 8/2006 | Rutherford et al. |
| 2006/0206118 A1 | 9/2006 | Kim et al. |
| 2006/0206178 A1 | 9/2006 | Kim |
| 2008/0154154 A1 | 6/2008 | Sarvazyan et al. |
| 2009/0018507 A1 | 1/2009 | Schmitz et al. |
| 2009/0131832 A1 | 5/2009 | Sacristan et al. |
| 2009/0157044 A1 | 6/2009 | Liyanagama et al. |
| 2009/0270759 A1 | 10/2009 | Wilson et al. |
| 2010/0256483 A1 | 10/2010 | Wall et al. |
| 2011/0054353 A1 | 3/2011 | Hulvershorn et al. |
| 2011/0066078 A1 | 3/2011 | Sarvazyan et al. |
| 2011/0092818 A1 | 4/2011 | Sarvazyan |
| 2011/0166442 A1 | 7/2011 | Sarvazyan |
| 2012/0046531 A1 | 2/2012 | Hua |
| 2012/0143029 A1 | 6/2012 | Silverstein et al. |
| 2012/0296213 A1 | 11/2012 | Mauldin, Jr. et al. |
| 2013/0023880 A1 | 1/2013 | Tramboo et al. |
| 2013/0085413 A1 | 4/2013 | Tsamir et al. |
| 2014/0046186 A1 | 2/2014 | Mauldin, Jr. et al. |
| 2014/0276925 A1 | 9/2014 | Alves et al. |
| 2014/0277045 A1 | 9/2014 | Fazio et al. |
| 2014/0288408 A1 | 9/2014 | Deutsch |
| 2014/0288427 A1 | 9/2014 | Wall |
| 2014/0303494 A1 | 10/2014 | Janicki et al. |
| 2015/0025363 A1 | 1/2015 | Hulvershorn et al. |
| 2015/0342635 A1 | 12/2015 | Tsamir et al. |
| 2015/0359563 A1 | 12/2015 | Kume et al. |
| 2016/0008007 A1 | 1/2016 | Taha |
| 2016/0157816 A1 | 6/2016 | Denny |
| 2016/0270810 A1 | 9/2016 | Vardi et al. |
| 2017/0020540 A1 | 1/2017 | Chou et al. |
| 2018/0206781 A1 | 7/2018 | Moskowitz et al. |

FOREIGN PATENT DOCUMENTS

| | | |
|---|---|---|
| CN | 104140066 A | 11/2014 |
| CN | 104523297 A | 4/2015 |
| CN | 204318870 U | 5/2015 |
| EP | 0303824 A2 | 2/1989 |
| EP | 0413588 A2 | 2/1991 |
| EP | 2223662 A1 | 9/2010 |
| WO | WO-9215256 A1 | 9/1992 |
| WO | WO-2007022599 A1 | 3/2007 |
| WO | WO-2007024399 A2 | 3/2007 |
| WO | WO-2009009621 A2 | 1/2009 |
| WO | WO-2009066972 A1 | 5/2009 |
| WO | WO-2010018536 A2 | 2/2010 |
| WO | WO-2011084788 A2 | 7/2011 |
| WO | WO-2011158227 A2 | 12/2011 |
| WO | WO-2013054165 A1 | 4/2013 |
| WO | WO-2013056243 A1 | 4/2013 |
| WO | WO-2014097301 A1 | 6/2014 |
| WO | WO-2015200712 A1 | 12/2015 |
| WO | WO-2016007527 A1 | 1/2016 |
| WO | WO-2016034910 A1 | 3/2016 |
| WO | WO-2017192596 A1 | 11/2017 |
| WO | WO-2018148456 A1 | 8/2018 |
| WO | WO-2019084502 A1 | 5/2019 |

OTHER PUBLICATIONS

International Application No. PCT/US2018/057860 International Search Report and Written Opinion dated Mar. 11, 2019.
PCT/US2017/030650 International Search Report and Written Opinion dated Sep. 21, 2017.
PCT/US2018/017487 International Search Report and Written Opinion dated May 21, 2018.
U.S. Appl. No. 15/584,875 First Action Interview Office Action Summary dated Oct. 12, 2017.
U.S. Appl. No. 15/584,875 First Action Interview Pilot Program, Pre-Interview Communication dated Jul. 17, 2017.

* cited by examiner

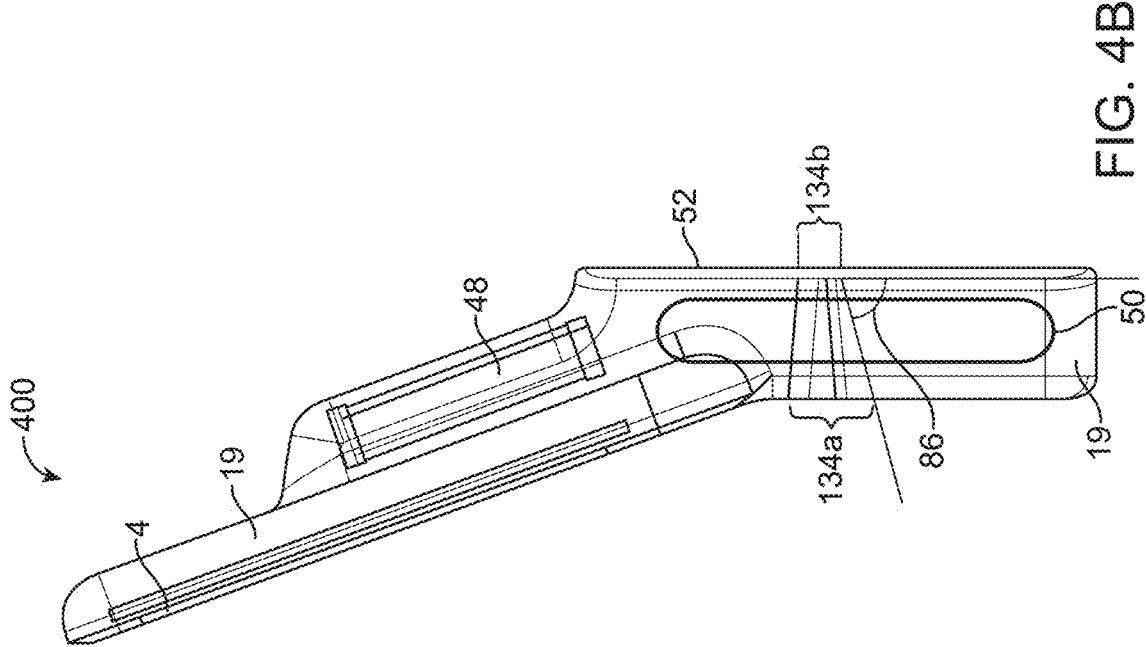
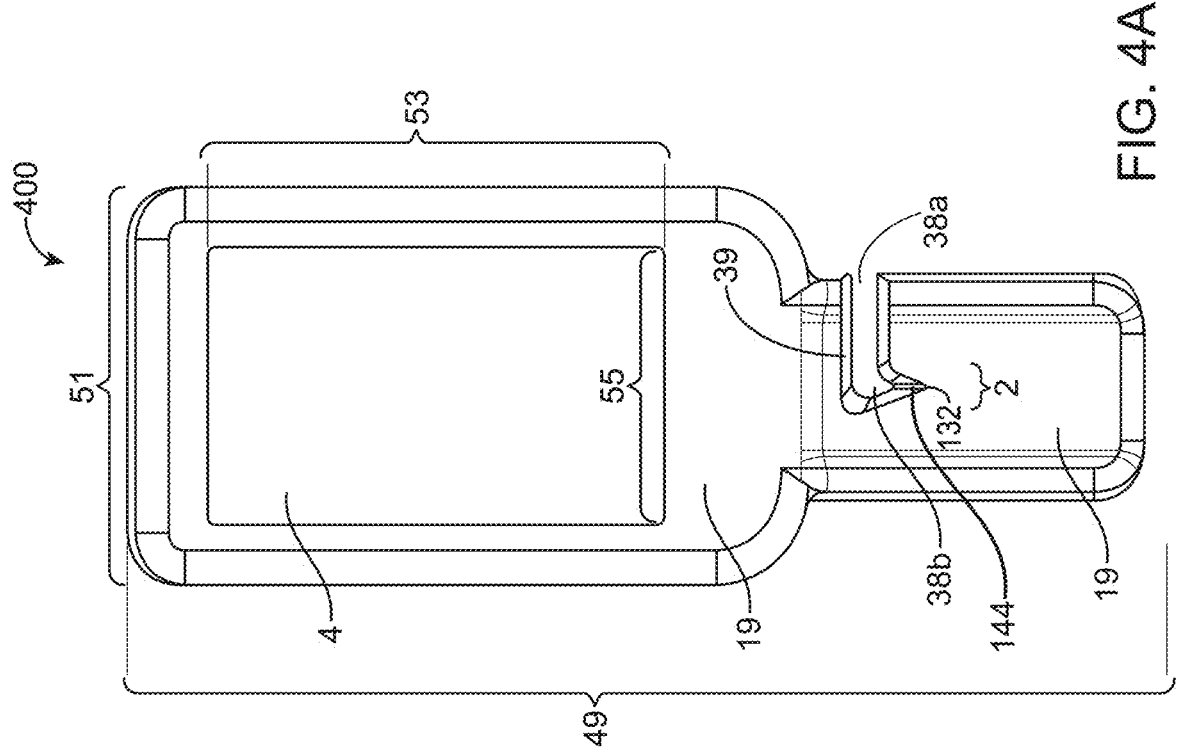

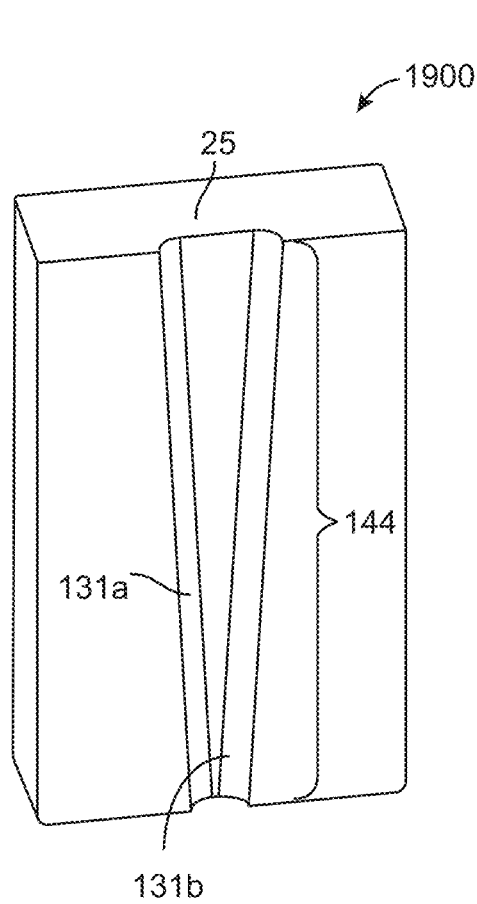
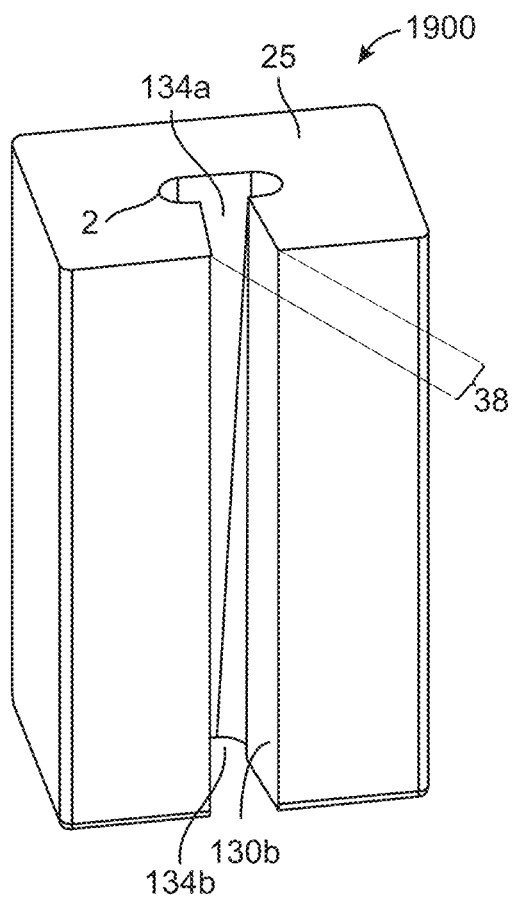
FIG. 19B
FIG. 19C
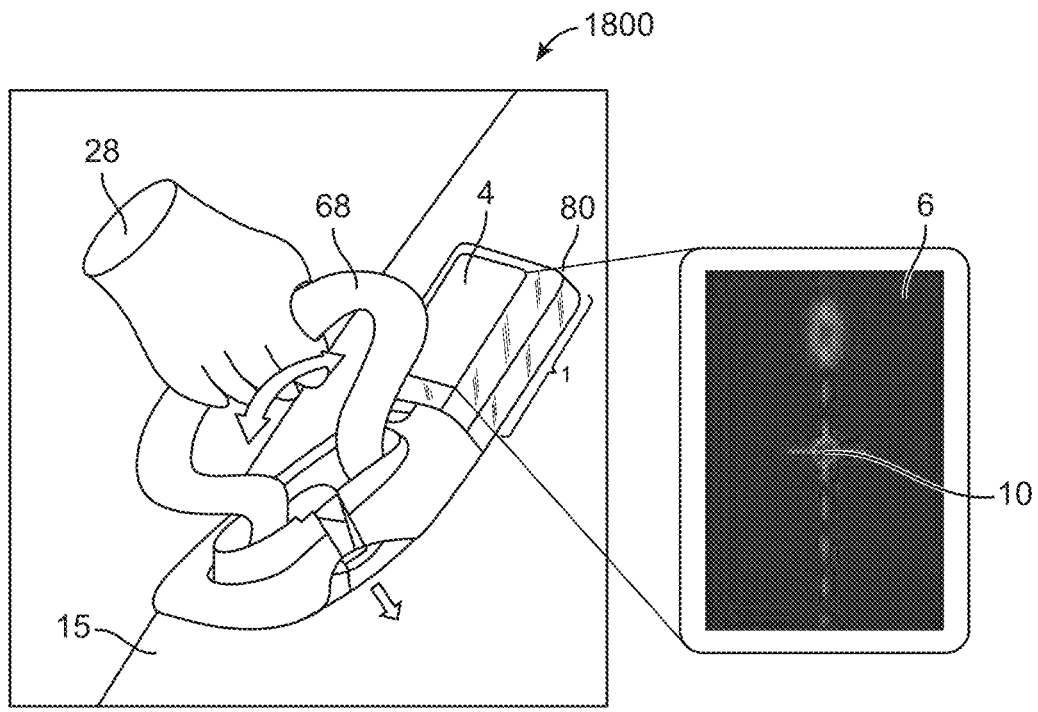
FIG. 20A

TACTILE SENSING AND NEEDLE GUIDANCE DEVICE

CROSS-REFERENCE

This application is a continuation of U.S. application Ser. No. 16/230,566, filed on Dec. 21, 2018, which is a continuation of International Application No. PCT/US2018/057860, filed on Oct. 26, 2018, which claims benefit of U.S. Provisional Application No. 62/578,147, filed Oct. 27, 2017 and U.S. Provisional Application No. 62/700,505, filed Jul. 19, 2018, each of which are incorporated herein by reference in their entireties.

SUMMARY

Disclosed herein, in certain embodiments, are tactile sensing devices, comprising: a frame comprising a needle guide comprising a proximal opening and a distal opening and a track therebetween configured to guide a needle; and a slot in open connection with the needle guide, the slot comprising a first slot wall, a second slot wall, a slot opening and a slot terminus at the proximal opening of the needle guide; and a sensor array, the sensor array comprising: a first sensor comprising a first surface, a second sensor comprising a second surface, and a sensor array slit aligned with the slot of the frame and extending from a boundary of the sensor array to the distal opening of the needle guide, wherein the distal opening is positioned in between the first sensor and the second sensor, wherein the first sensor is configured to output a first voltage signal in response to a first change in a first pressure applied to the first surface, and the second sensor is configured to output a second voltage signal in response to a second change in a second pressure applied to the second surface.

In some embodiments, the needle guide comprises a notch configured to reversibly and temporarily secure the needle in place during needle insertion. In some embodiments, the needle guide is fixed. In some embodiments, the frame comprises a needle alignment guide. In some embodiments, the needle alignment guide is a notch or a marking on the surface of the tactile sensing device. In some embodiments, the sensor array is a matrix array. In some embodiments, the sensor array is a flexible sensor array. In some embodiments, the track is angled at a treatment angle ranging between about 40° to about 90° with respect to the sensor array. In some embodiments, the treatment angle is a cephalad angle between about 0° to about 15° with respect to an individual. In some embodiments, the slot is perpendicular to the needle guide. In some embodiments, the sensor array is attached to a sensor array attachment area. In some embodiments, the frame comprises a handle. In some embodiments, the handle is a curved handle, a power grip handle, or a pinch grip. In some embodiments, the handle comprises a grip feature. In some embodiments, the tactile sensing device comprises a pressure sensor connector, the pressure sensor connector operatively connecting the tactile sensing device with a fluid pressure sensor. In some embodiments, the tactile sensing device comprises a scanhead comprising the sensor array and wherein the frame comprises a scanning track along which the scanhead comprising the sensor array is configured to move relative to the frame. In some embodiments, a part of the frame surrounding the needle guide is made out of clear plastic. In some embodiments, a posterior surface of the tactile sensing device has a curvature about a longitudinal axis. In some embodiments, the posterior surface of the tactile sensing device has a curvature about a lateral axis. In some embodiments, the slot and the sensor array slit are substantially a same width from the boundary of the sensor array to the needle guide distal opening. In some embodiments, the sensor array is adhered to a posterior surface of the tactile sensing device.

Disclosed herein, in certain embodiments, are tactile sensing systems, comprising: a frame comprising a sensor unit and an electronic unit; the sensor unit comprising: a needle guide comprising a proximal opening and a distal opening and a track therebetween configured to guide a needle; a slot in open connection with the needle guide, the slot comprising a first slot wall, a second slot wall, an slot opening and a slot terminus at the proximal opening of the needle guide; and a sensor array, the sensor array comprising: a first sensor comprising a first surface, a second sensor comprising a second surface, and a sensor array slit aligned with the slot of the frame and extending from a boundary of the sensor array to the distal opening of the needle guide, wherein the distal opening is positioned in between the first sensor and the second sensor, wherein the first sensor is configured to output a first voltage signal in response to a first change in a first pressure applied to the first surface, and the second sensor is configured to output a second voltage signal in response to a second change in a second pressure applied to the second surface, the electronic unit, comprising: a display screen operatively coupled to the sensor array, the display screen configured to display: a pressure map representing a target tissue location in an individual in need thereof based upon the first voltage signal and the second voltage signal from the sensor array and a projected subcutaneous needle location to be inserted into the individual; and a connector configured to operatively connect the electronic unit to the sensor unit; and a computing device comprising a processor operatively coupled to the sensor unit and the electronic unit, and a non-transitory computer readable storage medium with a computer program including instructions executable by the processor causing the processor to: i) convert the first voltage signal and the second voltage signal received from the sensor array into the pressure map and display the pressure map on the display screen and ii) calculate the projected subcutaneous needle location to be inserted into the individual and output the projected subcutaneous needle location on the display screen.

In some embodiments, the needle guide comprises a notch configured to reversibly and temporarily secure the needle in the needle guide from slipping along the slot during needle insertion. In some embodiments, the needle guide is fixed. In some embodiments, the frame comprises a needle alignment guide. In some embodiments, the needle alignment guide is a notch or a marking on the surface of the tactile sensing device. In some embodiments, the sensor array is a matrix array. In some embodiments, the sensor array is a flexible sensor array. In some embodiments, the track is angled at a treatment angle ranging between about 40° to about 90° with respect to the sensor array. In some embodiments, the treatment angle is a cephalad angle between about 0° to about 15° with respect to the individual. In some embodiments, the slot is perpendicular to the needle guide. In some embodiments, the sensor array is attached to a sensor array attachment area. In some embodiments, the frame comprises a handle. In some embodiments, the handle is a curved handle, a power grip handle, or a pinch grip. In some embodiments, the handle comprises a grip feature. In some embodiments, the tactile sensing device comprises a pressure sensor connector, the pressure sensor connector operatively connecting the tactile sensing device with a fluid pressure sensor. In some embodiments, the tactile sensing device comprises a scanhead comprising the sensor array and wherein the frame comprises a scanning track along which the scanhead comprising the sensor array is configured to move relative to the frame. In some embodiments, a part of the frame surrounding the needle guide is made out of clear plastic. In some embodiments, a posterior surface of the tactile sensing device has a curvature about a longitudinal axis. In some embodiments, the posterior surface of the tactile sensing device has a curvature about a lateral axis. In some embodiments, the slot and the sensor array slit are directly aligned with one another. In some embodiments, the sensor array is adhered to a posterior surface of the tactile sensing device. In some embodiments, the electronic unit comprises a printed circuit board. In some embodiments, the tactile sensing device comprises a sleeve configured for receiving the electronic unit. In some embodiments, the tactile sensing device comprises a power source. In some embodiments, the power source is a battery. In some embodiments, the battery is located underneath the display screen. In some embodiments, the sensor unit or the electronic unit are disposable. In some embodiments, the sensor unit and the electronic unit are reversibly connected. In some embodiments, the tactile sensing device comprises a wireless transmitter, the wireless transmitter operatively connected to the sensor array, for remotely transmitting the first voltage signal generated by the first voltage sensor and the second voltage signal generated by the second sensor. In some embodiments, the processor is configured with instructions to display the target tissue location and the projected subcutaneous needle location on the display screen in real time. In some embodiments, the processor is configured with instructions to display the target tissue location and the projected subcutaneous needle location on the display screen while the needle is advanced along the needle guide through the distal opening toward the target tissue location.

Disclosed herein, in certain embodiments, are methods of positioning a needle in the tactile sensing device, comprising: a) inserting the needle into the slot opening; b) guiding the needle along an axis of the slot by sliding the needle in between the first slot wall and the second slot wall towards the needle guide, c) contacting the needle with the track of needle guide, and d) sliding the needle along the track towards the distal opening of the needle guide.

Disclosed herein, in certain embodiments, are methods of positioning a needle, comprising: a) inserting the needle into the needle guide of the tactile sensing device, b) contacting the needle with the track of needle guide, c) sliding the needle along the track towards the distal opening of the needle guide and into a patient at an angle defined by the track, and d) removing the device while the needle is in the patient by guiding the device such that the needle is travels along the slot between the first slot wall and the second slot wall toward and out of the slot opening.

Disclosed herein, in certain embodiments, are tactile sensing devices, comprising: a frame comprising a needle guide comprising a proximal opening and a distal opening and a track therebetween configured to guide a needle; and a sensor array, the sensor array comprising: a first sensor comprising a first surface and a second sensor comprising a second surface, wherein the first sensor is configured to output a first voltage signal in response to a first change in a first pressure applied to the first surface, and the second sensor is configured to output a second voltage signal in response to a second change in a second pressure applied to the second surface.

In some embodiments, the needle guide comprises a notch configured to reversibly and temporarily secure the needle in place during needle insertion. In some embodiments, the needle guide is fixed. In some embodiments, the needle guide is reversibly attached to the tactile sensing device. In some embodiments, the frame comprises a needle alignment guide. In some embodiments, the needle alignment guide is a notch or a marking on the surface of the tactile sensing device. In some embodiments, the sensor array is a matrix array. In some embodiments, the sensor array is a flexible sensor array. In some embodiments, the track is angled at a treatment angle ranging between about 40° to about 90° with respect to the sensor array. In some embodiments, the treatment angle is a cephalad angle between about 0° to about 15° with respect to an individual. In some embodiments, the tactile sensing device comprises a slot in open connection with the needle guide, the slot comprising a first slot wall, a second slot wall, a slot opening and a slot terminus at the proximal opening of the needle guide. In some embodiments, the slot is perpendicular to the needle guide. In some embodiments, the sensor array comprises a sensor array slit aligned with the slot of the frame and extending from a boundary of the sensor array to the distal opening of the needle guide. In some embodiments, the slot and the sensor array slit are substantially a same width from the boundary of the sensor array to the needle guide distal opening. In some embodiments, the sensor array is attached to a sensor array attachment area. In some embodiments, the frame comprises a handle. In some embodiments, the handle is a curved handle, a power grip handle, or a pinch grip. In some embodiments, the handle comprises a grip feature. In some embodiments, the tactile sensing device comprises a pressure sensor connector, the pressure sensor connector operatively connecting the tactile sensing device with a fluid pressure sensor. In some embodiments, the tactile sensing device comprises a scanhead comprising the sensor array and wherein the frame comprises a scanning track along which the scanhead comprising the sensor array is configured to move relative to the frame. In some embodiments, a part of the frame surrounding the needle guide is made out of clear plastic. In some embodiments, a posterior surface of the tactile sensing device has a curvature about a longitudinal axis. In some embodiments, the posterior surface of the tactile sensing device has a curvature about a lateral axis. In some embodiments, the slot and the sensor array slit are substantially a same width from the boundary of the sensor array to the needle guide distal opening. In some embodiments, the sensor array is adhered to a posterior surface of the tactile sensing device. In some embodiments, the distal opening is positioned in between the first sensor and the second sensor.

Disclosed herein, in certain embodiments, are tactile sensing systems, comprising: a frame comprising a sensor unit and an electronic unit; the sensor unit comprising: a needle guide comprising a proximal opening and a distal opening and a track therebetween configured to guide a needle; and a sensor array, the sensor array comprising: a first sensor comprising a first surface, a second sensor comprising a second surface, wherein the first sensor is configured to output a first voltage signal in response to a first change in a first pressure applied to the first surface, and the second sensor is configured to output a second voltage signal in response to a second change in a second pressure applied to the second surface, the electronic unit, comprising: a display screen operatively coupled to the sensor array, the display screen configured to display: a pressure map representing a target tissue location in an individual in need thereof based upon the first voltage signal and the second voltage signal from the sensor array and a projected subcutaneous needle location to be inserted into the individual; and a connector configured to operatively connect the electronic unit to the sensor unit; and a computing device comprising a processor operatively coupled to the sensor unit and the electronic unit, and a non-transitory computer readable storage medium with a computer program including instructions executable by the processor causing the processor to: i) convert the first voltage signal and the second voltage signal received from the sensor array into the pressure map and display the pressure map on the display screen and ii) calculate the projected subcutaneous needle location to be inserted into the individual and output the projected subcutaneous needle location on the display screen.

In some embodiments, the needle guide comprises a notch configured to reversibly and temporarily secure the needle in the needle guide from slipping along the slot during needle insertion. In some embodiments, the needle guide is fixed. In some embodiments, the needle guide is reversibly attached to the tactile sensing device. In some embodiments, the frame comprises a needle alignment guide. In some embodiments, the needle alignment guide is a notch or a marking on the surface of the tactile sensing device. In some embodiments, the sensor array is a matrix array. In some embodiments, the sensor array is a flexible sensor array. In some embodiments, the track is angled at a treatment angle ranging between about 40° to about 90° with respect to the sensor array. In some embodiments, the treatment angle is a cephalad angle between about 0° to about 15° with respect to the individual. In some embodiments, the tactile sensing device comprises a slot in open connection with the needle guide, the slot comprising a first slot wall, a second slot wall, a slot opening and a slot terminus at the proximal opening of the needle guide. In some embodiments, the slot is perpendicular to the needle guide. In some embodiments, the sensor array comprises a sensor array slit aligned with the slot of the frame and extending from a boundary of the sensor array to the distal opening of the needle guide. In some embodiments, the slot and the sensor array slit are substantially a same width from the boundary of the sensor array to the needle guide distal opening. In some embodiments, the sensor array is attached to a sensor array attachment area. In some embodiments, the frame comprises a handle. In some embodiments, the handle is a curved handle, a power grip handle, or a pinch grip. In some embodiments, the handle comprises a grip feature. In some embodiments, the tactile sensing device comprises a pressure sensor connector, the pressure sensor connector operatively connecting the tactile sensing device with a fluid pressure sensor. In some embodiments, the tactile sensing device comprises a scanhead comprising the sensor array and wherein the frame comprises a scanning track along which the scanhead comprising the sensor array is configured to move relative to the frame. In some embodiments, a part of the frame surrounding the needle guide is made out of clear plastic. In some embodiments, a posterior surface of the tactile sensing device has a curvature about a longitudinal axis. In some embodiments, the posterior surface of the tactile sensing device has a curvature about a lateral axis. In some embodiments, the slot and the sensor array slit are directly aligned with one another. In some embodiments, the sensor array is adhered to a posterior surface of the tactile sensing device. In some embodiments, the electronic unit comprises a printed circuit board. In some embodiments, the tactile sensing device comprises a sleeve configured for receiving the electronic unit. In some embodiments, the tactile sensing device comprises a power source. In some embodiments, the power source is a battery. In some embodiments, the battery is located underneath the display screen. In some embodiments, the sensor unit or the electronic unit are disposable. In some embodiments, the sensor unit and the electronic unit are reversibly connected. In some embodiments, the tactile sensing device comprises a wireless transmitter, the wireless transmitter operatively connected to the sensor array, for remotely transmitting the first voltage signal generated by the first voltage sensor and the second voltage signal generated by the second sensor. In some embodiments, the processor is configured with instructions to display the target tissue location and the projected subcutaneous needle location on the display screen in real time. In some embodiments, the processor is configured with instructions to display the target tissue location and the projected subcutaneous needle location on the display screen while the needle is advanced along the needle guide through the distal opening toward the target tissue location. In some embodiments, the distal opening is positioned in between the first sensor and the second sensor.

Disclosed herein, in certain embodiments, are methods of positioning a needle in the tactile sensing device, comprising: a) inserting the needle into the needle guide opening; b) contacting the needle with the track of needle guide, and c) sliding the needle along the track towards the distal opening of the needle guide.

BRIEF DESCRIPTION OF THE DRAWINGS

The novel features of the subject matter disclosed herein are set forth with particularity in the appended claims. A better understanding of the features and advantages of the subject matter disclosed herein will be obtained by reference to the following detailed description that sets forth illustrative embodiments, in which the principles of the subject matter disclosed herein are utilized, and the accompanying drawings of which:

FIG. 1A shows a perspective view of the tactile sensing device 100 with an exemplary output image displayed on its display screen 4. FIG. 1B shows an additional perspective view of the tactile sensing device 100.

FIG. 2A shows a perspective view of the tactile sensing device 200 with an exemplary output image displayed on its display screen 4. FIG. 2B shows a front view of the tactile sensing device 200.

FIGS. 4A and 4B show an embodiment of the tactile sensing device 400 comprising a battery and a printed circuit board. FIG. 4A shows a front view of the tactile sensing device 400. FIG. 4B shows a side, wire frame view of the tactile sensing device 400.

FIG. 12A shows a front view of the tactile sensing device 1200 comprising a sliding sleeve and a sliding electronic unit 34. FIG. 12B shows a front view of the tactile sensing device 1200 comprising a handle comprising an indent specific for a left thumb. FIG. 12C shows a front view of the tactile sensing device 1200 comprising a snap-on disposable sleeve.

FIG. 18A shows a perspective view of the tactile sensing device. FIG. 18B shows a side view of the tactile sensing device comprising a curved sensor applicator. FIG. 18C shows a side, cutaway view of the tactile sensing device.

FIGS. 19A-C shows an embodiment curved sensor applicator and needle guide insert of the tactile sensing device comprising a rocker design. FIG. 19A shows an isometric view of an embodiment curved sensor applicator. FIG. 19B shows a cutaway view of an embodiment needle guide insert comprising a needle guide. FIG. 19C shows a front view of an embodiment needle guide insert comprising a needle guide.

FIGS. 20A-E show the workflow of an embodiment rocker tactile sensing device. FIG. 20A shows a user applying an embodiment rocker tactile sensing device against the skin surface of a patient. FIG. 20B shows the user moving an embodiment rocker tactile sensing device in a rocking motion. FIG. 20C shows the user identifying the correct needle insertion position. FIG. 20D shows the user removing an embodiment handle. FIG. 20E shows the user securing the needle with an embodiment needle retention gate 17.

FIG. 21A shows an isometric view of an embodiment slider tactile sensing device. FIG. 21B shows a side, cutaway view of an embodiment slider tactile sensing device with an undepressed scanhead. FIG. 21C shows a side, cutaway view of an embodiment slider tactile sensing device with a depressed scanhead.

FIG. 22A shows a front, isometric view of the scanhead subassembly. FIG. 22B shows a back, isometric view of the scanhead subassembly. FIG. 22C shows a back, cutaway view of the scanhead subassembly.

FIG. 23A shows an isometric view of the scanhead subassembly. FIG. 23B shows an exploded view of the scanhead subassembly.

FIG. 24A shows a scanning knob with ribs. FIG. 24B shows a concave scanning knob. FIG. 24C shows a convex scanning knob.

FIG. 25A shows an isometric view of the scanhead. FIG. 25B shows the scanhead of FIG. 25A, cut away through the needle track.

FIG. 26A shows a user inserting the scanning knob into the tactile sensing device. FIG. 26B shows the user sliding the scanning knob. FIG. 26C shows the user identifying the correct needle insertion position. FIG. 26D shows the user removing the scanning knob.

DETAILED DESCRIPTION

Figure 1A:
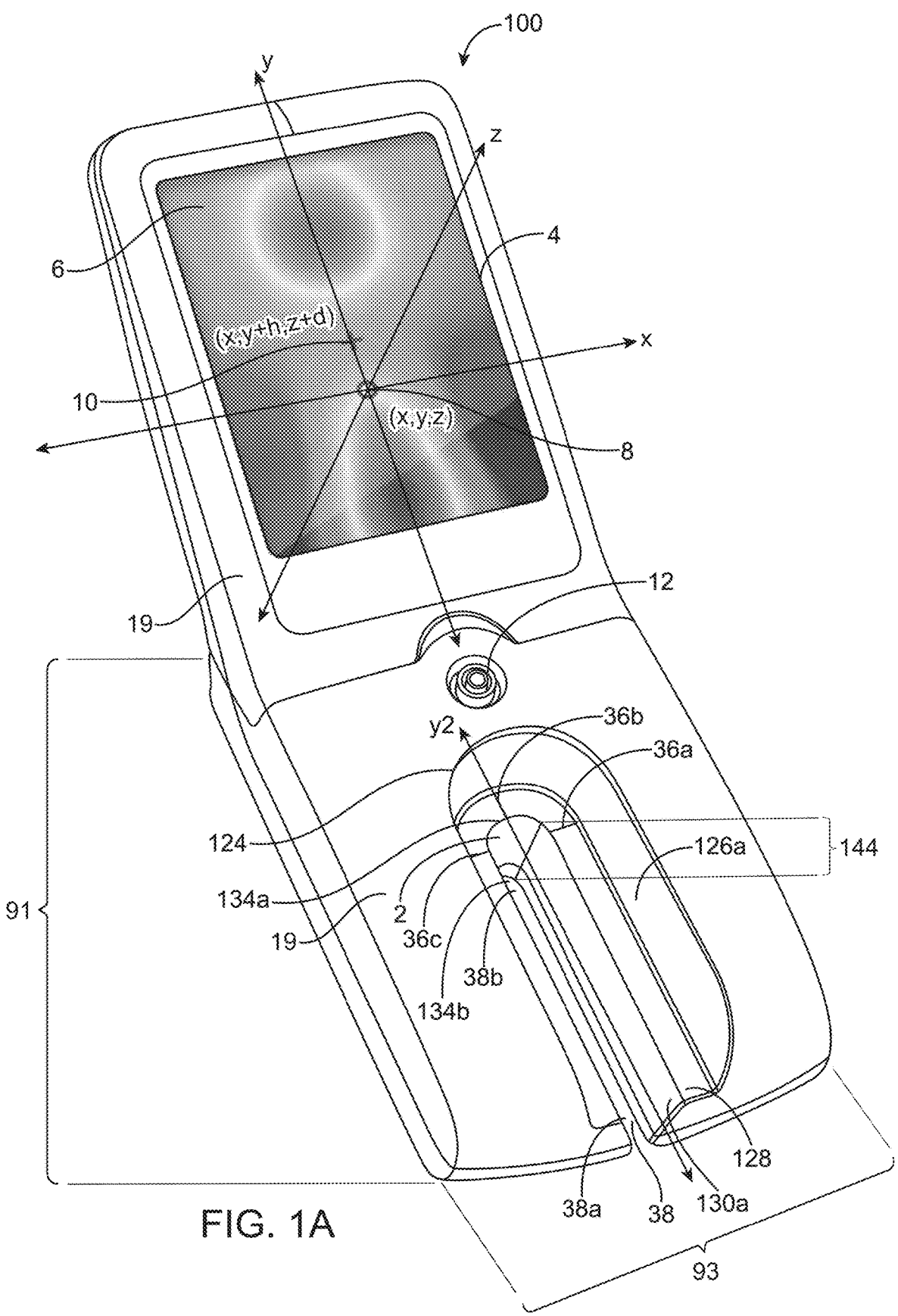
FIGS. 1A and 1B illustrate a tactile sensing device with a needle guide comprising a slot and track.

While preferred embodiments of the subject matter disclosed herein have been shown and described herein, it will be obvious to those skilled in the art that such embodiments are provided by way of example only. Numerous variations, changes, and substitutions will now occur to those skilled in the art without departing from the subject matter disclosed herein. It should be understood that various alternatives to the embodiments of the subject matter disclosed herein may be employed in practicing the subject matter disclosed herein. It is intended that the following claims define the scope of the subject matter disclosed herein and that methods and structures within the scope of these claims and their equivalents be covered thereby.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, e.g., the limitations of the measurement system. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 20.0 degrees, 15.0 degrees, 10.0 degrees, 9.0 degrees, 8.0 degrees, 7.0 degrees, 6.0 degrees, 5.0 degrees, 4.0 degrees, 3.0 degrees, 2.0 degrees, 1.0 degrees, 0.9 degrees, 0.8 degrees, 0.7 degrees, 0.6 degrees, 0.5 degrees, 0.4 degrees, 0.3 degrees, 0.2 degrees, 0.1 degrees, 0.09 degrees, 0.08 degrees, 0.07 degrees, 0.06 degrees, 0.05 degrees, 0.04 degrees, 0.03 degrees, 0.02 degrees or 0.01 degrees of a given value or range.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "user," "health care worker," "doctor," and "physician" are used interchangeably. These terms refer to any person that operates the devices described herein. Additional non-liming examples of a user include "registered nurse," "nurse practitioner," and "physician's assistant."

The terms "intracranial pressure (ICP)" and "cerebrospinal fluid (CSF) pressure" are used interchangeably. ICP is the pressure inside a skull and thus, it is the pressure in the brain tissue and CSF.

The terms "lumbar puncture" and "spinal tap" and "spinal puncture" are used interchangeably herein. Generally speaking, a "spinal puncture" is used herein to refer to lumbar puncture, spinal tap, epidural spinal injection, spinal injection, and/or neuraxial anesthesia, and thus is interchangeably therewith. The use of any one of these terms herein does not limit the devices, systems, or methods described herein to only the stated use or type of injection, but is exemplary only and such uses and interchangeable with any other type of injection or puncture for which a device or system or method described herein would be helpful or appropriate.

The term "needle hub," as used herein, refers to the hub at one end of a needle that commonly attaches to a syringe. The shaft of the needle is an elongated, slender stem of the needle that extends from the needle hub and is beveled at the end opposite to the needle hub end.

The term "proximal," as used herein, is defined as being closest or nearer to the user holding and/or operating the tactile sensing device, unless otherwise indicated. For example, a user pressing the tactile sensing device onto a patient.

The term "distal," as used herein, is defined as being farthest to the user holding and/or operating the tactile sensing device, unless otherwise indicated. For example, pressing the tactile sensing device onto a patient.

The terms "frame" and "main housing frame" are used interchangeable herein.

Accessing a Target Tissue Location

Accessing a target tissue location, for example, the epidural or subarachnoid space via a spinal puncture is a technically challenging procedure that is performed quite commonly in the clinic, especially in the Emergency Room. The procedure involves "blindly" landmarking, or landmarking by manually palpating, the lumbar spine, to identify a gap between two spinous processes through which a needle is inserted into the epidural or subarachnoid space for fluid collection or injection. The "blind" landmarking technique improves with time and practice therefore, physicians with limited experience find the spinal puncture procedure challenging. Furthermore, regardless of experience, the spinal puncture procedure becomes difficult to perform with obese patients or patients with a high body mass index (BMI) because their high accumulation of subcutaneous adipose tissue prevents the physician to accurately landmark the lumbar spine via manual palpation. Current landmarking techniques only have a 30% accuracy, making it necessary for an average of >4 attempts to properly puncture the space, and resulting in >25% of patients having traumatic spinal punctures and >32% of patients left with post-dural puncture headaches (PDPHs). Additionally, elderly patients or pregnant patients have limited flexibility and are unable to maximally flex the hips, knees, and back, as is required during a spinal puncture procedure in order to increase the opening space between the intervertebral disks.

Beyond just landmarking and localization, other functional steps of performing a diagnostic spinal puncture, where cerebrospinal fluid (CSF) samples are collected and intracranial pressure is measured, are severely inefficient. In order to obtain an intracranial pressure reading, physicians use a two-piece manometer connected to a needle hub by a three-way stopcock, which requires estimation of fluid levels in determining intracranial pressure. To simultaneously balance a manometer and one or more cerebrospinal fluid collection tubes requires significant dexterity and/or sometimes more than one pair of hands. Thus, the risk of CSF spillages is high and further increases the risk of contamination. Accordingly, there is a need for improved or alternative devices, methods, systems, and kits to perform a spinal puncture.

There is also a need for improved or alternative devices, methods, systems and kits to visualize bone and non-bone structures at any given target tissue location. In view of these deficiencies in the current state of the art, the subject matter presented herein addresses these and other needs. The devices, systems, and methods disclosed herein are highly advantageous. Some examples of advantages provided by the devices, systems, and methods disclosed herein include, but are not limited to, providing highly accurate imaging system as means for needle guidance to a target tissue location, imaging a target tissue location in real time, while a user simultaneously advances a needle into the target tissue location, and providing features that help guide, align, and secure the needle at a specific treatment angle.

Lumbar Punctures and Spinal Punctures

A spinal puncture (alternatively referred to as a lumbar puncture) is an invasive procedure performed in a clinical setting for diagnostic or therapeutic purposes. A diagnostic spinal puncture, also known as "spinal tap," is one of the most commonly invasive tests performed in the clinic. Every year, approximately 400,000 diagnostic spinal punctures are performed in the United States. During a spinal puncture, cerebrospinal fluid is collected and in some cases, cerebrospinal fluid (CSF) opening pressure is measured. Therapeutic spinal punctures are most commonly performed to deliver spinal anesthesia, intrathecal chemotherapeutics, intrathecal pain killers, intrathecal antibiotics, and contrast agents.

In some instances, a spinal puncture is performed with a patient in a lateral decubitus position or lying down on their side, knees bent, and head in a neutral position. In some instances, a spinal puncture is performed with a patient upright, seated with the chin down and feet supported. Aseptic technique is used when performing a spinal puncture. In some instances, to perform a spinal puncture, a practitioner performs a series of steps including: identifying an intraspineous process space between the $4^{th}$ and $5^{th}$ lumbar vertebrae (L4 and L5), between L3 and L4, or between L2 and L3; cleaning the patient's skin in the lumbar area with iodinated solution, ethanol or isopropyl alcohol, and chlorhexidine; administering a local anesthetic such as, but not limited to, xylocaine or lidocaine, in a manner such that it raises a small bleb on the skin; administering additional local anesthetic, such as lidocaine, to deeper subcutaneous and intraspinous tissues; slowly inserting a spinal needle angling towards the patient's head until the epidural or subarachnoid space is entered.

A critical component of a spinal puncture is the recording of intracranial (ICP) pressure, represented by the ultra-low pressure of the cerebrospinal fluid. ICP or cerebrospinal fluid pressure is typically in the 8-15 mmHg (10-20 mbar) range. Cerebrospinal fluid pressure is typically determined using a two-piece manometer attached to a 3-way stopcock valve which is connected to a spinal needle.

During a diagnostic spinal puncture, alternatively called a spinal tap or a spinal puncture, a needle is inserted between two lumbar vertebrae and into the spinal canal in order to remove a sample(s) of cerebrospinal fluid (CSF), which surrounds the brain and the spinal cord. In some instances, the CSF is collected and its physical, chemical, microscopic, and infectious properties are inspected. Physical properties of CSF that are checked include: color, turbidity, and viscosity. Chemical components of CSF that are routinely tested for include glucose and proteins. However, additional testing includes: protein electrophoresis to distinguish different types of protein; immunoglobulin G (IgG) detection; myelin basic protein detection; lactic acid detection; lactate dehydrogenase detection; glutamine detection; C-reactive protein detection; tumor markers such as carcinoembryonic antigen (CEA), alpha-fetoprotein (AFP), and human chorionic gonadotropin (hCG); amyloid beta 42 (Aβ42) protein detection; and tau protein detection. Microscopic examination of CSF comprises analyzing the sample for total cell counts including red and white blood cells; additionally, in some instances, a cytology test is performed to determine the presence or absence of abnormal cells such as tumor cells or immature blood cells. Infectious tests performed include: CSF gram stain, culture, and sensitivity test to detect microorganisms and predict best choices for antimicrobial therapy; detection of viruses using polymerase chain reaction (PCR); detection of CSF cryptococcal antigen to detect a fungal infection caused by yeast; detection of specific antibodies; CSF acid-fast bacilli (AFB) test to detect mycobacteria such as Mycobacterium tuberculosis; detection of parasites; and CSF syphilis test.

In some instances, diagnostic spinal punctures are used to diagnose: bacterial, fungal, and viral infections including meningitis, encephalitis, and neurosyphilis or syphilis; bleeding around the brain or spinal cord including subarachnoid hemorrhages; inflammation of the brain, spinal cord, or bone marrow including myelitis; cancer including brain cancer, spinal cord cancer, and leukemia; neurological disorders including demyelinating diseases such as multiple sclerosis and demyelination polyneuropathy, Guillain-Barr syndrome, mitochondrial disorders, leukencephalopathies, paraneoplastic syndromes, Reye syndrome; headaches of unknown cause; and intracranial pressure disorders including pseudotumor cerebri also known as idiopathic intracranial hypertension (IIH), spontaneous intracranial hypotension, and normal pressure hydrocephalus.

Therapeutic lumbar punctures (alternatively called therapeutic spinal punctures) are performed in the same manner as diagnostic spinal punctures however, instead of collecting a sample of CSF, a therapeutic agent is delivered to the subarachnoid space. In some embodiments, therapeutic agents delivered via a spinal puncture include but are not limited to: anesthetics such as bupivacaine, lidocaine, tetracaine, procaine, ropivacaine, levobupivacaine, prilocaine, and cinchocaine; opioids such as morphine, fentanyl, diamorphine, buprenorphine, and pethidine or meperidine; non-opioids such as clonidine; chemotherapeutic agents such as methotrexate, cytarabine, hydrocortisone, and thiotepa; contrast agents or dyes such as iohexol, metrizamide, iopamidol, ioversol, iopromide, iodixanol, iolotran, and iodophenylundecylic acid; anti-spasmodic agents such as baclofen; antibiotics such as gentamicin sulphate; proteins such as idursulfase.

Tactile Sensing Devices and Systems

Disclosed herein, in certain embodiments, are tactile sensing devices comprising: a) a frame comprising a needle guide, the needle guide having a proximal opening and a distal opening and a track therebetween configured to guide a needle, the track comprising a notch configured to reversibly and/or temporarily secure the needle in place; wherein the needle guide is in open connection with a slot such that a needle is moved toward the track along the slot until the needle reaches the notch of the track, the slot comprising a first slot wall and a second slot wall configured to guide a needle towards the needle guide; and b) a sensor array, the sensor array comprising: a first sensor comprising a first surface, a second sensor comprising a second surface, and a sensor array slit positioned in between the first sensor and the second sensor, the first sensor configured to output a first voltage signal in response to a first change in a first pressure applied to the first surface, and the second sensor configured to output a second voltage signal in response to a second change in a second pressure applied to the second surface; wherein the sensor array is coupled to and positioned directly underneath the needle guide.

Disclosed herein, in certain embodiments, are tactile sensing systems, comprising: a frame comprising a sensor unit and an electronic unit; the sensor unit comprising: i) a needle guide, the needle guide having a proximal opening and a distal opening and a track therebetween configured to guide a needle, the track comprising a notch configured to secure the needle in place; wherein the needle guide is in open connection with a slot, the slot comprising a first slot wall and a second slot wall configured to guide a needle towards the needle guide; and ii) a sensor array, the sensor array comprising: a first sensor comprising a first surface, a second sensor comprising a second surface, and a sensor array slit positioned in between the first sensor and the second sensor, the first sensor configured to output a first voltage signal in response to a first change in a first pressure applied to the first surface, and the second sensor configured to output a second voltage signal in response to a second change in a second pressure applied to the second surface; wherein the sensor array is positioned directly underneath the needle guide; the electronic unit, comprising: i) a display screen operatively coupled to the sensor array, the display screen configured to display: a pressure map representing a target tissue location in an individual in need thereof based upon the first voltage signal and the second voltage signal from the sensor array and a projected subcutaneous needle location to be inserted into the individual; and ii) a connector configured to operatively connect the electronic unit to the sensor unit; and a computing device comprising a processor operatively coupled to the sensor unit and the electronic unit, and a non-transitory computer readable storage medium with a computer program including instructions executable by the processor causing the processor to: i) convert the first voltage signal and the second voltage signal received from the sensor array into the pressure map and display the pressure map on the display screen and ii) calculate the projected subcutaneous needle location to be inserted into the individual and output the projected needle location on the display screen.

Figure 1B:
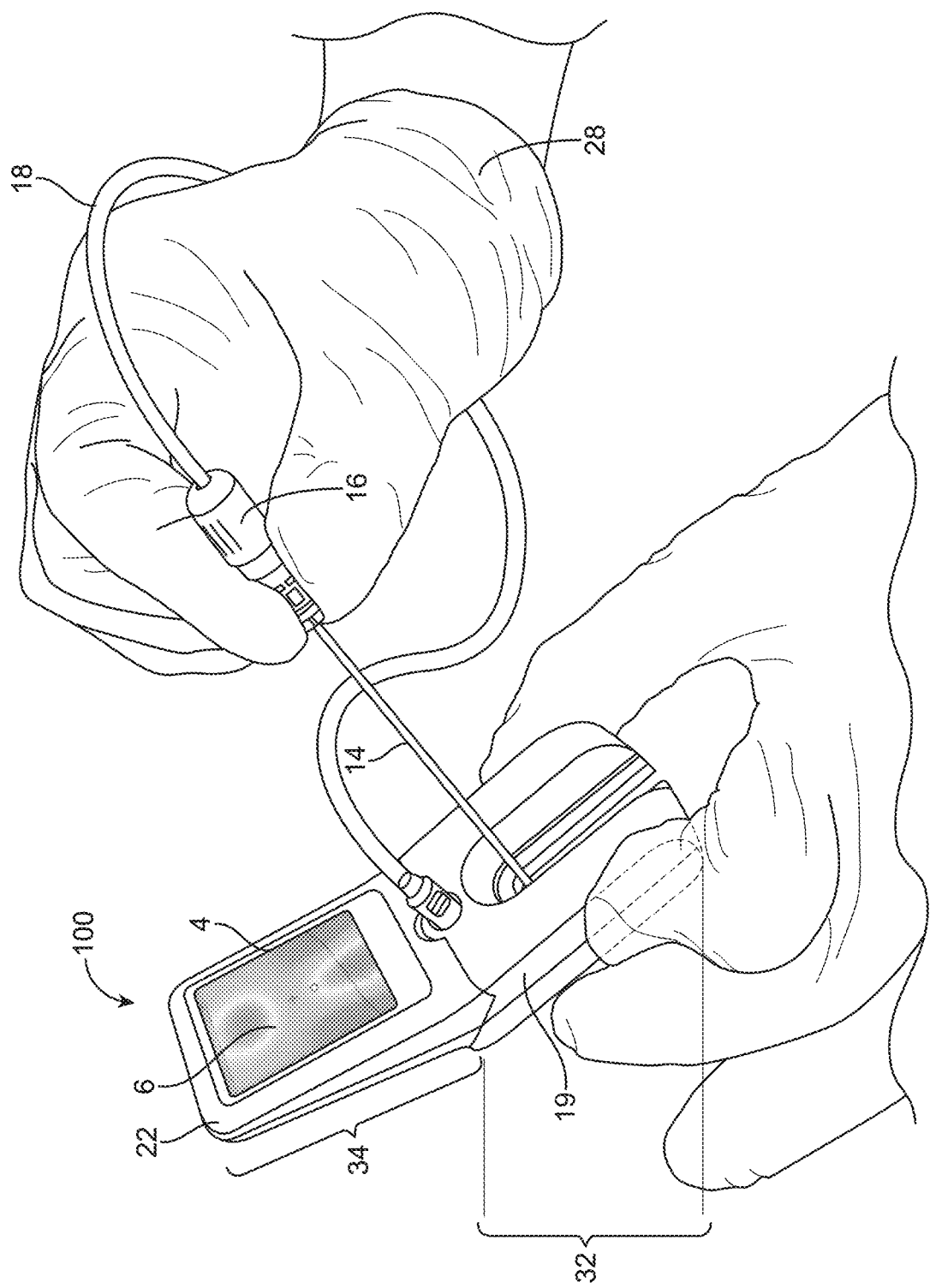

FIGS. 1A and 1B show an illustration of one embodiment of the tactile sensing device 100. In some embodiments, the tactile sensing device 100 comprises a sensor array (not shown in FIGS. 1A-B), a display screen 4, a needle guide 2, and a pressure sensor connector 12. In some embodiments, the tactile sensing device 100 is configured to image a desired target tissue location and guide a needle to the desired target tissue location. In some embodiments, the tactile sensing device 100 provides the user with targeted needle placement. In some embodiments, the tactile sensing device 100 provides the user with visual needle guidance.

Target Tissue Location

In some embodiments, the tactile sensing device images a target tissue location. In some embodiments, the desired target tissue location is the bone marrow. In some embodiments, the desired target tissue location is the epidural or subarachnoid space. In some embodiments, the desired target tissue location is gap between two spinous processes. In some embodiments, the tactile sensing device images bone and non-bone structures around a target tissue location. In some embodiments, the tactile sensing device images the lumbar vertebrae and the non-bone structures surrounding the lumbar vertebrae. In some embodiments, the tactile sensing device images the sacral vertebrae and the non-bone structures surrounding the sacral vertebrae. In some embodiments, the tactile sensing device images the lumbar and sacral vertebrae and the non-bone structures surrounding the lumbar and sacral vertebrae. In some embodiments, the tactile sensing device images the spinous processes and the non-bone structures surrounding the spinous processes. In some embodiments, the tactile sensing device images the L3 and L4 spinous processes and the non-bone structures surrounding the L3 and L4 spinous processes. In some embodiments, the tactile sensing device images the L4 and L5 spinous processes and the non-bone structures surrounding the L4 and L5 spinous processes. In some embodiments, the tactile sensing device images the L5 and S1 spinous processes and the non-bone structures surrounding the L5 and S1 spinous processes.

In some embodiments, the tactile sensing device images a first and second bone and non-bone structures. In some embodiments, the tactile sensing device images a plurality of bone and non-bone structures. In some embodiments, a bone structure is a rib. In some embodiments, a bone structure is an articular surface. In some embodiments an articular surface is a vertebral articulation, an articulation of a first bone of a hand with a second bone of the hand, an elbow joint, a wrist joint, an axillary articulation of a first bone of a shoulder with a second bone of the shoulder, a sternoclavicular joint, a temporomandibular joint, a sacroiliac joint, a hip joint, a knee joint, or an articulations of a first bone of a foot with a second bone of the foot. In some instances, a vertebral articulation is a spinous process. In some embodiments, a non-bone structure is subcutaneous tissue, a muscle, a ligament, adipose tissue, a cyst, or a cavity.

FIG. 1A shows a perspective view of the tactile sensing device 100. FIG. 1B shows an additional perspective view of the tactile sensing device 100 illustrating a user 28 actively using the tactile sensing device 100 in conjunction with a needle 14 and a pressure sensor 16. The user 28 is shown holding the needle 14 with the right hand while holding the tactile sensing device 100 with the left hand. In some embodiments, the user 28 holds the needle 14 with the left hand while holding the tactile sensing device 100 with the right hand. In some embodiments, the tactile sensing device 100 accommodates left and right handedness.

Needles

In some embodiments, the systems disclosed herein further comprise a needle 14, a stylet, or a catheter. In some embodiments, the needle is an atraumatic, also known as pencil-point type needle, or a traumatic needle, also known as a classic needle or a Quincke type needle. In some embodiments, the system further comprises a spinal needle. In some embodiments, the spinal needle is a Quincke spinal needle, a Whitacre spinal needle, or a Sprotte spinal needle. In some embodiments, the system further comprises an epidural needle. In some embodiments, the epidural needle is a Weiss epidural needle, a Tuohy epidural needle, or a Hustead epidural needle. In some embodiments, the needle incudes, by way of non-limiting examples, a 6-gauge needle, an 8-gauge needle, a 13-gauge needle, a 15-gauge needle, a 17-gauge needle, an 18-gauge needle, a 19-gauge needle, a 20-gauge needle, a 21-gauge needle, a 22-gauge needle, a 23-gauge needle, a 24-gauge needle, a 25-gauge needle, a 26-gauge needle, a 27-gauge needle, a 28-gauge needle, a 29-gauge needle, a 30-gauge needle, a 31-gauge needle, and a 32-gauge needle. In some embodiments, the needle is a spinal needle ranging between 1-10 inches in length. In some embodiments, the needle contains a stylet, also known as an obturator or an introducer, which is a fine wire, a slender probe, or a solid rod with a metal hub fitted to match a needle's bevel. In diagnostic spinal punctures, a stylet is withdrawn from the needle to allow cerebrospinal fluid to flow out from the spinal canal and through the needle hub.

In some embodiments, the system further comprises a catheter. In some embodiments, the catheter is an epidural tunneled catheter, which is implanted into the epidural space as a medication delivery port. In some embodiments, the catheter is used to monitor intracranial pressure during a diagnostic spinal puncture procedure. In some embodiments, the catheter is used as means to continuously remove cerebrospinal fluid and relieve pressure on the brain of a patient suffering from hydrocephalus.

In some embodiments, the pressure sensor 16 is operatively connected to the tactile sensing device 100 by a pressure sensor cable 18 that operatively couples the pressure sensor 16 to the tactile sensing device 100 via a pressure sensor connector 12. In some embodiments, the pressure sensor connector 12 operatively connects the tactile sensing device with a fluid pressure sensor. In some embodiments, the pressure sensor connector 12 is located distally away from the needle guide 2. In some embodiments, the pressure sensor connector 12 is a male connector. In some embodiments, the pressure sensor connector 12 is a female connector. In some embodiments, the pressure sensor connector 12 is a pressure sensor port.

In some embodiments, pressure sensor 16 is operatively connected to the tactile sensing device 100 and configured to measure a cerebrospinal fluid pressure. In some embodiments, the pressure sensor is an electronic pressure sensor. In some embodiments, the electronic pressure sensor is medical grade. In some embodiments, the electronic pressure sensor is a Honeywell TruStability®, board mount pressure sensor, which is capable of sensing 0-60 mbar. In some embodiments, the electronic pressure sensor is an uncompensated and unamplified piezoresistive silicon pressure sensor. In some embodiments, the pressure sensor 16 provides feedback of internal needle pressure during needle insertion.

In some embodiments, the pressure sensor 16 is a digital pressure sensor. In some embodiments, pressure sensor 16 is a pressure gauge. In some instances, pressure sensor 16 is a piezoresistive, capacitive, electromagnetic, piezoelectric, optical, or potentiometric pressure sensor. In some embodiments, a cerebrospinal fluid pressure measured with the pressure sensor 16 is displayed digitally. In some embodiments, a cerebrospinal fluid pressure measured with pressure sensor 16 is displayed on display screen 4 in real-time. In some embodiments, the display screen 4 provides visual needle guidance. In some embodiments, a cerebrospinal fluid pressure measured with the pressure sensor 16 is displayed digitally on an external display screen. In some embodiments, a cerebrospinal fluid pressure measured with the pressure sensor 16 is displayed digitally on an external display screen of a computing device operatively connected to the tactile sensing device 100. In some embodiments, a cerebrospinal fluid pressure measured with pressure sensor 16 is displayed on display screen 4 in real-time, while user 28 simultaneous advances the needle 14 into a desired target tissue location.

In some embodiments, once the needle is guided to and inserted into a desired target tissue location and the tactile sensing device 100 is no longer needed, user 28 slides the tactile sensing device 100 distally away from himself or herself in order to maintain the needle in place while removing the tactile sensing device 100 and optionally disconnects the pressure sensor 16.

In some embodiments, the tactile sensing device 100 comprises a main housing frame 19. In some embodiments, the main housing frame 19 is the housing of the tactile sensing device 100. In some embodiments, the main housing frame 19 protects internal elements of the tactile sensing device 100 such as, but not limited to, electric circuitry, a power source, and sensor array electric connections. In some embodiments, the main housing frame 19 is composed of a plastic or elastomer material including, but not limited to: polyethylene; polypropylene; polystyrene; polyester; polylactic acid (PLA); polycarbonate, polyvinyl chloride, polyethersulfone, polyacrylate or acrylic or polymethylmethacrylate (PMMA); polysulfone; polyetheretherketone (PEEK); thermoplastic elastomers or thermoplastic urethanes; or poly-p-xylylene or parylene.

In some embodiments, the main housing frame 19 comprises an electronic unit 34 and a sensor unit 32, as shown in FIG. 1B. In some embodiments, the main housing frame 19 encompasses, surrounds, protects, supports, encases, or houses the electronic unit 34 and the sensor unit 32. In some embodiments, the electronic unit 34 is disposable. In some embodiments, the electronic unit 34 is reusable. In some embodiments, the electronic unit 34 is durable. In some embodiments, the tactile sensing device 100 comprises a sleeve (not shown in FIGS. 1A-B) that is configured to receive the electronic unit 34. In some embodiments, the sleeve is a vacuum-formed sleeve. In some embodiments, the sleeve is sterile. In some embodiments, the sleeve is composed of a plastic or elastomer material including, but not limited to: polyethylene; polypropylene; polystyrene; polyester; polylactic acid (PLA); polycarbonate, polyvinyl chloride, polyethersulfone, polyacrylate or acrylic or polymethylmethacrylate (PMMA); polysulfone; polyetheretherketone (PEEK); thermoplastic elastomers or thermoplastic urethanes; or poly-p-xylylene or parylene. In some embodiments, the sleeve is composed of a rubber material including, but not limited to: silicone rubber, natural rubber, acrylonitrile-butadiene rubber, hydrogenated acrylonitrile-butadiene rubber, ethylene propylene diene rubber, fluorocarbon rubber, chloroprene rubber, fluorosilicone rubber, polyacrylate rubber, ethylene acrylic rubber, styrene-butadiene rubber, polyester urethane rubber, or polyether urethane rubber. In some embodiments, a part of the main housing frame 19 surrounding the needle guide 2 is made out of clear plastic. In some embodiments, the main housing frame 19 is made out of clear plastic. In some embodiments, having the main housing frame 19 or part of the main housing frame 19 near the needle guide be made out of clear plastic, enables user 28 to better visualize and guide the needle 14 as it penetrates the skin of the individual. In some embodiments, the frame 20 comprises a handle (not shown in FIGS. 1A-B). In some embodiments, the handle is a curved handle, a power grip handle, or a pinch grip. In some embodiments, the handle comprises a grip feature.

In some embodiments, the sensor unit has a length 91, as shown in FIG. 1A. In some embodiments, the length 91 of the sensor unit is about 130 mm. In some embodiments, the length 91 of the sensor unit is about 100 mm. In some embodiments, the length 91 of the sensor unit is about 50 mm. In some embodiments, the length 91 of the sensor unit is about 150 mm. In some embodiments, the length 91 of the sensor unit is about 25 mm. In some embodiments, the length 91 of the sensor unit is about 200 mm.

In some embodiments, the sensor unit has a width 93, as shown in FIG. 1A. In some embodiments, the width 93 of the sensor unit is at least about 25 mm to about 200 mm at most. In some embodiments, the width 93 of the sensor unit is at least about 25 mm to about 150 mm at most. In some embodiments, the sensor unit is at least about 25 mm to about 130 mm at most. In some embodiments, the width 93 of the sensor unit is at least about 25 mm to about 50 mm at most. In some embodiments, the width 93 of the sensor unit is at least about 50 mm to about 200 mm at most. In some embodiments, the width 93 of the sensor unit is at least about 50 mm to about 150 mm at most. In some embodiments, the width 93 of the sensor unit is at least about 50 mm to about 130 mm at most. In some embodiments, the width 93 of the sensor unit is at least about 130 mm to about 200 mm at most. In some embodiments, the width 93 of the sensor unit is at least about 130 mm to about 150 mm at most. In some embodiments, the width 93 of the sensor unit is at least about 150 mm to about 200 mm at most.

In some embodiments, the electronic unit 34 comprises the display screen 4. In some embodiments, the display screen 4 is operatively coupled to the sensor array (not shown in FIGS. 1A-B). In some embodiments, sensor array 24 is located on the posterior surface of the tactile sensing device 100. In some embodiments, sensor array 24 is coupled to the posterior surface of the tactile sensing device 100. In some embodiments, sensor array 24 is adhered to the posterior surface of the tactile sensing device 100. In some embodiments, sensor array 24 is connected to the posterior surface of the tactile sensing device 100. In some embodiments, the posterior surface of the tactile sensing device 100 has a curvature about a longitudinal axis (not shown in FIGS. 1A-B). In some embodiments, the posterior surface of the tactile sensing device 100 has a curvature about a lateral axis (not shown in FIGS. 1A-B). In some embodiments, the curvature about a longitudinal axis is designed to reduce adverse effects of surrounding muscle. In some embodiments, the curvature about a lateral axis helps the user comprehend the need to rock the device in instances where there is significant spinal flexion.

Sensor Arrays

In some embodiments, the tactile sensing device comprises an array of sensors. In some embodiments, the sensor array is a tactile sensor array. In some embodiments, the sensor array comprises sensors that are piezoresistive sensors. In some embodiments, the sensor array comprises sensors are piezoelectric sensors. In some embodiments, the sensor array comprises sensors are piezoresistive sensors. In some embodiments, the sensor array comprises sensors that are optical sensors. In some embodiments, the sensor array comprises sensors that are electromagnetic sensors. In some embodiments, the sensor array comprises sensors that are capacitive sensors. In some embodiments, the sensor array comprises sensors that are potentiometric sensors.

In some embodiments, the sensor array 8 comprises pressure sensors. In some embodiments, the pressure sensors are force-sensitive resistors. Force-sensitive resistors (FSRs) change their resistance in response to a change in pressure applied to their surface. In some embodiments, the force-sensitive resistors decrease their resistance with an increase in pressure applied the surface of the sensor. In some embodiments, the sensor array comprises at least one sensor configured to output a signal in response to a change in pressure applied to its surface. Force-sensitive resistors are two wire devices with a resistance that depends on applied force. In some embodiments, the force-sensitive resistors comprise a voltage divider. In some embodiments, the voltage divider outputs a voltage value that is correlated to the resistance; thus, the output voltage value also changes in response to a pressure applied to the surface of the sensor. In some embodiments, an increase in voltage indicates an increase in a pressure applied to the surface of the sensor. In some instances, the force-sensitive resistors output voltage signals. In some embodiments, the array of force-sensitive resistors is a 6×3 array comprising eighteen force-sensitive resistors. In some embodiments, the array of force-sensitive resistors is an 8×4 array comprising thirty two force-sensitive resistors. In some embodiments, the size of the array of force-sensitive resistors is dependent upon the surface area of the individual's body to be examined. In some embodiments, the array of force-sensitive resistors is configured in a way that is sufficient to visualize the bone and non-bone structures in the individual.

In some embodiments, the sensor array is a screen-printed pressure sensor array. In some embodiments, the screen-printed pressure sensor array is also known as a matrix. In some embodiments, screen-printed pressure sensor arrays offer enhanced construction, resolution, sensitivity, and customizability, all at a reduced cost. In some embodiments, the screen-printed pressure sensor array comprises a ThruMode configuration. As used herein, a ThruMode configuration refers to an array comprising two parallel sheets, one with conductive rows; the other with conductive columns; the locations at which these overlap form sensing cells (sensels). In some embodiments, the screen-printed pressure sensor array comprises two parallel sheets, one with conductive rows; the other with conductive columns; the locations at which these overlap form sensing cells (sensels). In some embodiments, the screen-printed pressure sensor array comprises a ShuntMode configuration. In some embodiments, the drive electronics to support these arrays necessitate a 16-line shift register and 16-channel multiplexer. In some embodiments, the 16-line shift register and 16-channel multiplexer are driven by a microcontrolled.

In some embodiments, the sensor array is an array of sensor elements also known as "sensels." In some embodiments, the sensels are not discrete sensors. In some embodiments, the sensor elements or sensels are configured to connect to each other. In some embodiments, the sensor elements are arranged in a grid, with each sensor element (or "sensel") located at the intersection of a row and column. In some embodiments, the rows and columns are pinned out, rather than individual sensors being pinned out, as is the case with an array of discrete sensors. In some embodiments, the sensor array is an array of cells. In some embodiments, the sensor array is an array of sensing cells. In some embodiments, the sensor array slit is positioned between two rows of sensels. In some embodiments, the sensor array slit is positioned between two columns of sensels. In some embodiments, the sensor array slit is within the bounds of the sensor array, and/or within the bounds of the sensor array outer edges, and/or within the edges bounding of the sensor array. In some embodiments, the distal opening of the needle guide opening is positioned between two rows of sensels. In some embodiments, the distal opening of the needle guide is positioned between two columns of sensels. In some embodiments the distal opening of the needle guide is within the bounds of the sensor array, and/or within the bounds of the sensor array outer edges, and/or within the edges bounding of the sensor array.

In some embodiments, the screen-printed pressure sensor array comprises a plurality of sensors. In some embodiments, the sensors are sensing elements or sensels. In some embodiments, the sensels comprise interdigitated fingers. In some embodiments, the screen-printed pressure sensor array is a 10×5 array. In some embodiments, the screen-printed pressure sensor array comprises about 10 columns of sensels and about 5 rows of sensels. In some embodiments, the screen-printed pressure sensor array comprises about 5 columns of sensels and about 10 rows of sensels. In some embodiments, the screen-printed pressure sensor array is designed to accommodate a slot for needle guidance and device removal. In some embodiments, the slot interrupts the sensor array. In some embodiments, the slot extends from a bounding edge of the array to the distal opening of the track, and is sized and configured to allow the needle to stay in place once inserted into the subject while the device itself is removed from the treatment area on the subject. That is, the spacing at the distal end of the slot is designed to accommodate a needle, which is angled at a range of 0-30 degrees cephalad. For example, in some embodiments, the slot comprises a minimum width from a first slot wall to a second slot wall of 0.5 mm to 15 mm, from 0.5 mm to 10 mm, from 0.5 mm to 6 mm, from 0.25 mm to 10 mm, from 0.25 mm to 5 mm, about 1.5 mm, about 2 mm, about 2.5 mm, about 3 mm, 2 mm, 3 mm, 2.5 mm, 1.5 mm or about 1-3 mm. For example, in some embodiments, the slot comprises a minimum width at the slot terminus from a first slot wall to a second slot wall of 0.5 mm to 15 mm, from 0.5 mm to 10 mm, from 0.5 mm to 6 mm, from 0.25 mm to 10 mm, from 0.25 mm to 5 mm, about 1.5 mm, about 2 mm, about 2.5 mm, about 3 mm, 2 mm, 3 mm, 2.5 mm, 1.5 mm or about 1-3 mm. For example, in some embodiments, the slot comprises a notch width at the track from a first slot wall to the notch at the distal opening of 0.5 mm to 15 mm, from 0.5 mm to 10 mm, from 0.5 mm to 6 mm, from 0.25 mm to 10 mm, from 0.25 mm to 5 mm, about 1.5 mm, about 2 mm, about 2.5 mm, about 3 mm, 2 mm, 3 mm, 2.5 mm, 1.5 mm or about 1-3 mm. For example, in some embodiments, the slot comprises a distal track width at the distal opening of the track from a first slot wall to the distal opening of the track of 0.5 mm to 15 mm, from 0.5 mm to 10 mm, from 0.5 mm to 6 mm, from 0.25 mm to 10 mm, from 0.25 mm to 5 mm, about 1.5 mm, about 2 mm, about 2.5 mm, about 3 mm, 2 mm, 3 mm, 2.5 mm, 1.5 mm or about 1-3 mm. In some embodiments of the device, the slot comprises a distal end that is between two sensors or between two sensels. In some embodiments, the sensor array comprises a slit that substantially corresponds in size and shape with the distal end of the slot of the device, and the slit terminates at the distal opening of the needle guide. In some embodiments the slit of the sensor array comprises a minimum width along the length of the slit from a first slit wall to a second slit wall of 0.5 mm to 15 mm, from 0.5 mm to 10 mm, from 0.5 mm to 6 mm, from 0.25 mm to 10 mm, from 0.25 mm to 5 mm, about 1.5 mm, about 2 mm, about 2.5 mm, about 3 mm, 2 mm, 3 mm, 2.5 mm, 1.5 mm or about 1-3 mm. The position of the slot and or of the slit may be various, depending on the embodiment. That is, depending on the embodiment, the slot and slit may be leftward extending from a right boundary of the sensor array, upward extending from a bottom boundary of the sensor array, downward extending from a top boundary of the sensor array, rightward extending from a left boundary of the sensor array, or diagonally extending from any boundary of the array that is not only leftward extending, rightward extending, upward extending, or downward extending from a boundary of the sensor array toward the needle guide distal opening, all of which directions of extension are relative to the sensor array when the array is positioned against a subject and the top boundary is closest to the head of the subject. In some embodiments, the screen-printed pressure sensor array comprises increased spacing between the upper and lower 5 rows of sensels. In some embodiments, the screen-printed pressure sensor array comprises a symmetric cutout or sensor array slit in that space. In some embodiments, the cutout or slit in the sensor array is designed for a slot, which accommodates leftward sliding of the device off the patient. In some embodiments, the screen-printed pressure sensor array comprises an opening or an orifice through which a needle is inserted therethrough. In some embodiments, the tactile sensing device does not comprise a slot. For example, in certain embodiments, the tactile sensing device comprises a needle guide that is reversibly attached to the tactile sensing device, in which case there is no need for a slot. In some embodiments, the sensor array does not comprise a slit.

In some embodiments, the sensor array slit is about 2 mm wide at the slit minimum width from a first slit wall to a second slit wall. In some embodiments, the sensor array slit is about 1 mm wide at the slit minimum width from a first slit wall to a second slit wall. In some embodiments, the sensor array slit is about 0.5 mm wide at the slit minimum width from a first slit wall to a second slit wall. In some embodiments, the sensor array slit is about 3 mm wide at the slit minimum width from a first slit wall to a second slit wall. In some embodiments, the sensor array slit is about 0.1 mm wide at the slit minimum width from a first slit wall to a second slit wall. In some embodiments, the sensor array slit is about 4 mm wide at the slit minimum width from a first slit wall to a second slit wall. In some embodiments, the sensor array slit is about 5 mm wide at the slit minimum width from a first slit wall to a second slit wall. In some embodiments, the sensor array slit is about 6 mm wide at the slit minimum width from a first slit wall to a second slit wall. In some embodiments, the sensor array slit is about 6 mm wide at the slit minimum width from a first slit wall to a second slit wall. In some embodiments, the sensor array slit is about 7 mm wide at the slit minimum width from a first slit wall to a second slit wall. In some embodiments, the sensor array slit is about 8 mm wide at the slit minimum width from a first slit wall to a second slit wall. In some embodiments, the sensor array slit is about 9 mm wide at the slit minimum width from a first slit wall to a second slit wall. In some embodiments, the sensor array slit is about 10 mm wide at the sensor boundary. In some embodiments, the sensor array slit is about 15 mm wide at the sensor boundary. In some embodiments, the sensor array slit is about 20 mm wide at the sensor boundary. In some embodiments, the sensor array slit is about 30 mm wide or more at the sensor boundary. In some embodiments, the array slit is a constant width from the distal opening to the sensor array boundary. In some embodiments, the array slit gets narrower from the sensor array boundary to the distal opening of the needle guide. In some embodiments, the array slit gets wider from the sensor array boundary to the needle guide distal opening. In some embodiments, the array slit width varies from the sensor array boundary to the distal opening of the needle guide.

In some embodiments, the sensor array slit is at least about 0.1 mm to about 30 mm wide at most from a first slit wall to a second slit wall. In some embodiments, the sensor array slit is at least about 0.1 mm to about 25 mm wide at most from a first slit wall to a second slit wall. In some embodiments, the sensor array slit is at least about 0.1 mm to about 20 mm wide at most from a first slit wall to a second slit wall. In some embodiments, the sensor array slit is at least about 0.1 mm to about 15 mm wide at most from a first slit wall to a second slit wall. In some embodiments, the sensor array slit is at least about 0.1 mm to about 10 mm wide at most from a first slit wall to a second slit wall. In some embodiments, the sensor array slit is at least about 0.1 mm to about 9 mm wide at most from a first slit wall to a second slit wall. In some embodiments, the sensor array slit is at least about 0.1 mm to about 8 mm wide at most from a first slit wall to a second slit wall. In some embodiments, the sensor array slit is at least about 0.1 mm to about 7 mm wide at most from a first slit wall to a second slit wall. In some embodiments, the sensor array slit is at least about 0.1 mm to about 6 mm wide at most from a first slit wall to a second slit wall. In some embodiments, the sensor array slit is at least about 0.1 mm to about 5 mm wide at most from a first slit wall to a second slit wall. In some embodiments, the sensor array slit is at least about 0.1 mm to about 4 mm wide at most from a first slit wall to a second slit wall. In some embodiments, the sensor array slit is at least about 0.1 mm to about 3 mm wide at most from a first slit wall to a second slit wall. In some embodiments, the sensor array slit is at least about 0.1 mm to about 2 mm wide at most from a first slit wall to a second slit wall. In some embodiments, the sensor array slit is at least about 0.1 mm to about 1 mm wide at most from a first slit wall to a second slit wall. In some embodiments, the sensor array slit is at least about 0.1 mm to about 0.5 mm wide at most from a first slit wall to a second slit wall.

In some embodiments, the screen-printed pressure sensor array detects a plurality of spinous processes in the lumbar region. In some embodiments, the screen-printed pressure sensor array has a center-to-center (C2C) distance of about 6.86 mm between sensels. In some embodiments, the screen-printed pressure sensor array has a center-to-center (C2C) distance of about 6.86 mm between sensels. In some embodiments, the screen-printed pressure sensor array has a center-to-center (C2C) distance of about at least 0.5 mm to about 7 mm between sensels. In some embodiments, the screen-printed pressure sensor array has a center-to-center (C2C) distance of about 1 mm between sensels. In some embodiments, the screen-printed pressure sensor array has a center-to-center (C2C) distance of about 2 mm between sensels. In some embodiments, the screen-printed pressure sensor array has a center-to-center (C2C) distance of about 3 mm between sensels. In some embodiments, the screen-printed pressure sensor array has a center-to-center (C2C) distance of about 4 mm between sensels. In some embodiments, the screen-printed pressure sensor array has a center-to-center (C2C) distance of about 5 mm between sensels. In some embodiments, the screen-printed pressure sensor array has a center-to-center (C2C) distance of about 6 mm between sensels. In some embodiments, the screen-printed pressure sensor array has a center-to-center (C2C) distance of about 7 mm between sensels. In some embodiments, the screen-printed pressure sensor array has a center-to-center (C2C) distance of about 8 mm between sensels. In some embodiments, the screen-printed pressure sensor array has a center-to-center (C2C) distance of about 9 mm between sensels. In some embodiments, the screen-printed pressure sensor array has a center-to-center (C2C) distance of about 10 mm between sensels.

In some embodiments, the screen-printed pressure sensor array has an effective resolution of about 13.72 mm. In some embodiments, the screen-printed pressure sensor array has an effective resolution of at least about 1 mm to at most about 15 mm. In some embodiments, the screen-printed pressure sensor array has an effective resolution of at least about 5 mm to at most about 10 mm. In some embodiments, the screen-printed pressure sensor array has an effective resolution of at least about 1 mm to at most about 2.5 mm. In some embodiments, the screen-printed pressure sensor array has an effective resolution of about 1 mm. In some embodiments, the screen-printed pressure sensor array has an effective resolution of about 2 mm. In some embodiments, the screen-printed pressure sensor array has an effective resolution of about 3 mm. In some embodiments, the screen-printed pressure sensor array has an effective resolution of about 4 mm. In some embodiments, the screen-printed pressure sensor array has an effective resolution of about 5 mm. In some embodiments, the screen-printed pressure sensor array has an effective resolution of about 6 mm. In some embodiments, the screen-printed pressure sensor array has an effective resolution of about 7 mm. In some embodiments, the screen-printed pressure sensor array has an effective resolution of about 8 mm. In some embodiments, the screen-printed pressure sensor array has an effective resolution of about 9 mm. In some embodiments, the screen-printed pressure sensor array has an effective resolution of about 10 mm. In some embodiments, the screen-printed pressure sensor array has an effective resolution of about 11 mm. In some embodiments, the screen-printed pressure sensor array has an effective resolution of about 12 mm. In some embodiments, the screen-printed pressure sensor array has an effective resolution of about 13 mm. In some embodiments, the screen-printed pressure sensor array has an effective resolution of about 14 mm. In some embodiments, the screen-printed pressure sensor array has an effective resolution of about 15 mm. In some embodiments, the effective resolution of the screen-printed pressure sensor array is determined by Nyquist criterion. In some embodiments, the effective resolution of the screen-printed pressure sensor array is determined by the total number of sensels in the sensor array. In some embodiments, the sensitivity of the screen-printed pressure sensor array is defined by array construction (i.e. related to spacer depth, silver-ink conductivity, and FSR thickness).

In some embodiments, the sensor array visualizes two vertebral gaps. In some embodiments, the sensor array visualizes the upper- and lower-most spinous processes (SPs) in the imaged area under the sensor array or within range of the sensor array. In some embodiments, the sensor array resolves the midline of a spine. In some embodiments, the active area imaged by the sensor array is rectangular (for example comprising a 50 mm×20 mm active area) a polygonal, triangular, circular, or another shape generally corresponding to the shape of the sensor array shape. In some embodiments, the screen-printed pressure sensor array visualizes only two SPs. In some embodiments, height of the screen-printed pressure sensor array is the sum of the height of two SPs (average in addition to one standard deviation) and the interspinous process distance (IPD) (higher-end average in addition to one standard deviation). In some embodiments, the width of the screen-printed pressure sensor array is defined as the caudal width of an SP (though the cranial width, which is significantly smaller than the caudal width of an SP, is the more superficial feature). In some embodiments, width of the screen-printed pressure sensor array is defined is by the shallowest area between the muscle on either side of the vertebral column. In some embodiments, the caudal width of an SP is at least about at least 6 mm to about 16 mm at most. In some embodiments, the cranial width of an SP is at least at least about 2 mm to about 10 mm at most. In some embodiments, the caudal width is about 90% larger than the cranial width. In some embodiments, the caudal width is about 80% larger than the cranial width. In some embodiments, the caudal width is about 70% larger than the cranial width. In some embodiments, the caudal width is about 60% larger than the cranial width. In some embodiments, the caudal width is about 50% larger than the cranial width. In some embodiments, the caudal width is about 40% larger than the cranial width. In some embodiments, the width of the screen-printed pressure sensor array is at least about 6 mm to about 16 mm at most. In some embodiments, the width of the screen-printed pressure sensor array is at least about 7 mm to about 16 mm at most. In some embodiments, the width of the screen-printed pressure sensor array is at least about 8 mm to about 16 mm at most. In some embodiments, the width of the screen-printed pressure sensor array is at least about 9 mm to about 16 mm at most. In some embodiments, the width of the screen-printed pressure sensor array is at least about 10 mm to about 16 mm at most. In some embodiments, the width of the screen-printed pressure sensor array is at least about 11 mm to about 16 mm at most. In some embodiments, the width of the screen-printed pressure sensor array is at least about 12 mm to about 16 mm at most. In some embodiments, the width of the screen-printed pressure sensor array is at least about 13 mm to about 16 mm at most. In some embodiments, the width of the screen-printed pressure sensor array is at least about 14 mm to about 16 mm at most. In some embodiments, the width of the screen-printed pressure sensor array is at least about 15 mm to about 16 mm at most.

In some embodiments, the width of the screen-printed pressure sensor array is at least about 6 mm. In some embodiments, the width of the screen-printed pressure sensor array is at least about 7 mm. In some embodiments, the width of the screen-printed pressure sensor array is at least about 8 mm. In some embodiments, the width of the screen-printed pressure sensor array is at least about 9 mm. In some embodiments, the width of the screen-printed pressure sensor array is at least about 10 mm. In some embodiments, the width of the screen-printed pressure sensor array is at least about 11 mm. In some embodiments, the width of the screen-printed pressure sensor array is at least about 12 mm. In some embodiments, the width of the screen-printed pressure sensor array is at least about 13 mm. In some embodiments, the width of the screen-printed pressure sensor array is at least about 14 mm. In some embodiments, the width of the screen-printed pressure sensor array is at least about 15 mm. In some embodiments, the width of the screen-printed pressure sensor array is at least about 16 mm. In some embodiments, the width of the screen-printed pressure sensor array is at least about 17 mm. In some embodiments, the width of the screen-printed pressure sensor array is at least about 18 mm. In some embodiments, the width of the screen-printed pressure sensor array is at least about 19 mm. In some embodiments, the width of the screen-printed pressure sensor array is at least about 20 mm. In some embodiments, the width of the screen-printed pressure sensor array is at least about 25 mm.

Multiplexer

In some embodiments, the tactile sensing device further comprises a multiplexer. In some embodiments, there may be more than one multiplexer. The multiplexer selects voltage output signals from the sensor and forwards the selected voltage output signals into a single line. In some embodiments, the multiplexer is an analog multiplexer. In some embodiments, the analog multiplexer is a 16:1 or an 8:1 multiplexer. In some embodiments, the analog multiplexer is a frequency division multiplexer or a wave division multiplexer. In various further embodiments, the multiplexer is a digital multiplexer. In some instances, the digital multiplexer is a time division multiplexer. In some embodiments, the time division multiplexer is a synchronous time division multiplexer or an asynchronous time division multiplexer. In some embodiments, the multiplexer is mounted onto a printed circuit board.

Voltage Divider

In some embodiments, the tactile sensing device further comprises a voltage divider. In some embodiments, the voltage divider is a component of a pressure sensor such as a resistive force sensor or of an array of sensors. In some embodiments, there may be more than one voltage divider. In some embodiments, the pressure sensor array or a sensor thereof which may be a resistive sensor is coupled to a measuring resistor $R_M$ in a voltage divider. In some embodiments, the output voltage signal from the force-sensitive resistors is read out using a voltage divider. In some embodiments, the output voltage signal read out using the voltage divider is described by Equation 1 below.

Equation 1: $V_{OUT}=(R_M V_{IN})/(R_M+R_{FSR})$; wherein $V_{OUT}$ is the output voltage signal, $R_M$ is the measuring resistor, $V_{IN}$ is the input voltage signal, and $R_{FSR}$ is the resistance detected by the pressure-sensitive resistor. In some embodiments, the voltage divider is a resistive voltage divider, a low-pass RC filter voltage divider, an inductive voltage divider, or a capacitive voltage divider.

Voltage Source

In some embodiments, the tactile sensing device further comprises a voltage source. In some embodiments, the voltage source is a battery. In some embodiments, the voltage source is rechargeable. In some embodiments, the voltage source is removable. In some embodiments, the voltage source includes, but is not limited to: a nickel cadmium (NiCd) battery, nickel-metal hydride (NiMH) battery, a nickel zinc (NiZn) battery, a lead acid battery, a lithium ion battery (Li-ion), or a lithium ion polymer (Li-ion polymer) battery.

In some embodiments, the electronic unit 34 comprises the display screen 4 and a connector (not shown in FIGS. 1A-B) configured to operatively connect the electronic unit 34 to the sensor unit 32. In some embodiments, the display screen 4 is configured to display: a pressure map 6 representing a target tissue location in an individual in need thereof based upon a first voltage signal and a second voltage signal from the sensor array 24, a projected subcutaneous needle location 10 to be inserted into the individual, and an original skin level needle location 8.

Display Screen

In some embodiments, the tactile sensing device 100 comprises a display screen 4 to provide visual information to a user. In some embodiments, the display screen 4 is operatively connected to the tactile sensing device 100. In some embodiments, the display screen 4 is a computer screen, a mobile device screen, or a portable device screen. In some embodiments, the display screen 4 is a liquid crystal display (LCD). In further embodiments, the display screen 4 is a thin film transistor liquid crystal display (TFT-LCD). In some embodiments, the display screen 4 is an organic light emitting diode (OLED) display. In various further embodiments, an OLED display is a passive-matrix OLED (PMOLED) or active-matrix OLED (AMOLED) display. In some embodiments, the display screen 4 is a plasma display. In some embodiments, the display screen 4 is a video projector. In still further embodiments, the display screen 4 is a combination of devices such as those disclosed herein. In some embodiments, the display screen 4 is a full color display. In some embodiments, the display screen 4 is a monochromatic display.

In some embodiments, the visual information provided to the user via a display screen 4 is a pressure map 6 representing bone and non-bone structures. In some embodiments, the pressure map 6 is a heat map. In some embodiments, the sensor array comprises at least one sensor configured to output a signal in response to a change in pressure applied to its surface, wherein the signal is represented as a heat map 6. In some embodiments, the heat map 6 is a graphical representation of voltage signals wherein the individual voltage output signals are represented as a plurality of colors, color hues, color saturations, graphical patterns, shading, geometrical figures, or any combination thereof. In some embodiments, high voltage output signals are represented in a red-based color and low voltage output signals are represented in blue-based color. In some embodiments, high voltages are about 5V. In some embodiments, high voltages in a heat map correspond to a bone. In some embodiments, high voltages in a heat map correspond to spinous processes. In some embodiments, the heat map displays high voltages in a red color. In some embodiments, the heat map displays low voltages in a blue color. In some embodiments, low voltages in a heat map correspond to tissue softer than bone. In some embodiments, low voltages in a heat map correspond to inter interspinous ligaments.

In some embodiments, the pressure map is overlaid onto a second image. In some embodiments, the second image is a type of diagnostic image including, but not limited to: radiography image, magnetic resonance imaging (MRI) image, computed tomography (CT) image, nuclear medicine image, ultrasound image, photoacoustic image, or thermography image. In some embodiments, the second image is an image of bone and non-bone structures. In some embodiments, the second image of a bone and non-bone structure is an image of a rib; an articular surface such as, a vertebral articulation, an articulation of a first bone of a hand with a second bone of the hand, an elbow joint, a wrist joint, an axillary articulation of a first bone of a shoulder with a second bone of the shoulder, a sternoclavicular joint, a temporomandibular joint, a sacroiliac joint, a hip joint, a knee joint, or an articulations of a first bone of a foot with a second bone of the foot; non-bone structure is subcutaneous tissue, a muscle, a ligament, adipose tissue, a cyst, or a cavity.

In some embodiments, the pressure map 6 is a heat map. In some embodiments, the pressure map 6 shows the needle position of the needle 14 at the skin level ("original"), and its adjusted, projected location, accounting for the depth of the subcutaneous tissue. In some embodiments, the pressure map 6 displays the original skin level location of the needle 8. In some embodiments, the pressure map 6 displays the projected subcutaneous position of the needle 10, adjusted for the depth of the subcutaneous tissue. In some embodiments, the pressure map 6 shown in FIG. 1A is generated by using the tactile sensing device on a lumbar spine model. In some embodiments, the pressure map 6 shown in FIG. 1A is generated by using the tactile sensing device on the lumbar region of a patient. In some embodiments, the pressure map 6 shown in FIG. 1A displays two spinous processes (darker areas) and the soft tissue (lighter areas) surrounding the spinous processes. In some embodiments, pressing the tactile sensing device 100 against bone, outputs a higher voltage signal compared to the voltage signal output when pressing the tactile sensing device 100 against soft tissue. In some embodiments, the pressure map 6 enables a user to correctly identify and distinguish hard tissue (e.g. bone and bony landmarks) from soft tissue (e.g. adipose tissue, muscle, ligaments, and tendons).

In some embodiments, the original skin level needle location 8 is the location at which the needle penetrates the skin of the individual. In some embodiments, the original skin level needle location 8 is also termed the original needle location, the original skin level needle location, or the needle entry location. In some embodiments, the original skin level needle location 8 is depicted with a circle. In some embodiments, the projected subcutaneous needle location 10 is depicted with a cross shape or a star shape or a crosshair display indicator. In some embodiments, the original skin level needle location 8 and the projected subcutaneous needle location 10 are labeled with words, such as "original" and "projected" or "adjusted," or abbreviations, such as "O" and "P" in order for a user to identify them correctly on the display screen 4. In some embodiments, the original skin level needle location (for example, which is indicated by a crosshair display indicator) stays at the center of the display, and the heat map itself is translated based on algorithm output (by the same factor the crosshair would be in an embodiment where the crosshair moves based on the movement of the sensor array on the subject/patient).

In some embodiments, a trigonometric algorithm, as shown in Equation 2 below, is used to determine the projected subcutaneous needle location 10 at which the needle will be once it traverses the subcutaneous tissue. Equation 2: $h = \tan(\theta) \cdot d$; wherein h is solved for in this equation, d refers to the tissue depth; and $\theta$ is the cephalad angle in radians at which the needle is inserted. FIG. 1A shows representative X-, Y-, and Z-axes defining an origin at the original skin level needle location 8. In some embodiments, h is the distance along the Y-axis between the original skin level needle location 8 and the projected subcutaneous location of the needle 10. That is, while the features such as bones are shown are in their correct locations, due to the depth the needle will have to traverse, it will not hit those features at the angle it's inserted due to adjustment the device provides in angle and insertion location. Similarly, while the target location is in its correct location, due to the depth the needle will traverse, without the adjustment of angle and insertion direction at the skin level that the device provides, the needle might otherwise miss its target location subcutaneously. In some embodiments, the projected subcutaneous needle location 10 is located distally away from the original skin level needle location 8. In some embodiments, the original skin level needle location 8 has coordinates (x, y, z), as shown in FIG. 1A. In some embodiments, the Z-axis, shown in FIG. 1A, represents the tissue depth at which the needle is inserted into a patient. In some embodiments, the original skin level needle location 8 has coordinates (x, y, 0), wherein z=0 represents the needle has not penetrated the subcutaneous tissue and is at the level of the skin. In some embodiments, the projected subcutaneous needle location 10 has coordinates (x, y+h, z+d), as shown in FIG. 1A. In some embodiments, z+d represents z-coordinate of the point in space where the tip of the needle is located once it traverses the subcutaneous tissue. In some embodiments, d represents the tissue depth. In some embodiments, 0 is assumed to be the angulation (i.e. cephalad angulation, that is, $h \cdot \tan(\text{treatment angle}) = d$; tangent of complementary angles). In some embodiments, 0 is the treatment angle defined as the space between the posterior face of the sensor array and the needle.

In some embodiments, the (x, y, z) coordinates (x, y+h, z+d) of the projected subcutaneous location of the needle 10 are displayed on the display screen 4. In some embodiments, the (x,y) coordinates (x, y+h) of the projected subcutaneous needle location 10 are displayed on the display screen 4. In some embodiments, the y-coordinate y+h of the projected subcutaneous needle location 10 are displayed on the display screen 4. In some embodiments, the projected subcutaneous needle location 10 is displayed two-dimensionally on the display screen 4, as shown in FIGS. 1A and 1B. In some embodiments, the projected subcutaneous needle location 10 is displayed two-dimensionally on the display screen 4 by displaying the (x, y) coordinates (x, y+h). In some embodiments, the projected subcutaneous needle location 10 is displayed three-dimensionally on the display screen 4. In some embodiments, the projected subcutaneous needle location 10 is displayed three-dimensionally on the display screen 4 by displaying the coordinates (x, y+h, z+d). In some embodiments, a 3D representation of the needle, terminating at the projected, subcutaneous site, is displayed on the display.

In some embodiments, the depth, d, at which the needle will be once it traverses the subcutaneous tissue (e.g. adipose tissue, muscle, ligaments, and/or tendons) is calculated. In some embodiments, the depth, d, is calculated based on the signal output of the sensor array. In some embodiments, the depth, d, is calculated based on a voltage signal ratio, $V_{max}/V_{min}$ produced by the sensor array. In some embodiments, the voltage signal ratio, $V_{max}/V_{min}$ is defined as the ratio between a maximum voltage reading, $V_{max}$, (for example, over a spinous process) and a minimum voltage reading (for example, over subcutaneous tissue). In some embodiments, the voltage signal ratio $V_{max}/V_{min}$ is determined by aligning the sensor array such that the Y-axis shown in FIG. 1A vertically traverses the midline of the spinous processes (i.e. the Y-axis shown in FIG. 1A represents the midline of the spinous processes). In some embodiments, the maximum voltage reading, $V_{max}$, and the minimum voltage reading, $V_{min}$, are determined by selecting the maximum and minimum voltage readings detected along the midline of the active area subjected to tactile sensing by the sensor array (e.g. along the Y-axis shown in FIG. 1A). In some embodiments, the voltage signal ratio $V_{max}/V_{min}$ is determined by using the voltage signal readings located along the midline of a pressure map 6 (i.e. along the Y-axis shown in FIG. 1A).

In some embodiments, the depth, d, is calculated based on a first voltage signal ratio $V_{max1}/V_{min1}$ and a second voltage signal $V_{max2}/V_{min2}$ produced by the sensor array. In some embodiments, the voltage signal ratio $V_{max1}/V_{min1}$ is acquired by placing the tactile sensing device (i.e. the sensor array) on the skin surface of a patient. In some embodiments, the second voltage signal $V_{max2}/V_{min2}$ is an empirically determined ratio of the maximum voltage reading, $V_{max2}$, to the minimum voltage reading, $V_{min2}$. In some embodiments, the empirically determined second voltage signal ratio $V_{max2}/V_{min2}$ corresponds to a known depth, d. In some embodiments, a plurality of second voltage signal ratios $V_{max2}/V_{min2}$ are empirically obtained using the tactile sensing device and correlated to a known tissue depth. In some embodiments, a plurality of second voltage signal ratios, $V_{max2}/V_{min2}$, are empirically obtained using the tactile sensing device and correlating the second voltage signal ratios to a plurality of corresponding tissue depths in a spinal lumbar model. In some embodiments, a plurality of second voltage signal ratios, $V_{max2}/V_{min2}$, are empirically obtained using the tactile sensing device and correlating the second voltage signal ratios to a plurality of corresponding tissue depths in a human cadaver. In some embodiments, the plurality of empirically determined second voltage signal ratios, $V_{max2}/V_{min2}$, and corresponding tissue depths are compiled in a tissue depth database. In some embodiments, the tissue depth database is accessed by the computing device of the tactile sensing system. In some embodiments, the computing device obtains a first voltage signal ratio, $V_{max1}/V_{min1}$, accesses the tissue depth database, compares the first voltage signal ratio, $V_{max1}/V_{min1}$ to an empirically determined second voltage signal ratio $V_{max2}/V_{min2}$, obtains the tissue depth corresponding to the second voltage signal ratio $V_{max2}/V_{min2}$ (and consequently, also corresponding to the first voltage signal ratio $V_{max1}/V_{min1}$), and uses the obtained tissue depth to calculate the subcutaneous projected needle location 10 based on Equation 2.

In some embodiments, the tissue depth, d, used in Equation 2 (i.e. the level at which the needle will be once it traverses the subcutaneous tissue) is calculated based on a machine-learning algorithm. In some embodiments, the machine-learning algorithm is selected from a plurality of machine-learning algorithms. In some embodiments, the machine-learning algorithm selected to calculate tissue depth, d, used in Equation 2, is the machine-learning algorithm that outputs the best approximation of the tissue depth (i.e. that outputs the least amount of error). In some embodiments, the machine-learning algorithm learns a target function (f) that best maps a voltage signal ratio $V_{max}/V_{min}$ to a tissue depth. In some embodiments, the machine-learning algorithm learns a target function (f) that predicts a tissue depth based on a voltage signal ratio $V_{max}/V_{min}$. In some embodiments, the machine-learning algorithm includes an irreducible error to account for not having sufficient attributes to predict the tissue depth. In some embodiments, the function (f) is linear. In some embodiments, the function (f) is nonlinear.

In some embodiments, the tactile sensing device comprises a machine-learning system. In some embodiments, the machine-learning system comprises a machine-learning model, a set of parameters, and a learner. In some embodiments, the machine-learning model makes predictions or approximations of a tissue depth. In some embodiments, the parameters are the input that is used by the model to make its approximations. In some embodiments, the parameters are the first voltage signal ratio $V_{max1}/V_{min1}$, the second voltage signal ratio $V_{max2}/V_{min2}$, and the known tissue depths (e.g. obtained from human cadavers, patients (e.g. actual outcome), and/or spinal lumbar models). In some embodiments, the learner is the system that adjusts the parameters, and in turn the machine-learning model, by looking at differences in the predictions versus actual outcome. In some embodiments, the machine-learning system uses a mathematical equation to express the relationship between the second voltage signal ratio $V_{max2}/V_{min2}$ and a known tissue depth. In some embodiments, the first voltage signal ratio $V_{max1}/V_{min1}$ is given to the machine-learning system. In some embodiments, the first voltage signal ratio $V_{max1}/V_{min1}$ is the training data used by the learner to train the machine-learning model and improve the predicted approximations of the tissue depth. In some embodiments, the learner makes adjustments to the parameters in order to refine the machine-learning model. In some embodiments, the machine-learning model predicts a tissue depth by: a) having the machine-learning model receive input data or training data (i.e. the first voltage signal ratio $V_{max1}/V_{min1}$), b) using a mathematical equation to represent the training data, c) having the learner compare the training data to the mathematical equation; d) having the learner adjust the training data to reshape the machine-learning model (i.e. to adjust the mathematical equation used by the machine-learning model in step b)), repeating steps a)-d) until a high degree of confidence is achieved on the predicted tissue depth.

In some embodiments, the machine-learning algorithm enhances the accuracy of the displayed, projected subcutaneous needle location. In some embodiments, the visualization of a projected subcutaneous needle location helps the user optimally gauge when they have positioned the sensor array at a location that will allow them to accurately and reliably reach the midline of the target tissue location (e.g. the spine) with the needle.

In some embodiments, the sensor unit 32 is disposable. In some embodiments, the sensor unit 32 is reusable. In some embodiments, the sensor unit 32 comprises the needle guide 2. In some embodiments, the sensor unit 32 comprises a sensor array 24. In some embodiments, the sensor array 24 comprises: a first sensor comprising a first surface, a second sensor comprising a second surface, the first sensor configured to output a first voltage signal in response to a first change in a first pressure applied to the first surface, and the second sensor configured to output a second voltage signal in response to a second change in a second pressure applied to the second surface. In some embodiments, the sensor array 24 is coupled to and positioned directly underneath the needle guide 2. In some embodiments, the sensor array 24 is a matrix array. In some embodiments, the sensor array 24 is a flexible sensor array. In some embodiments, the sensor array 24 is attached to a sensor array attachment area (not shown in FIGS. 1A-B). In some embodiments, the sensor array 24 is adhered to the posterior surface of the tactile sensing device 100.

In some embodiments, the tactile sensing device 100 comprises a recess 124 comprising a first recess wall 126a and a second recess wall (not shown in FIGS. 1A and 1B). In some embodiments, the first recess wall 126a and the second recess wall are connecting walls. In some embodiments, the first recess wall 126a and the second recess wall form a first "U" shape. In some embodiments, the needle guide 2 comprises a slot 38. In some embodiments, the needle guide 2 comprises a first slot wall 130a and a second slot wall (not shown in FIGS. 1A and 1B). In some embodiments, the first slot wall 130a and the second slot wall are connecting. In some embodiments, the first slot wall 130a and the second slot wall form a second "U" shape. In some embodiments, the needle guide 38 comprises a slot opening 38a and a slot terminus 38b. In some embodiments, the needle guide 2 has a proximal opening 134a and a distal opening 134b and a track therebetween configured to guide the needle 14 at a predetermined angle relative to the surfaces of the sensors and/or relative to the face of the sensor array as the needle 14 travels into the subject.

In some embodiments, the sensor array (not shown in FIGS. 1A-B) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIGS. 1A-B), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIGS. 1A-B) is an array of cells. In some embodiments, the sensor array (not shown in FIGS. 1A-B) is an array of sensing cells. In some embodiments, the sensor array slit (not shown in FIGS. 1A-B) is positioned between two rows or more of sensels. In some embodiments, the sensor array slit (not shown in FIGS. 1A-B) is positioned between two columns or more of sensels. In some embodiments, the sensor array slit (not shown in FIGS. 1A-B) is within the bounds of the sensor array, and/or within the bounds of the sensor array outer edges, and/or within the edges bounding of the sensor array. In some embodiments, the distal opening 134b of the needle guide 2 is positioned between two rows of sensels. In some embodiments, the distal opening 134b of the needle guide 2 is positioned between two columns of sensels. In some embodiments the distal opening 134b of the needle guide 2 is within the bounds of the sensor array, and/or within the bounds of the sensor array outer edges, and/or within the edges bounding of the sensor array. In some embodiments, the distal opening 134b is between two or more sensors of the sensor array. In some embodiments, the distal opening 134b is positioned between two rows or more of sensels. In some embodiments, the distal opening 134b is positioned between two columns or more of sensels.

In some embodiments, track is shaped as a "V." In some embodiments, track is shaped as a "U." In some embodiments, the track comprises a lip that protrudes from one of the slot walls (i.e., from the first slot wall 130a or from the second slot wall (not shown in FIGS. 1A and 1B)). In some embodiments, the lip aligns with an arm of the V or of the U shape. The track shape and the lip thereof allows the needle to be seated in the track and not slip toward the opening of the slot prior to or during insertion of the needle into the subject.

In some embodiments, the needle guide 2 is flexible. In some embodiments, the needle guide 2 comprises a flexible catch. In some embodiments, the flexible catch comprises a flexible material. In some embodiments, the first slot wall 130a and the second slot wall 130b are composed of a soft, flexible material. Non-limiting examples of the soft, flexible materials include: silicone rubber, natural rubber, acrylonitrile-butadiene rubber, hydrogenated acrylonitrile-butadiene rubber, ethylene propylene diene rubber, fluorocarbon rubber, chloroprene rubber, fluorosilicone rubber, polyacrylate rubber, ethylene acrylic rubber, styrene-butadiene rubber, polyester urethane rubber, or polyether urethane rubber. In some embodiments, the catch is shaped as a disc with a slit therein that aligns with an axis of the slot that extends from the terminus to the opening of the slot. In some embodiments, the catch allows for reversible and temporary holding of the needle or of the injector device and results in alignment with and seating of the needle in the track such that the needle does not slip toward the opening of the slot prior to or during the movement of the needle into the subject.

In some embodiments, the recess 124 has an axis Y2, as shown in FIG. 1A, that extends from the base of the first "U" to between the first recess wall 126a and the second recess wall. In some embodiments, the slot 38 shares the axis Y2 of the recess 124. In some embodiments, the needle guide 2 is located at the apex of the second "U." In some embodiments, the needle guide 2 is located at the apex of the first "U." In some embodiments, the recess 124 provides a stop for the needle 14 such that the syringe barrel and/or the needle hub have a limited distal distance that they are advanced along the slot 38. In some embodiments, the needle 14 rests on the recess 124.

In some embodiments, the pressure sensor connector 12 is located along axis Y2. In some embodiments, the pressure sensor connector 12 is located at an offset relative to axis Y2. In some embodiments, the pressure sensor connector 12 is located distally away from the recess 124, between the posterior end of the display screen 4 and the recess 124. In some embodiments, the recess 124 comprises the needle guide 2. In some embodiments, the first recess wall 126a or the second recess wall, or both, comprise a top bevel 128, such that the recess 124 is narrower closer to the slot 38 than the recess 124 is further from the slot 38. In some embodiments, the tactile sensing device 100 does not comprise a slot 38. In some embodiments, the needle 14 is inserted in the recess 124, along the edges of the top bevel 128, when the tactile sensing device 100 does not comprise a slot 38. In some embodiments, the top bevel 128 is positioned on top of the anterior surface of the sensor array.

In some embodiments, one or more of the walls of the slot 38 are perpendicular to the track. In some embodiments, the track comprises a notch (not shown in FIGS. 1A-B) or catch configured to reversibly or temporarily secure the needle in place. In some embodiments, the slot 38 is parallel to the track. In some embodiments, one or more of the walls of the slot 38 parallel to the top bevel 128, as shown in FIG. 1A. In some embodiments, the slot 38 is enclosed by the first slot wall 130a and the second slot wall, (the second slot wall is not shown in FIGS. 1A-B). In some embodiments, the needle guide 2 is in open connection with the slot 38. In some embodiments, the slot 38 comprises a first slot wall and a second slot wall (not shown in FIGS. 1A-B). In some embodiments, the slot walls are configured to guide a needle 14 towards the needle guide 2. In some embodiments, the needle guide 2 is fixed.

In some embodiments, the track 144 is angled at a treatment angle ranging between about 40° to about 90° with respect to the posterior face of the sensor array 24. In some embodiments, the track 144 is angled at a treatment angle ranging between about 69° to about 81° with respect to the posterior face of the sensor array 24. In some embodiments, the track 144 is angled at a treatment angle ranging between about 75° to about 90° with respect to the posterior face of the sensor array 24.

In some embodiments, the top bevel 128 comprises a first needle alignment guide 36a, a second needle alignment guide 36b, and a third needle alignment guide 36c. In some embodiments, the needle alignment guide 36 is a marking, a notch, an indentation, a sticker, a light, a light bulb, a light emitting diode (LED), or any combination of these, configured to provide the user with an alignment reference tool to align the needle along a proper axis or in a proper location that is adequate for needle insertion into an individual along the track. In some embodiments, the needle alignment guide 36 is a visual cue for midline alignment. In some embodiments, the needle alignment guide 36 is a mechanical feature (e.g., a notch) in the area located along an edge of the needle guide 2 and/or slot 38. In some embodiments, the frame comprises a needle alignment guide. In some embodiments, the needle alignment guide is a notch or a marking on the surface of the tactile sensing device. In some embodiments, the needle alignment guide 36 alerts the user when the needle is or is not in a proper or correct alignment or position. For instance, in one embodiment, the needle alignment guide 36 is an LED that turns on and emits a green light when the needle is aligned properly or in the correct position for insertion. For instance, in some embodiments, the needle alignment guide 36 is an LED that turns on and emits a red light when the needle is aligned improperly or is not in the correct position for insertion. In some embodiments, the needle alignment guide 36 is an LED that only turns on when the needle is aligned properly or in the correct position for insertion. In some embodiments, the needle alignment guide 36 is an LED that only turns on when the needle is not aligned properly or is not in the correct position for insertion.

Figure 2A:
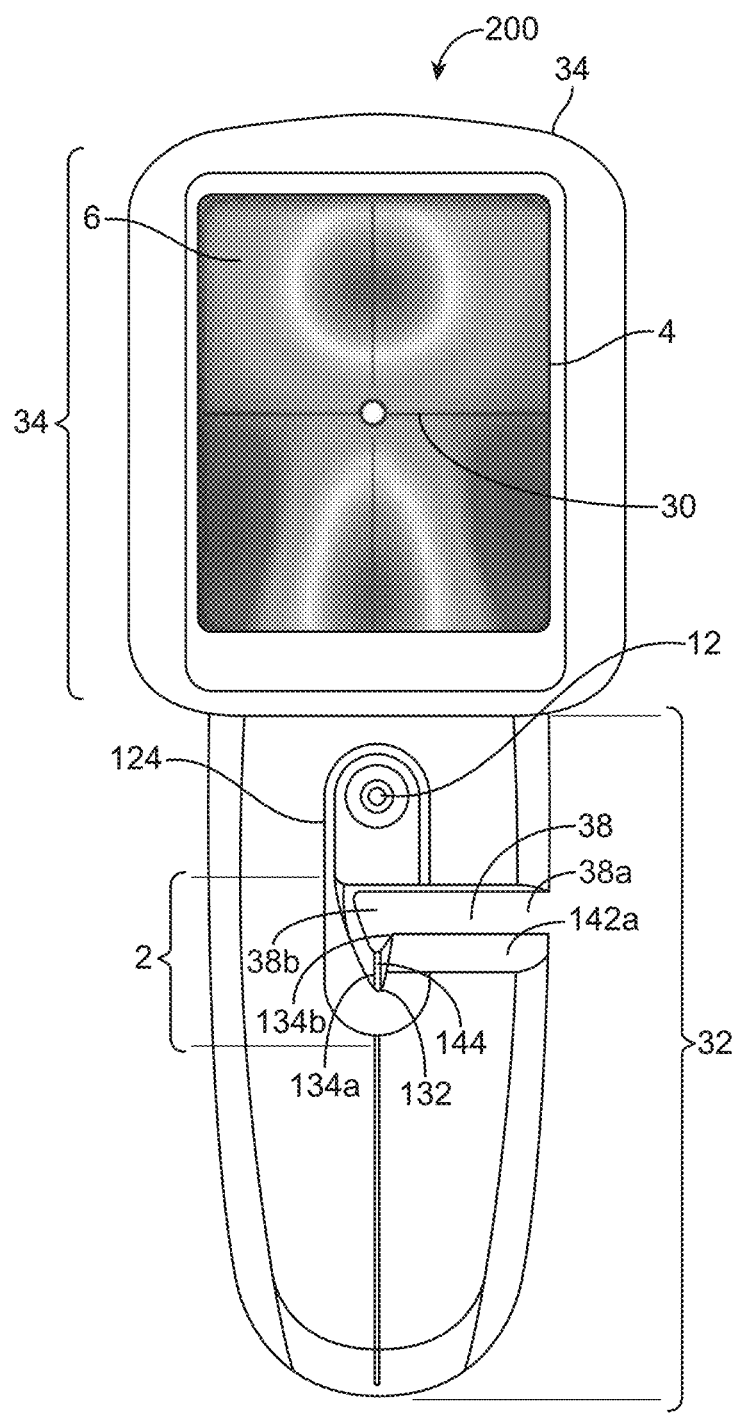
FIGS. 2A and 2B illustrate an embodiment of a tactile sensing device 200 comprising a lateral slot and a needle guide comprising a notch.
Figure 2B:
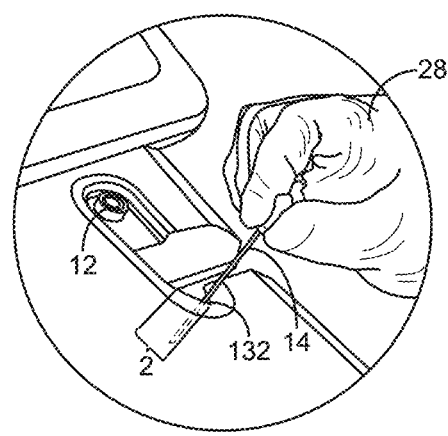

FIGS. 2A and 2B show an illustration of an embodiment of the tactile sensing device 200. In some embodiments, the tactile sensing device 200 comprises a sensor array (not shown in FIGS. 2A-B), a display screen 4, a needle guide 2, and a pressure sensor connector 12. In some embodiments, the display screen 4 comprises pressure map features, such as a simple centerline, or a plurality of active lines, which connect detected peaks and offer a visual indication of alignment (e.g. flashing or an once it's within 5° of the centerline). In some embodiments, the pressure map 6 displayed on the display screen 4 comprises visual cues such as crosshairs 30, as shown in FIG. 2A. In some embodiments, the crosshairs 30 provide the user with a visual indication of midline alignment (i.e. alignment both along longitudinal and lateral axes on the display screen 4). In some embodiments, the tactile sensing device 200 provides visual, auditory, and/or haptic cues to indicate to a user when the tactile sensing device 200 and/or the needle are aligned or not aligned with the target tissue location.

In some embodiments, the tactile sensing device 200 comprises a needle guide 2. In some embodiments, the needle guide 2 comprises a proximal opening 134a and a distal opening 134b. In some embodiments, a track 144 is in between the proximal opening 134a and the distal opening 134b. In some embodiments, the track 144 is configured to guide a needle into a target tissue location at a predetermined treatment angle. FIGS. 2A-B show the tactile sensing device 200 comprising a slot 38. In some embodiments, the slot 38 is perpendicular to the needle guide 2, as shown in FIG. 2A. FIG. 2A shows the tactile sensing device 200 comprising a recess 124. In some embodiments, the recess 124 comprises a pressure sensor connector 12. In some embodiments, the recess 124 ends on a second slot wall (not shown in FIGS. 2A-B).

FIG. 2B shows a user 28 resting a needle 14 on notch 132 and on the track 144 (not shown in FIG. 2B, but shown in FIG. 2A). In some embodiments, the notch 132 reversibly secures the needle onto the track 144. In some embodiments, the notch 132 reversibly secures the needle in place. In some embodiments, the notch 132 aligns the needle at a correct angle aligned with the angle of the track. In some embodiments, the notch 132 aligns the needle with a target tissue location. In some embodiments, the notch 132 comprises a lip that interrupts and protrudes from one or more slot wall and temporarily and reversibly reduces the chance of or prevents the needle from moving off the track 144. In some embodiments, the notch 132 prevents the needle from being inserted off center into the target tissue location. In some embodiments, the needle 14 rides over and/or along the notch (not shown in FIGS. 2A-B).

In some embodiments, the notch 132 is or comprises a lip. In some embodiments, the notch 132 comprises a rubber or plastic lip that must be overcome by the needle in order to move the needle 14 along the track 144 and toward the distal opening 134b. In some embodiments, the lip is shaped as a "U" and comprises an opening. In some embodiments, the lip is flexible. In some embodiments, the lip is rigid. In some embodiments, the opening of the lip is narrower than the proximal opening 134a in order to prevent a needle 14 from moving off the track 144 once inserted through the notch 132. In some embodiments, the notch 132 comprises more than one lips or rings positioned along the track 144. In some embodiments, the notch 132 comprises at least two lips or rings positioned along the track 144. In some embodiments, the notch 132 comprises at least three lips or rings positioned along the track 144. In some embodiments, the notch 132 comprises at least four lips or rings positioned along the track 144. In some embodiments, the notch 132 comprises at least five lips or rings positioned along the track 144. In some embodiments, the notch 132 comprises at least ten lips or rings positioned along the track 144.

In some embodiments, the notch 132 comprises a groove. In some embodiments, the groove has a "U" shaped form and has a first lateral wall and a second lateral wall that have both extremities (or arms) open. In some embodiments, one pair of projections are located in the first lateral wall and in the second lateral wall, opposite from one another and with a profile that defines the continuation of the curved wall of each groove, in a way that accommodates the cylindrical cannula of the needle 14. In some embodiments, the user inserts the needle 14 into the groove by pushing the needle into the groove, with a light force so that the body of the needle overcomes the projections of the groove. In some embodiments, the user releases the needle 14, by pulling on its proximal extremity, with a light force so that the body of the needle passes the projections of the groove. In some embodiments, alternatively, the user releases the needle 14, by sliding the needle 14 along the track 144, towards the proximal opening 134a. In some embodiments, the groove is composed of a soft, flexible material in order to enable separation of the extremities of the "U" when the needle 14 is either inserted or released.

In some embodiments, the notch 132 comprises a beveled edge. In some embodiments, the beveled edge must be overcome in order to move the needle 14 along the track 144 and toward the distal opening 134b. In some embodiments, the notch 132 comprises more than beveled edges positioned along the track 144. In some embodiments, the beveled edge is positioned at the proximal opening 134a. In some embodiments, the beveled edge is positioned at the distal opening 134b.

In some embodiments, the notch 132 comprises a bump. In some embodiments, the bump is positioned at the proximal opening 134a. In some embodiments, the bump is positioned at the distal opening 134b. In some embodiments, the bump is composed of a soft, flexible material such as, but not limited to rubber or silicone. In some embodiments, the bump is shaped as a "U." In some embodiments, the bump is shaped as a "V." In some embodiments, the bump mates with the notch 132. In some embodiments, the bump interrupts the wall of the slot or protrudes from the wall of the slot.

In some embodiments, the notch 132 is a plastic piece. In some embodiments, the notch 132 is a rubber piece. In some embodiments, the notch 132 is a stopper notch. In some embodiments, the notch 132 is a grip.

In some embodiments, the notch 132 is a snap-on notch. In some embodiments, the user snaps the needle into the snap-on notch to secure the needle in the track 144. In some embodiments, the snap-on notch has a "U" shaped form and has a first lateral wall and a second lateral wall that have both ends open. In some embodiments, one pair of projections are located in the first lateral wall and in the second lateral wall, opposite from one another and with a profile that defines the continuation of the curved wall of each snap-on notch, in a way that perfectly accommodates the cylindrical cannula of the needle 14. In some embodiments, the user inserts the needle 14 into the snap-on notch by pushing the needle into the snap-on notch, with a light force so that the cannula of the needle overcomes the projections of the snap-on notch. In some embodiments, the user releases the needle 14, by pulling on its proximal end, with a light force so that the body of the needle passes the projections of the snap-on notch. In some embodiments, alternatively, the user releases the needle 14, by sliding the needle 14 along the track 144, towards the proximal opening 134a. In some embodiments, the snap-on notch is composed of a soft, flexible material in order to enable separation of the ends of the "U" when the needle 14 is either inserted or released. In some embodiments, the snap-on notch is composed of a rigid material.

In some embodiments, the notch 132 comprises a magnet located at the proximal opening 134a. In some embodiments, the notch 132 comprises a magnet located at the distal opening 134b. In some embodiments, the notch 132 comprises a magnet located along the track 144. In some embodiments, the notch 132 comprises a magnet located along the track and shaped as a "U." In some embodiments, the notch 132 comprises a magnet located along the track and shaped as a cylinder. In some embodiments, the needle 14 comprises a magnet. In some embodiments, the needle 14 comprises a magnet located on the needle hub. In some embodiments, the needle 14 comprises a magnet that is coaxially aligned with the needle cannula. In some embodiments, the needle 14 comprises a magnet located on the tip of the needle 14. In some embodiments, the magnet on the notch 132 defines a magnetic axis that is aligned in a desired predetermined orientation with respect to the needle. In some embodiments, the magnet on the needle 14 defines a magnetic axis that is aligned in a desired predetermined orientation with respect to the notch 132. In some embodiments, the desired predetermined orientation is the desired treatment angle. In some embodiments, the magnet on the notch 132 attracts the magnet on the needle 14 and secures the needle onto the track 144. In some embodiments, the position of the needle 14 is tracked by tracking the magnet on the notch 132 and by tracking the magnet on the needle 14. In some embodiments, the tactile sensing system comprises a magnetic tracking system to track the position of a needle in real time.

In some embodiments, the sensor array (not shown in FIGS. 2A-B) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIGS. 2A-B), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIGS. 2A-B) is an array of cells. In some embodiments, the sensor array (not shown in FIGS. 2A-B) is an array of sensing cells. In some embodiments, the sensor array slit (not shown in FIGS. 2A-B) is positioned between two rows or more of sensels. In some embodiments, the sensor array slit (not shown in FIGS. 2A-B) is positioned between two columns or more of sensels. In some embodiments, the sensor array slit (not shown in FIGS. 2A-B) is within the bounds of the sensor array, and/or within the bounds of the sensor array outer edges, and/or within the edges bounding of the sensor array. In some embodiments, the distal opening 134b of the needle guide 2 is positioned between two rows of sensels. In some embodiments, the distal opening 134b of the needle guide 2 is positioned between two columns of sensels. In some embodiments the distal opening 134b of the needle guide 2 is within the bounds of the sensor array, and/or within the bounds of the sensor array outer edges, and/or within the edges bounding of the sensor array. In some embodiments, the distal opening 34b is between two or more sensors of the sensor array. In some embodiments, the distal opening 34b is positioned between two rows or more of sensels. In some embodiments, the distal opening 34b is positioned between two columns or more of sensels.

Tactile Sensing Device Methods

Disclosed herein, in certain embodiments, are methods of positioning a needle in the tactile sensing device, comprising: inserting the needle through the slot; guiding the needle in the slot by sliding the needle in between the first slot wall and the second slot wall towards the needle guide, wherein a first needle guide wall connects to the second needle guide wall at the proximal opening of the needle guide to form a notch at the proximal opening; securing the needle in place by inserting the needle into the notch; and sliding the needle along the track that extends from the notch at the proximal opening to the distal opening of the needle guide.

Spinal Puncture Methods

In some embodiments, methods for performing a spinal puncture in an individual in need thereof, comprise: placing a tactile sensing device on a lumbar region of the individual; applying force to the tactile sensing device against the lumbar region; viewing voltage signals, corresponding to vertebral articulations, detected by the tactile sensing device resulting from the application of force to the tactile sensing device against the lumbar region, on a display screen; localizing two spinous processes on the image; identifying a gap between a first spinous process and a second spinous process of the individual; using a needle guide to insert a needle between the first and second spinous processes of the individual and into a subarachnoid space; and collecting cerebrospinal fluid or administering a therapeutic agent. In some embodiments, the method comprises use of an operatively connected pressure sensor for fluid-pressure measurement.

Epidural Methods

In some embodiments, methods for administering a therapeutic agent to an epidural space of an individual in need thereof, comprise: placing a tactile sensing device on a lumbar region of the individual; applying force to the tactile sensing device against the lumbar region; viewing voltage signals, corresponding to vertebral articulations, detected by the tactile sensing device resulting from the application of force to the tactile sensing device against the lumbar region, on a display screen; localizing two spinous processes on the image; identifying a gap between a first spinous process and a second spinous process of the individual; using a needle guide to insert a needle between the first and second spinous processes and into the epidural space of the individual; and injecting a therapeutic agent into the epidural space. In some embodiments, this method comprises attachment of a loss-of-resistance syringe to facilitate detection of epidural-space entry.

Therapeutic Agents

In some embodiments, therapeutic agents are delivered via a spinal puncture. In some embodiments, therapeutic agents delivered via a spinal puncture include but are not limited to: anesthetics, analgesics, chemotherapeutic agents, contrast agents or dyes, anti-spasmodic agents, antibiotics, or proteins. In some embodiments, anesthetics delivered via a spinal puncture include but are not limited to: bupivacaine, lidocaine, tetracaine, procaine, ropivacaine, levobupivacaine, prilocaine, and cinchocaine. In some embodiments, analgesics delivered via a spinal puncture include but are not limited to: opioids such as morphine, fentanyl, diamorphine, buprenorphine, and pethidine or meperidine; and non-opioids such as clonidine. In some embodiments, chemotherapeutic agents delivered via a spinal puncture include but are not limited to: methotrexate, cytarabine, hydrocortisone, and thiotepa. In some embodiments, contrast agents or dyes delivered via a spinal puncture include but are not limited to: iohexol, metrizamide, iopamidol, ioversol, iopromide, iodixanol, iolotran, and iodophenylundecylic acid. In some embodiments, anti-spasmodic agents delivered via a spinal puncture include baclofen. In some embodiments, antibiotics delivered via a spinal puncture include gentamicin sulphate. In some embodiments, proteins delivered via a spinal puncture include idursulfase.

Spinous Processes

In some embodiments, methods for performing a spinal puncture in an individual in need thereof comprise using a needle guide to insert a needle between the first and second spinous processes and into the subarachnoid space of the individual. In some embodiments, methods for administering a therapeutic agent to an epidural space of an individual in need thereof comprise using a needle guide to insert a needle between the first and second spinous processes and into the epidural space of the individual. In some embodiments, the first spinous process is a part of the first lumbar vertebra (L1), L2, L3, or L4 lumbar vertebrae and the second spinous process is a part of L2, L3, L4, or L5 lumbar vertebrae. In some further embodiments, the first and spinous process is a part In some embodiments, a kit for performing a diagnostic spinal puncture in an individual in need thereof, comprises: a tactile sensing device to image bone and non-bone structures in the individual; a computer to process voltage signals detected by the tactile sensing device; a display screen to visualize the bone and non-bone structures; an electronic pressure sensor to measure cerebrospinal fluid pressure; and a sleeve.

In some embodiments, the slot 38 is the entry point or entrance for the needle 14. In some embodiments, the user first inserts the needle 14 through the slot opening 38a. In some embodiments, the user guides the needle 14 in the slot 38 towards the slot terminus 38b, by sliding the needle 14 in between the first slot wall 142a and the second slot wall (not shown in FIGS. 2A-B). In some embodiments, the user guides the needle 14 in the slot 38 t towards the needle guide 2. In some embodiments, the needle guide 2 comprises a first needle guide wall and a second needle guide wall (not shown in FIGS. 2A-B). In some embodiments, the first needle guide wall connects to the second needle guide wall. In some embodiments, the user contacts the needle 14 with the first needle guide wall and the second needle guide wall. In some embodiments, the user secures the needle 14 in place by inserting the needle 14 into the notch 32 located in between the first needle guide wall and the second needle guide wall. In some embodiments, the user slides the needle 14 along the track 144 towards the distal opening of the needle guide, in order to insert the needle into a target tissue location of an individual.

In some embodiments, the tactile sensing device 200 comprises an indentation in the frame 20. In some embodiments, the indentation is configured to act as a grip for a user. FIG. 2B demonstrates user 28 utilizing the indentation 42 to hold the tactile sensing device 200. In some embodiments, the tactile sensing device 200 comprises a sensor unit 32 and an electronic unit 34. In some embodiments, the sensor unit 32 and the electronic unit 34 are operatively coupled to each other. In some embodiments, the sensor unit 32 and the electronic unit 34 are non-reversibly, operatively coupled to each other. In some embodiments, the sensor unit 32 and the electronic unit 34 are reversibly, operatively coupled to each other. In some embodiments, the tactile sensing device 200 comprises a tab (not shown in FIGS. 2A-B) on one or more lateral sides of the sensor unit 32 configured to release the electronic unit 34 from the sensor unit 32, once it is depressed by a user. In some embodiments, the tactile sensing device 200 comprises one or more tabs configured to be pinched, depressed, or pushed by a user in order to detach the electronic unit 34 from the sensor unit 32. In some embodiments, the sensor unit 32 and the electronic unit 34 are reversibly, operatively coupled to each other via a mechanism that includes an audible indication, such as, but not limited to, a clicking noise, a recording, and/or a ding sound, that indicates when the sensor unit 32 and the electronic unit 34 are attached or detached by a user.

Figure 3:
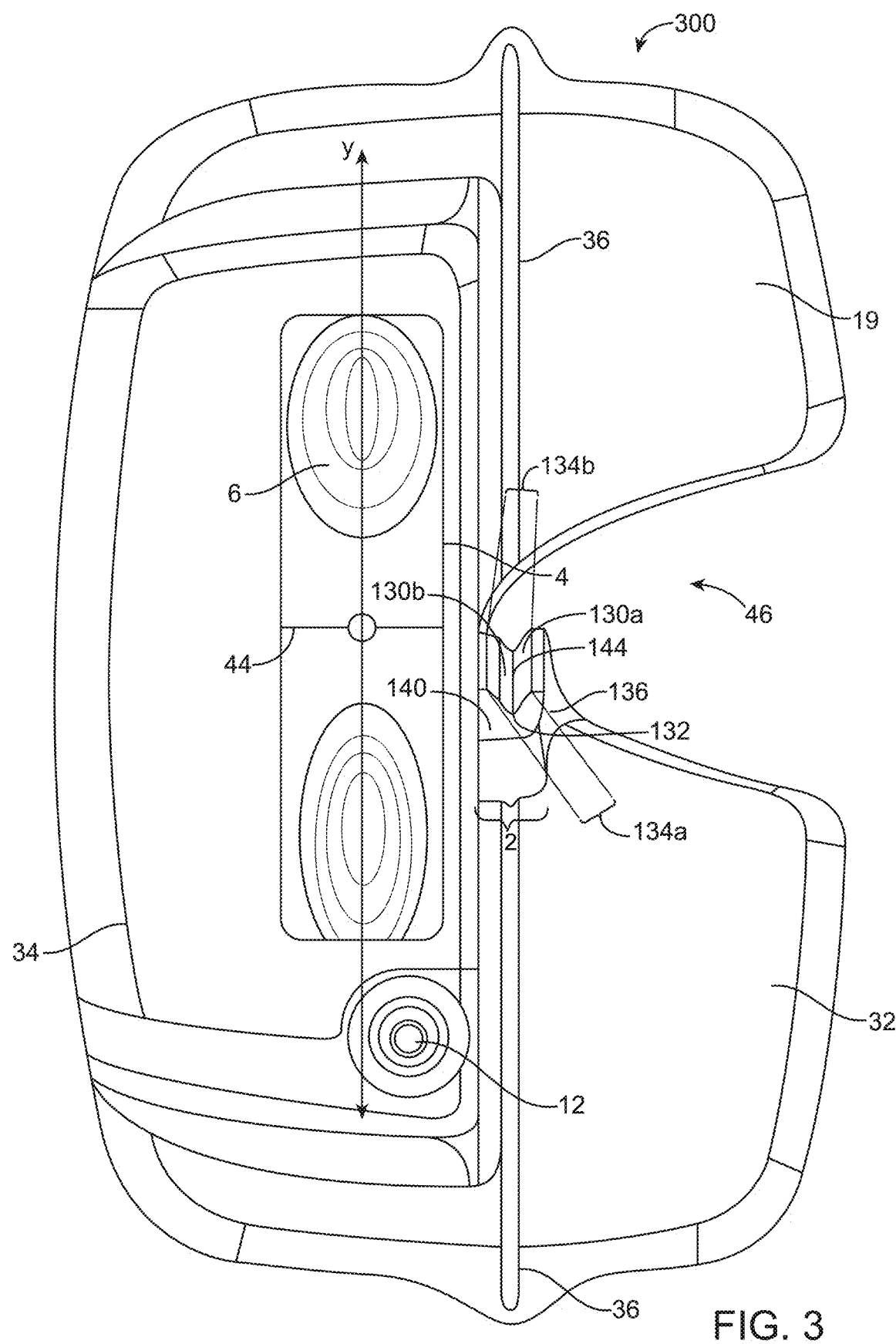
FIG. 3 exemplifies an embodiment of the tactile sensing device 300 comprising a wide cutout alternatively called a slot herein and a notch with a lip protruding from the slot wall to aid in retaining a needle in the track during insertion of the needle into the subject.

FIG. 3 shows an embodiment of the tactile sensing device 300. In some embodiments, the tactile sensing device 300 comprises a wide cutout 46 that enables the user to access the needle guide 2. In some embodiments, the wide cutout 46 enables the user to remove the tactile sensing device 300 by sliding the device laterally away from the needle, once the needle has been inserted into an individual.

In some embodiments, the tactile sensing device 300 comprises a display screen 4 located laterally from the needle guide 4, as shown in FIG. 3. In some embodiments, the tactile sensing device 300 comprises a display screen 4 located laterally from the needle alignment guide 36, as shown in FIG. 3. In some embodiments, the display screen 4 is a monochromatic screen. In some embodiments, the display screen 4 is a monochromatic OLED screen. In some embodiments, the display screen 4 comprises a real time, on-screen targeting 40. In some embodiments, the on-screen targeting 40 provides the user with a visual cue that shows the position of the needle in real time, as the user moves and adjusts the tactile sensing device 300 to a desired location. In some embodiments, the on-screen targeting 40 identifies the target tissue location and alerts the user via an auditory, visual, or haptic cue. In some embodiments, the on-screen targeting 40 identifies the midpoint between two spinous processes where a needle is to be inserted in order to access the epidural or the subarachnoid space.

In some embodiments, the pressure sensor connector 12 is positioned at an offset relative to the Y-axis shown in FIG. 3. In some embodiments, tactile sensing device 300 comprises an electronic unit 34 comprising the display screen 4 and the pressure sensor connector 12. In some embodiments, the electronic unit 34 is elevated and forms a C-grip where the user 28 is able to grip the device, as shown in FIG. 3. In some embodiments, tactile sensing device 300 comprises a sensor unit 32. In some embodiments, the sensor unit 32 acts as a mounting platform, wherein the sensor unit 32 receives the electronic unit 34. In some embodiments, the electronic unit 34 is non-reversibly mounted on top of the sensor unit 32. In some embodiments, the electronic unit 34 is reversibly mounted on top of the sensor unit 32. In some embodiments, the sensor unit 32 is disposable. In some embodiments, the sensor unit 32 comprises a bifurcated sensor array (not shown in FIG. 3). In some embodiments, the sensor unit 32 comprises a disposable sensor array.

In some embodiments, the tactile sensing device 300 comprises a needle guide platform 136 further comprising a lateral side needle guide platform wall (not shown in FIG. 3) and an anterior side needle guide platform wall 140. In some embodiments, the needle guide platform 136 elevates the needle guide 2. In some embodiments, the needle guide 2 is fixed. In some embodiments, the needle guide 2 is adjustable and a user is able to manually or automatically adjust the height and angle of the needle guide 2. In some embodiments, the slot of the needle guide 2 comprises a first slot wall 130a and a second slot wall 130b that connect with each other. In some embodiments, the first slot wall 130a connects to the second slot wall 130b to form the slot. In some embodiments, the slot has an opening and a terminus. In some embodiments, the proximal opening 134a is at the terminus of the slot on the side of the device not having the sensors thereon. In some embodiments, the needle guide 2 comprises a track 144. In some embodiments, the track 144 is positioned in between a proximal opening 134a and a distal opening 134b of the needle guide 2. In some embodiments, the needle guide 2 comprises a notch 132 positioned on the proximal opening 134a of the needle guide. In some embodiments, the notch 132 is directly aligned with the anterior side needle guide platform wall 140.

In some embodiments, notch 132 is at least about 1 mm to about 5 mm at most wide. In some embodiments, notch 132 is about 1 mm wide. In some embodiments, notch 132 is about 2 mm wide. In some embodiments, notch 132 is about 3 mm wide. In some embodiments, notch 132 is about 4 mm wide. In some embodiments, notch 132 is about 5 mm wide. In some embodiments, notch 132 is at least about 1 mm to about 5 mm at most wide. In some embodiments, notch 132 is about 6 mm wide. In some embodiments, notch 132 is about 7 mm wide. In some embodiments, notch 132 is about 8 mm wide. In some embodiments, notch 132 is about 9 mm wide. In some embodiments, notch 132 is about 10 mm wide. In some embodiments, notch 132 is at least about 6 mm to about 15 mm at most wide. In some embodiments, notch 132 is wider than notch 132. In some embodiments, notch 132 is 90% wider than notch 132. In some embodiments, notch 132 is 80% wider than notch 132. In some embodiments, notch 132 is 70% wider than notch 132. In some embodiments, notch 132 is 60% wider than notch 132. In some embodiments, notch 132 is 50% wider than notch 132. In some embodiments, notch 132 is 40% wider than notch 132. In some embodiments, notch 132 is 30% wider than notch 132. In some embodiments, notch 132 is 20% wider than notch 132. In some embodiments, notch 132 is 10% wider than notch 132.

In some embodiments, notch 132 is shaped as a wide "V." In some embodiments, notch 132 is shaped as a wide "U." In some embodiments, the notch comprises a lip that protrudes from one of the slot walls 130a or 130b, and in some embodiments aligns with an arm of the V or of the U shape. The notch and the lip thereof allow the needle to be seated in the track and not slip toward the opening of the slot prior to or during insertion of the needle into the subject.

In some embodiments, the tactile sensing device 300 comprises a needle alignment guide 36. In some embodiments, the needle alignment guide 36 is a notch traversing the center of the tactile sensing device 300 through a longitudinal axis that is parallel to the track 144, as shown in FIG. 3.

In some embodiments, the sensor array (not shown in FIG. 3) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIG. 3), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIG. 3) is an array of cells. In some embodiments, the sensor array (not shown in FIG. 3) is an array of sensing cells. In some embodiments, the sensor array slit (not shown in FIG. 3) is positioned between two rows or more of sensels. In some embodiments, the sensor array slit (not shown in FIG. 3) is positioned between two columns or more of sensels. In some embodiments, the sensor array slit (not shown in FIG. 3) is within the bounds of the sensor array, and/or within the bounds of the sensor array outer edges, and/or within the edges bounding of the sensor array. In some embodiments, the distal opening 134b of the needle guide 2 is positioned between two rows of sensels. In some embodiments, the distal opening 134b of the needle guide 2 is positioned between two columns of sensels. In some embodiments the distal opening 134b of the needle guide 2 is within the bounds of the sensor array, and/or within the bounds of the sensor array outer edges, and/or within the edges bounding of the sensor array. In some embodiments, the distal opening 34b is between two or more sensors of the sensor array. In some embodiments, the distal opening 34b is positioned between two rows or more of sensels. In some embodiments, the distal opening 34b is positioned between two columns or more of sensels.

In some embodiments, the tactile sensing device comprises a display screen 4 that is adjacent to the needle guide 2, as shown in FIG. 3. In some embodiments, the display screen 4 is adjacent to the track 144. In some embodiments, the tactile sensing device comprises a display screen 4 that is laterally offset from the midline of the tactile sensing device. In some embodiments, the display screen 4 is adjacent to the needle alignment guide 36. In some embodiments, the display screen 4 comprises on-screen targeting 44. In some embodiments, the on-screen targeting 44 is one or more axes (e.g., an x-axis and a y-axis) that appear on the display screen 4 and help the user to align the tactile sensing device with the target tissue location, an insertion site of the needle, and/or a projected subcutaneous location of a needle. In some embodiments, the on-screen targeting 44 is a software tool that helps the user with alignment of the needle and/or the tactile sensing device. In some embodiments, the on-screen targeting 44 comprises crosshairs, as shown in FIG. 3. In some embodiments, the on-screen targeting 44 responds in real time to any movement of the needle and/or the tactile sensing device carried out by the user. For example, in some embodiments, the crosshairs displayed on the display screen 4 moves on the display screen 4 as the user adjusts the position of the tactile sensing device. In some embodiments, the on-screen targeting 44 indicates the proximity of the crosshairs (and/or the target circle at the center of the crosshairs) to the calculated needle insertion point. In some embodiments, the on-screen targeting 44 uses a light, a sound (e.g., a beeping sound), a visual cue (e.g., blinking of the crosshairs on the display screen), or any other suitable indicator to inform the user of an accurate alignment between the insertion device (e.g., the needle guide) and the calculated needle insertion point.

FIGS. 4A-B show a high-level concept configuration of the tactile sensing device 400. FIG. 4A shows a front view of the tactile sensing device 400. In some embodiments, the tactile sensing device 400 comprises a frame 20 that comprises a display screen 4 and a needle guide 2. In some embodiments, the needle guide 2 comprises a slot 38. In some embodiments, the slot 38 comprises a lateral entrance area (i.e., the slot opening 38*a*) and a medial area (i.e. the slot terminus 38*b*). In some embodiments, the slot terminus 38*b* is in open connection with the needle guide 2. In some embodiments, the needle guide 2 is a fixed needle guide. In some embodiments, the display screen 4 is angled with respect to the skin surface of the patient. In some embodiments, the display screen is flat. In some embodiments, the angle of the display screen 4 is adjustable. In some embodiments, the tactile sensing device comprises one or more hinges at the junction of the sensor unit 32 and the electronic unit 34, which allows the user to adjust the angle of the display screen.

In some embodiments, the tactile sensing device 400 has a length 49 of about 198 millimeters (mm). In some embodiments, the tactile sensing device 400 has a length 49 of about 150 mm to about 300 mm. In some embodiments, the tactile sensing device 400 has a length 49 of at least about 150 mm. In some embodiments, the tactile sensing device 400 has a length 49 of at most about 300 mm. In some embodiments, the tactile sensing device 400 has a length 49 of about 150 mm to about 160 mm, about 150 mm to about 170 mm, about 150 mm to about 180 mm, about 150 mm to about 190 mm, about 150 mm to about 200 mm, about 150 mm to about 210 mm, about 150 mm to about 220 mm, about 150 mm to about 230 mm, about 150 mm to about 240 mm, about 150 mm to about 250 mm, about 150 mm to about 300 mm, about 160 mm to about 170 mm, about 160 mm to about 180 mm, about 160 mm to about 190 mm, about 160 mm to about 200 mm, about 160 mm to about 210 mm, about 160 mm to about 220 mm, about 160 mm to about 230 mm, about 160 mm to about 240 mm, about 160 mm to about 250 mm, about 160 mm to about 300 mm, about 170 mm to about 180 mm, about 170 mm to about 190 mm, about 170 mm to about 200 mm, about 170 mm to about 210 mm, about 170 mm to about 220 mm, about 170 mm to about 230 mm, about 170 mm to about 240 mm, about 170 mm to about 250 mm, about 170 mm to about 300 mm, about 180 mm to about 190 mm, about 180 mm to about 200 mm, about 180 mm to about 210 mm, about 180 mm to about 220 mm, about 180 mm to about 230 mm, about 180 mm to about 240 mm, about 180 mm to about 250 mm, about 180 mm to about 300 mm, about 190 mm to about 200 mm, about 190 mm to about 210 mm, about 190 mm to about 220 mm, about 190 mm to about 230 mm, about 190 mm to about 240 mm, about 190 mm to about 250 mm, about 190 mm to about 300 mm, about 200 mm to about 210 mm, about 200 mm to about 220 mm, about 200 mm to about 230 mm, about 200 mm to about 240 mm, about 200 mm to about 250 mm, about 200 mm to about 300 mm, about 210 mm to about 220 mm, about 210 mm to about 230 mm, about 210 mm to about 240 mm, about 210 mm to about 250 mm, about 210 mm to about 300 mm, about 220 mm to about 230 mm, about 220 mm to about 240 mm, about 220 mm to about 250 mm, about 220 mm to about 300 mm, about 230 mm to about 240 mm, about 230 mm to about 250 mm, about 230 mm to about 300 mm, about 240 mm to about 250 mm, about 240 mm to about 300 mm, or about 250 mm to about 300 mm. In some embodiments, the tactile sensing device 400 has a length 49 of about 150 mm, about 160 mm, about 170 mm, about 180 mm, about 190 mm, about 200 mm, about 210 mm, about 220 mm, about 230 mm, about 240 mm, about 250 mm, or about 300 mm.

In some embodiments, the tactile sensing device 400 has a width 51 of about 78 mm. In some embodiments, the tactile sensing device 400 has a width 51 of about 50 mm to about 200 mm. In some embodiments, the tactile sensing device 400 has a width 51 of at least about 50 mm. In some embodiments, the tactile sensing device 400 has a width 51 of at most about 200 mm. In some embodiments, the tactile sensing device 400 has a width 51 of about 50 mm to about 60 mm, about 50 mm to about 70 mm, about 50 mm to about 80 mm, about 50 mm to about 90 mm, about 50 mm to about 100 mm, about 50 mm to about 110 mm, about 50 mm to about 120 mm, about 50 mm to about 130 mm, about 50 mm to about 140 mm, about 50 mm to about 150 mm, about 50 mm to about 200 mm, about 60 mm to about 70 mm, about 60 mm to about 80 mm, about 60 mm to about 90 mm, about 60 mm to about 100 mm, about 60 mm to about 110 mm, about 60 mm to about 120 mm, about 60 mm to about 130 mm, about 60 mm to about 140 mm, about 60 mm to about 150 mm, about 60 mm to about 200 mm, about 70 mm to about 80 mm, about 70 mm to about 90 mm, about 70 mm to about 100 mm, about 70 mm to about 110 mm, about 70 mm to about 120 mm, about 70 mm to about 130 mm, about 70 mm to about 140 mm, about 70 mm to about 150 mm, about 70 mm to about 200 mm, about 80 mm to about 90 mm, about 80 mm to about 100 mm, about 80 mm to about 110 mm, about 80 mm to about 120 mm, about 80 mm to about 130 mm, about 80 mm to about 140 mm, about 80 mm to about 150 mm, about 80 mm to about 200 mm, about 90 mm to about 100 mm, about 90 mm to about 110 mm, about 90 mm to about 120 mm, about 90 mm to about 130 mm, about 90 mm to about 140 mm, about 90 mm to about 150 mm, about 90 mm to about 200 mm, about 100 mm to about 110 mm, about 100 mm to about 120 mm, about 100 mm to about 130 mm, about 100 mm to about 140 mm, about 100 mm to about 150 mm, about 100 mm to about 200 mm, about 110 mm to about 120 mm, about 110 mm to about 130 mm, about 110 mm to about 140 mm, about 110 mm to about 150 mm, about 110 mm to about 200 mm, about 120 mm to about 130 mm, about 120 mm to about 140 mm, about 120 mm to about 150 mm, about 120 mm to about 200 mm, about 130 mm to about 140 mm, about 130 mm to about 150 mm, about 130 mm to about 200 mm, about 140 mm to about 150 mm, about 140 mm to about 200 mm, or about 150 mm to about 200 mm. In some embodiments, the tactile sensing device 400 has a width 51 of about 50 mm, about 60 mm, about 70 mm, about 80 mm, about 90 mm, about 100 mm, about 110 mm, about 120 mm, about 130 mm, about 140 mm, about 150 mm, or about 200 mm.

In some embodiments, the display screen 4 has a display screen length 53 of about 99 mm. In some embodiments, the display screen 4 has a display screen length 53 of about 40 mm to about 150 mm. In some embodiments, the display screen 4 has a display screen length 53 of at least about 40 mm. In some embodiments, the display screen 4 has a display screen length 53 of at most about 150 mm. In some embodiments, the display screen 4 has a display screen length 53 of about 40 mm to about 50 mm, about 40 mm to about 60 mm, about 40 mm to about 70 mm, about 40 mm to about 90 mm, about 40 mm to about 100 mm, about 40 mm to about 110 mm, about 40 mm to about 120 mm, about 40 mm to about 130 mm, about 40 mm to about 140 mm, about 40 mm to about 150 mm, about 50 mm to about 60 mm, about 50 mm to about 70 mm, about 50 mm to about 90 mm, about 50 mm to about 100 mm, about 50 mm to about 110 mm, about 50 mm to about 120 mm, about 50 mm to about 130 mm, about 50 mm to about 140 mm, about 50 mm to about 150 mm, about 60 mm to about 70 mm, about 60 mm to about 90 mm, about 60 mm to about 100 mm, about 60 mm to about 110 mm, about 60 mm to about 120 mm, about 60 mm to about 130 mm, about 60 mm to about 140 mm, about 60 mm to about 150 mm, about 70 mm to about 90 mm, about 70 mm to about 100 mm, about 70 mm to about 110 mm, about 70 mm to about 120 mm, about 70 mm to about 130 mm, about 70 mm to about 140 mm, about 70 mm to about 150 mm, about 90 mm to about 100 mm, about 90 mm to about 110 mm, about 90 mm to about 120 mm, about 90 mm to about 130 mm, about 90 mm to about 140 mm, about 90 mm to about 150 mm, about 100 mm to about 110 mm, about 100 mm to about 120 mm, about 100 mm to about 130 mm, about 100 mm to about 140 mm, about 100 mm to about 150 mm, about 110 mm to about 120 mm, about 110 mm to about 130 mm, about 110 mm to about 140 mm, about 110 mm to about 150 mm, about 120 mm to about 130 mm, about 120 mm to about 140 mm, about 120 mm to about 150 mm, about 130 mm to about 140 mm, about 130 mm to about 150 mm, or about 140 mm to about 150 mm. In some embodiments, the display screen 4 has a display screen length 53 of about 40 mm, about 50 mm, about 60 mm, about 70 mm, about 90 mm, about 100 mm, about 110 mm, about 120 mm, about 130 mm, about 140 mm, or about 150 mm.

In some embodiments, the display screen 4 has a display screen width 55 of about 57 mm. In some embodiments, the display screen 4 has a display screen width 55 of about 40 mm to about 150 mm. In some embodiments, the display screen 4 has a display screen width 55 of at least about 40 mm. In some embodiments, the display screen 4 has a display screen width 55 of at most about 150 mm. In some embodiments, the display screen 4 has a display screen width 55 of about 40 mm to about 50 mm, about 40 mm to about 60 mm, about 40 mm to about 70 mm, about 40 mm to about 90 mm, about 40 mm to about 100 mm, about 40 mm to about 110 mm, about 40 mm to about 120 mm, about 40 mm to about 130 mm, about 40 mm to about 140 mm, about 40 mm to about 150 mm, about 50 mm to about 60 mm, about 50 mm to about 70 mm, about 50 mm to about 90 mm, about 50 mm to about 100 mm, about 50 mm to about 110 mm, about 50 mm to about 120 mm, about 50 mm to about 130 mm, about 50 mm to about 140 mm, about 50 mm to about 150 mm, about 60 mm to about 70 mm, about 60 mm to about 90 mm, about 60 mm to about 100 mm, about 60 mm to about 110 mm, about 60 mm to about 120 mm, about 60 mm to about 130 mm, about 60 mm to about 140 mm, about 60 mm to about 150 mm, about 70 mm to about 90 mm, about 70 mm to about 100 mm, about 70 mm to about 110 mm, about 70 mm to about 120 mm, about 70 mm to about 130 mm, about 70 mm to about 140 mm, about 70 mm to about 150 mm, about 90 mm to about 100 mm, about 90 mm to about 110 mm, about 90 mm to about 120 mm, about 90 mm to about 130 mm, about 90 mm to about 140 mm, about 90 mm to about 150 mm, about 100 mm to about 110 mm, about 100 mm to about 120 mm, about 100 mm to about 130 mm, about 100 mm to about 140 mm, about 100 mm to about 150 mm, about 110 mm to about 120 mm, about 110 mm to about 130 mm, about 110 mm to about 140 mm, about 110 mm to about 150 mm, about 120 mm to about 130 mm, about 120 mm to about 140 mm, about 120 mm to about 150 mm, about 130 mm to about 140 mm, about 130 mm to about 150 mm, or about 140 mm to about 150 mm. In some embodiments, the display screen 4 has a display screen width 55 of about 40 mm, about 50 mm, about 60 mm, about 70 mm, about 90 mm, about 100 mm, about 110 mm, about 120 mm, about 130 mm, about 140 mm, or about 150 mm.

FIG. 4B shows a side view of the tactile sensing device 400. In some embodiments, the tactile sensing device 400 comprises a sensor attachment area 52. In some embodiments, sensor attachment area 52 receives a sensor array (not shown in FIGS. 4A-B). In some embodiments, sensor attachment area 52 is located on the posterior surface of the tactile sensing device 400. In some embodiments, the sensor attachment area 52 comprises a slit corresponding in shape and size to the slot opening 38a and needle guide 2. In some embodiments, needle guide 2 has a proximal opening 134a and a distal opening 134b, with respect to the user, as shown in FIG. 4B. In some embodiments, the frame 20 comprises a battery 48. In some embodiments, the battery 48 is located on the posterior side of the tactile sensing device 400, as shown in FIG. 4B. In some embodiments, the battery 48 is located within the frame 20, in the handle area. In some embodiments, the battery 48 is located on the posterior surface of the display screen 4, as shown in FIG. 4B. In some embodiments, the battery 48 is located beneath the display screen 4. In some embodiments, the tactile sensing device 400 comprises a printed circuit board (PCB) 50 sitting on the anterior surface of the sensor attachment area 52, within the frame 20. In some embodiments, the tactile sensing device 400 comprises a printed circuit board (PCB) 50 located directly sitting on the anterior surface of the sensor array, within the frame 20. In some embodiments, the PCB 50 is located over the sensor array, within the frame 20. In some embodiments, the printed circuit board (PCB) 50 is located within the frame 20. In some embodiments, an additional printed circuit board is located between the battery 48 and the display screen 4.

In some embodiments, the needle guide 2 is angled. In some embodiments, the needle guide 2 is at an angle with respect to the sensor array (not shown in FIGS. 4A-B). In some embodiments, the needle guide 2 is at an angle with respect to the sensor attachment area 52. In some embodiments, the needle guide 2 is at an angle with respect to the posterior or bottom surface of the tactile sensing device 400. In some embodiments, the angle is a treatment angle 86, as shown in FIG. 4B. In some embodiments, the needle guide forms a treatment angle 86 with respect to the sensor array. In some embodiments, the needle guide forms a treatment angle 86 with respect to the posterior surface of the tactile sensing device 400. In some embodiments, the track (not shown in FIGS. 4A-B) forms a treatment angle 86 with respect to the sensor array. In some embodiments, the track forms a treatment angle 86 with respect to the posterior surface of the tactile sensing device 400. In some embodiments, the needle is guided at a treatment angle 86 when inserted in the needle guide 2 and advanced along the track of the needle guide. In some embodiments, the treatment angle 86 is a cephalad angle. In some embodiments, the needle is pointed towards the head or the anterior end of the body of a patient when guided at a cephalad angle. In some embodiments, the treatment angle 86 is a cephalad angle when the user places the tactile sensing device 400 such that the anterior end of the tactile sensing device 400 is pointed towards the anterior end of the body of the patient. In some embodiments, the treatment angle 86 is a cephalad angle when the user places the needle in the needle guide and angles the needle away from the upper face 39 of the slot. In some embodiments, the treatment angle 86 is a caudal angle. In some embodiments, the needle is pointed towards the feet or the posterior end of the body of a patient when guided at a cephalad angle. In some embodiments, the treatment angle 86 is a caudal angle when the patient is in a lateral decubitus position. In some embodiments, the treatment angle 86 is a caudal angle when the user places the tactile sensing device 400 such that the anterior end of the tactile sensing device 400 is pointed towards the posterior end of the body of the patient.

In some embodiments, the treatment angle is about 30 degrees to about 90 degrees. In some embodiments, the treatment angle is about 69 degrees to about 81 degrees. In some embodiments, the treatment angle is at least about 30 degrees. In some embodiments, the treatment angle is at most about 90 degrees. In some embodiments, the treatment angle is about 30 degrees to about 35 degrees, about 30 degrees to about 40 degrees, about 30 degrees to about 45 degrees, about 30 degrees to about 50 degrees, about 30 degrees to about 55 degrees, about 30 degrees to about 60 degrees, about 30 degrees to about 65 degrees, about 30 degrees to about 70 degrees, about 30 degrees to about 75 degrees, about 30 degrees to about 80 degrees, about 30 degrees to about 90 degrees, about 35 degrees to about 40 degrees, about 35 degrees to about 45 degrees, about 35 degrees to about 50 degrees, about 35 degrees to about 55 degrees, about 35 degrees to about 60 degrees, about 35 degrees to about 65 degrees, about 35 degrees to about 70 degrees, about 35 degrees to about 75 degrees, about 35 degrees to about 80 degrees, about 35 degrees to about 90 degrees, about 40 degrees to about 45 degrees, about 40 degrees to about 50 degrees, about 40 degrees to about 55 degrees, about 40 degrees to about 60 degrees, about 40 degrees to about 65 degrees, about 40 degrees to about 70 degrees, about 40 degrees to about 75 degrees, about 40 degrees to about 80 degrees, about 40 degrees to about 90 degrees, about 45 degrees to about 50 degrees, about 45 degrees to about 55 degrees, about 45 degrees to about 60 degrees, about 45 degrees to about 65 degrees, about 45 degrees to about 70 degrees, about 45 degrees to about 75 degrees, about 45 degrees to about 80 degrees, about 45 degrees to about 90 degrees, about 50 degrees to about 55 degrees, about 50 degrees to about 60 degrees, about 50 degrees to about 65 degrees, about 50 degrees to about 70 degrees, about 50 degrees to about 75 degrees, about 50 degrees to about 80 degrees, about 50 degrees to about 90 degrees, about 55 degrees to about 60 degrees, about 55 degrees to about 65 degrees, about 55 degrees to about 70 degrees, about 55 degrees to about 75 degrees, about 55 degrees to about 80 degrees, about 55 degrees to about 90 degrees, about 60 degrees to about 65 degrees, about 60 degrees to about 70 degrees, about 60 degrees to about 75 degrees, about 60 degrees to about 80 degrees, about 60 degrees to about 90 degrees, about 65 degrees to about 70 degrees, about 65 degrees to about 75 degrees, about 65 degrees to about 80 degrees, about 65 degrees to about 90 degrees, about 70 degrees to about 75 degrees, about 70 degrees to about 80 degrees, about 70 degrees to about 90 degrees, about 75 degrees to about 80 degrees, about 75 degrees to about 90 degrees, or about 80 degrees to about 90 degrees.

In some embodiments, the treatment angle is about 30 degrees. In some embodiments, the treatment angle is about 35 degrees. In some embodiments, the treatment angle is about 40 degrees. In some embodiments, the treatment angle is about 45 degrees. In some embodiments, the treatment angle is about 50 degrees. In some embodiments, the treatment angle is about 55 degrees. In some embodiments, the treatment angle is about 60 degrees. In some embodiments, the treatment angle is about 65 degrees. In some embodiments, the treatment angle is about 70 degrees. In some embodiments, the treatment angle is about 75 degrees. In some embodiments, the treatment angle is about 80 degrees. In some embodiments, the treatment angle is about 90 degrees.

In some embodiments, the treatment angle is about 69 degrees. In some embodiments, the treatment angle is about 70 degrees. In some embodiments, the treatment angle is about 71 degrees. In some embodiments, the treatment angle is about 72 degrees. In some embodiments, the treatment angle is about 73 degrees. In some embodiments, the treatment angle is about 74 degrees. In some embodiments, the treatment angle is about 75 degrees. In some embodiments, the treatment angle is about 76 degrees. In some embodiments, the treatment angle is about 77 degrees. In some embodiments, the treatment angle is about 78 degrees. In some embodiments, the treatment angle is about 79 degrees. In some embodiments, the treatment angle is about 80 degrees. In some embodiments, the treatment angle is about 81 degrees.

In some embodiments, the treatment angle 86 is a cephalad angle between about 0° to about 15° with respect to the individual. In some embodiments, the treatment angle 86 is a cephalad angle between about 9° to about 21°. In some embodiments, the treatment angle 86 is a cephalad angle that is at least about 0 degrees. In some embodiments, the treatment angle 86 is a cephalad angle that is at most about 15 degrees. In some embodiments, the treatment angle 86 is a cephalad angle that is about 0 degrees to about 1 degree, about 0 degrees to about 2 degrees, about 0 degrees to about 3 degrees, about 0 degrees to about 4 degrees, about 0 degrees to about 5 degrees, about 0 degrees to about 6 degrees, about 0 degrees to about 7 degrees, about 0 degrees to about 8 degrees, about 0 degrees to about 9 degrees, about 0 degrees to about 10 degrees, about 0 degrees to about 15 degrees, about 1 degree to about 2 degrees, about 1 degree to about 3 degrees, about 1 degree to about 4 degrees, about 1 degree to about 5 degrees, about 1 degree to about 6 degrees, about 1 degree to about 7 degrees, about 1 degree to about 8 degrees, about 1 degree to about 9 degrees, about 1 degree to about 10 degrees, about 1 degree to about 15 degrees, about 2 degrees to about 3 degrees, about 2 degrees to about 4 degrees, about 2 degrees to about 5 degrees, about 2 degrees to about 6 degrees, about 2 degrees to about 7 degrees, about 2 degrees to about 8 degrees, about 2 degrees to about 9 degrees, about 2 degrees to about 10 degrees, about 2 degrees to about 15 degrees, about 3 degrees to about 4 degrees, about 3 degrees to about 5 degrees, about 3 degrees to about 6 degrees, about 3 degrees to about 7 degrees, about 3 degrees to about 8 degrees, about 3 degrees to about 9 degrees, about 3 degrees to about 10 degrees, about 3 degrees to about 15 degrees, about 4 degrees to about 5 degrees, about 4 degrees to about 6 degrees, about 4 degrees to about 7 degrees, about 4 degrees to about 8 degrees, about 4 degrees to about 9 degrees, about 4 degrees to about 10 degrees, about 4 degrees to about 15 degrees, about 5 degrees to about 6 degrees, about 5 degrees to about 7 degrees, about 5 degrees to about 8 degrees, about 5 degrees to about 9 degrees, about 5 degrees to about 10 degrees, about 5 degrees to about 15 degrees, about 6 degrees to about 7 degrees, about 6 degrees to about 8 degrees, about 6 degrees to about 9 degrees, about 6 degrees to about 10 degrees, about 6 degrees to about 15 degrees, about 7 degrees to about 8 degrees, about 7 degrees to about 9 degrees, about 7 degrees to about 10 degrees, about 7 degrees to about 15 degrees, about 8 degrees to about 9 degrees, about 8 degrees to about 10 degrees, about 8 degrees to about 15 degrees, about 9 degrees to about 10 degrees, about 9 degrees to about 15 degrees, or about 10 degrees to about 15 degrees. In some embodiments, the treatment angle 86 is a cephalad angle that is about 0 degrees, about 1 degree, about 2 degrees, about 3 degrees, about 4 degrees, about 5 degrees, about 6 degrees, about 7 degrees, about 8 degrees, about 9 degrees, about 10 degrees, or about 15 degrees. In some embodiments, the treatment angle 86 is a cephalad angle that is about 10 degrees to about 15 degrees. In some embodiments, the treatment angle 86 is a cephalad angle that is at least about 10 degrees. In some embodiments, the treatment angle 86 is a cephalad angle that is at most about 15 degrees. In some embodiments, the treatment angle 86 is a cephalad angle that is about 10 degrees to about 11 degrees, about 10 degrees to about 12 degrees, about 10 degrees to about 13 degrees, about 10 degrees to about 14 degrees, about 10 degrees to about 15 degrees, about 11 degrees to about 12 degrees, about 11 degrees to about 13 degrees, about 11 degrees to about 14 degrees, about 11 degrees to about 15 degrees, about 12 degrees to about 13 degrees, about 12 degrees to about 14 degrees, about 12 degrees to about 15 degrees, about 13 degrees to about 14 degrees, about 13 degrees to about 15 degrees, or about 14 degrees to about 15 degrees.

In some embodiments, the treatment angle 86 is a cephalad angle that is about 9 degrees. In some embodiments, the treatment angle 86 is a cephalad angle that is about 10 degrees. In some embodiments, the treatment angle 86 is a cephalad angle that is about 11 degrees. In some embodiments, the treatment angle 86 is a cephalad angle that is about 12 degrees. In some embodiments, the treatment angle 86 is a cephalad angle that is about 13 degrees. In some embodiments, the treatment angle 86 is a cephalad angle that is about 14 degrees. In some embodiments, the treatment angle 86 is a cephalad angle that is about 15 degrees. In some embodiments, the treatment angle 86 is a cephalad angle that is about 16 degrees. In some embodiments, the treatment angle 86 is a cephalad angle that is about 17 degrees. In some embodiments, the treatment angle 86 is a cephalad angle that is about 18 degrees. In some embodiments, the treatment angle 86 is a cephalad angle that is about 19 degrees. In some embodiments, the treatment angle 86 is a cephalad angle that is about 20 degrees. In some embodiments, the treatment angle 86 is a cephalad angle that is about 21 degrees.

In some embodiments, the sensor array (not shown in FIGS. 4A-B) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIGS. 4A-B), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIGS. 4A-B) is an array of cells. In some embodiments, the sensor array (not shown in FIGS. 4A-B) is an array of sensing cells. In some embodiments, the sensor array slit (not shown in FIGS. 4A-B) is positioned between two rows or more of sensels. In some embodiments, the sensor array slit (not shown in FIGS. 4A-B) is positioned between two columns or more of sensels. In some embodiments, the sensor array slit (not shown in FIGS. 4A-B) is within the bounds of the sensor array, and/or within the bounds of the sensor array outer edges, and/or within the edges bounding of the sensor array. In some embodiments, the sensor array does not comprise a slit. In some embodiments, the distal opening 134b of the needle guide 2 is positioned between two rows of sensels. In some embodiments, the distal opening 134b of the needle guide 2 is positioned between two columns of sensels. In some embodiments the distal opening 134b of the needle guide 2 is within the bounds of the sensor array, and/or within the bounds of the sensor array outer edges, and/or within the edges bounding of the sensor array. In some embodiments, the distal opening 34b is between two or more sensors of the sensor array. In some embodiments, the distal opening 34b is positioned between two rows or more of sensels. In some embodiments, the distal opening 34b is positioned between two columns or more of sensels.

FIGS. 5-12 show the tactile sensing device comprising a display screen, a needle guide, and a handle. Specifically, FIGS. 5-12 show different variations and types of handles and/or grips.

Figure 5:
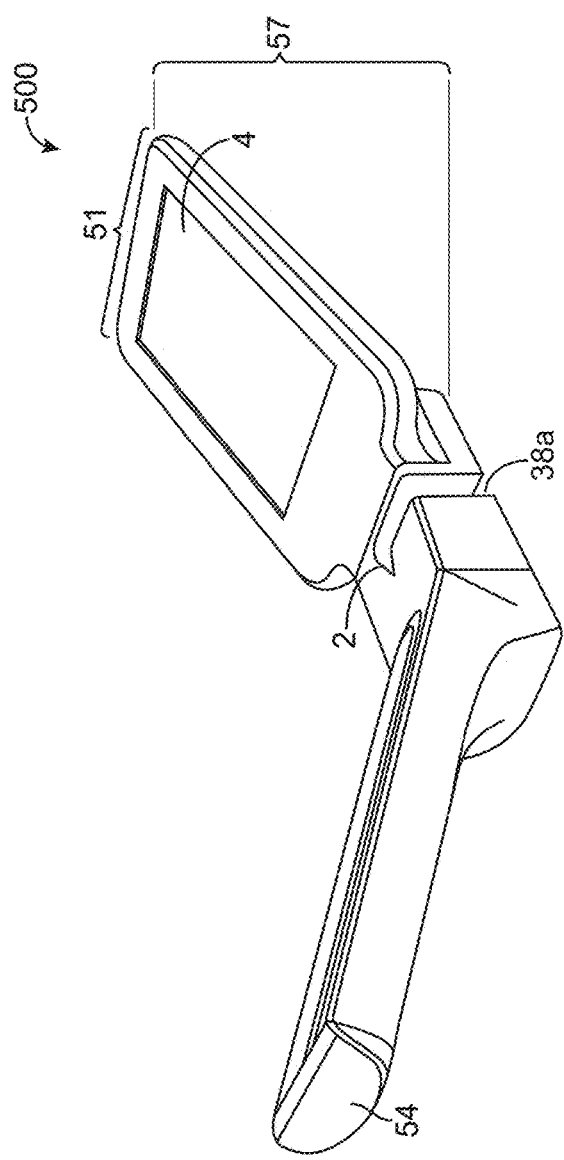
FIG. 5 shows an embodiment of the tactile sensing device 500 comprising an extended handle.

FIG. 5 shows the tactile sensing device 500 comprising a handle 54 that is an extended handle. In some embodiments, the extended handle provides numerous advantages which include, but are not limited to, maximizing the ability to apply force, better balance and linear movement control, separate handling area from interaction point, accommodating both left and right handed users, easy to be used when used on both a seated and a lateral decubitus-positioned individual. In some embodiments, a battery is located inside or within the handle 54. In some embodiments, the extended handle accommodates all fingers of a user to better hold the device. In some embodiments, the extended handle allows the user to use his/her thumb to apply more force on the surface where the tactile sensing device 500 is being pressed upon. In some embodiments, the tactile sensing device 500 comprises a needle guide 2 that is a fixed needle guide. In some embodiments, the tactile sensing device 500 comprises a slot opening 38a. In some embodiments, the slot opening 38a c provides the user (i.e., holding a syringe and/or needle) with access to the needle guide 2. In some embodiments, the slot opening 38a provides an opening to remove the tactile sensing device from a needle resting on the needle guide 2.

In some embodiments, the tactile sensing device 500 has a length 49 of about 296 mm. In some embodiments, the tactile sensing device 500 has a length 49 of about 250 mm to about 400 mm. In some embodiments, the tactile sensing device 500 has a length 49 of at least about 250 mm. In some embodiments, the tactile sensing device 500 has a length 49 of at most about 400 mm. In some embodiments, the tactile sensing device 500 has a length 49 of about 250 mm to about 260 mm, about 250 mm to about 270 mm, about 250 mm to about 280 mm, about 250 mm to about 290 mm, about 250 mm to about 300 mm, about 250 mm to about 310 mm, about 250 mm to about 320 mm, about 250 mm to about 330 mm, about 250 mm to about 340 mm, about 250 mm to about 350 mm, about 250 mm to about 400 mm, about 260 mm to about 270 mm, about 260 mm to about 280 mm, about 260 mm to about 290 mm, about 260 mm to about 300 mm, about 260 mm to about 310 mm, about 260 mm to about 320 mm, about 260 mm to about 330 mm, about 260 mm to about 340 mm, about 260 mm to about 350 mm, about 260 mm to about 400 mm, about 270 mm to about 280 mm, about 270 mm to about 290 mm, about 270 mm to about 300 mm, about 270 mm to about 310 mm, about 270 mm to about 320 mm, about 270 mm to about 330 mm, about 270 mm to about 340 mm, about 270 mm to about 350 mm, about 270 mm to about 400 mm, about 280 mm to about 290 mm, about 280 mm to about 300 mm, about 280 mm to about 310 mm, about 280 mm to about 320 mm, about 280 mm to about 330 mm, about 280 mm to about 340 mm, about 280 mm to about 350 mm, about 280 mm to about 400 mm, about 290 mm to about 300 mm, about 290 mm to about 310 mm, about 290 mm to about 320 mm, about 290 mm to about 330 mm, about 290 mm to about 340 mm, about 290 mm to about 350 mm, about 290 mm to about 400 mm, about 300 mm to about 310 mm, about 300 mm to about 320 mm, about 300 mm to about 330 mm, about 300 mm to about 340 mm, about 300 mm to about 350 mm, about 300 mm to about 400 mm, about 310 mm to about 320 mm, about 310 mm to about 330 mm, about 310 mm to about 340 mm, about 310 mm to about 350 mm, about 310 mm to about 400 mm, about 320 mm to about 330 mm, about 320 mm to about 340 mm, about 320 mm to about 350 mm, about 320 mm to about 400 mm, about 330 mm to about 340 mm, about 330 mm to about 350 mm, about 330 mm to about 400 mm, about 340 mm to about 350 mm, about 340 mm to about 400 mm, or about 350 mm to about 400 mm. In some embodiments, the tactile sensing device 500 has a length 49 of about 250 mm, about 260 mm, about 270 mm, about 280 mm, about 290 mm, about 300 mm, about 310 mm, about 320 mm, about 330 mm, about 340 mm, about 350 mm, or about 400 mm.

In some embodiments, the tactile sensing device 500 has a width 51 of about 78 mm. In some embodiments, the tactile sensing device 500 has a width 51 of about 10 mm to about 200 mm. In some embodiments, the tactile sensing device 500 has a width 51 of at least about 10 mm. In some embodiments, the tactile sensing device 500 has a width 51 of at most about 200 mm. In some embodiments, the tactile sensing device 500 has a width 51 of about 50 mm to about 60 mm, about 50 mm to about 70 mm, about 50 mm to about 80 mm, about 50 mm to about 90 mm, about 50 mm to about 100 mm, about 50 mm to about 110 mm, about 50 mm to about 10 mm, about 50 mm to about 130 mm, about 50 mm to about 140 mm, about 50 mm to about 150 mm, about 50 mm to about 200 mm, about 60 mm to about 70 mm, about 60 mm to about 80 mm, about 60 mm to about 90 mm, about 60 mm to about 100 mm, about 60 mm to about 110 mm, about 60 mm to about 10 mm, about 60 mm to about 130 mm, about 60 mm to about 140 mm, about 60 mm to about 150 mm, about 60 mm to about 200 mm, about 70 mm to about 80 mm, about 70 mm to about 90 mm, about 70 mm to about 100 mm, about 70 mm to about 110 mm, about 70 mm to about 10 mm, about 70 mm to about 130 mm, about 70 mm to about 140 mm, about 70 mm to about 150 mm, about 70 mm to about 200 mm, about 80 mm to about 90 mm, about 80 mm to about 100 mm, about 80 mm to about 110 mm, about 80 mm to about 10 mm, about 80 mm to about 130 mm, about 80 mm to about 140 mm, about 80 mm to about 150 mm, about 80 mm to about 200 mm, about 90 mm to about 100 mm, about 90 mm to about 110 mm, about 90 mm to about 10 mm, about 90 mm to about 130 mm, about 90 mm to about 140 mm, about 90 mm to about 150 mm, about 90 mm to about 200 mm, about 100 mm to about 110 mm, about 100 mm to about 10 mm, about 100 mm to about 130 mm, about 100 mm to about 140 mm, about 100 mm to about 150 mm, about 100 mm to about 200 mm, about 110 mm to about 10 mm, about 110 mm to about 130 mm, about 110 mm to about 140 mm, about 110 mm to about 150 mm, about 110 mm to about 200 mm, about 10 mm to about 130 mm, about 10 mm to about 140 mm, about 10 mm to about 150 mm, about 10 mm to about 200 mm, about 130 mm to about 140 mm, about 130 mm to about 150 mm, about 130 mm to about 200 mm, about 140 mm to about 150 mm, about 140 mm to about 200 mm, or about 150 mm to about 200 mm. In some embodiments, the tactile sensing device 500 has a width 51 of about 50 mm, about 60 mm, about 70 mm, about 80 mm, about 90 mm, about 100 mm, about 110 mm, about 10 mm, about 130 mm, about 140 mm, about 150 mm, or about 200 mm.

In some embodiments, the tactile sensing device 500 has a height 57 of about 81 mm. In some embodiments, the tactile sensing device 500 has a height 57 of about 10 mm to about 150 mm. In some embodiments, the tactile sensing device 500 has a height 57 of at least about 10 mm. In some embodiments, the tactile sensing device 500 has a height 57 of at most about 150 mm. In some embodiments, the tactile sensing device 500 has a height 57 of about 50 mm to about 60 mm, about 50 mm to about 70 mm, about 50 mm to about 80 mm, about 50 mm to about 90 mm, about 50 mm to about 100 mm, about 50 mm to about 110 mm, about 50 mm to about 10 mm, about 50 mm to about 130 mm, about 50 mm to about 140 mm, about 50 mm to about 150 mm, about 60 mm to about 70 mm, about 60 mm to about 80 mm, about 60 mm to about 90 mm, about 60 mm to about 100 mm, about 60 mm to about 110 mm, about 60 mm to about 10 mm, about 60 mm to about 130 mm, about 60 mm to about 140 mm, about 60 mm to about 150 mm, about 70 mm to about 80 mm, about 70 mm to about 90 mm, about 70 mm to about 100 mm, about 70 mm to about 110 mm, about 70 mm to about 10 mm, about 70 mm to about 130 mm, about 70 mm to about 140 mm, about 70 mm to about 150 mm, about 80 mm to about 90 mm, about 80 mm to about 100 mm, about 80 mm to about 110 mm, about 80 mm to about 10 mm, about 80 mm to about 130 mm, about 80 mm to about 140 mm, about 80 mm to about 150 mm, about 90 mm to about 100 mm, about 90 mm to about 110 mm, about 90 mm to about 10 mm, about 90 mm to about 130 mm, about 90 mm to about 140 mm, about 90 mm to about 150 mm, about 100 mm to about 110 mm, about 100 mm to about 10 mm, about 100 mm to about 130 mm, about 100 mm to about 140 mm, about 100 mm to about 150 mm, about 110 mm to about 10 mm, about 110 mm to about 130 mm, about 110 mm to about 140 mm, about 110 mm to about 150 mm, about 10 mm to about 130 mm, about 10 mm to about 140 mm, about 10 mm to about 150 mm, about 130 mm to about 140 mm, about 130 mm to about 150 mm, or about 140 mm to about 150 mm. In some embodiments, the tactile sensing device 500 has a height 57 of about 50 mm, about 60 mm, about 70 mm, about 80 mm, about 90 mm, about 100 mm, about 110 mm, about 10 mm, about 130 mm, about 140 mm, or about 150 mm.

In some embodiments, the sensor array (not shown in FIG. 5) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIG. 5), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIG. 5) is an array of cells. In some embodiments, the sensor array (not shown in FIG. 5)

is an array of sensing cells. In some embodiments, the sensor array slit (not shown in FIG. 5) is positioned between two rows or more of sensels. In some embodiments, the sensor array slit (not shown in FIG. 5) is positioned between two columns or more of sensels. In some embodiments, the sensor array slit (not shown in FIG. 5) is within the bounds of the sensor array, and/or within the bounds of the sensor array outer edges, and/or within the edges bounding of the sensor array. In some embodiments, the sensor array does not comprise a slit. In some embodiments, the distal opening (not shown in FIG. 5) of the needle guide 2 is positioned between two rows of sensels. In some embodiments, the distal opening (not shown in FIG. 5) of the needle guide 2 is positioned between two columns of sensels. In some embodiments the distal opening (not shown in FIG. 5) of the needle guide 2 is within the bounds of the sensor array, and/or within the bounds of the sensor array outer edges, and/or within the edges bounding of the sensor array. In some embodiments, the distal opening (not shown in FIG. 5) is between two or more sensors of the sensor array. In some embodiments, the distal opening (not shown in FIG. 5) is positioned between two rows or more of sensels. In some embodiments, the distal opening (not shown in FIG. 5) is positioned between two columns or more of sensels.

Figure 6:
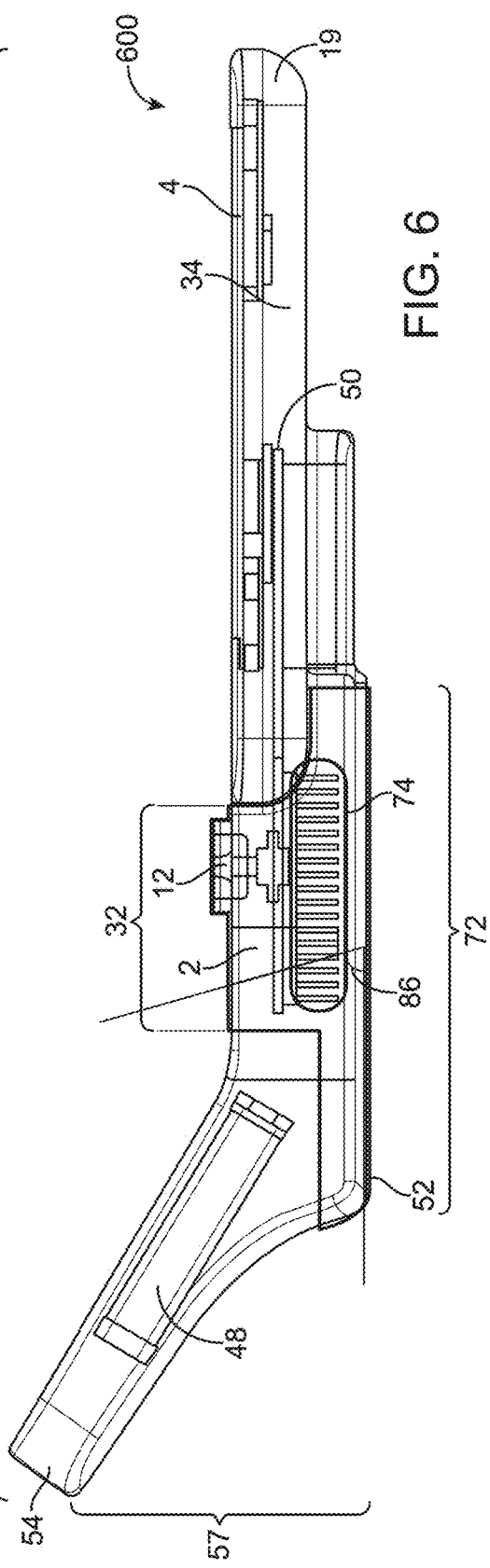
FIG. 6 shows an embodiment of the tactile sensing device 600 comprising a disposable sensor unit 32.

FIG. 6 shows the tactile sensing device 600 comprising a curved handle 56. In some embodiments, the curved handle 56 is a reduced-sized handle compared to the handle shown in FIG. 5. In some embodiments, the reduced-sized handle provides numerous advantages which include, but are not limited to, enhancing the ability to apply force using a thumb, better balance and linear movement control, separate handling area from penetration area (i.e. needle guide area), accommodating both left and right handed users, better hand posture when used on both a seated and a lateral decubitus-positioned individual. In some embodiments, a battery is located inside or within a curved handle 56. In some embodiments, the reduced-sized handle accommodates all fingers of a user to better hold the device. In some embodiments, the reduced-sized handle allows the user to use their prominent fingers to control the tactile sensing device 600. In some embodiments, the reduced-sized handle allows the user to use his/her thumb to apply more force on the surface where the tactile sensing device 600 is being pressed upon. In some embodiments, the tactile sensing device 600 comprises a tilted display.

FIG. 6 shows the architecture of different components of the tactile sensing device 600. In some embodiments, the tactile sensing device 600 comprises a frame 20 that encloses a sensor unit 32 and an electronic unit 34. In some embodiments, the sensor unit 32 is disposable. In some embodiments, the sensor unit 32 is detachable or reversibly attached to the tactile sensing device 1300. In some embodiments, the sensor unit 32 is sterile. In some embodiments, the sensor unit 32 comprises the needle guide (not shown in FIG. 6). In some embodiments, the sensor unit 32 that has a length of about 50 mm to about 100 mm.

In some embodiments, the sensor unit 32 comprises a sensor attachment area 52. In some embodiments, the sensor attachment area 52 is sterile. In some embodiments, the sensor attachment area 52 receives a sensor array. In some embodiments, the sensor array is adhered to the sensor attachment area 52. In some embodiments, the sensor array is a screen-printed force-sensitive resistor (FSR) array. In some embodiments, the frame 20 comprises a printed circuit board (PCB) 50 located underneath the display screen 4, as shown in FIG. 6.

In some embodiments, the tactile sensing device 600 comprises a screen (not shown in FIG. 6). In some embodiments, the display screen measures 99 mm by 57 mm.

In some embodiments, the sensor unit 32 comprises a pressure sensor connector 12, a needle guide 2, an electronic unit connector 74, and a sensor array area 72. In some embodiments, the needle guide 2 is sterile. In some embodiments, the needle guide 2 is at a treatment angle 86 with respect to the sensor array area 72. In some embodiments, the pressure sensor connector 12 is a pressure port. In some embodiments, the pressure sensor connector 12 is sterile. In some embodiments, the electronic unit connector 74 operatively couples the sensor unit 32 with the electronic unit 34. In some embodiments, a battery 48 is located inside a handle 54.

In some embodiments, the sensor unit 32 is a disposable cassette. In some embodiments, the disposable sensor unit is designed to minimize the overall size of the disposable part of the tactile sensing device while keeping the skin and needle contact areas sterile. In some embodiments, the disposable sensor unit is inserted from the bottom or from the side of the device. In some embodiments, the disposable sensor unit remains in place via a snapping mechanism. The disposable sensor unit is loaded into place in a multitude of ways. Non-limiting examples of loading the disposable sensor unit into the tactile sensing device, include, pressing the disposable sensor unit into the tactile sensing device, including snap fit features that allow the disposable sensor unit to stay in place once loaded onto the tactile sensing device, any magnetic means to hold the disposable sensor unit in place, any mechanical means to hold the disposable sensor unit in place. In some embodiments, a tugging string is used to snap the disposable sensor unit out of the tactile sensing device. In some embodiments the disposable sensor unit comprises snap ledges, or other reversible means of loading the disposable sensor unit into the tactile sensing device. In some embodiments, the disposable sensor unit remains in place simply because it abuts a ledge of the tactile sensing device. In some embodiments, one or more tabs are present on the external surface of the tactile sensing device. In some embodiments, the disposable sensor unit is reversibly loaded onto the tactile sensing device.

In some embodiments, the tactile sensing device 600 has a length 49 of about 248 mm. In some embodiments, the tactile sensing device 600 has a length 49 of about 200 mm to about 350 mm. In some embodiments, the tactile sensing device 600 has a length 49 of at least about 200 mm. In some embodiments, the tactile sensing device 600 has a length 49 of at most about 350 mm. In some embodiments, the tactile sensing device 600 has a length 49 of about 200 mm to about 210 mm, about 200 mm to about 220 mm, about 200 mm to about 230 mm, about 200 mm to about 240 mm, about 200 mm to about 250 mm, about 200 mm to about 260 mm, about 200 mm to about 270 mm, about 200 mm to about 280 mm, about 200 mm to about 290 mm, about 200 mm to about 300 mm, about 200 mm to about 350 mm, about 210 mm to about 220 mm, about 210 mm to about 230 mm, about 210 mm to about 240 mm, about 210 mm to about 250 mm, about 210 mm to about 260 mm, about 210 mm to about 270 mm, about 210 mm to about 280 mm, about 210 mm to about 290 mm, about 210 mm to about 300 mm, about 210 mm to about 350 mm, about 220 mm to about 230 mm, about 220 mm to about 240 mm, about 220 mm to about 250 mm, about 220 mm to about 260 mm, about 220 mm to about 270 mm, about 220 mm to about 280 mm, about 220 mm to about 290 mm, about 220 mm to about 300 mm, about 220 mm to about 350 mm, about 230 mm to about 240 mm, about 230 mm to about 250 mm, about 230 mm to about 260 mm, about 230 mm to about 270 mm, about 230 mm to about 280 mm, about 230 mm to about 290 mm, about 230 mm to about 300 mm, about 230 mm to about 350 mm, about 240 mm to about 250 mm, about 240 mm to about 260 mm, about 240 mm to about 270 mm, about 240 mm to about 280 mm, about 240 mm to about 290 mm, about 240 mm to about 300 mm, about 240 mm to about 350 mm, about 250 mm to about 260 mm, about 250 mm to about 270 mm, about 250 mm to about 280 mm, about 250 mm to about 290 mm, about 250 mm to about 300 mm, about 250 mm to about 350 mm, about 260 mm to about 270 mm, about 260 mm to about 280 mm, about 260 mm to about 290 mm, about 260 mm to about 300 mm, about 260 mm to about 350 mm, about 270 mm to about 280 mm, about 270 mm to about 290 mm, about 270 mm to about 300 mm, about 270 mm to about 350 mm, about 280 mm to about 290 mm, about 280 mm to about 300 mm, about 280 mm to about 350 mm, about 290 mm to about 300 mm, about 290 mm to about 350 mm, or about 300 mm to about 350 mm. In some embodiments, the tactile sensing device 600 has a length 49 of about 200 mm, about 210 mm, about 220 mm, about 230 mm, about 240 mm, about 250 mm, about 260 mm, about 270 mm, about 280 mm, about 290 mm, about 300 mm, or about 350 mm.

In some embodiments, the tactile sensing device 600 has a width of about 78 mm. In some embodiments, the tactile sensing device 600 has a width of about 40 mm to about 150 mm. In some embodiments, the tactile sensing device 600 has a width of at least about 40 mm. In some embodiments, the tactile sensing device 600 has a width of at most about 150 mm. In some embodiments, the tactile sensing device 600 has a width of about 40 mm to about 50 mm, about 40 mm to about 60 mm, about 40 mm to about 70 mm, about 40 mm to about 80 mm, about 40 mm to about 90 mm, about 40 mm to about 100 mm, about 40 mm to about 110 mm, about 40 mm to about 120 mm, about 40 mm to about 130 mm, about 40 mm to about 140 mm, about 40 mm to about 150 mm, about 50 mm to about 60 mm, about 50 mm to about 70 mm, about 50 mm to about 80 mm, about 50 mm to about 90 mm, about 50 mm to about 100 mm, about 50 mm to about 110 mm, about 50 mm to about 120 mm, about 50 mm to about 130 mm, about 50 mm to about 140 mm, about 50 mm to about 150 mm, about 60 mm to about 70 mm, about 60 mm to about 80 mm, about 60 mm to about 90 mm, about 60 mm to about 100 mm, about 60 mm to about 110 mm, about 60 mm to about 120 mm, about 60 mm to about 130 mm, about 60 mm to about 140 mm, about 60 mm to about 150 mm, about 70 mm to about 80 mm, about 70 mm to about 90 mm, about 70 mm to about 100 mm, about 70 mm to about 110 mm, about 70 mm to about 120 mm, about 70 mm to about 130 mm, about 70 mm to about 140 mm, about 70 mm to about 150 mm, about 80 mm to about 90 mm, about 80 mm to about 100 mm, about 80 mm to about 110 mm, about 80 mm to about 120 mm, about 80 mm to about 130 mm, about 80 mm to about 140 mm, about 80 mm to about 150 mm, about 90 mm to about 100 mm, about 90 mm to about 110 mm, about 90 mm to about 120 mm, about 90 mm to about 130 mm, about 90 mm to about 140 mm, about 90 mm to about 150 mm, about 100 mm to about 110 mm, about 100 mm to about 120 mm, about 100 mm to about 130 mm, about 100 mm to about 140 mm, about 100 mm to about 150 mm, about 110 mm to about 120 mm, about 110 mm to about 130 mm, about 110 mm to about 140 mm, about 110 mm to about 150 mm, about 120 mm to about 130 mm, about 120 mm to about 140 mm, about 120 mm to about 150 mm, about 130 mm to about 140 mm, about 130 mm to about 150 mm, or about 140 mm to about 150 mm. In some embodiments, the tactile sensing device 600 has a width of about 40 mm, about 50 mm, about 60 mm, about 70 mm, about 80 mm, about 90 mm, about 100 mm, about 110 mm, about 120 mm, about 130 mm, about 140 mm, or about 150 mm.

In some embodiments, the tactile sensing device 600 has a height 57 of about 72 mm. In some embodiments, the tactile sensing device 600 has a height 57 of about 10 mm to about 100 mm. In some embodiments, the tactile sensing device 600 has a height 57 of at least about 10 mm. In some embodiments, the tactile sensing device 600 has a height 57 of at most about 100 mm. In some embodiments, the tactile sensing device 600 has a height 57 of about 10 mm to about 20 mm, about 10 mm to about 30 mm, about 10 mm to about 40 mm, about 10 mm to about 50 mm, about 10 mm to about 60 mm, about 10 mm to about 70 mm, about 10 mm to about 80 mm, about 10 mm to about 90 mm, about 10 mm to about 100 mm, about 20 mm to about 30 mm, about 20 mm to about 40 mm, about 20 mm to about 50 mm, about 20 mm to about 60 mm, about 20 mm to about 70 mm, about 20 mm to about 80 mm, about 20 mm to about 90 mm, about 20 mm to about 100 mm, about 30 mm to about 40 mm, about 30 mm to about 50 mm, about 30 mm to about 60 mm, about 30 mm to about 70 mm, about 30 mm to about 80 mm, about 30 mm to about 90 mm, about 30 mm to about 100 mm, about 40 mm to about 50 mm, about 40 mm to about 60 mm, about 40 mm to about 70 mm, about 40 mm to about 80 mm, about 40 mm to about 90 mm, about 40 mm to about 100 mm, about 50 mm to about 60 mm, about 50 mm to about 70 mm, about 50 mm to about 80 mm, about 50 mm to about 90 mm, about 50 mm to about 100 mm, about 60 mm to about 70 mm, about 60 mm to about 80 mm, about 60 mm to about 90 mm, about 60 mm to about 100 mm, about 70 mm to about 80 mm, about 70 mm to about 90 mm, about 70 mm to about 100 mm, about 80 mm to about 90 mm, about 80 mm to about 100 mm, or about 90 mm to about 100 mm. In some embodiments, the tactile sensing device 600 has a height 57 of about 10 mm, about 20 mm, about 30 mm, about 40 mm, about 50 mm, about 60 mm, about 70 mm, about 80 mm, about 90 mm, or about 100 mm.

In some embodiments, the sensor array (not shown in FIG. 6) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIG. 6), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIG. 6) is an array of cells. In some embodiments, the sensor array (not shown in FIG. 6) is an array of sensing cells. In some embodiments, the sensor array slit (not shown in FIG. 6) is positioned between two rows or more of sensels. In some embodiments, the sensor array slit (not shown in FIG. 6) is positioned between two columns or more of sensels. In some embodiments, the sensor array slit (not shown in FIG. 6) is within the bounds of the sensor array, and/or within the bounds of the sensor array outer edges, and/or within the edges bounding of the sensor array. In some embodiments, the sensor array does not comprise a slit. In some embodiments, the distal opening (not shown in FIG. 6) of the needle guide 2 is positioned between two rows of sensels. In some embodiments, the distal opening (not shown in FIG. 6) of the needle guide 2 is positioned between two columns of sensels. In some embodiments the distal opening (not shown in FIG. 6) of the needle guide 2 is within the bounds of the sensor array, and/or within the bounds of the sensor array outer edges, and/or within the edges bounding of the sensor array. In some embodiments, the distal opening (not shown in FIG. 6) is between two or more sensors of the sensor array. In some embodiments, the distal opening (not shown in FIG. 6) is positioned between two rows or more of sensels. In some embodiments, the distal opening (not shown in FIG. 6) is positioned between two columns or more of sensels.

Figure 7:
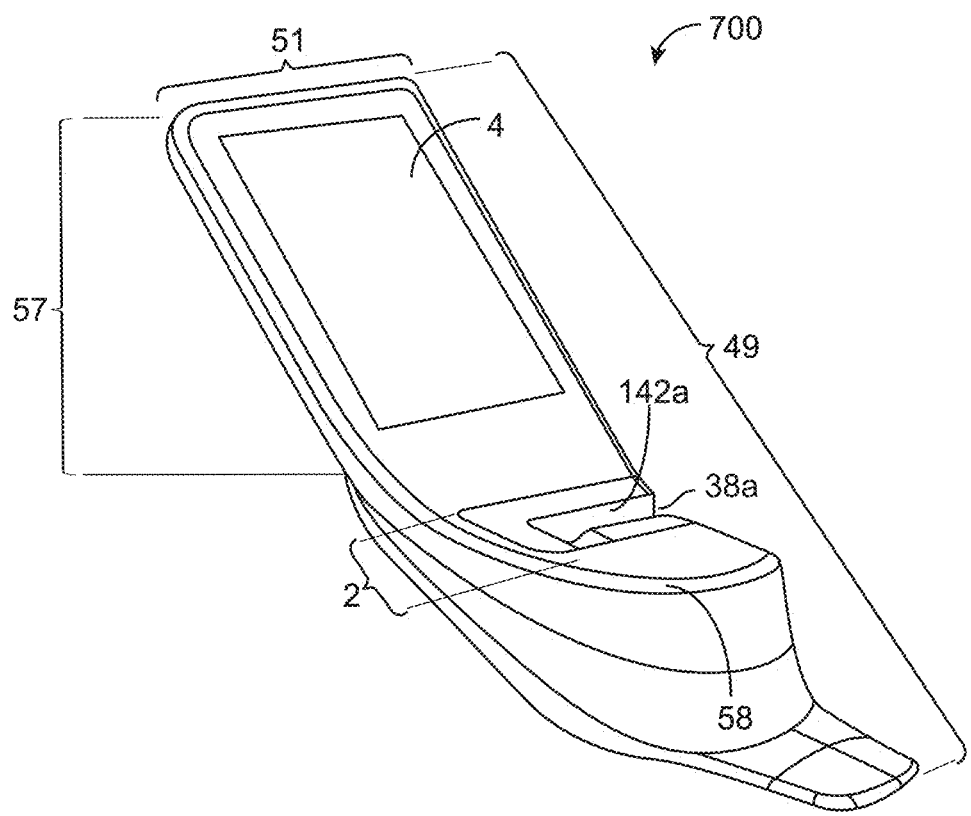
FIG. 7 shows an embodiment of the tactile sensing device 700 comprising an enhanced pinch grip.

FIG. 7 shows the tactile sensing device 700 comprising an enhanced support pinch grip 58. In some embodiments, the reduced-sized handle provides numerous advantages, which include, but are not limited to, enhancing the ability to apply moderate force, an increased, medium sized device, and using prominent fingers to hold the device. In some embodiments, a battery is located inside or within the enhanced support pinch grip 58. In some embodiments, the surface of the enhanced support pinch grip 58 comprises texture detail. In some embodiments, the surface of the enhanced support pinch grip 58 is textured. In some embodiments, the enhanced support pinch grip 58 provides the user with palm support. In some embodiments, the enhanced support pinch grip 58 allows the user to use prominent fingers to hold the tactile sensing device 700. In some embodiments, the tactile sensing device 700 comprises a fixed needle guide 2. In some embodiments, the tactile sensing device 700 comprises a slot further comprising a first slot wall 142a and a second slot wall (not shown in FIG. 7).

In some embodiments, the tactile sensing device 700 has a length 49 of about 223 mm. In some embodiments, the tactile sensing device 700 has a length 49 of about 150 mm to about 300 mm. In some embodiments, the tactile sensing device 700 has a length 49 of at least about 150 mm. In some embodiments, the tactile sensing device 700 has a length 49 of at most about 300 mm. In some embodiments, the tactile sensing device 700 has a length 49 of about 150 mm to about 200 mm, about 150 mm to about 210 mm, about 150 mm to about 220 mm, about 150 mm to about 230 mm, about 150 mm to about 240 mm, about 150 mm to about 250 mm, about 150 mm to about 270 mm, about 150 mm to about 280 mm, about 150 mm to about 290 mm, about 150 mm to about 300 mm, about 200 mm to about 210 mm, about 200 mm to about 220 mm, about 200 mm to about 230 mm, about 200 mm to about 240 mm, about 200 mm to about 250 mm, about 200 mm to about 270 mm, about 200 mm to about 280 mm, about 200 mm to about 290 mm, about 200 mm to about 300 mm, about 210 mm to about 220 mm, about 210 mm to about 230 mm, about 210 mm to about 240 mm, about 210 mm to about 250 mm, about 210 mm to about 270 mm, about 210 mm to about 280 mm, about 210 mm to about 290 mm, about 210 mm to about 300 mm, about 220 mm to about 230 mm, about 220 mm to about 240 mm, about 220 mm to about 250 mm, about 220 mm to about 270 mm, about 220 mm to about 280 mm, about 220 mm to about 290 mm, about 220 mm to about 300 mm, about 230 mm to about 240 mm, about 230 mm to about 250 mm, about 230 mm to about 270 mm, about 230 mm to about 280 mm, about 230 mm to about 290 mm, about 230 mm to about 300 mm, about 240 mm to about 250 mm, about 240 mm to about 270 mm, about 240 mm to about 280 mm, about 240 mm to about 290 mm, about 240 mm to about 300 mm, about 250 mm to about 270 mm, about 250 mm to about 280 mm, about 250 mm to about 290 mm, about 250 mm to about 300 mm, about 270 mm to about 280 mm, about 270 mm to about 290 mm, about 270 mm to about 300 mm, about 280 mm to about 290 mm, about 280 mm to about 300 mm, or about 290 mm to about 300 mm. In some embodiments, the tactile sensing device 700 has a length 49 of about 150 mm, about 200 mm, about 210 mm, about 220 mm, about 230 mm, about 240 mm, about 250 mm, about 270 mm, about 280 mm, about 290 mm, or about 300 mm.

In some embodiments, the tactile sensing device 700 has a width 51 of about 78 mm. In some embodiments, the tactile sensing device 700 has a width 51 of about 50 mm to about 150 mm. In some embodiments, the tactile sensing device 700 has a width 51 of at least about 50 mm. In some embodiments, the tactile sensing device 700 has a width 51 of at most about 150 mm. In some embodiments, the tactile sensing device 700 has a width 51 of about 50 mm to about 60 mm, about 50 mm to about 70 mm, about 50 mm to about 80 mm, about 50 mm to about 90 mm, about 50 mm to about 100 mm, about 50 mm to about 110 mm, about 50 mm to about 120 mm, about 50 mm to about 130 mm, about 50 mm to about 140 mm, about 50 mm to about 150 mm, about 60 mm to about 70 mm, about 60 mm to about 80 mm, about 60 mm to about 90 mm, about 60 mm to about 100 mm, about 60 mm to about 110 mm, about 60 mm to about 120 mm, about 60 mm to about 130 mm, about 60 mm to about 140 mm, about 60 mm to about 150 mm, about 70 mm to about 80 mm, about 70 mm to about 90 mm, about 70 mm to about 100 mm, about 70 mm to about 110 mm, about 70 mm to about 120 mm, about 70 mm to about 130 mm, about 70 mm to about 140 mm, about 70 mm to about 150 mm, about 80 mm to about 90 mm, about 80 mm to about 100 mm, about 80 mm to about 110 mm, about 80 mm to about 120 mm, about 80 mm to about 130 mm, about 80 mm to about 140 mm, about 80 mm to about 150 mm, about 90 mm to about 100 mm, about 90 mm to about 110 mm, about 90 mm to about 120 mm, about 90 mm to about 130 mm, about 90 mm to about 140 mm, about 90 mm to about 150 mm, about 100 mm to about 110 mm, about 100 mm to about 120 mm, about 100 mm to about 130 mm, about 100 mm to about 140 mm, about 100 mm to about 150 mm, about 110 mm to about 120 mm, about 110 mm to about 130 mm, about 110 mm to about 140 mm, about 110 mm to about 150 mm, about 120 mm to about 130 mm, about 120 mm to about 140 mm, about 120 mm to about 150 mm, about 130 mm to about 140 mm, about 130 mm to about 150 mm, or about 140 mm to about 150 mm. In some embodiments, the tactile sensing device 700 has a width 51 of about 50 mm, about 60 mm, about 70 mm, about 80 mm, about 90 mm, about 100 mm, about 110 mm, about 120 mm, about 130 mm, about 140 mm, or about 150 mm.

In some embodiments, the tactile sensing device 700 has a height 57 of about 70 mm. In some embodiments, the tactile sensing device 700 has a height 57 of about 10 mm to about 100 mm. In some embodiments, the tactile sensing device 700 has a height 57 of at least about 10 mm. In some embodiments, the tactile sensing device 700 has a height 57 of at most about 100 mm. In some embodiments, the tactile sensing device 700 has a height 57 of about 10 mm to about 20 mm, about 10 mm to about 30 mm, about 10 mm to about 40 mm, about 10 mm to about 50 mm, about 10 mm to about 60 mm, about 10 mm to about 70 mm, about 10 mm to about 80 mm, about 10 mm to about 90 mm, about 10 mm to about 100 mm, about 20 mm to about 30 mm, about 20 mm to about 40 mm, about 20 mm to about 50 mm, about 20 mm to about 60 mm, about 20 mm to about 70 mm, about 20 mm to about 80 mm, about 20 mm to about 90 mm, about 20 mm to about 100 mm, about 30 mm to about 40 mm, about 30 mm to about 50 mm, about 30 mm to about 60 mm, about 30 mm to about 70 mm, about 30 mm to about 80 mm, about 30 mm to about 90 mm, about 30 mm to about 100 mm, about 40 mm to about 50 mm, about 40 mm to about 60 mm, about 40 mm to about 70 mm, about 40 mm to about 80 mm, about 40 mm to about 90 mm, about 40 mm to about 100 mm, about 50 mm to about 60 mm, about 50 mm to about 70 mm, about 50 mm to about 80 mm, about 50 mm to about 90 mm, about 50 mm to about 100 mm, about 60 mm to about 70 mm, about 60 mm to about 80 mm, about 60 mm to about 90 mm, about 60 mm to about 100 mm, about 70 mm to about 80 mm, about 70 mm to about 90 mm, about 70 mm to about 100 mm, about 80 mm to about 90 mm, about 80 mm to about 100 mm, or about 90 mm to about 100 mm. In some embodiments, the tactile sensing device 700 has a height 57 of about 10 mm, about 20 mm, about 30 mm, about 40 mm, about 50 mm, about 60 mm, about 70 mm, about 80 mm, about 90 mm, or about 100 mm.

In some embodiments, the sensor array (not shown in FIG. 7) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIG. 7), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIG. 7) is an array of cells. In some embodiments, the sensor array (not shown in FIG. 7) is an array of sensing cells. In some embodiments, the sensor array slit (not shown in FIG. 7) is positioned between two rows or more of sensels. In some embodiments, the sensor array slit (not shown in FIG. 7) is positioned between two columns or more of sensels. In some embodiments, the sensor array slit (not shown in FIG. 7) is within the bounds of the sensor array, and/or within the bounds of the sensor array outer edges, and/or within the edges bounding of the sensor array. In some embodiments, the sensor array does not comprise a slit. In some embodiments, the distal opening (not shown in FIG. 7) of the needle guide 2 is positioned between two rows of sensels. In some embodiments, the distal opening (not shown in FIG. 7) of the needle guide 2 is positioned between two columns of sensels. In some embodiments the distal opening (not shown in FIG. 7) of the needle guide 2 is within the bounds of the sensor array, and/or within the bounds of the sensor array outer edges, and/or within the edges bounding of the sensor array. In some embodiments, the distal opening (not shown in FIG. 7) is between two or more sensors of the sensor array. In some embodiments, the distal opening (not shown in FIG. 7) is positioned between two rows or more of sensels. In some embodiments, the distal opening (not shown in FIG. 7) is positioned between two columns or more of sensels.

Figure 8:
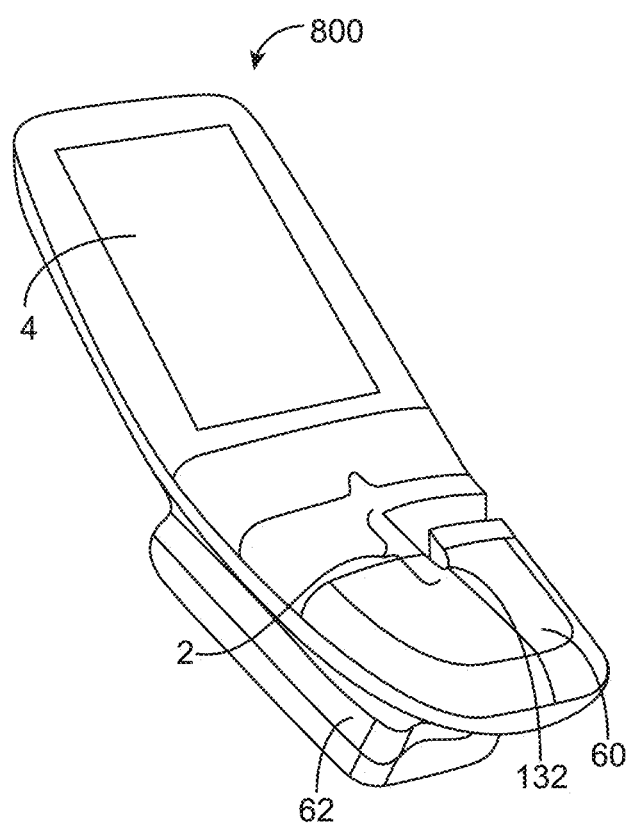
FIG. 8 shows an embodiment of the tactile sensing device 800 comprising an exaggerated undercut grip.

FIG. 8 shows the tactile sensing device 800 comprising an exaggerated undercut grip 60. In some embodiments, the exaggerated undercut grip 60 provides numerous advantages which include, but are not limited to, the ability to apply more force with the palm of the user's hand, offering a surface area that is larger than the surface area of handle 56 shown in FIGS. 6A-D, for example, which the user uses to press or apply a force, and an integrated form factor. In some embodiments, the exaggerated undercut grip 60 comprises a three-sided undercut wall 62 for grip. In some embodiments, the tactile sensing device 800 measures approximately 213 mm in length, 79 mm in width, and 72 mm in height.

In some embodiments, the sensor array (not shown in FIG. 8) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIG. 8), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIG. 8) is an array of cells. In some embodiments, the sensor array (not shown in FIG. 8) is an array of sensing cells. In some embodiments, the sensor array slit (not shown in FIG. 8) is positioned between two rows or more of sensels. In some embodiments, the sensor array slit (not shown in FIG. 8) is positioned between two columns or more of sensels. In some embodiments, the sensor array slit (not shown in FIG. 8) is within the bounds of the sensor array, and/or within the bounds of the sensor array outer edges, and/or within the edges bounding of the sensor array. In some embodiments, the sensor array does not comprise a slit. In some embodiments, the distal opening (not shown in FIG. 8) of the needle guide 2 is positioned between two rows of sensels. In some embodiments, the distal opening (not shown in FIG. 8) of the needle guide 2 is positioned between two columns of sensels. In some embodiments the distal opening (not shown in FIG. 8) of the needle guide 2 is within the bounds of the sensor array, and/or within the bounds of the sensor array outer edges, and/or within the edges bounding of the sensor array. In some embodiments, the distal opening (not shown in FIG. 8) is between two or more sensors of the sensor array. In some embodiments, the distal opening (not shown in FIG. 8) is positioned between two rows or more of sensels. In some embodiments, the distal opening (not shown in FIG. 8) is positioned between two columns or more of sensels.

Figure 9:
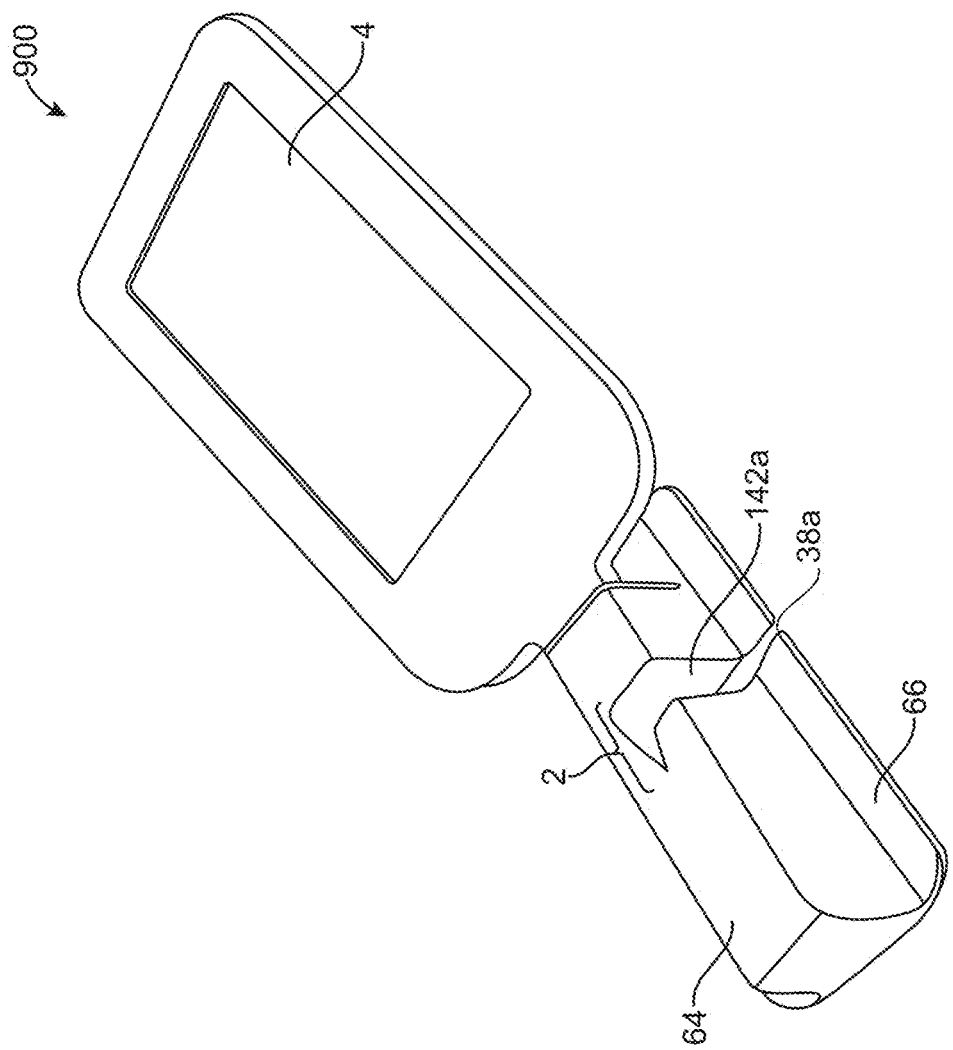
FIG. 9 shows an embodiment of the tactile sensing device 900 comprising a pinch grip control.

FIG. 9 shows the tactile sensing device 900 comprising a pinch grip 64. In some embodiments, the pinch grip 64 provides numerous advantages which include, but are not limited to, better control to make small adjustments in positioning of the tactile sensing device 900 with fingers, compact size, ability to apply force or press directly over the sensor array, and better control when used on a lateral decubitus-positioned individual. In some embodiments, the pinch grip 64 comprises a pressing support 66 that has an increased posterior surface area that allows for a user to apply force directly over the sensor array. In some embodiments, the tactile sensing device 900 measures approximately 213 mm in length, 78 mm in width, and 72 mm in height.

In some embodiments, the sensor array (not shown in FIG. 9) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIG. 9), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIG. 9) is an array of cells. In some embodiments, the sensor array (not shown in FIG. 9) is an array of sensing cells. In some embodiments, the sensor array slit (not shown in FIG. 9) is positioned between two rows or more of sensels. In some embodiments, the sensor array slit (not shown in FIG. 9) is positioned between two columns or more of sensels. In some embodiments, the sensor array slit (not shown in FIG. 9) is within the bounds of the sensor array, and/or within the bounds of the sensor array outer edges, and/or within the edges bounding of the sensor array. In some embodiments, the sensor array does not comprise a slit. In some embodiments, the distal opening (not shown in FIG. 9) of the needle guide 2 is positioned between two rows of sensels. In some embodiments, the distal opening (not shown in FIG. 9) of the needle guide 2 is positioned between two columns of sensels. In some embodiments the distal opening (not shown in FIG. 9) of the needle guide 2 is within the bounds of the sensor array, and/or within the bounds of the sensor array outer edges, and/or within the edges bounding of the sensor array. In some embodiments, the distal opening (not shown in FIG. 9) is between two or more sensors of the sensor array. In some embodiments, the distal opening (not shown in FIG. 9) is positioned between two rows or more of sensels. In some embodiments, the distal opening (not shown in FIG. 9) is positioned between two columns or more of sensels.

Figure 10:
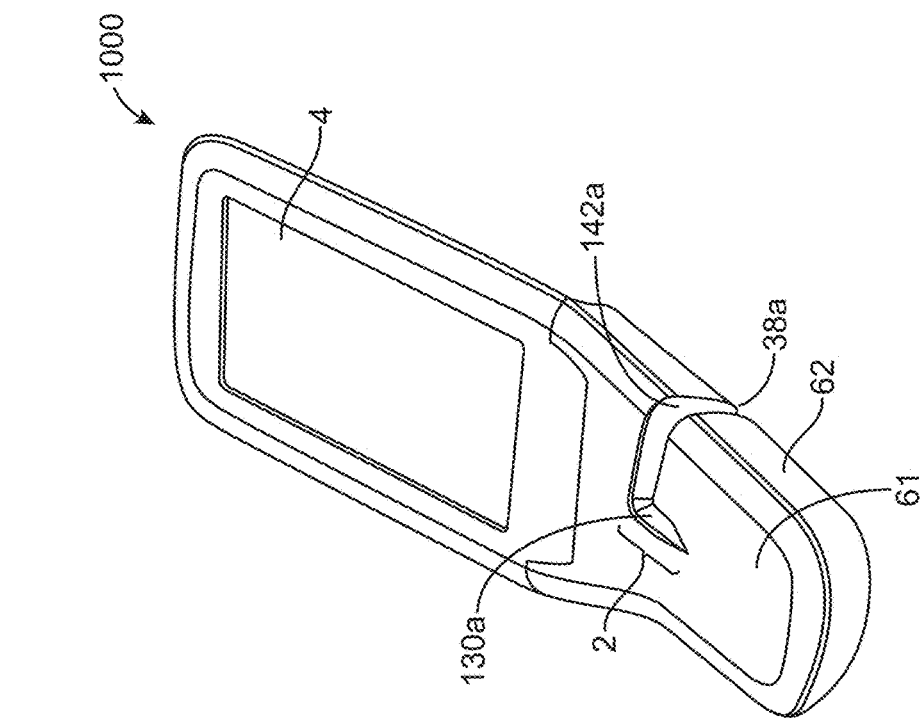
FIG. 10 shows an embodiment of the tactile sensing device 1000 comprising an undercut body grip.

FIG. 10 show the tactile sensing device 1000 comprising an undercut body grip 61. In some embodiments, the undercut body grip 61 provides numerous advantages which include, but are not limited to, better control to make small adjustments in positioning of the tactile sensing device 1000 with fingers, compact size of device, integrated form factor, and ability of a user to apply force or press directly over the sensor array. In some embodiments, the undercut body grip 61 comprises an undercut wall 62 on its lateral side that enables the user to have improved handling of the device. In some embodiments, the tactile sensing device 1000 measures approximately 207 mm in length, 78 mm in width, and 72 mm in height.

In some embodiments, the sensor array (not shown in FIG. 10) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIG. 10), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIGS. 10) is an array of cells. In some embodiments, the sensor array (not shown in FIG. 10) is an array of sensing cells. In some embodiments, the sensor array slit (not shown in FIG. 10) is positioned between two rows or more of sensels. In some embodiments, the sensor array slit (not shown in FIG. 10) is positioned between two columns or more of sensels. In some embodiments, the sensor array slit (not shown in FIG. 10) is within the bounds of the sensor array, and/or within the bounds of the sensor array outer edges, and/or within the edges bounding of the sensor array. In some embodiments, the sensor array does not comprise a slit. In some embodiments, the distal opening (not shown in FIG. 10) of the needle guide 2 is positioned between two rows of sensels. In some embodiments, the distal opening (not shown in FIG. 10) of the needle guide 2 is positioned between two columns of sensels. In some embodiments the distal opening (not shown in FIG. 10) of the needle guide 2 is within the bounds of the sensor array, and/or within the bounds of the sensor array outer edges, and/or within the edges bounding of the sensor array. In some embodiments, the distal opening (not shown in FIG. 10) is between two or more sensors of the sensor array. In some embodiments, the distal opening (not shown in FIG. 10) is positioned between two rows or more of sensels. In some embodiments, the distal opening (not shown in FIG. 10) is positioned between two columns or more of sensels.

Figure 11:
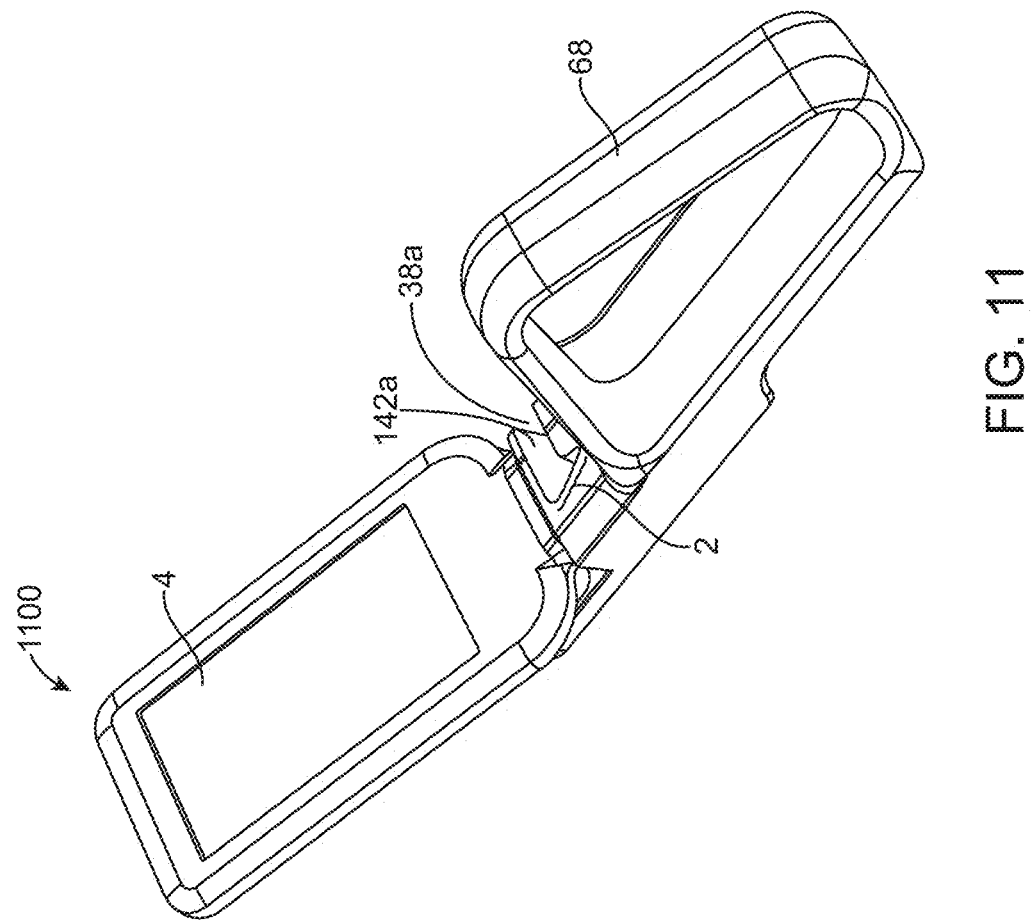
FIG. 11 shows an embodiment of the tactile sensing device 1100 comprising a power grip.

FIG. 11 shows the tactile sensing device 1100 comprising a power grip handle 68. In some embodiments, the power grip handle 68 enhances the ability of a user to apply force or press directly over the sensor array. In some embodiments, the power grip handle 68. In some embodiments, the tactile sensing device 1100 measures approximately 286 mm in length, 78 mm in width, and 95 mm in height.

In some embodiments, the tactile sensing device measures at least about 150 mm to at most about 350 mm in length. In some embodiments, the tactile sensing device measures at least about 150 mm to at most about 200 mm in length. In some embodiments, the tactile sensing device measures at least about 200 mm to at most about 250 mm in length. In some embodiments, the tactile sensing device measures at least about 250 mm to at most about 300 mm in length. In some embodiments, the tactile sensing device measures about 150 mm in length. In some embodiments, the tactile sensing device measures about 160 mm in length. In some embodiments, the tactile sensing device measures about 170 mm in length. In some embodiments, the tactile sensing device measures about 180 mm in length. In some embodiments, the tactile sensing device measures about 190 mm in length. In some embodiments, the tactile sensing device measures about 200 mm in length. In some embodiments, the tactile sensing device measures about 210 mm in length. In some embodiments, the tactile sensing device measures about 220 mm in length. In some embodiments, the tactile sensing device measures about 230 mm in length. In some embodiments, the tactile sensing device measures about 240 mm in length. In some embodiments, the tactile sensing device measures about 250 mm in length. In some embodiments, the tactile sensing device measures about 260 mm in length. In some embodiments, the tactile sensing device measures about 270 mm in length. In some embodiments, the tactile sensing device measures about 280 mm in length. In some embodiments, the tactile sensing device measures about 290 mm in length. In some embodiments, the tactile sensing device measures about 300 mm in length. In some embodiments, the tactile sensing device measures about 350 mm in length. In some embodiments, the tactile sensing device measures about 316 mm in length.

In some embodiments, the tactile sensing device measures at least about 50 mm to at most about 150 mm in width. In some embodiments, the tactile sensing device measures at least about 50 mm to at most about 100 mm in width. In some embodiments, the tactile sensing device measures at least about 100 mm to at most about 150 mm in width. In some embodiments, the tactile sensing device measures at least about 50 mm to at most about 80 mm in width. In some embodiments, the tactile sensing device measures about 70 mm in width. In some embodiments, the tactile sensing device measures about 75 mm in width. In some embodiments, the tactile sensing device measures about 80 mm in width. In some embodiments, the tactile sensing device measures about 85 mm in width. In some embodiments, the tactile sensing device measures about 100 mm in width. In some embodiments, the tactile sensing device measures about 150 mm in width. In some embodiments, the tactile sensing device measures about 50 mm in width. In some embodiments, the tactile sensing device measures about 60 mm in width. In some embodiments, the tactile sensing device measures about 78 mm in width. In some embodiments, the tactile sensing device measures about 79 mm in width. In some embodiments, the tactile sensing device measures about 77 mm in width.

In some embodiments, the sensor array (not shown in FIG. 11) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIG. 11), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIG. 11) is an array of cells. In some embodiments, the sensor array (not shown in FIG. 11) is an array of sensing cells. In some embodiments, the sensor array slit (not shown in FIG. 11) is positioned between two rows or more of sensels. In some embodiments, the sensor array slit (not shown in FIG. 11) is positioned between two columns or more of sensels. In some embodiments, the sensor array slit (not shown in FIG. 11) is within the bounds of the sensor array, and/or within the bounds of the sensor array outer edges, and/or within the edges bounding of the sensor array. In some embodiments, the sensor array does not comprise a slit. In some embodiments, the distal opening (not shown in FIG. 11) of the needle guide 2 is positioned between two rows of sensels. In some embodiments, the distal opening (not shown in FIG. 11) of the needle guide 2 is positioned between two columns of sensels. In some embodiments the distal opening (not shown in FIG. 11) of the needle guide 2 is within the bounds of the sensor array, and/or within the bounds of the sensor array outer edges, and/or within the edges bounding of the sensor array. In some embodiments, the distal opening (not shown in FIG. 11) is between two or more sensors of the sensor array. In some embodiments, the distal opening (not shown in FIG. 11) is positioned between two rows or more of sensels. In some embodiments, the distal opening (not shown in FIG. 11) is positioned between two columns or more of sensels.

In some embodiments, the tactile sensing device comprises an angled display screen. In some embodiments, the display screen 4 is at a display angle with respect to the sensor array. In some embodiments, the angled display screen is at a display angle with respect to the posterior surface of the tactile sensing device. In some embodiments, the angled display screen provides more visibility when used on a seated individual compared to when used on a lateral decubitus-positioned individual. In some embodiments, the tactile sensing device comprises a flat display screen. In some embodiments, the flat display screen is parallel to the sensor array. In some embodiments, the flat display screen is parallel to the posterior surface of the tactile sensing device. In some embodiments, the flat display screen is at a display angle of zero degrees with respect to the posterior surface of the tactile sensing device. In some embodiments, the display angle is adjustable. In some embodiments, the display is manually or automatically adjustable. In some embodiments, the flat display screen provides good visibility when used on a seated individual and when used on a lateral decubitus-positioned individual.

Figure 12A:
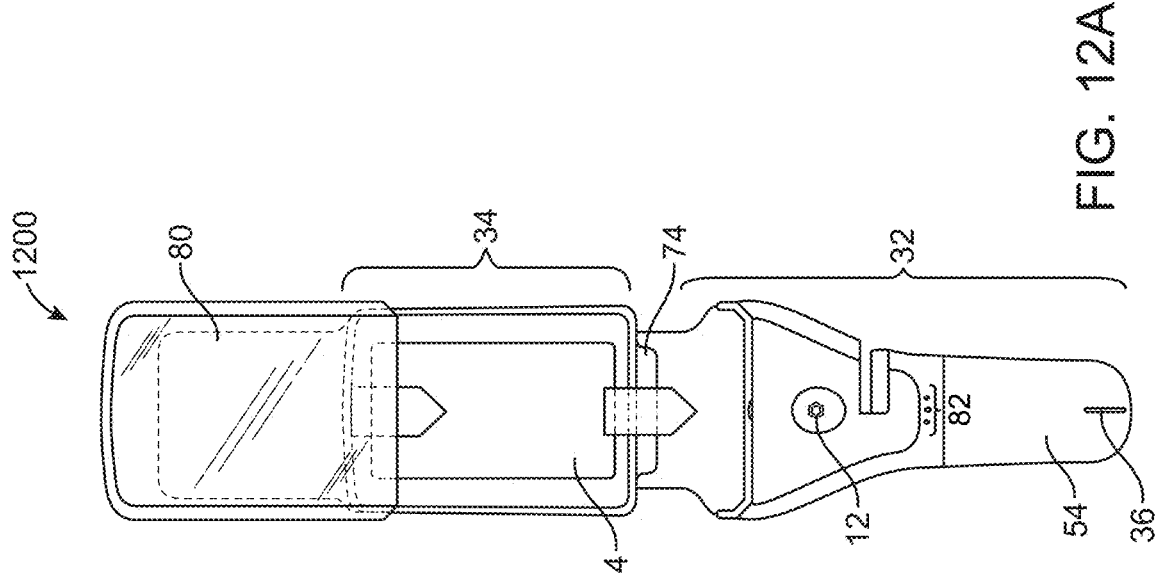
FIGS. 12A, 12B, and 12C show an embodiment of the tactile sensing device 1200 comprising an electronic unit 34 and a sensor unit 32 that includes the handle 54.
Figure 12B:
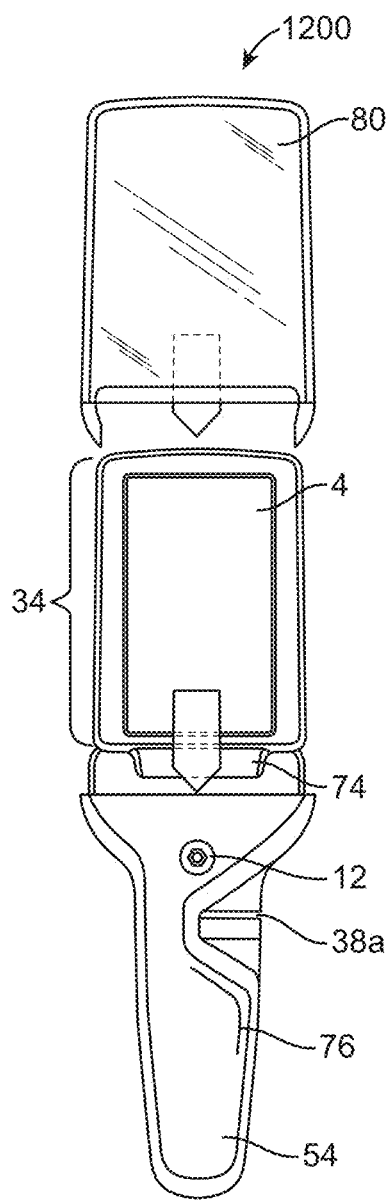
Figure 12C:
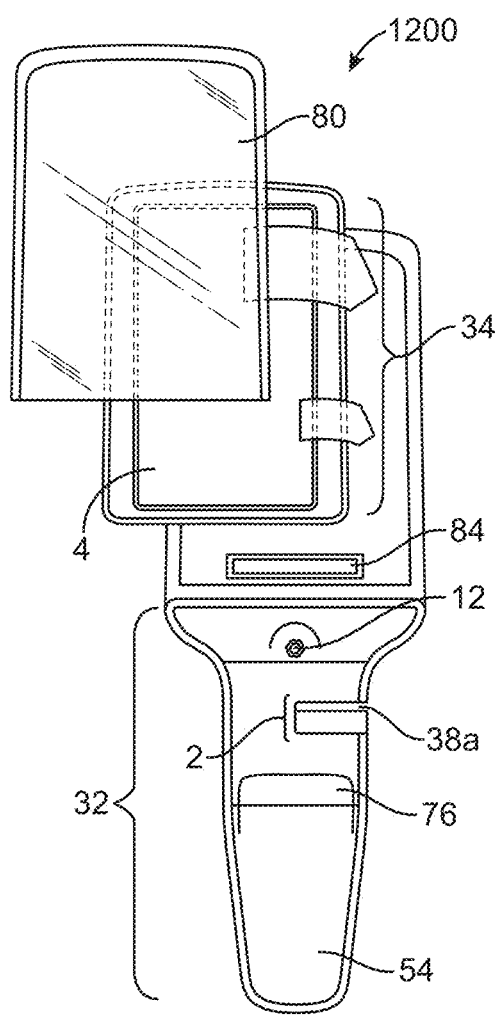

FIGS. 12A-C show a tactile sensing device 1200 comprising a sleeve 80, an electronic unit 34, and a sensor unit 32. FIGS. 12A-C show different designs of the tactile sensing device 1200, particularly different features of the handle 54. For example, in some embodiments, the tactile sensing device 1200 comprises a handle 54 comprising a texture feature 82 and a needle alignment guide 36, as shown in FIG. 12A. In some embodiments, the texture feature 82 provides a textured surface to increase traction on and enhance a thumb grip. In some embodiments, the tactile sensing device 1200 comprises a grip feature 76, as shown in FIGS. 12B-C. In some embodiments, the grip feature 76 is an indentation on the handle 54 that enhances grip.

In some embodiments, the tactile sensing device comprises a larger sterile area compared to the embodiments presented in FIG. 6. In some embodiments, the sensor unit 32 is disposable. In some embodiments, the sensor unit 32 comprises a handle 54. In some embodiments, the sensor unit 32 comprises a pressure sensor connector 12, a needle guide 2, an electronic unit connector 74, and a sensor array area 72. In some embodiments, the sensor unit 32 comprises the main body of the tactile sensing device 1400. In some embodiments, the electronic unit connector 74 is positioned distally away from the pressure sensor connector 12. In some embodiments, the electronic unit connector 74 operatively couples the sensor unit 32 with the electronic unit 34. In some embodiments, the electronic unit connector 74 is a male connector. In some embodiments, the sensor unit 32 comprises a port or female connector configured to receive the electronic unit connector 74. In some embodiments, the electronic unit connector 74 operatively couples the sensor unit 32 with the electronic unit 34 when the electronic unit connector 74 is inserted into a port or female connector located in the sensor unit 32. In some embodiments, the sensor unit 32 is operatively coupled to the electronic unit 34 by sliding the sensor unit 32 into a socket in the electronic unit 34, where the electronic connectors are located.

In some embodiments, the tactile sensing device comprises a sleeve 80. In some embodiments, the sleeve 80 enables the tactile sensing device to achieve complete sterility during use. In some embodiments, having two sterile disposable units completely covers the electronic unit connector and a sensor unit connector.

FIGS. 12 A-B are front views of two different embodiments of the tactile sensing device 1200 that illustrate how the sleeve 80 slides onto the electronic unit 34. Additionally, in some embodiments, FIGS. 12 A-B illustrate how the electronic unit 34 inserts into the sensor unit 32 (note the arrows in FIGS. 12 A-C indicate the direction of movement of each element during assembly). FIG. 12C illustrates yet another embodiment of the tactile sensing device 1200 where the electronic unit 34 snaps onto the distal portion of the tactile sensing device 1200, and the sleeve 80 snaps onto the electronic unit 34, as shown by the arrows. In some embodiments, the sleeve 80 is loaded onto the electronic unit via a snap-on mechanism, as shown in FIG. 12C. In some embodiments, the electronic unit 34 is loaded onto the sensor unit via a snap-on mechanism, as shown in FIG. 12C.

In some embodiments, the electronic unit 34 is reversibly loaded onto the sensor unit from the top of the device. In some embodiments, the electronic unit 34 reversibly and operatively connects to the sensor unit 32 and/or the tactile sensing device via a magnetic force. In some embodiments, the electronic unit 34 comprises a magnet. In some embodiments, the distal portion of the tactile sensing device comprises a magnet. In some embodiments, the sleeve 80 reversibly attaches to the electronic unit 34 and/or to the tactile sensing device via a magnetic force. In some embodiments, the sleeve 80 comprises a magnet. In some embodiments, the electronic unit 34 is reversibly and operatively connected to the tactile sensing device and/or to the sensor unit 32 by any other suitable means (e.g., by using one or more clips, one or more fasteners, and/or one or more clamps). In some embodiments, the sleeve 80 is reversibly and operatively connected to the tactile sensing device and/or to the electronic unit 34 by any other suitable means (e.g., by using one or more clips, one or more fasteners, and/or one or more clamps).

In some embodiments, the electronic unit 34 comprises an electronic unit connector 74. In some embodiments, the electronic unit connector 74 is a tab. In some embodiments, the sleeve 80 is composed of clear plastic. In some embodiments, the sleeve 80 is a disposable sleeve. In some embodiments, the sleeve 80 is a plastic sleeve. In some embodiments, the sleeve 80 is a reusable sleeve. In some embodiments, the sleeve 80 is a sterile sleeve. In some embodiments the tactile sensing device 1200 comprises a needle guide 2 comprising a rectangular shape. In some embodiments the tactile sensing device 1200 comprises a needle guide 2, wherein the needle guide 2 does not comprise a notch. In some embodiments the tactile sensing device 1200 comprises a needle guide 2, wherein the needle guide 2 only comprises a slot 38. In some embodiments the tactile sensing device 1200 comprises a needle guide 2, wherein the needle guide 2 does not comprise a track. In some embodiments the tactile sensing device 1200 comprises a needle guide 2 comprising a flared proximal opening.

In some embodiments, the sensor array (not shown in FIGS. 12A-C) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIGS. 12A-C), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIGS. 12A-C) is an array of cells. In some embodiments, the sensor array (not shown in FIGS. 12A-C) is an array of sensing cells. In some embodiments, the sensor array slit (not shown in FIGS. 12A-C) is positioned between two rows or more of sensels. In some embodiments, the sensor array slit (not shown in FIGS. 12A-C) is positioned between two columns or more of sensels. In some embodiments, the sensor array slit (not shown in FIGS. 12A-C) is within the bounds of the sensor array, and/or within the bounds of the sensor array outer edges, and/or within the edges bounding of the sensor array. In some embodiments, the sensor array does not comprise a slit. In some embodiments, the distal opening (not shown in FIGS. 12A-C) of the needle guide 2 is positioned between two rows of sensels. In some embodiments, the distal opening (not shown in FIGS. 12A-C) of the needle guide 2 is positioned between two columns of sensels. In some embodiments the distal opening (not shown in FIGS. 12A-C) of the needle guide 2 is within the bounds of the sensor array, and/or within the bounds of the sensor array outer edges, and/or within the edges bounding of the sensor array. In some embodiments, the distal opening (not shown in FIGS. 12A-C) is between two or more sensors of the sensor array. In some embodiments, the distal opening (not shown in FIGS. 12A-C) is positioned between two rows or more of sensels. In some embodiments, the distal opening (not shown in FIGS. 12A-C) is positioned between two columns or more of sensels.

Figure 13:
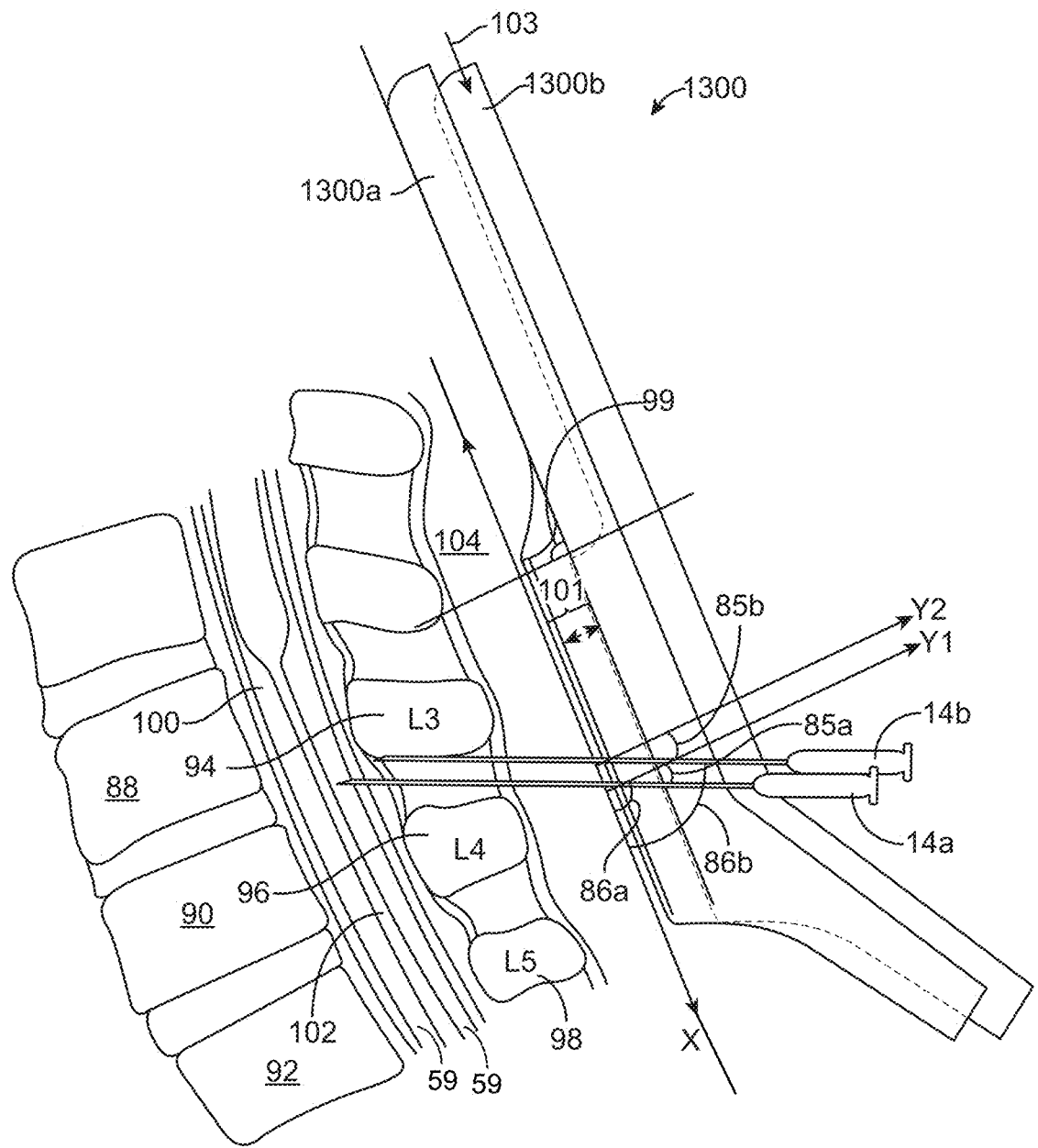
FIG. 13 shows a needle being inserted into a spinal canal or an epidural space 100 using the tactile sensing device 1300.

FIG. 13 illustrates a sagittal section of the lumbar spine of an individual with a first needle 14a in the spinal canal 100, in the subarachnoid space. The illustration of the sagittal section of the lumbar spine shows a third lumbar vertebra 88, a fourth lumbar vertebra 90, and a fifth lumbar vertebra 92. FIG. 13 further shows a spinous process of the third lumbar vertebra (L3) 94, a spinous process of the fourth lumbar vertebra (L4) 96, and a spinous process of the fifth lumbar (L5) vertebra 98, which are located laterally across from the third lumbar vertebra 88, from the fourth lumbar vertebra 90, and from the fifth lumbar vertebra 92, respectively. The illustration of the sagittal section of the lumbar spine further shows a spinal cord 102 located in the space between the lumbar vertebrae and the spinous processes (i.e., the spinal canal). Additionally, FIG. 13 shows a subarachnoid space 100 located in the space between the lumbar vertebrae and the spinous processes and surrounding the spinal cord 102. FIG. 13 shows an epidural space 59, which is shown as encasing the subarachnoid space 100. FIG. 13 further shows a tissue 104 of the individual located laterally across from the spinous processes. In some embodiments, the tissue 104 is soft tissue. In some embodiments, the tissue 104 is subcutaneous adipose tissue, muscle, ligaments, tendons, and/or skin. In some embodiments, the surface of tissue 104, as shown by the X-axis on FIG. 13, is skin.

FIG. 13 shows a first tactile sensing device 1300a and a second tactile sensing device 1300b placed on top of the skin of an individual. The second tactile sensing device in this image is not meant to indicate that there is a system with two devices, rather, it is meant to show how the location the needle gets inserted into the subject might differ in cases of different spinous process depths. FIG. 13 shows a first Y1-axis and a second Y2-axis that are both perpendicular to the X-axis. In some embodiments, a first needle 14a is inserted at a first treatment angle 86a, as shown in FIG. 13. In some embodiments, the first treatment angle 86a is defined as the space measured in degrees between the X-axis and the first needle 14a. In some embodiments, the first treatment angle 86a is defined as the space measured in degrees between the posterior surface of the tactile sensing device 1900a and the first needle 14a. In some embodiments, the first treatment angle 86a is defined as the space measured in degrees between a posterior face of the sensor array and the first needle 14a.

In some embodiments, a second needle 14b is inserted at a second treatment angle 86b. In some embodiments, the second treatment angle 86b is defined as the space measured in degrees between the X-axis and the second needle 14b. In some embodiments, the second treatment angle 86b is defined as the space measured in degrees between the posterior surface of the second tactile sensing device 1900b and the second needle 14b. In some embodiments, the second treatment angle 86b is defined as the space measured in degrees between a posterior face of the sensor array and the first needle 14b.

In some embodiments, a first needle 14a is inserted at a first cephalad angle 85a. In some embodiments, the first cephalad angle 85a is defined as the space measured in degrees between the first Y1-axis and the first needle 14a. In some embodiments, a second needle 14b is shown as being inserted at a second cephalad angle 85b. In some embodiments, the second cephalad angle 85b is defined as the space measured in degrees between the second Y2-axis and the second needle 14b. In some embodiments, the treatment angle is a cephalad angle. In some embodiments, the treatment angle is a caudal angle.

In addition, FIG. 13 shows the first tactile sensing device 1300a being moved in the direction of arrow 103 resulting in the tactile sensing device being positioned as illustrated by the second tactile second device 1300b. In some embodiments, the user moves the tactile sensing device in the direction of arrow 103 in order to adjust the level at which the needle enters the epidural space 100. In some embodiments, the user does not need to tilt the tactile sensing device in order to adjust the level at which the needle enters the epidural space 100.

Furthermore, FIG. 13 shows a display screen offset 101. In some embodiments, the display screen (not shown in FIG. 13) is raised at a display screen offset 101 from the posterior surface of the tactile sensing device 1900. In some embodiments, the display screen is raised at a display screen offset 101 from the posterior face of the sensor array. In some embodiments, the display screen is raised at a display screen offset 101 from the skin surface of the patient when pressing the tactile sensing device against the patient.

In some embodiments, the display screen offset 101 is about 17 mm. In some embodiments, the display screen offset 101 is about 5 mm. In some embodiments, the display screen offset 101 is about 10 mm. In some embodiments, the display screen offset 101 is about 11 mm. In some embodiments, the display screen offset 101 is about 12 mm. In some embodiments, the display screen offset 101 is about 13 mm. In some embodiments, the display screen offset 101 is about 14 mm. In some embodiments, the display screen offset 101 is about 15 mm. In some embodiments, the display screen offset 101 is about 16 mm. In some embodiments, the display screen offset 101 is about 18 mm. In some embodiments, the display screen offset 101 is about 19 mm. In some embodiments, the display screen offset 101 is about 20 mm. In some embodiments, the display screen offset 19101 is about 25 mm. In some embodiments, the display screen offset 101 is about 30 mm. In some embodiments, the display screen offset 101 is about 35 mm. In some embodiments, the display screen offset 101 is about 40 mm. In some embodiments, the display screen offset 101 is about 45 mm. In some embodiments, the display screen offset 101 is about 50 mm.

In some embodiments, the display screen offset 101 is at least about 1 mm to about 5 mm at most. In some embodiments, the display screen offset 101 is at least about 5 mm to about 10 mm at most. In some embodiments, the display screen offset 101 is at least about 10 mm to about 15 mm at most. In some embodiments, the display screen offset 101 is at least about 15 mm to about 20 mm at most. In some embodiments, the display screen offset 101 is at least about 20 mm to about 25 mm at most. In some embodiments, the display screen offset 101 is at least about 25 mm to about 30 mm at most. In some embodiments, the display screen offset 101 is at least about 30 mm to about 35 mm at most. In some embodiments, the display screen offset 101 is at least about 35 mm to about 40 mm at most. In some embodiments, the display screen offset 101 is at least about 40 mm to about 45 mm at most. In some embodiments, the display screen offset 101 is at least about 45 mm to about 50 mm at most. In some embodiments, the display screen offset 101 is at least about 50 mm to about 55 mm at most. In some embodiments, the display screen offset 101 is at least about 55 mm to about 60 mm at most. In some embodiments, the display screen offset 101 is at least about 1 mm to about 100 mm or more.

In some embodiments, the display screen is at a display screen angle 99 with respect to the display screen offset 101. In some embodiments, the display screen rotates relative to the sensor array around a hinge to adjust the display screen angle 99. In some embodiments, the display screen rotates relative to the sensor unit around a hinge to adjust the display screen angle 99. In some embodiments, the display screen is pivotally mounted to the tactile sensing device via hinges (not shown in FIG. 13). In some embodiments, the display screen angle 99 is manually adjusted by moving the display screen around a hinge (not shown).

In some embodiments, the display screen is fixed to a rotary shaft that is further connected to the sensor array (not shown in FIG. 13). In some embodiments, the display screen is fixed to a rotary shaft that is further connected to the sensor unit. In some embodiments, the display screen rotates freely and multidirectionally relative to the sensor array. In some embodiments, the display screen rotates freely and multidirectionally relative to the sensor unit. In some embodiments, the display screen rotates bidirectionally relative to the sensor array. In some embodiments, the display screen rotates bidirectionally relative to the sensor unit. In some embodiments, the display screen rotates clockwise or counterclockwise relative to the sensor array. In some embodiments, the display screen rotates clockwise or counterclockwise relative to the sensor unit.

In some embodiments, the display screen angle 99 is about 90 degrees. In some embodiments, the display screen angle 99 is about 100 degrees. In some embodiments, the display screen angle 99 is about 110 degrees. In some embodiments, the display screen angle 99 is about 120 degrees. In some embodiments, the display screen angle 99 is about 130 degrees. In some embodiments, the display screen angle 99 is about 135 degrees. In some embodiments, the display screen angle 99 is about 140 degrees. In some embodiments, the display screen angle 99 is about 80 degrees. In some embodiments, the display screen angle 99 is about 70 degrees. In some embodiments, the display screen angle 99 is about 60 degrees. In some embodiments, the display screen angle 99 is about 50 degrees. In some embodiments, the display screen angle 99 is about 45 degrees. In some embodiments, the display screen angle 99 is at least about 45 degrees to about 140 degrees or more. In some embodiments, the display screen angle 99 is at least about 45 degrees to about 90 degrees at most. In some embodiments, the display screen angle 99 is at least about 90 degrees to about 140 degrees at most.

In some embodiments, the sensor array (not shown in FIG. 13) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIG. 13), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIG. 13) is an array of cells. In some embodiments, the sensor array (not shown in FIG. 13) is an array of sensing cells. In some embodiments, the sensor array slit (not shown in FIG. 13) is positioned between two rows or more of sensels. In some embodiments, the sensor array slit (not shown in FIG. 13) is positioned between two columns or more of sensels. In some embodiments, the sensor array slit (not shown in FIG. 13) is within the bounds of the sensor array, and/or within the bounds of the sensor array outer edges, and/or within the edges bounding of the sensor array. In some embodiments, the sensor array does not comprise a slit. In some embodiments, the distal opening (not shown in FIG. 13) of the needle guide (not shown in FIG. 13) is positioned between two rows of sensels. In some embodiments, the distal opening (not shown in FIG. 13) of the needle guide (not shown in FIG. 13) is positioned between two columns of sensels. In some embodiments the distal opening (not shown in FIG. 13) of the needle guide (not shown in FIG. 13) is within the bounds of the sensor array, and/or within the bounds of the sensor array outer edges, and/or within the edges bounding of the sensor array. In some embodiments, the distal opening (not shown in FIG. 13) is between two or more sensors of the sensor array. In some embodiments, the distal opening (not shown in FIG. 13) is positioned between two rows or more of sensels. In some embodiments, the distal opening (not shown in FIG. 13) is positioned between two columns or more of sensels.

Figure 14:
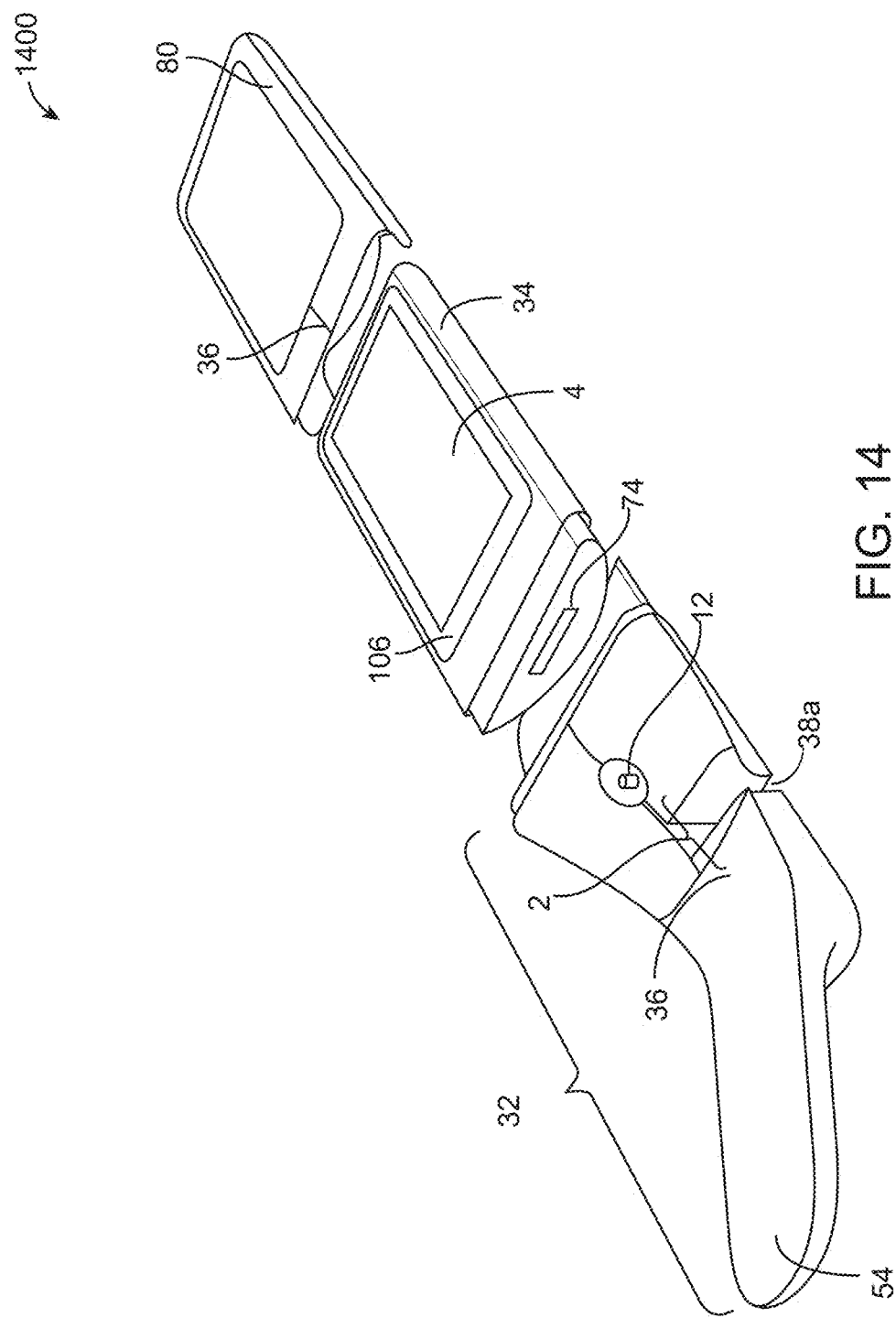
FIG. 14 shows an exploded view of an embodiment tactile sensing device 1400.

FIG. 14 shows the assembly of the various elements of the tactile sensing device 1400. In some embodiments, the tactile sensing device 1400 comprises a sleeve 80 that is slipped onto the electronic unit 34. In some embodiments, the electronic unit 34 comprises a display screen 4, a graphic overlay 106, and an electronic unit connector 74. In some embodiments, the electronic unit 34 is inserted into a sensor unit 32 comprising a sensor unit port (not shown in FIG. 14). In some embodiments, the sensor unit 32 comprises a needle guide 2, a pressure sensor connector 12, a slot opening 38a, a needle alignment guide 36, and a handle 54. In some embodiments, the handle 54 comprises a grip feature 76 to enhance grip. In some embodiments, the grip feature 76 is an indentation in the underside of the handle 54.

In some embodiments, the sensor array (not shown in FIG. 14) is an array of sensor elements also known as "sensels." In some embodiments, the sensels are not discrete sensors. In some embodiments, the sensor elements or sensels are configured to connect to each other. In some embodiments, the sensor elements are arranged in a grid (not shown in FIG. 14), with each sensor element (or "sensel") located at the intersection of a row and column. In some embodiments, the rows and columns are pinned out, rather than individual sensors being pinned out, as is the case with an array of discrete sensors. In some embodiments, the sensor array (not shown in FIG. 14) is an array of cells. In some embodiments, the sensor array (not shown in FIG. 14) is an array of sensing cells. In some embodiments, the sensor array slit (not shown in FIG. 14) is positioned between two rows or more of sensels. In some embodiments, the sensor array slit (not shown in FIG. 14) is positioned between two columns or more of sensels. In some embodiments, the sensor array slit (not shown in FIG. 14) is within the bounds of the sensor array, and/or within the bounds of the sensor array outer edges, and/or within the edges bounding of the sensor array. In some embodiments, the sensor array does not comprise a slit. In some embodiments, the distal opening (not shown in FIG. 14) of the needle guide 2 is positioned between two rows or more of sensels. In some embodiments, the distal opening (not shown in FIG. 14) of the needle 2 is positioned between two columns of sensels. In some embodiments the distal opening (not shown in FIG. 20) of the needle guide 2 is within the bounds of the sensor array, and/or within the bounds of the sensor array outer edges, and/or within the edges bounding of the sensor array. In some embodiments, the distal opening (not shown in FIG. 14) is between two or more sensors of the sensor array. In some embodiments, the distal opening (not shown in FIG. 14) is positioned between two rows or more of sensels. In some embodiments, the distal opening (not shown in FIG. 14) is positioned between two columns or more of sensels.

Figure 15:
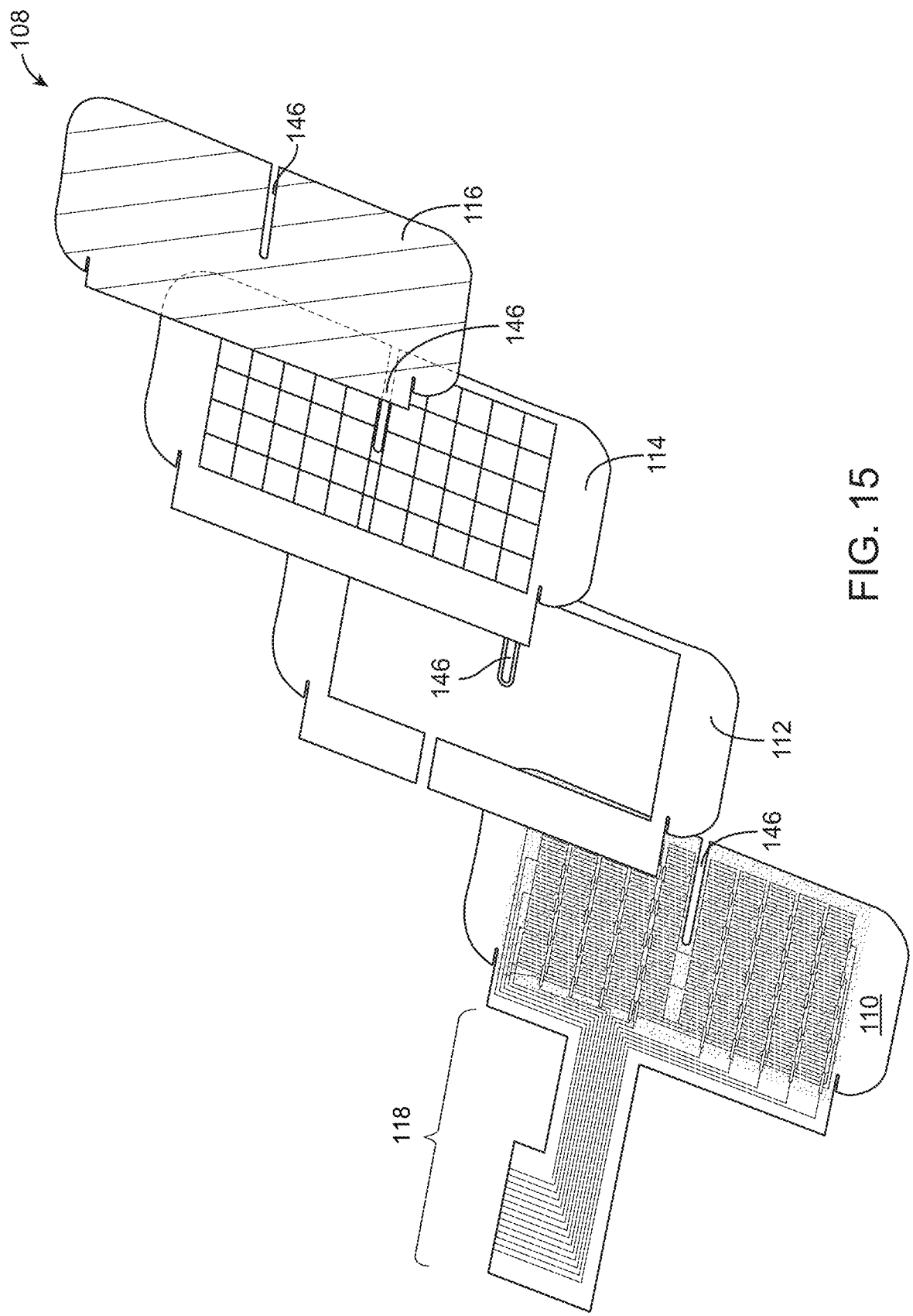
FIG. 15 shows an exploded view of the screen-printed force-sensitive resistor (FSR) array 108.

FIG. 15 shows an exploded view of the sensor array. In some embodiments, the sensor array comprises an elastomer on the patient-facing side to improve force output and/or tissue displacement. In some embodiments, the sensor array is a screen-printed force-sensitive resistor (FSR) array 108. In some embodiments, the screen-printed force-sensitive resistor (FSR) array 108 comprises a lower circuit 110, a spacer 112, an FSR layer 114, and an adhesive 116. In some embodiments, the screen-printed force-sensitive resistor (FSR) array 108 is constructed by first placing the spacer 112 directly over the lower circuit 110, then placing the FSR layer 114 directly over the spacer 112, and finally placing the adhesive 116 directly over the FSR layer 114. In some embodiments, the screen-printed force-sensitive resistor (FSR) array 108 is adhered to the posterior surface of the tactile sensing device by using the adhesive 116. In some embodiments, the screen-printed force-sensitive resistor (FSR) array 108 comprises a sensor array slit 146. In some embodiments, the screen-printed force-sensitive resistor (FSR) array 108 does not comprise a sensor array slit 146. In some embodiments, the sensor array slit 146 is directly aligned with slot featured in some of the embodiments, presented herein (e.g. slot opening 38a in FIG. 14). In some embodiments, the sensor array slit 146 matches the posterior surface design and shape of the tactile sensing device.

In some embodiments, the sensor array slit 146 is positioned between two rows or more of sensels. In some embodiments, the sensor array slit 146 is positioned between two columns or more of sensels. In some embodiments, the sensor array slit 146 is within the bounds of the sensor array, and/or within the bounds of the sensor array outer edges, and/or within the edges bounding of the sensor array. In some embodiments, the distal opening (not shown in FIG. 15) of the needle guide (not shown in FIG. 15) is positioned between two rows of sensels. In some embodiments, the distal opening (not shown in FIG. 15) of the needle (not shown in FIG. 15) is positioned between two columns of sensels. In some embodiments the distal opening (not shown in FIG. 15) of the needle guide (not shown in FIG. 15) is within the bounds of the sensor array, and/or within the bounds of the sensor array outer edges, and/or within the edges bounding of the sensor array. In some embodiments, the distal opening (not shown in FIG. 15) is between two or more sensors of the sensor array. In some embodiments, the distal opening (not shown in FIG. 15) is positioned between two rows or more of sensels. In some embodiments, the distal opening (not shown in FIG. 15) is positioned between two columns or more of sensels.

Figure 16:
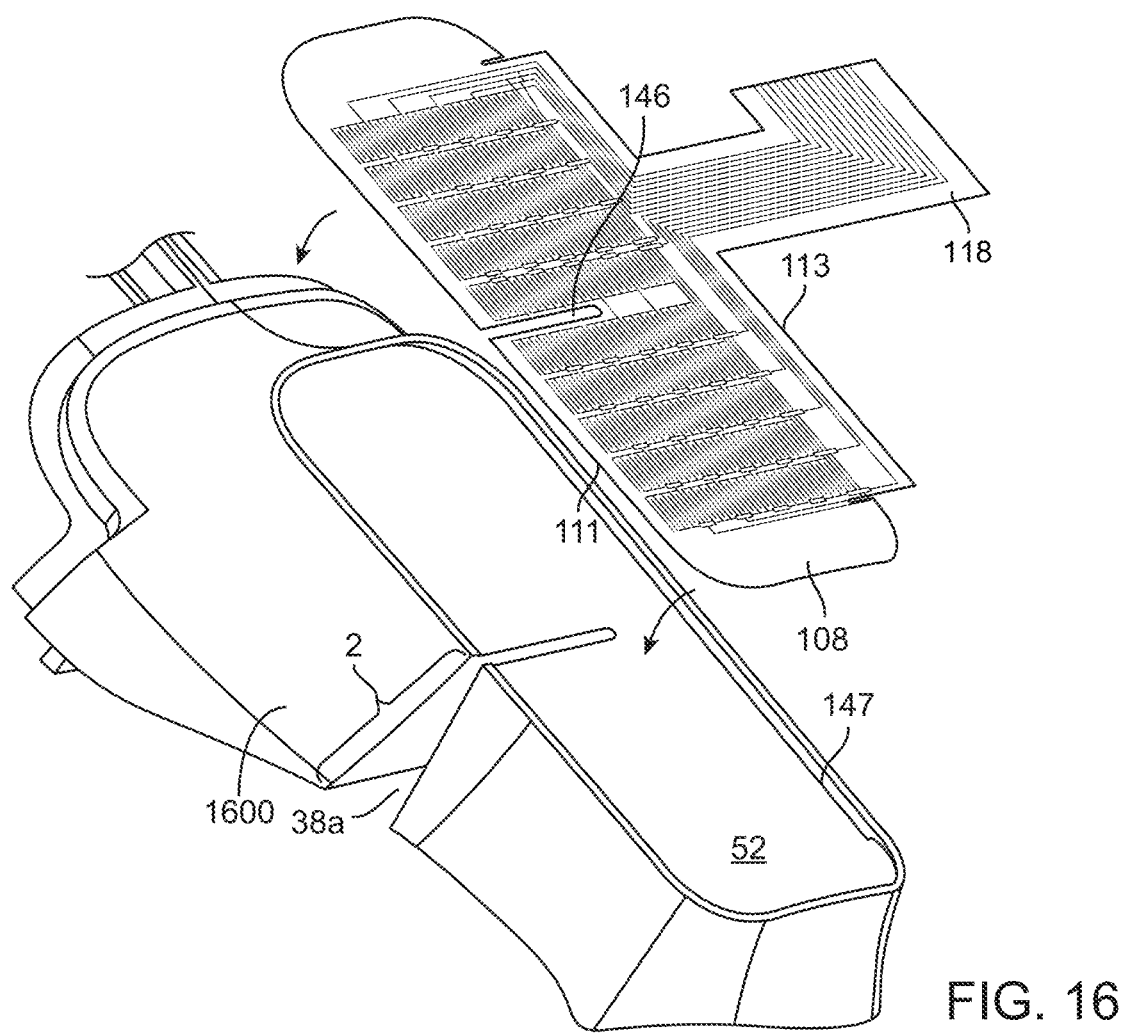
FIG. 16 shows a perspective view of a screen-printed force-sensitive resistor (FSR) array 108 being adhered onto the tactile sensing device 1600.

FIG. 16 shows how the screen-printed force-sensitive resistor (FSR) array 108 is adhered onto the posterior surface of the tactile sensing device 2200. In some embodiments, the screen-printed force-sensitive resistor (FSR) array 108 is adhered onto the sensor attachment area 52. As seen in FIG. 16, the sensor array slit 146 is the same shape and size as the slot 38 of the device, which enables the user to slide the needle through the slot 38 without any obstructions. In some embodiments, the screen-printed force-sensitive resistor (FSR) array 108 comprises a conductive adhesive 118 configured to operatively couple the screen-printed force-sensitive resistor (FSR) array 108 with a printed circuit board (not shown in FIG. 16). In dome embodiments, the screen-printed force-sensitive resistor (FSR) array 108 comprises a connector configured to operatively couple the array 108 with the printed circuit board, such as a zero insertion force electrical connector. In some embodiments, the part of the screen-printed force-sensitive resistor (FSR) array 108 comprising (i.e., the part resembles a tab in FIG. 16) a conductive adhesive 118 is folded into a sensor array slot 147 of the tactile sensing device. In some embodiments, the sensor array slot 147 is slot located along a lateral edge of the bottom surface of the tactile sensing device, as shown in FIG. 16. In some embodiments, the sensor array slot 147 is located along any edge of the bottom surface of the tactile sensing device. In some embodiments, the sensor array slot 147 is a slot that is configured to receive the conductive adhesive 118. In some embodiments, the conductive adhesive 118 is inserted into the sensor array slot 147 in order to operatively connect the FSR array to one or more electronic components of the tactile sensing device. Also shown in FIG. 16, is a posterior face 109 of the sensor array 108. In some embodiments, the posterior face 109 comes in contact with the skin surface of a patient. In some embodiments, the posterior face 109 is located on the posterior surface of the tactile sensing device 2200. In some embodiments, a tail of the sensor array will terminate with a connector, which will further be assembled with an intermediary PCBA in disposable versions of the device described herein (requiring some sort of connector, e.g. a zero insertion force connector, or a Z-axis adhesive). In some embodiments, the intermediary PCBA will comprise a durable connector, that facilitates connection with the reusable portion of the device (e.g. via a card-edge connector).

In some embodiments, the sensor array slit 146 is positioned between two rows or more of sensels. In some embodiments, the sensor array slit 146 is positioned between two columns or more of sensels. In some embodiments, the sensor array slit 146 is within the bounds of the sensor array, and/or within the bounds of the sensor array outer edges, and/or within the edges bounding of the sensor array. In some embodiments, the distal opening (not shown in FIG. 16) of the needle guide (not shown in FIG. 16) is positioned between two rows of sensels. In some embodiments, the distal opening (not shown in FIG. 16) of the needle (not shown in FIG. 16) is positioned between two columns of sensels. In some embodiments the distal opening (not shown in FIG. 16) of the needle guide (not shown in FIG. 16) is within the bounds of the sensor array, and/or within the bounds of the sensor array outer edges, and/or within the edges bounding of the sensor array. In some embodiments, the distal opening (not shown in FIG. 16) is between two or more sensors of the sensor array. In some embodiments, the distal opening (not shown in FIG. 16) is positioned between two rows or more of sensels. In some embodiments, the distal opening (not shown in FIG. 16) is positioned between two columns or more of sensels.

In some embodiments, the sensor array is a tactile sensor array. In some embodiments, the sensor array is an ultrasound sensor array. In some embodiments, the sensor array is an infrared radiation (IR) sensor array. Sensor array is a sensor array cartridge that is pressed into a sensor array holder. In some embodiments, the sensor array turns on once it is loaded into the sensor array holder.

The sensors in the sensor array generate output voltage signals when the user applies a force using the tactile sensing device onto a surface, for example, onto a tissue of a patient. The sensor array is operatively connected to the display screen and a computing device (not shown in in the figures). The sensor array relays its output voltage signals to the computing device (not shown in FIGS. 1A and 1B), the computing device processes the output voltage signals, and an image of the output voltage signals is visualized on the display screen.

In some embodiments, a method of using a tactile sensing device to obtain an image comprises a first step comprising pressing the tactile sensing device against an area that is to be imaged and pressing or applying force to the sensor array of the tactile sensing device. In some embodiments, in second a step, a computing device is provided, and the computing device is operatively connected to the tactile sensing device. In some embodiments, the computing device is operatively connected to the display screen, the sensor array, and optionally connected to a pressure sensor. In some embodiments, the computing device collects voltage signals that are generated by the sensor array of the tactile sensing device after a force is applied onto the surface of the sensors in the sensor array. In a third step, the computing device processes the collected voltage signals such that the voltage signals are converted into an image. In fourth step, the image is displayed on a display screen of the tactile sensing device. In some embodiments, the image displayed is a heat map. In some embodiments, the image displayed provides the user feedback regarding the uniformity of their application of force to the tactile sensing device. In some embodiments, the image displayed includes the approximate position of a needle at the skin surface as well as the approximate depth of a needle. In some embodiments, the pressure map is a three-dimensional display of a target tissue location (e.g. vertebral features). In some embodiments, the three-dimensional display entails acquiring, registering, and visualizing pressure data at varying depths. In some embodiments, the three-dimensional display is achieved with an actuated system. In some embodiments, the depth detection algorithm facilitates a collection of depth (i.e. z-axis) layers, resulting in a three-dimensional display.

Computer Control Systems

Figure 17:
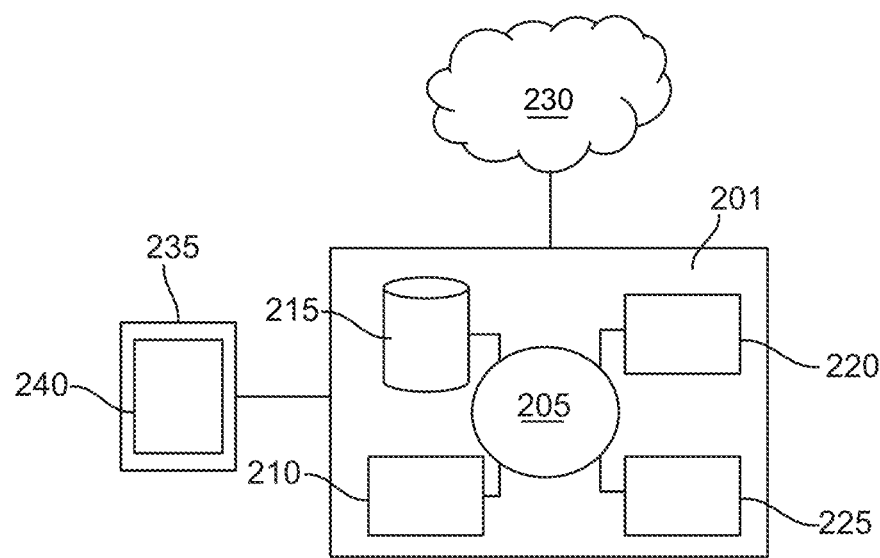
FIG. 17 shows a computer control system that is programmed or otherwise configured to implement methods provided herein.

The present disclosure provides computer control systems that are programmed to implement methods of the disclosure. FIG. 17 shows a computer system 201 that is programmed or otherwise configured to output a signal in response to a change in pressure applied to its surface; wherein the signal is converted to a pressure map. In some embodiments, the computer system 201 regulates various aspects of the tactile sensing device of the present disclosure, such as, for example, calculate a projected subcutaneous needle location, display the projected subcutaneous location of a needle in real time, display the original insertion site of the needle (i.e., original needle location) in real time, and output a pressure map corresponding to the output signals transmitted by the sensor array also in real time. In some embodiments, the computer system 201 is an electronic device of a user or a computer system that is remotely located with respect to the electronic device. In some embodiments, the electronic device is a mobile electronic device. In some embodiments, the electronic device is located within the tactile sensing device.

The computer system 201 includes a central processing unit (CPU, also "processor" and "computer processor" herein) 205. In some embodiments, the CPU20 205 is a single core or multi core processor. In some embodiments, the computer system 201 includes a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. In some embodiments, the memory 210, storage unit 215, interface 220 and peripheral devices 225 are in communication with the CPU 205 through a communication bus (solid lines), such as a motherboard. In some embodiments, the storage unit 215 is a data storage unit (or data repository) for storing data. In some embodiments, the computer system 201 is operatively coupled to a computer network ("network") 230 with the aid of the communication interface 220. In some embodiments, the network 230 is the Internet, an internet and/or extranet, or an intranet and/or extranet that is in communication with the Internet. In some embodiments, the network 230 in some cases is a telecommunication and/or data network. In some embodiments, the network 230 includes one or more computer servers, which enable distributed computing, such as cloud computing. In some embodiments, the network 230, in some cases with the aid of the computer system 201, implements a peer-to-peer network, which enables devices coupled to the computer system 201 to behave as a client or a server.

In some embodiments, the CPU 205 executes a sequence of machine-readable instructions, which are embodied in a program or software. In some embodiments, the instructions may be stored in a memory location, such as the memory 210. In some embodiments, the instructions are directed to the CPU 205, which subsequently program or otherwise configure the CPU 205 to implement methods of the present disclosure. Examples of operations performed by the CPU 205 include fetch, decode, execute, and writeback.

In some embodiments, the CPU 205 is part of a circuit, such as an integrated circuit. In some embodiments, one or more other components of the system 201 are included in the circuit. In some cases, the circuit is an application specific integrated circuit (ASIC).

In some embodiments, the storage unit 215 stores files, such as drivers, libraries and saved programs. In some embodiments, the storage unit 205 stores user data, e.g., user preferences and user programs. In some embodiments, the computer system 201 in some cases includes one or more additional data storage units that are external to the computer system 201, such as located on a remote server that is in communication with the computer system 201 through an intranet or the Internet.

In some embodiments, the computer system 201 communicates with one or more remote computer systems through the network 230. For instance, the computer system 201 communicates with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. In some embodiments, the user accesses the computer system 201 via the network 230.

Methods as described herein are implemented by way of machine (e.g., computer processor) executable code stored on an electronic storage location of the computer system 1, such as, for example, on the memory 210 or electronic storage unit 215. In some embodiments, the machine executable or machine-readable code is provided in the form of software. In some embodiments, during use, the code is executed by the processor 5. In some cases, the code is retrieved from the storage unit 215 and stored on the memory 210 for ready access by the processor 5. In some situations, the electronic storage unit 215 is precluded, and machine-executable instructions are stored on memory 210.

In some embodiments, the code is pre-compiled and configured for use with a machine having a processor adapted to execute the code, or is compiled during runtime. In some embodiments, the code is supplied in a programming language that is selected to enable the code to execute in a pre-compiled or as-compiled fashion.

Aspects of the systems and methods provided herein, such as the computer system 1, are embodied in programming. In some embodiments, various aspects of the technology are thought of as "products" or "articles of manufacture" typically in the form of machine (or processor) executable code and/or associated data that is carried on or embodied in a type of machine-readable medium. In some embodiments, the machine-executable code is stored on an electronic storage unit, such as memory (e.g., read-only memory, random-access memory, flash memory) or a hard disk. In some embodiments, "storage" type media includes any or all of the tangible memory of the computers, processors or the like, or associated modules thereof, such as various semiconductor memories, tape drives, disk drives and the like, which provide non-transitory storage at any time for the software programming. In some embodiments, the entirety of the software or portions of the software, at times, is communicated through the Internet or various other telecommunication networks. Such communications, for example, enable loading of the software from one computer or processor into the other, for example, from a management server or host computer into the computer platform of an application server. Thus, another type of media that bears the software elements includes optical, electrical and electromagnetic waves, such as used across physical interfaces between local devices, through wired and optical landline networks and over various air-links. In some embodiments, the physical elements that carry such waves, such as wired or wireless links, optical links or the like, also are considered as media bearing the software. As used herein, unless restricted to non-transitory, tangible "storage" media, terms such as computer or machine "readable medium" refer to any medium that participates in providing instructions to a processor for execution.

Hence, in some embodiments, a machine-readable medium, such as computer-executable code, takes many forms, including but not limited to, a tangible storage medium, a carrier wave medium or physical transmission medium. Non-volatile storage media include, for example, optical or magnetic disks, such as any of the storage devices in any computer(s) or the like, such as are used to implement the databases, etc. shown in the drawings. In some embodiments, volatile storage media include dynamic memory, such as main memory of such a computer platform. In some embodiments, tangible transmission media include coaxial cables; copper wire and fiber optics, including the wires that comprise a bus within a computer system. In some embodiments, carrier-wave transmission media takes the form of electric or electromagnetic signals, or acoustic or light waves such as those generated during radio frequency (RF) and infrared (IR) data communications. In some embodiments, common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. In some embodiments, many of these forms of computer readable media are involved in carrying one or more sequences of one or more instructions to a processor for execution.

The computer system 1 includes or is in communication with an electronic display 235 that comprises a user interface (UI) 1 (alternatively called a user interface (UI) module elsewhere herein) for providing, for example, a real time pressure map, a real time fluid pressure reading, a real time location of a needle once it is inserted into an individual, and a projected subcutaneous location of a needle prior to insertion. Examples of UI's include, without limitation, a graphical user interface (GUI) and web-based user interface.

Methods and systems of the present disclosure are implemented by way of one or more algorithms. In some embodiments, an algorithm is implemented by way of software upon execution by the central processing unit 205. In some embodiments, the algorithm, for example, calculates a real time projected subcutaneous needle location prior to insertion, acquires a plurality of voltage signals, and converts them into a pressure sensor array.

In some embodiments, a sensor array comprising at least one sensor is configured to output a signal in response to a change in pressure applied to its surface; wherein the signal is converted to a pressure map. In a first step, the output voltage signals generated by the force-sensitive resistors via a voltage divider are inputted into the computing device via a multiplexer. In a second step, the inputted voltage signals are written to a serial monitor. In some embodiments, the second step further comprises organizing the inputted voltage signals. In some embodiments, a first computer program that includes instructions executable by a processor performs the second step. In some embodiments, the instructions to perform the second step, which are included in the computer program, are written in Arduino programming language. In third step, a second computer program includes instructions to acquire the inputted voltage signals that were written to the serial monitor and generates an array of sensor data. In some embodiments, the instructions to perform the third step, which are included in the second computer program, are executable by a processor. In a fourth step, a second computer program includes instructions to process the inputted voltage signals that were written to the serial monitor and rescales the previously generated array of sensor data to a second array of sensor data. In some embodiments, the instructions to perform the fourth step use cubic interpolation methods to rescale the array of sensor data. In some embodiments, the instructions to perform the fourth step, which are included in the second computer program, are executable by a processor. In a fifth step, a second computer program includes instructions to update the display for real-time target tissue visualization. In some embodiments, the instructions to perform the third, fourth, and fifth steps, which are included in the second computer program are written in Python programming language. In some embodiments, the display is updated for real-time visualization of a patient's spine. In some embodiments, these five steps comprise the process of transforming a sensor output into a visual display. In some embodiments, the visual display is a pressure map.

Computing Device

In some embodiments, the tactile sensing device further comprises a computing device. In some embodiments, the computing device is a microcontroller. In some embodiments, the microcontroller is an 8-bit, 16-bit, or 32-bit microcontroller. In some embodiments, the microcontroller is an 8051 microcontroller, a programmable interface controller (PIC), an AVR or Advanced Virtual RISC microcontroller, or an ARM® microcontroller. In some embodiments, the microcontroller is, by way of non-limiting examples, an Arduino Uno microcontroller or a Raspberry Pi microcontroller.

In some embodiments, the computing device is a microprocessor. In some embodiments, the microprocessor is manufactured by AMD®, Intel®, or ARM®. In some embodiments, the AMD® microprocessors include, but are not limited to: AMD Sempron™, AMD Turion II™ AMD Athlon II™, AMD Sempron™, AMD Phenom II™, AMD A-Series, or AMD FX™. In some embodiments, the Intel® microprocessors include, but are not limited to: Intel Atom™, Intel Celeron™, Intel Pentium™, Intel Core i3™, Intel Core i5™, or Intel Core i7™. In some embodiments, the ARM® microprocessors include, but are not limited to: ARM OMAP 3, ARM MAP 4, ARM OMAP 5, ARM SnapDragon S2, ARM SnapDragon S, ARM SnapDragon S4, ARM Tegra, ARM Tegra 2, ARM Tegra 3, ARM Exynos 3 Single, ARM Exynos 4 Dual, ARM Exynos 4 Quad, ARM Exynos 5 Dual, ARM A4, ARM A5, or ARM A5X.

In some embodiments, the computing device further comprises a memory device. In some embodiments, the processing device includes a memory device. A memory device is one or more physical apparatus used to store data or programs on a temporary basis, a permanent basis, or combinations thereof. In some embodiments, a memory device is volatile and requires power to maintain stored information. In some embodiments, a memory device is non-volatile and retains stored information and does not require power to maintain stored information.

In some embodiments, the computing device further comprises a non-transitory computer readable storage medium with a computer program including instructions executable by the processor causing the processor to convert the voltage signals into an image. In some embodiments, the computer program includes instructions executable by the processor that cause the processor to encode the voltage signals into a first and second computer signals.

In some embodiments, the computer program includes instructions executable by the processor that cause the processor to calculate a projected needle position (i.e. location) and display it on the display screen. In some embodiments, the computer program includes instructions executable by the processor that cause the processor to calculate a projected needle position (i.e. location) for any potential needle guide when using a tactile sensing device 200 comprising a needle guide cartridge 12, as shown in FIGS. 2A and 2B. In some embodiments, a needle projection calculation is a trigonometric algorithm. In some embodiments, the trigonometric algorithm determines the depth of the needle once it traverses subcutaneous adipose tissue. In some embodiments, the needle projection calculation is adjusted based on amount of subcutaneous adipose tissue.

In some embodiments, the computer program includes instructions executable by the processor causing the processor to: determine, as a first requirement, a location of a bone detected by the tactile sensing device; ii) determine, as a second requirement, the space between said bone structures; and iii) perform predictive analysis based on application of machine-learning. In some embodiments, the predictive analysis performed by the processor enhances the accuracy of a needle projection calculation. In some embodiments, the predictive analysis performed by the processor locates a desired bone and non-bone structure. In some embodiments, the predictive analysis performed by the processor locates a gap between bone and non-bone structures. In some embodiments, the predictive analysis performed by the processor suggests a needle insertion location to the user based on the voltage signals detected by the tactile sensing device. In some embodiments, the predictive analysis performed by the processor comprises midline alignment (e.g. determining rotation of detected peaks about the device's midline, thereby alerting user to align the device).

The computer program is, for example, software, including computer algorithms, computer codes, programs, and data, which manages the device's hardware and provides services for execution of instructions. Suitable computer program languages include, by way of non-limiting examples, C, C++, C#, Objective C, Perl, Scala, Haskell, Go, Arduino C, Python, Java, SQL, JavaScript, PHP, iOS Swift, or Ruby.

In some embodiments, the computing device is a desktop computer or a laptop computer. In some embodiments, the computing device is a mobile device. In some embodiments, the mobile device is a smart phone or a smart watch. In some embodiments, the computing device is a portable device. In accordance with the description herein, suitable computing devices further include, by way of non-limiting examples, notebook computers, tablet computers, netbook computers, smart book computers, subnotebook computers, ultra-mobile PCs, handheld computers, personal digital assistants, Internet appliances, smart phones, music players, and portable video game systems. Many mobile smart phones are suitable for use in the systems described herein. Suitable tablet computers include those with booklet, slate, and convertible configurations. Suitable portable video game systems include, by way of non-limiting examples, Nintendo DS™ and Sony PSP™

Signal Transmitter and Receiver

In some embodiments, the processor encodes the voltage signals into a first and second computer signals. In some embodiments, the tactile sensing device comprises a signal transmitter. In some embodiments, the tactile sensing device comprises a signal receiver. In some embodiments, a transmitter is configured to transmit the first computer signal to a computing device. In some embodiments, a receiver is configured to receive the second computer signal from a tactile sensing device. In some embodiments, the first and second computer signals are transmitted via a USB (Universal Serial Bus) cable. In some embodiments, the first and second computer signals are wireless signals.

In some embodiments, the signal receiver is a wireless element. In some embodiments, the signal transmitter is a wireless element. In some embodiments, the wireless element is configured to receive a signal from a computing device, for example, a mobile device. In some embodiments, the signal receiver is a wireless element which is configured to receive a signal from the tactile sensing device. In some embodiments, the wireless element is a wireless network technology. In some embodiments, the wireless network technology is ANT, ANT+, INSTEON, IrDA, Wireless USB, Bluetooth, Z-Wave, or ZigBee, IEEE 802.15.4, 6LoWPAN, or Wi-Fi.

Marking Tools

In some embodiments, the tactile sensing device further comprises a marking tool. The marking tool helps the user identify the tissue target location. In some embodiments, the marking tool enables the user to mark the entry point of a needle on the skin surface of the patient. In some embodiments, the marking tool enables the user to mark or label a tissue target location. In some embodiments, marking or labeling the tissue target location is done subcutaneously, intramuscularly, or on the skin surface. In some embodiments, the marked tissue location is detected by a medical imaging device. In some embodiments, the marking tool enables the user to mark or label a target tissue location in order to be identified by a medical imaging device or system. In some embodiments, the target tissue location is marked by indenting the skin over the target tissue location. In some embodiments, the skin over the target tissue location is indented using the posterior surface of the tactile sensing device. In some embodiments, the skin over the target tissue location is indented using a mechanism attached to the tactile sensing device. In some embodiments, the mechanism attached to the tactile sensing device is an indenting tool. In some embodiments, the skin over the target tissue location is indented by placing an indenting tool through the needle guide. In some embodiments, the marking tool is a light, an ink, a hydrogel, a nanoparticle. In some embodiments, the light is a laser light or a light emitting diode (LED). In some embodiments, the ink is a permanent ink, a gentian violent ink, a water-based ink, an oil-based in, a liquid ink, or a gel ink. In some embodiments, the hydrogel further comprises a contrast agent. In some embodiments, the nanoparticle further comprises a contrast agent. In some embodiments, the contrast agent includes, but is not limited to: a magnetic contrast agent, a radiocontrast agent, a radioactive contrast agent, a magnetic resonance imaging contrast agent, and a microbubble contrast agent. Non-limiting examples of the magnetic contrast agent include: gadolinium-based agents or nanoparticles, iron oxide-based agents or nanoparticles, iron platinum-based agents or nanoparticles, and manganese-based agents or nanoparticles. Non-limiting examples of the radiocontrast agent include: iodine-based agents or nanoparticles, air, thorium dioxide, carbon dioxide, gastrografin, and barium-based agents or nanoparticles. Non-limiting examples of the radioactive contrast agent include: $^{64}Cu$ diacetyl-bis($N^4$-methylthiosemicarbazone), also called ATSM or Copper 64, $^{18}F$-fluorodeoxyglucose (FDG), $^{18}F$-fluoride, 3'-deoxy-3'fluorothymidine (FLT), $^{18}F$-fluoromisonidazole, gallium, techtenium-99m, and thallium.

Rocker Tactile Sensing Device

In some embodiments, the tactile sensing device is a rocker tactile sensing device 1800, as shown in embodiments shown in FIGS. 18A-C, 19A-C, and 20A-E, alternatively referred to herein as embodiment tactile sensing devices having rocker designs. In such embodiments, the tactile sensing devices include aspects and functionality described elsewhere herein, with the substitution of a curved sensor applicator in place of a flat-faced sensor array, and including historical and real time visualization as described herein. In some embodiments, the rocker tactile sensing device comprises a main housing frame 19. In some embodiments, the main housing frame 19 comprises a needle alignment guide 36. In some embodiments, the needle alignment guide 36 is an indicator for the midline of the device to facilitate alignment with the spine. In some embodiments, the needle alignment guide 36 is a colored line. In some embodiments, the needle alignment guide 36 is a colored notch. In some embodiments, the main housing frame 19 is reusable. In some embodiments, the main housing frame 19 is disposable. In some embodiments, the main housing frame 19 is made of medical-grade, injection-molded plastic. In some embodiments, the main housing frame 19 is comprised of two parts.

Figure 18A:
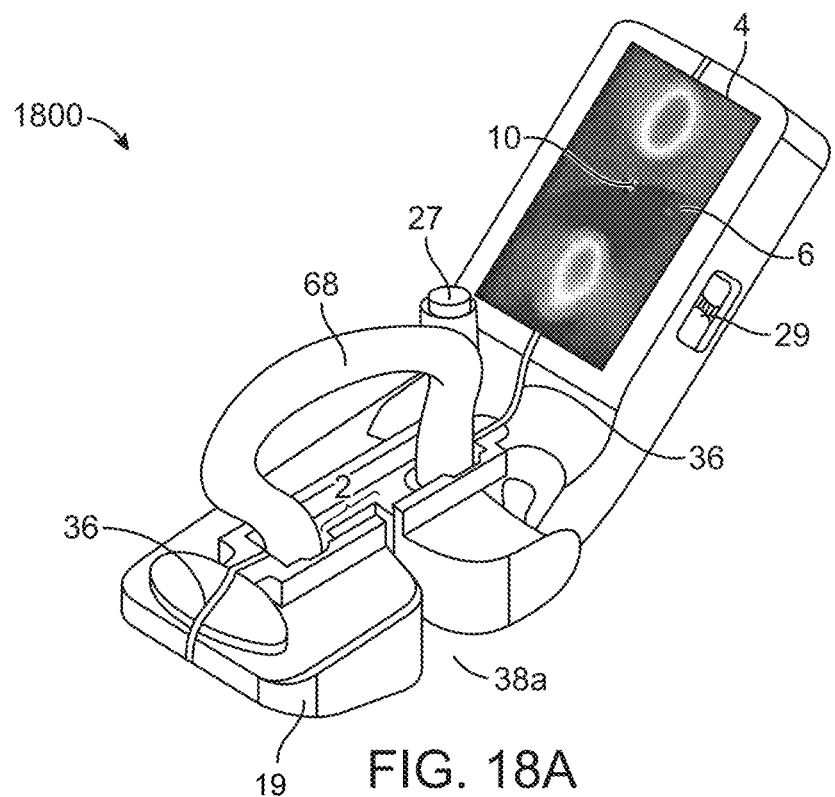
FIGS. 18A-C show an embodiment rocker tactile sensing device.
Figure 18B:
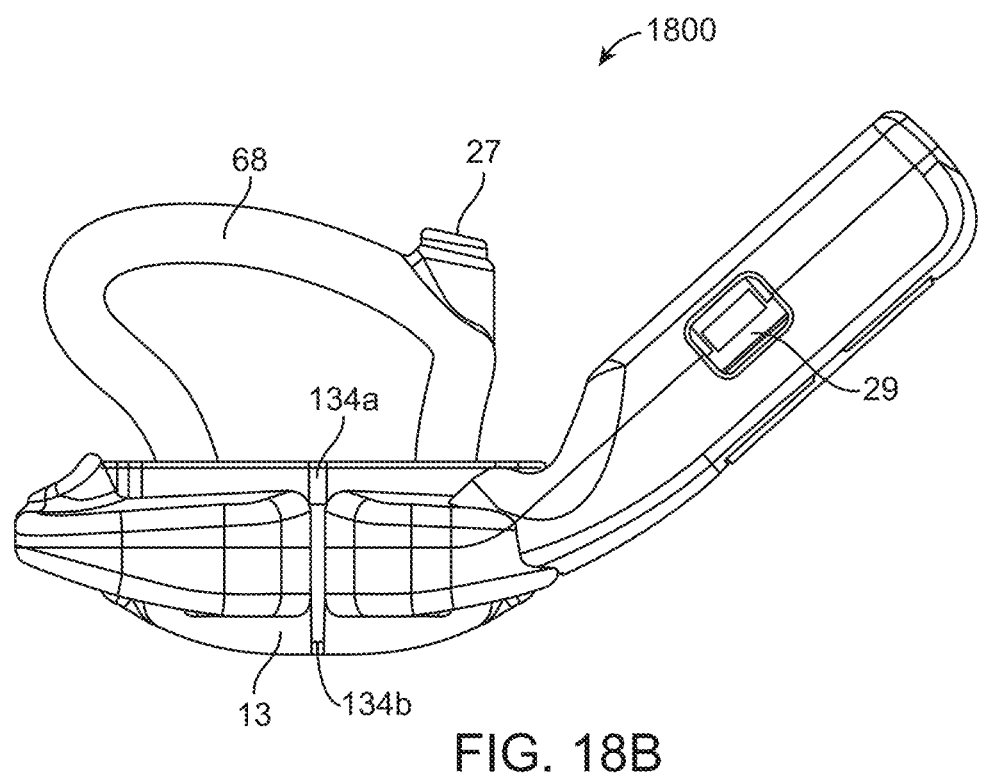

In some embodiments, the rocker tactile sensing device comprises a curved sensor applicator 13, as shown in FIG. 18B. In some embodiments, the curved sensor applicator 13 has a curvature with a radius of about 1.5 inches to about 3.5 inches. In some embodiments, the curved sensor applicator 13 is part of the main housing frame 19. In some embodiments, the curved sensor applicator 13 is assembled with the main housing frame 19. In some embodiments, the curved sensor applicator 13 protrudes from the main housing frame 19 to allow for more concentrated application of force. In some embodiments, the curved sensor applicator 13 is rocked relative to a fixed main housing frame 19. In some embodiments, the curved sensor applicator 13 is pressed against the skin surface of the patient. In some embodiments, the sensor array captures a series of images when the user "rocks" the curved sensor applicator 13 against the skin surface of a patient (e.g., against the lower back of a patient, if the target tissue location is the lumbar vertebrae). In some embodiments, partial images of captured areas are displayed as the rocking cycle is completed. In some embodiments, portions of the image currently being acquired are highlighted for clarity.

Figure 19A:
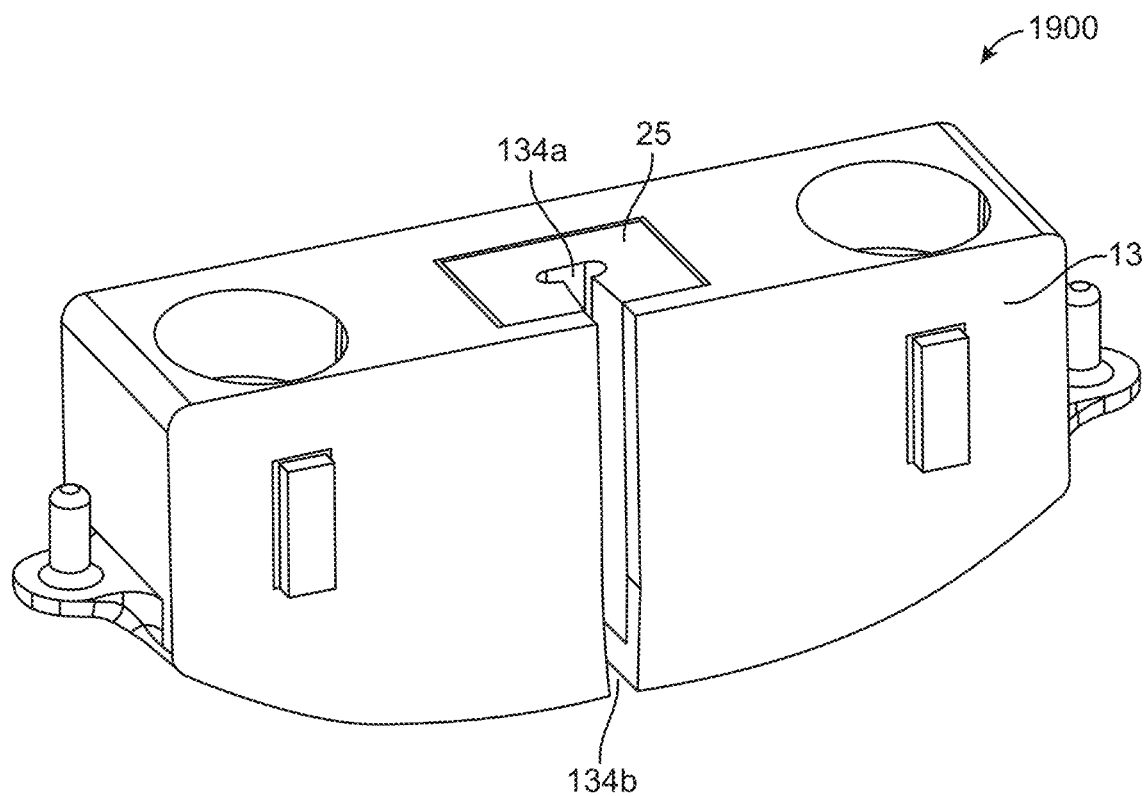

In some embodiments, the tactile sensing device comprises a needle guide 2 to facilitate insertion of a needle or marking tool or removal of the tactile sensing device. In some embodiments, the needle guide facilitates insertion of a needle that is attached to a syringe. In some embodiments, the syringe is a fluid-filled syringe or an air-filled syringe. In some embodiments, the needle guide is transparent to allow for maximal visibility of the target tissue. In some embodiments, the needle guide 2 is part of the curved sensor applicator. In some embodiments, the curved sensor applicator 13 comprises a needle guide insert 25, as shown in FIG. 19A. In some embodiments, the needle guide insert 25 comprises a needle guide 2, as shown in FIGS. 19B-C. In some embodiments, the needle guide 2 comprises a first needle guide wall 131*a* and a second needle guide wall 131*b*. In some embodiments, the first needle guide wall 131*a* and a second needle guide wall 131*b* are in contact with a needle that is inserted into the needle guide 2. In some embodiments, the first needle guide wall 130*a* and a second needle guide wall 131*b* guide the angle of a needle that is inserted into the needle guide 2. In some embodiments, the first needle guide wall 131*a* and a second needle guide wall 131*b* restrict the angle of a needle that is inserted into the needle guide 2. In some embodiments, the needle guide is reversibly attached to the tactile sensing device. In some embodiments, the needle comprises a notch.

In some embodiments, the needle guide insert 25 comprises a slot 38. In some embodiments, the slot 38 comprises a first slot wall 130*a* (not shown in FIGS. 19B-C) and a second slot wall 130*b* (shown in FIG. 19C). In some embodiments, the slot 38 provides the user with lateral access to the needle guide 2, as described elsewhere herein in other embodiments. In some embodiments, the first needle guide wall 131*a* and a second needle guide wall 131*b* connect and form the track 144 of the needle guide 2.

In some embodiments, the main housing frame 19 comprises a needle guide recess 31 configured to receive the needle guide insert 25. In some embodiments, the needle guide insert 25 is removable and is assembled with the curved sensor applicator 13. In some embodiments, the needle guide insert 25 is inserted into a needle guide recess 31. In some embodiments, the portion of the curved sensor surrounding the needle guide slot is flat to facilitate stabilization of the device during needle insertion. In some embodiments, the flat surface is about 0.1 inches to about 1 inch in length. In some embodiments, the needle guide comprises a needle guide opening 134*a* and a needle guide terminus 134*b*. In some embodiments, the slot extends from the center of the sensor applicator to the left edge of the sensor applicator, when viewed from the back of the device. In some embodiments, the needle guide 2 comprises a wall to restrict lateral needle movement. In some embodiments, the needle guide 2 comprises a needle retention gate 17, which is engaged to prevent the needle from sliding out of the slot and disengaged to allow the device to be removed from the needle after insertion. In some embodiments, the needle guide 2 is a fixed angle needle guide. In some embodiments, the needle guide allows for about 3° of flexibility. In some embodiments, the needle guide 2 is oriented at about 15° cephalad.

In some embodiments, the needle guide contains a mechanism that secures the needle. In some embodiments, the securing mechanism restricts the needle to the midline plane. In some embodiments, the securing mechanism is part of the needle guide. In some embodiments, the securing mechanism is attached to the needle guide. In some embodiments, the proximal end of the securing mechanism is filleted to allow for greater travel of the needle hub. In some embodiments, the securing mechanism is telescopic, to allow for greater travel of the needle hub. In some embodiments, the width of the securing mechanism is adjusted to accommodate a variety of needle gauges. In some embodiments, the securing mechanism comprises one or more parallel sets of tabs, which are separated or brought together via a scissor mechanism to accommodate a variety of gauges. In some embodiments, the tabs are elastic, such that smaller needles are easily accommodated. In some embodiments, a separation of the tabs is tracked with an electronic sensor. In some embodiments, a separation of the tabs is determined based on markers. In some embodiments, the tabs are orientated such the distance between their outer edges is greater than the distance between their inner edges, which allows for support of the needle, and facilitates easier removal of the device from the needle. In some embodiments, separate securing mechanisms are available for different needle gauges. In some embodiments, the needle is advanced through the securing mechanism and into the target tissue. In some embodiments, the securing mechanism is fixed relative to the needle guide. In some embodiments, the needle guide and/or the securing mechanism are rotated relative to the device. In some embodiments, the securing mechanism is rotated relative to the needle guide. In some embodiments, the securing mechanism is rotated to allow for insertion at any angle between about 0° and 30° cephalad. In some embodiments, the needle guide contains markers to indicate insertion angle. In some embodiments, the securing mechanism is locked at increments between about 0° and 30° cephalad to allow for fixed movement. In some embodiments, the securing mechanism is locked at about 1° increments. In some embodiments, increments for rotation of the securing mechanism are adjusted. In some embodiments, the axis of rotation of the securing mechanism is located at the midpoint of the securing mechanism. In some embodiments, the axis of rotation of the securing mechanism is located at the distal end of the securing mechanism. In some embodiments, the needle guide comprises a tab that is used to rotate the securing mechanism. In some embodiments, the needle guide comprises a dial that is rotated to rotate the securing mechanism. In some embodiments, the securing mechanism is automatically rotated based on input to the device. In some embodiments, the needle guide comprises a mechanism that allows the securing mechanism to release the needle after insertion. In some embodiments, minimal retaining force allows the device to be pulled away from the needle without the need for a release mechanism. In some embodiments, the needle guide contains a separate channel for insertion of a needle or other tool that is inserted offset from the target tissue location. In some embodiments, the needle guide contains a channel laterally offset from the securing mechanism that allows for insertion of a needle for local-anesthetic injection. In some embodiments, the sensor applicator is assembled with a main housing frame 19, which contains a slot extending from the slot in the sensor applicator to the left edge of the main housing frame 19 when viewed from the back of the device.

In some embodiments, the curved sensor applicator 13 comprises a sensor array. In some embodiments the sensor array is mounted on the curved bottom surface of the sensor applicator via an adhesive layer spanning its active area. In some embodiments, the non-active area of the sensor further comprises through holes for registration with the sensor applicator or the main housing frame 19 during assembly. In some embodiments, the sensor terminates in a zero-insertion force (ZIF) connector to connect with device sensor circuitry.

In some embodiments, the sensor array features a slot to facilitate insertion of a needle or marking tool, and device removal. In some embodiments, the slot extends from the center of the array to the outer left edge of the array, when observed print-side up. In some embodiments, the slot in the sensor array aligns with the needle guide slot in the sensor applicator. In some embodiments, the inner edge of the slot terminates in a through hole of about 2.1 millimeters (mm) in diameter at the center of the array to accommodate a needle or other marking tool.

In some embodiments, the sensor array (not shown in FIGS. 18-26) is a calibrated, custom screen-printed sensor array that detects pressure. In some embodiments, the sensor array comprises two thin, polyester sheets, with conductive silver traces deposited in row and column patterns on the inner surface of each sheet, respectively. In some embodiments, the polyester sheets are about 3 mil (i.e., 0.003 inches) in depth. In some embodiments, each intersection of the columns and rows forms a sensing element (i.e., a sensel), which acts as a variable resistor. In some embodiments, the resistance of each sensel varies inversely with an applied load. In some embodiments, the sequentially scanning of these sensels via voltage-divider circuitry enables for 2D mapping of the pressure distribution over a target tissue location (e.g., vertebrae). In some embodiments, traces and spaces are about 1.9 mm in width. In some embodiments, the center-to-center spacing of rows and columns in the sensor array is about 1.9 millimeters (mm). In some embodiments, the sensor array has a spatial resolution of about 3.8 mm.

In some embodiments, the center-to-center spacing of rows and columns in the sensor array is about 0.5 mm to about 5 mm. In some embodiments, the center-to-center spacing of rows and columns in the sensor array is at least about 0.5 mm. In some embodiments, the center-to-center spacing of rows and columns in the sensor array is at most about 5 mm. In some embodiments, the center-to-center spacing of rows and columns in the sensor array is about 0.5 mm to about 1 mm, about 0.5 mm to about 1.5 mm, about 0.5 mm to about 2 mm, about 0.5 mm to about 2.5 mm, about 0.5 mm to about 3 mm, about 0.5 mm to about 3.5 mm, about 0.5 mm to about 4 mm, about 0.5 mm to about 4.5 mm, about 0.5 mm to about 5 mm, about 1 mm to about 1.5 mm, about 1 mm to about 2 mm, about 1 mm to about 2.5 mm, about 1 mm to about 3 mm, about 1 mm to about 3.5 mm, about 1 mm to about 4 mm, about 1 mm to about 4.5 mm, about 1 mm to about 5 mm, about 1.5 mm to about 2 mm, about 1.5 mm to about 2.5 mm, about 1.5 mm to about 3 mm, about 1.5 mm to about 3.5 mm, about 1.5 mm to about 4 mm, about 1.5 mm to about 4.5 mm, about 1.5 mm to about 5 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 3 mm to about 3.5 mm, about 3 mm to about 4 mm, about 3 mm to about 4.5 mm, about 3 mm to about 5 mm, about 3.5 mm to about 4 mm, about 3.5 mm to about 4.5 mm, about 3.5 mm to about 5 mm, about 4 mm to about 4.5 mm, about 4 mm to about 5 mm, or about 4.5 mm to about 5 mm. In some embodiments, the center-to-center spacing of rows and columns in the sensor array is about 0.5 mm, about 1 mm, about 1.5 mm, about 2 mm, about 2.5 mm, about 3 mm, about 3.5 mm, about 4 mm, about 4.5 mm, or about 5 mm.

In some embodiments, a center-to-center spacing of about 1.9 mm effectively resolves the lowest extreme of observed interspinous spaces. In some embodiments, the sensor array produces an image with an effective resolution of an interspinous space of about 3 mm to about 6.5 mm. In some embodiments, the sensor array produces an image with an effective resolution of an interspinous space of at least about 3 mm. In some embodiments, the sensor array produces an image with an effective resolution of an interspinous space of at most about 6.5 mm. In some embodiments, the sensor array produces an image with an effective resolution of an interspinous space of about 3 mm to about 3.5 mm, about 3 mm to about 4 mm, about 3 mm to about 4.5 mm, about 3 mm to about 5 mm, about 3 mm to about 5.5 mm, about 3 mm to about 6 mm, about 3 mm to about 6.5 mm, about 3.5 mm to about 4 mm, about 3.5 mm to about 4.5 mm, about 3.5 mm to about 5 mm, about 3.5 mm to about 5.5 mm, about 3.5 mm to about 6 mm, about 3.5 mm to about 6.5 mm, about 4 mm to about 4.5 mm, about 4 mm to about 5 mm, about 4 mm to about 5.5 mm, about 4 mm to about 6 mm, about 4 mm to about 6.5 mm, about 4.5 mm to about 5 mm, about 4.5 mm to about 5.5 mm, about 4.5 mm to about 6 mm, about 4.5 mm to about 6.5 mm, about 5 mm to about 5.5 mm, about 5 mm to about 6 mm, about 5 mm to about 6.5 mm, about 5.5 mm to about 6 mm, about 5.5 mm to about 6.5 mm, or about 6 mm to about 6.5 mm. In some embodiments, the sensor array produces an image with an effective resolution of an interspinous space of about 3 mm, about 3.5 mm, about 4 mm, about 4.5 mm, about 5 mm, about 5.5 mm, about 6 mm, or about 6.5 mm.

In some embodiments, the pressure rating of the sensor array is about 20 psi. In some embodiments, the pressure rating of the sensor array is about 1 psi to about 150 psi. In some embodiments, the pressure rating of the sensor array is at least about 1 psi. In some embodiments, the pressure rating of the sensor array is at most about 150 psi. In some embodiments, the pressure rating of the sensor array is about 1 psi to about 7 psi, about 1 psi to about 25 psi, about 1 psi to about 50 psi, about 1 psi to about 75 psi, about 1 psi to about 100 psi, about 1 psi to about 125 psi, about 1 psi to about 150 psi, about 7 psi to about 25 psi, about 7 psi to about 50 psi, about 7 psi to about 75 psi, about 7 psi to about 100 psi, about 7 psi to about 125 psi, about 7 psi to about 150 psi, about 25 psi to about 50 psi, about 25 psi to about 75 psi, about 25 psi to about 100 psi, about 25 psi to about 125 psi, about 25 psi to about 150 psi, about 50 psi to about 75 psi, about 50 psi to about 100 psi, about 50 psi to about 125 psi, about 50 psi to about 150 psi, about 75 psi to about 100 psi, about 75 psi to about 125 psi, about 75 psi to about 150 psi, about 100 psi to about 125 psi, about 100 psi to about 150 psi, or about 125 psi to about 150 psi. In some embodiments, the pressure rating of the sensor array is about 1 psi, about 7 psi, about 25 psi, about 50 psi, about 75 psi, about 100 psi, about 125 psi, or about 150 psi. In some embodiments, a pressure rating of 20 psi effectively resolves a target tissue location (e.g., an interspinous space). In some embodiments, a pressure rating of about 20 psi effectively resolves bony landmarks as deep as about 60 mm. In some embodiments, a depth of about 60 mm corresponds to a tissue depth of an obese patient having a body mass index (BMI) of about 40 kg/m$^2$.

In some embodiments, the sensor array comprises about 38 rows and about 9 columns, which corresponds to an active sensing area comprising about 7.05 mm in length by about 15.2 mm in width. In some embodiments, the sensor array comprises an active sensing area with a width of about 5 mm to about 30 mm. In some embodiments, the sensor array comprises an active sensing area with a width of at least about 5 mm. In some embodiments, the sensor array comprises an active sensing area with a width of at most about 30 mm. In some embodiments, the sensor array comprises an active sensing area with a width of about 5 mm to about 6 mm, about 5 mm to about 7 mm, about 5 mm to about 8 mm, about 5 mm to about 9 mm, about 5 mm to about 10 mm, about 5 mm to about 15 mm, about 5 mm to about 20 mm, about 5 mm to about 25 mm, about 5 mm to about 30 mm, about 6 mm to about 7 mm, about 6 mm to about 8 mm, about 6 mm to about 9 mm, about 6 mm to about 10 mm, about 6 mm to about 15 mm, about 6 mm to about 20 mm, about 6 mm to about 25 mm, about 6 mm to about 30 mm, about 7 mm to about 8 mm, about 7 mm to about 9 mm, about 7 mm to about 10 mm, about 7 mm to about 15 mm, about 7 mm to about 20 mm, about 7 mm to about 25 mm, about 7 mm to about 30 mm, about 8 mm to about 9 mm, about 8 mm to about 10 mm, about 8 mm to about 15 mm, about 8 mm to about 20 mm, about 8 mm to about 25 mm, about 8 mm to about 30 mm, about 9 mm to about 10 mm, about 9 mm to about 15 mm, about 9 mm to about 20 mm, about 9 mm to about 25 mm, about 9 mm to about 30 mm, about 10 mm to about 15 mm, about 10 mm to about 20 mm, about 10 mm to about 25 mm, about 10 mm to about 30 mm, about 15 mm to about 20 mm, about 15 mm to about 25 mm, about 15 mm to about 30 mm, about 20 mm to about 25 mm, about 20 mm to about 30 mm, or about 25 mm to about 30 mm. In some embodiments, the sensor array comprises an active sensing area with a width of about 5 mm, about 6 mm, about 7 mm, about 8 mm, about 9 mm, about 10 mm, about 15 mm, about 20 mm, about 25 mm, or about 30 mm.

In some embodiments, the sensor array comprises an active sensing area with a length of about 30 mm to about 90 mm. In some embodiments, the sensor array comprises an active sensing area with a length of at least about 30 mm. In some embodiments, the sensor array comprises an active sensing area with a length of at most about 90 mm. In some embodiments, the sensor array comprises an active sensing area with a length of about 30 mm to about 35 mm, about 30 mm to about 40 mm, about 30 mm to about 45 mm, about 30 mm to about 50 mm, about 30 mm to about 55 mm, about 30 mm to about 60 mm, about 30 mm to about 65 mm, about 30 mm to about 70 mm, about 30 mm to about 75 mm, about 30 mm to about 80 mm, about 30 mm to about 90 mm, about 35 mm to about 40 mm, about 35 mm to about 45 mm, about 35 mm to about 50 mm, about 35 mm to about 55 mm, about 35 mm to about 60 mm, about 35 mm to about 65 mm, about 35 mm to about 70 mm, about 35 mm to about 75 mm, about 35 mm to about 80 mm, about 35 mm to about 90 mm, about 40 mm to about 45 mm, about 40 mm to about 50 mm, about 40 mm to about 55 mm, about 40 mm to about 60 mm, about 40 mm to about 65 mm, about 40 mm to about 70 mm, about 40 mm to about 75 mm, about 40 mm to about 80 mm, about 40 mm to about 90 mm, about 45 mm to about 50 mm, about 45 mm to about 55 mm, about 45 mm to about 60 mm, about 45 mm to about 65 mm, about 45 mm to about 70 mm, about 45 mm to about 75 mm, about 45 mm to about 80 mm, about 45 mm to about 90 mm, about 50 mm to about 55 mm, about 50 mm to about 60 mm, about 50 mm to about 65 mm, about 50 mm to about 70 mm, about 50 mm to about 75 mm, about 50 mm to about 80 mm, about 50 mm to about 90 mm, about 55 mm to about 60 mm, about 55 mm to about 65 mm, about 55 mm to about 70 mm, about 55 mm to about 75 mm, about 55 mm to about 80 mm, about 55 mm to about 90 mm, about 60 mm to about 65 mm, about 60 mm to about 70 mm, about 60 mm to about 75 mm, about 60 mm to about 80 mm, about 60 mm to about 90 mm, about 65 mm to about 70 mm, about 65 mm to about 75 mm, about 65 mm to about 80 mm, about 65 mm to about 90 mm, about 70 mm to about 75 mm, about 70 mm to about 80 mm, about 70 mm to about 90 mm, about 75 mm to about 80 mm, about 75 mm to about 90 mm, or about 80 mm to about 90 mm. In some embodiments, the sensor array comprises an active sensing area with a length of about 30 mm, about 35 mm, about 40 mm, about 45 mm, about 50 mm, about 55 mm, about 60 mm, about 65 mm, about 70 mm, about 75 mm, about 80 mm, or about 90 mm.

Figure 18C:
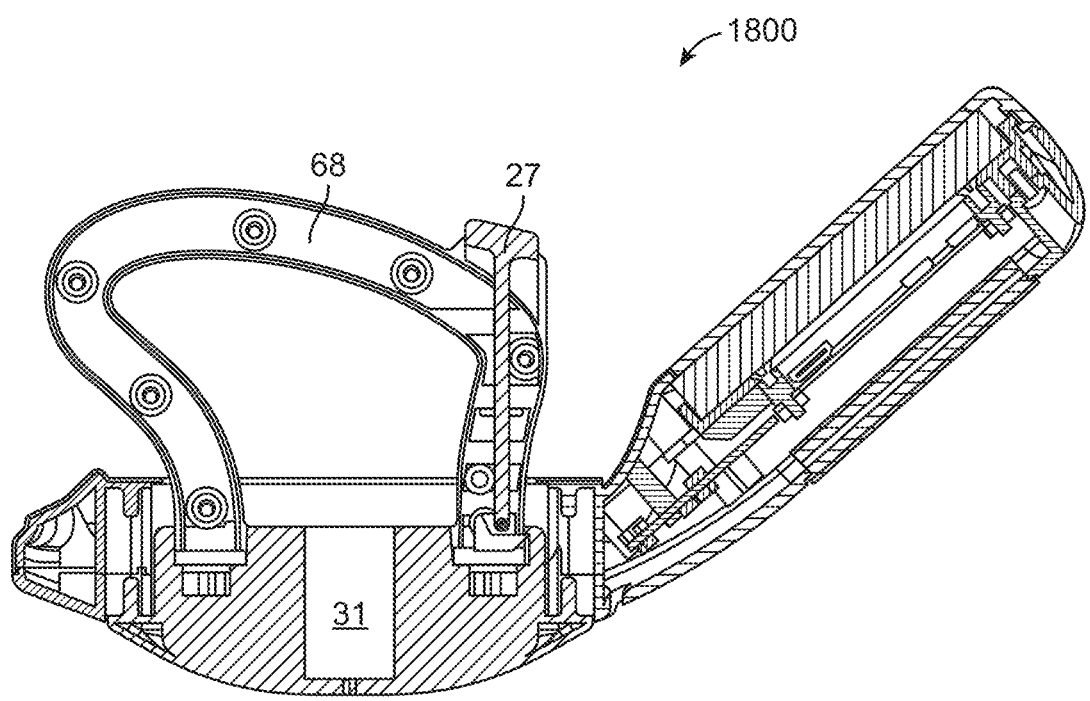

In some embodiments, the tactile sensing device is a rocker tactile sensor device 1800 comprising a removable handle 68, as shown in FIGS. 18A-C. In some embodiments, the removable handle is a power grip handle. In some embodiments, the removable handle is similar to the power grip handle 68 shown in FIG. 11. In some embodiments, the removable handle is removed to expose the needle guide 2. In some embodiments, the removable handle comprises a first post and a second post that are inserted into a first opening and a second opening in the top surface of the sensor applicator or main housing frame 19 of the tactile sensing device 1800. In some embodiments, the handle and the main housing frame 19 are reversibly coupled to each other via a mechanism that includes an audible indication, such as, but not limited to, a clicking noise. In some embodiments, the handle has a handle release button 27, as shown in FIGS. 18A-C. In some embodiments, the handle release button 27 is located at the posterior or anterior end of the handle. In some embodiments, the handle release button 27 is pushed to disengage the handle from the curved sensor applicator 13 or main housing frame 19. In some embodiments, the handle is comprised of a two-part housing. In some embodiments, the posts of the handle comprise a skirt that secures the posts in the openings after insertion.

In some embodiments, the tactile sensing device is a rocker tactile sensing device 2400 comprising a reusable user interface (UI) module 1. In some embodiments, the UI module 1 is part of a main housing frame 19. In some embodiments the UI module is comprised of a two-part housing. In some embodiments the UI module has a back plate for access to electronics. In some embodiments, the UI module is assembled with the main housing frame 19. In some embodiments, the UI module 1 is a non-sterile, non-patient-contacting part, to be made of medical-grade, injection-molded plastic. In some embodiments, the main housing frame 19 comprises hubs for UI module attachment at the top and bottom when the device is viewed from the top to facilitate use in right- and left-handed users. In some embodiments, the UI module 1 comprises a printed circuit board assembly (PCBA). In some embodiments, the PCBA serves as the motherboard of the system of the tactile sensing device. In some embodiments, the PCBA comprises a microprocessor. In some embodiments, the PCBA interfaces to the sensor breakout board, display module, external sensors, and user-input mechanisms. In some embodiments, the PCBA comprises the fusing, charging, and protection circuitry for the rechargeable battery. In some embodiments, the PCBA processes and displays pressure sensor data. In some embodiments, the PCBA handles interrupts, such as a physical or touchscreen menu button press and physical or touchscreen refresh button press. In some embodiments, a sample runtime task for live imaging (about 50 milliseconds (ms)) comprises data capture, data analysis, error checks, frame drawing, and frame display. In some embodiments, the PCBA comprises circuitry to support adjustment of maximum sensor pressure between a factor of ⅐ and a factor of 3 of the sensor's pressure rating. In some embodiments, sensitivity is adjusted via a dial or external buttons, or a touchscreen display. In some embodiments drive voltage is automatically adjusted based on an equilibration file. In some embodiments, the PCBA comprises sensors and circuitry to track device orientation and trigger alerts to device movement during rocking. In some embodiments, the UI module is powered on by a switch.

In some embodiments, the tactile sensing device comprises a sensor breakout board (not shown in the figures). In some embodiments, the sensor breakout board comprises minimal electronics that are disposable. In some embodiments, the sensor breakout board is configured to connect the sensor driver and acquisition circuitry from the UI module to the sensor array. In some embodiments, the sensor breakout board comprises a zero insertion force (ZIF) connector for sensor array connection. In some embodiments, the sensor breakout board comprises an analog multiplexer (MUX) and a bit shifter to support scanning and output. In some embodiments, position sensors to track device movement are comprised in the disposable breakout board. In some embodiments, the UI module is powered on upon connection to the breakout board.

In some embodiments, the UI module comprises a display screen. In some embodiments, the display screen is a touchscreen. In some embodiments, the display screen has an adjustable angle. In some embodiments, the display screen is a full-color LCD display. In some embodiments, the display screen is connected to the PCBA and mechanically integrated in the anterior surface of the housing of the module, to allow for output visualization. In some embodiments, the tactile sensing device wirelessly interfaces with an external display, such as a tablet or computer. In some embodiments, the display is collapsed to reduce tactile sensing device footprint.

In some embodiments, the tactile sensing device is a rocker tactile sensing device 2400 comprising a sleeve 80. In some embodiments, the sleeve is a single-component part that is sterile. In some embodiments, the sleeve shrouds the reusable UI module during use. In some embodiments, the sleeve is made of medical-grade polyethylene terephthalate glycol-modified (PETG). In some embodiments, the sleeve is vacuum-formed to a mold of the reusable UI module. In some embodiments, the sleeve comprises a low-reflectivity, transparent component over the display area. In some embodiments, the sleeve has openings for user-input buttons.

In some embodiments, the UI module comprises a battery. In some embodiments, the battery is a rechargeable battery. In some embodiments, the rechargeable battery interfaces with the PCBA. In some embodiments, the tactile sensing device comprises a battery indicator. In some embodiments, the battery indicator is a charging indicator. In some embodiments, the charging indicator alerts the user of a low battery. In some embodiments, the charging indicator alerts the user of the amount of battery charged during the charging process. In some embodiments, the battery indicator is on-screen. In some embodiments, the battery indicator is an LED. In some embodiments, the device is powered via USB connection to a computer.

In some embodiments, the rechargeable battery located within the tactile sensing device is charged using a reusable charging station (not shown in the figures). In some embodiments, the charging unit comprises standard electronics, including electrical contacts for mating with the computing unit (i.e., with PCBA). In some embodiments, the charging station is housed in a two-part injection molded plastic. In some embodiments, the charging station comprises a charging indicator. In some embodiments, the charging station employs induction charging.

FIGS. 18-21 show embodiments of a tactile sensing device 2400 comprising a rocker design, referred to herein as rocker tactile sensing devices. In some embodiments, the rocker tactile sensing device 1800 comprises a UI module 1, a power grip handle 68, and a main housing frame 19. In some embodiments, the UI module 1 comprises a display screen 4, a pressure map 6, and a UI module connector 9. In some embodiments, a sleeve 80 shrouds the UI module 1. In some embodiments, the main housing frame 19 comprises a first handle opening 5*a* and a second handle opening 5*b* configured to receive the power grip handle 68. In some embodiments, the handle and the main housing frame are reversibly coupled to each other via a mechanism that includes an audible indication, such as, but not limited to, a clicking noise. In some embodiments, the power grip handle 68 comprises a first handle notch 3*a* and a second handle notch 3*b*. In some embodiments, the power grip handle 68 comprises a handle skirt 11. In some embodiments, the handle skirt 11 is configured to secure the power grip handle 68 once inserted into the first handle opening 5*a* and the second handle opening 5*b*. In some embodiments, the main housing frame 19 comprises a UI module slot 7 configured to receive the UI module connector 9. In some embodiments, the UI module 1 is powered upon connection with the housing comprising the sensor platform and array. In some embodiments, the UI module is powered by a switch.

As shown in FIGS. 18B, the tactile sensing device comprising the rocker design comprises a curved sensor applicator 13. In some embodiments, the curved sensor applicator comprises the sensor array. In some embodiments, the sensor array is adhered to the surface of the curved sensor applicator. In some embodiments, the curved sensor platform 13 and the sensor array comprise a slot to facilitate needle insertion and tactile sensing device removal. As shown in FIG. 18A, the tactile sensing device comprises a needle guide. In some embodiments, the needle guide is a slot 38. In some embodiments, the slot 38 comprises a first needle guide wall 131*a* and a second needle guide wall 131*b*. In some embodiments, the needle guide comprises a slot opening 38*a* and a slot terminus 38*b*.

Figure 20B:
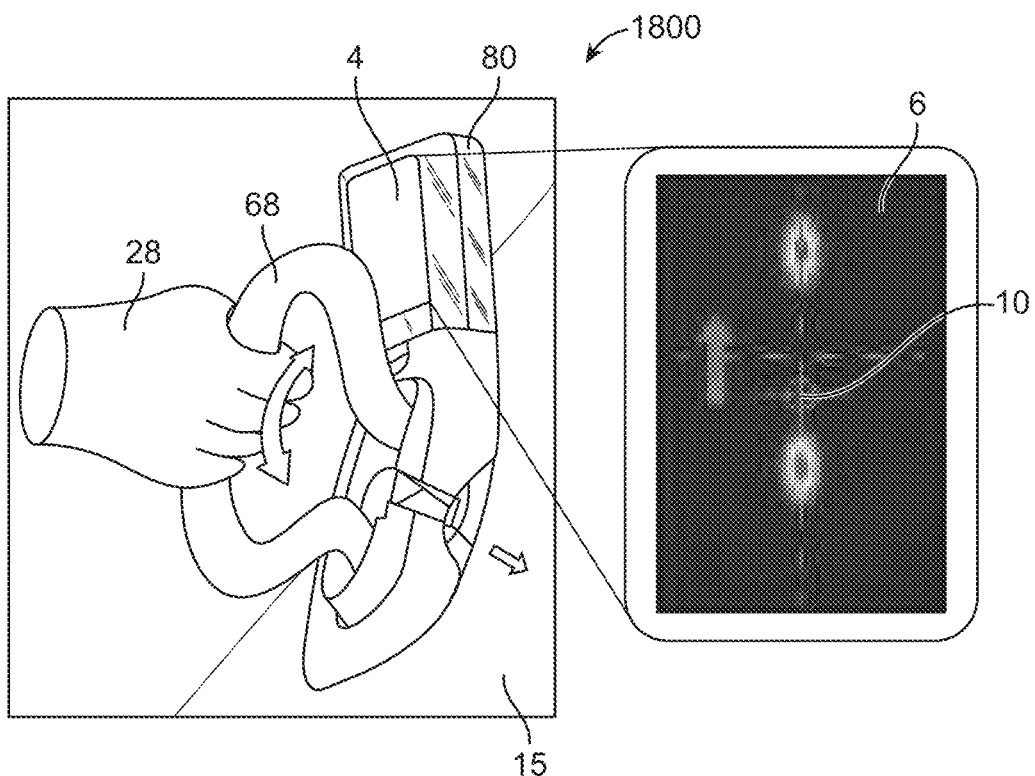

FIGS. 20A-E show the workflow of how a user utilizes the tactile sensing device 1800 comprising the rocker design, alternatively referred to a rocker tactile sensing device, when imaging a target tissue location of a patient. In some embodiments, the user inserts the handle 68 into the main housing frame 19 via the handle openings. Next, in some embodiments, the user visually locates the general area of the target tissue location (e.g., spinous processes). Next, in some embodiments, the user places the tactile sensing device on the skin surface of the patient, ensuring the midline of the device aligns with the target tissue location (i.e., the spine). FIG. 20A shows the user 28 applying a constant downward pressure on the power grip handle 68, through the sensor array, and onto the skin surface of the patient. Furthermore, FIG. 20A illustrates how the user 28 obtains a first image of the target tissue location when exerting a forward rocking motion of the device while pressing against the skin surface of the patient 15. In some embodiments, the sleeve 80 is used as a sterile barrier between the patient 15 and the reusable UI module 1.

FIG. 20B shows how the user 28 obtains a second image of the target tissue location when exerting a backward rocking motion of the device while pressing against the skin surface of the patient 15. In some embodiments, the user partially images the target tissue location when exerting either a forward or backward rocking motion of the device while pressing it against the patient. In some embodiments, a complete image of the target tissue location is acquired once the user exerts both a forward or backward rocking motion of the device while pressing it against the patient. In some embodiments, the user rocks the tactile sensing device forward to its maximum position and subsequently rocks the tactile sensing device backward to the maximum downward position, and then back to center in order to fully image the target tissue location (e.g., spinous processes). In some embodiments, the user continues to rock the tactile sensing device as necessary until the display screen displays the hotspots of the target tissue location (e.g., the spinous processes) and the midline. In some embodiments, the display screen displays a line corresponding to the midline. In some embodiments, the display screen displays a crosshair corresponding to location of the needle guide relative to the spine. In some embodiments, the display screen displays an arrow indicating to the user the direction in which the tactile sensing device needs to be moved in order to localize the target tissue location. In some embodiments, the user refreshes the device output and starts the imaging process again at another location along the spine.

Figure 20C:
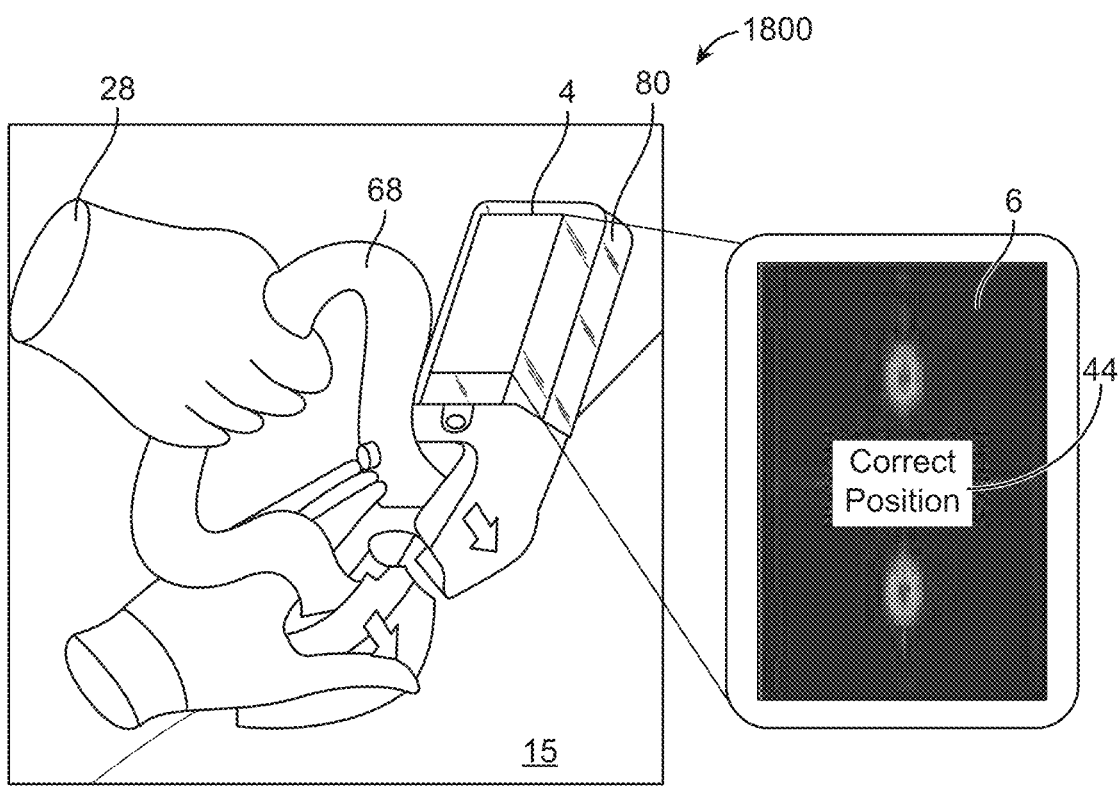
Figure 20D:
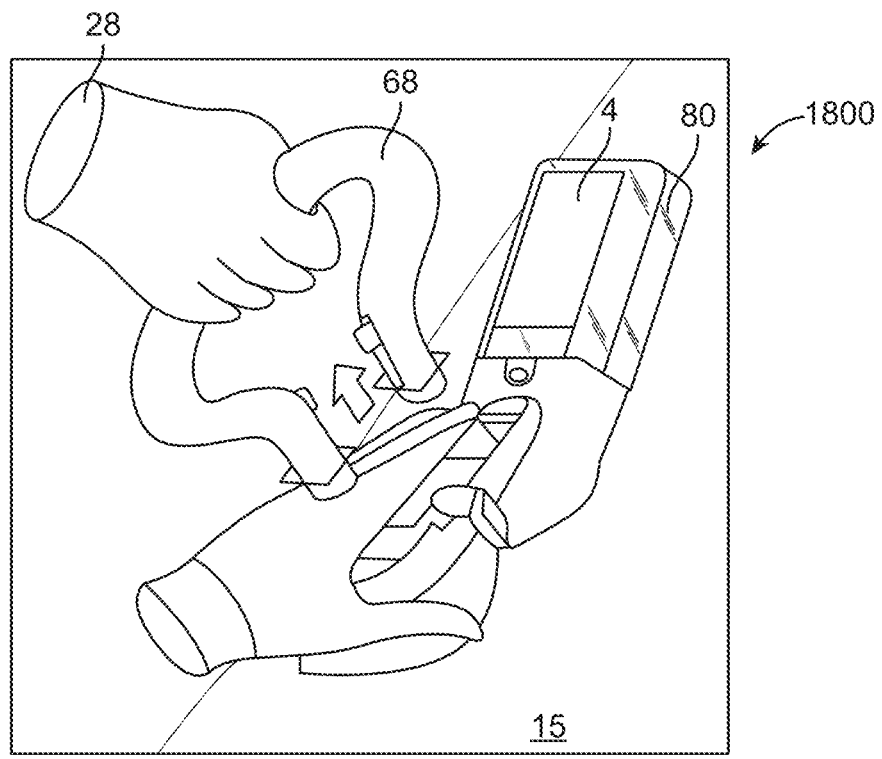
Figure 20E:
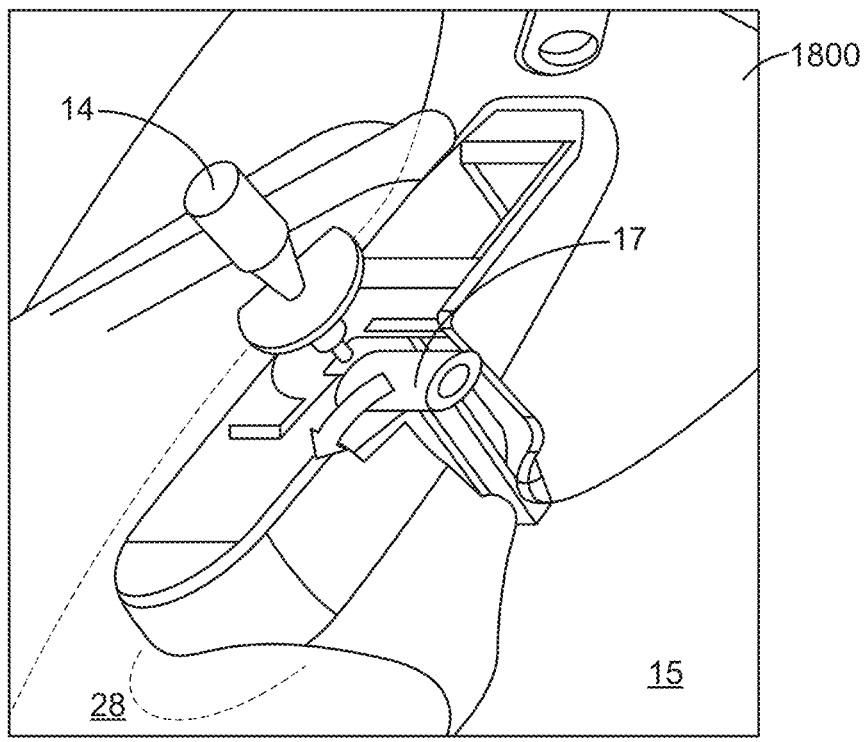

In some embodiments, once the complete image of the target tissue location is acquired, the tactile sensing device prompts the user when the needle guide is at correct location, as shown in FIG. 20C. In some embodiments, upon correct alignment of the needle guide, the user 28 detaches the power grip handle 68 by pulling the handle up in order to release it from the main housing frame 19, as shown in FIG. 20D. In some embodiments, the handle is detached by pressing at least one button that releases the handle from the main housing frame 19. Next, in some embodiments, the user proceeds to insert the needle or marking tool into the needle guide. In some embodiments, the needle guide allows for a certain degree of angular movement that enables the user to pinpoint the exact needle insertion position required. In some embodiments, the tactile sensing device is removed after needle insertion by sliding the device leftward along the skin surface. In some embodiments, the tactile sensing device comprises a needle retention clip 17, as shown in FIG. 20E. The needle retention clip 17 is configured to keep the needle 14 fixed in place. In some embodiments, the needle retention clip is disengaged to allow release the needle from the device in order to slide the device off the skin surface.

Slider Tactile Sensing Device

In some embodiments, the tactile sensing device is a slider tactile sensing device 2100, as shown in the embodiments depicted in FIGS. 21A-B, 22A-C, 23A-B, 24A-C, 25A-B, and 26A-D alternatively referred to a tactile sensing device including a slider design herein. In embodiments of the tactile sensing device that are slider tactile sensing devices, the devices include aspects and functionality of the tactile sensing devices described elsewhere herein with the sensor array being movable relative to the body of the device and that uses and includes historical and real time image visualization thereby requiring a smaller sensor array to build an image for display of the anatomy of a subject as compared to a non-sliding tactile sensing device, and as compared to a rocker tactile sensing device sensor array.

Figure 21A:
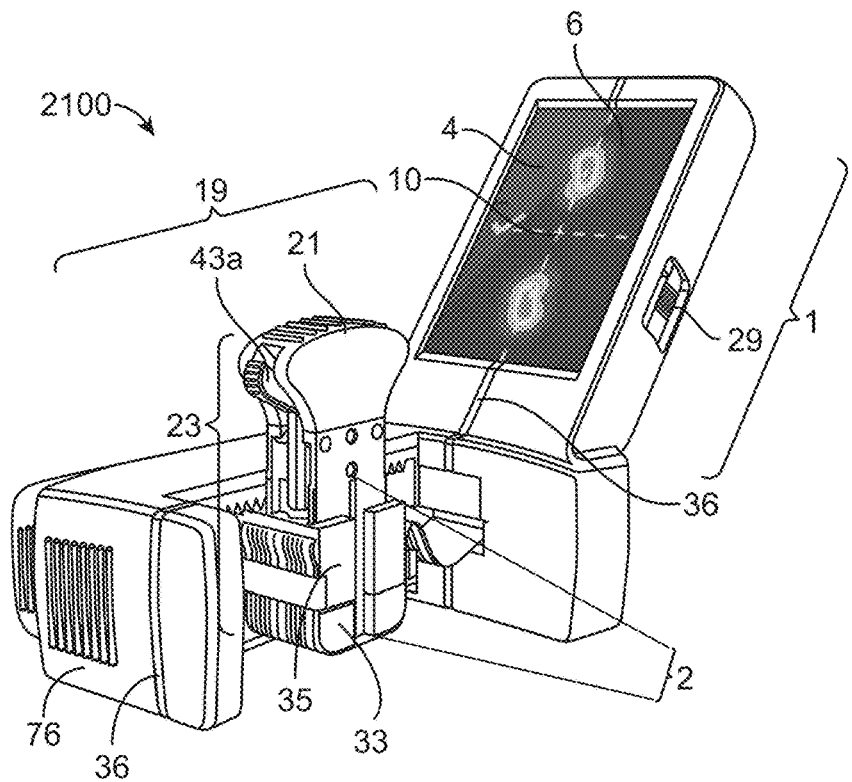
FIGS. 21A-C show an embodiment slider tactile sensing device.

FIG. 21A shows an isometric view of the slider tactile sensing device 2100. In some embodiments, the slider tactile sensing device 2100 comprises a scanning knob 21. In some embodiments, the slider tactile sensing device 2100 comprises a scanhead subassembly 23. In some embodiments, the scanning knob 21 is configured to enable the user to translate the carriage-scanhead subassembly along a distance (e.g., along the vertebrae of a patient). In some embodiments, the scanning knob 21 is configured to enable the user to press the sensor array onto the surface of the skin of the patient. In some embodiments, the scanning knob 21 is configured to lock the scanhead 33 in place once a target tissue insertion site is identified. In some embodiments, the scanning knob 21 is supplied as a separate component.

In some embodiments, the scanhead 33 allows the sensor array to be translated over a distance (e.g., along a 3 inch distance along the vertebrae). In some embodiments, the scanhead 33 is translated over a distance of about 0.5 inches (in.) to about 10 in. In some embodiments, the scanhead 33 is translated over a distance of at least about 0.5 in. In some embodiments, the scanhead 33 is translated over a distance of at most about 10 in. In some embodiments, the scanhead 33 is translated over a distance of about 0.5 in. to about 1 in., about 0.5 in. to about 2 in., about 0.5 in. to about 3 in., about 0.5 in. to about 4 in., about 0.5 in. to about 5 in., about 0.5 in. to about 6 in., about 0.5 in. to about 7 in., about 0.5 in. to about 8 in., about 0.5 in. to about 9 in., about 0.5 in. to about 10 in., about 1 in. to about 2 in., about 1 in. to about 3 in., about 1 in. to about 4 in., about 1 in. to about 5 in., about 1 in. to about 6 in., about 1 in. to about 7 in., about 1 in. to about 8 in., about 1 in. to about 9 in., about 1 in. to about 10 in., about 2 in. to about 3 in., about 2 in. to about 4 in., about 2 in. to about 5 in., about 2 in. to about 6 in., about 2 in. to about 7 in., about 2 in. to about 8 in., about 2 in. to about 9 in., about 2 in. to about 10 in., about 3 in. to about 4 in., about 3 in. to about 5 in., about 3 in. to about 6 in., about 3 in. to about 7 in., about 3 in. to about 8 in., about 3 in. to about 9 in., about 3 in. to about 10 in., about 4 in. to about 5 in., about 4 in. to about 6 in., about 4 in. to about 7 in., about 4 in. to about 8 in., about 4 in. to about 9 in., about 4 in. to about 10 in., about 5 in. to about 6 in., about 5 in. to about 7 in., about 5 in. to about 8 in., about 5 in. to about 9 in., about 5 in. to about 10 in., about 6 in. to about 7 in., about 6 in. to about 8 in., about 6 in. to about 9 in., about 6 in. to about 10 in., about 7 in. to about 8 in., about 7 in. to about 9 in., about 7 in. to about 10 in., about 8 in. to about 9 in., about 8 in. to about 10 in., or about 9 in. to about 10 in.. In some embodiments, the scanhead 33 is translated over a distance of about 0.5 in., about 1 in., about 2 in., about 3 in., about 4 in., about 5 in., about 6 in., about 7 in., about 8 in., about 9 in., or about 10 in.

In some embodiments, the surface of the distal end with respect to the user (i.e., the bottom surface) of the scanhead subassembly 23 comprises the sensor array. In some embodiments, the scanhead 33 is configured to receive the scanning knob 21. In some embodiments, the sensor array (not shown in FIGS. 21A-B) is mounted on the bottom surface of the scanhead 33. In some embodiments, the scanhead 33 has a size and curvature designed to mimic palpation and optimize vertebral resolution. As shown in FIG. 21A, the slider tactile sensing device 2100 comprises a grip feature 76. In some embodiments, the grip feature 76 is the outer portion of the main housing frame 19. In some embodiments, the user uses the grip feature 76 to press the device against the patient. In some embodiments, the grip feature 76 is any of the previously described grip features.

In some embodiments, the slider device comprises a main housing frame 19. In some embodiments, the main housing frame 19 comprises an indicator for the midline of the tactile sensing device to facilitate alignment with the spine. In some embodiments the indicator for the midline of the tactile sensing device is a needle alignment guide 36. In some embodiments, the indicator is a colored notch. In some embodiments, the main housing frame 19 is reusable. In some embodiments, the main housing frame 19 is disposable. In some embodiments, the main housing frame 19 is made of medical-grade, injection-molded plastic. In some embodiments, the main housing frame 19 is comprised of two parts. In some embodiments, the main housing frame 19 comprises a patient-attachment mechanism on the bottom surface. In some embodiments the patient-attachment feature employs a vacuum, an adhesive, or a belt mechanism. In some embodiments, the patient-contacting surface of the main housing frame 19 is curved. In some embodiments, the patient-contacting surface of the main housing frame 19 has a downward concave curvature to conform to one or more vertebrae in flexion. In some embodiments, the patient-contacting surface of the main housing frame 19 has an upward concave curvature to conform to the tissue between the thoracolumbar fascia. In some embodiments, the patient-contacting surface of the main housing frame 19 has an M-shaped curvature to optimize conformance in the mediolateral direction. In some embodiments, the main housing frame 19 comprises a grip area for the user's non-dominant hand. In some embodiments, the grip area is on the left side of the main housing frame 19 when viewed from the front. In some embodiments, the grip area is rounded. In some embodiments the grip area comprises multiple materials. In some embodiments, the grip area comprises an undercut to improve purchase. In some embodiments, the grip area is a removable palm pad that is assembled with the main housing frame 19. In some embodiments, removable palm pads are available in different sizes and grips.

Figure 21B:
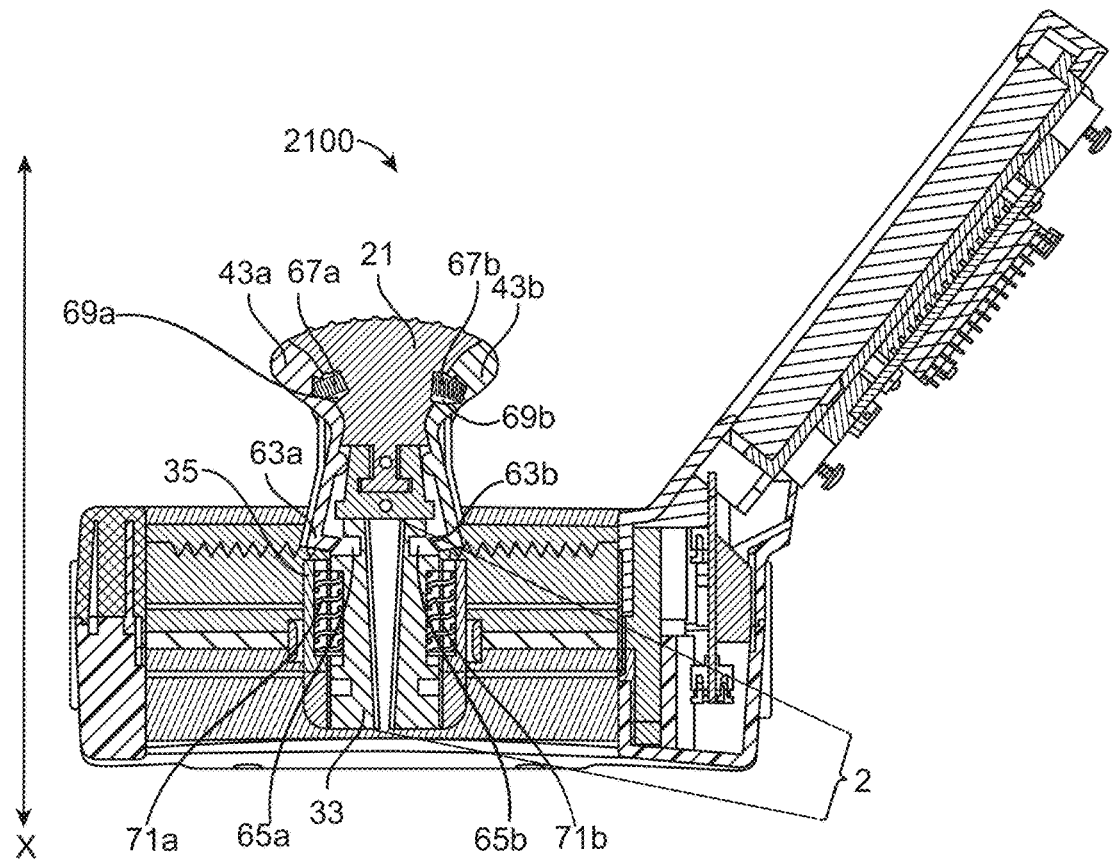
Figure 21C:
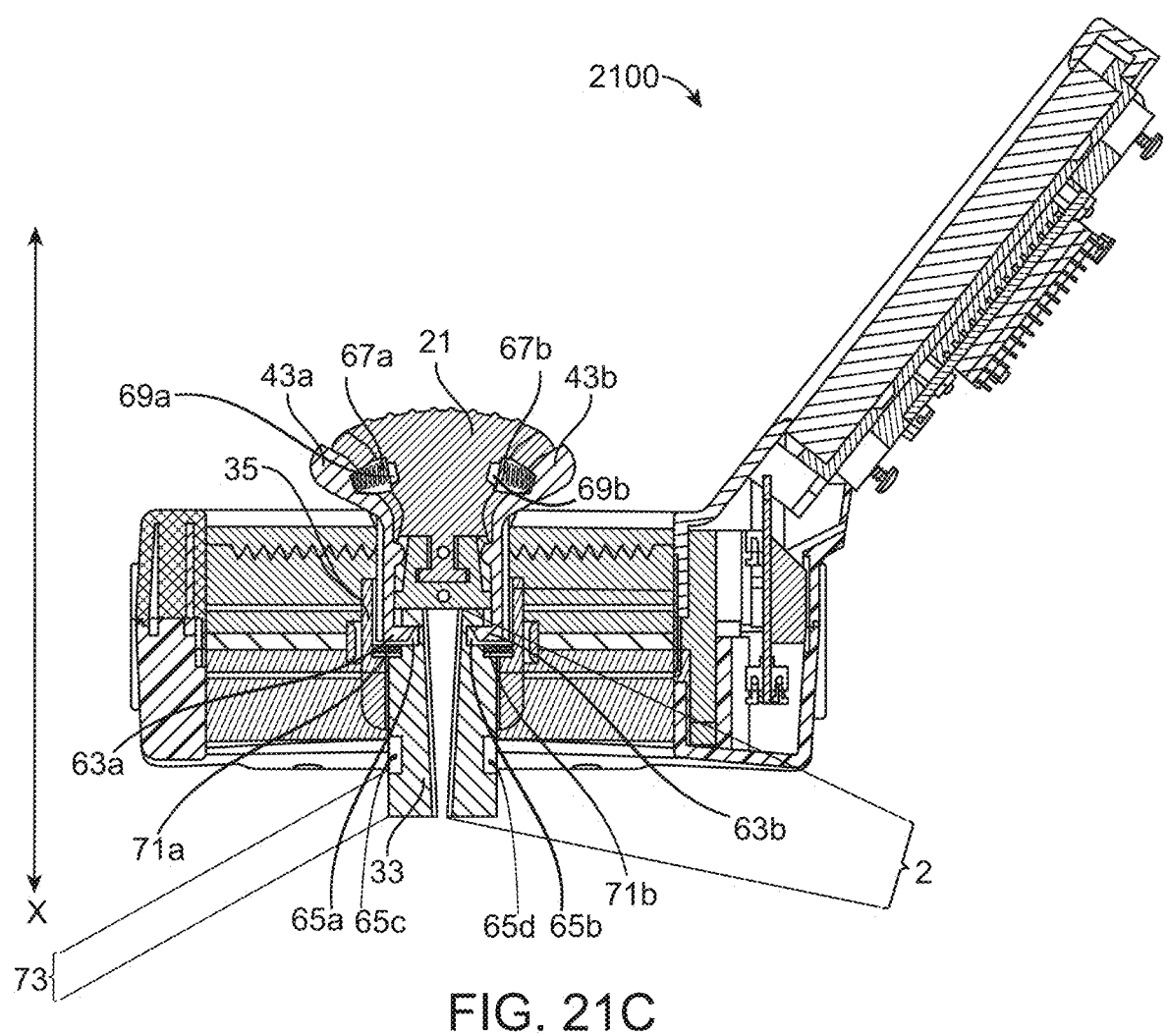

FIG. 21B shows a cut away view of the slider tactile sensing device 2100 with no force being applied onto the proximal end (with respect to the user) of the scanning knob 21. In contrast, FIG. 21C shows a cut away view of the slider tactile sensing device 2100 while a force is being applied onto the proximal end (with respect to the user) of the scanning knob 21. In other words, FIG. 21C shows the tactile sensing device 2100 as a user (not shown in FIGS. 21A-B) presses down onto the scanning knob 21 and depresses the entire scanhead subassembly 23 (e.g., onto the surface of the skin of a patient). In some embodiments, the scanning knob 21 is reversibly attached to the tactile sensing device 2100 via a first release clip 43*a* and a second release clip 43*b* at the top of the scanhead 33, as shown in FIG. 21B. In some embodiments, the first release clip 43*a* comprises a first foot 63*a*. In some embodiments, the first release clip 43*a* comprises a second foot 63*b*. In some embodiments, the slider tactile sensing device 2100 comprises a first ledge 65*a*. In some embodiments, the slider tactile sensing device 2100 comprises a second ledge 65*b*. In some embodiments, the first ledge 65*a* is configured to receive the first foot 63*a*. Likewise, in some embodiments, the second ledge 65*b* is configured to receive the second foot 63*b*.

In some embodiments, the slider tactile sensing device 2100 comprises a first retention clip spring 67*a*. In some embodiments, the slider tactile sensing device 2100 comprises a second retention clip spring 67*b*. In some embodiments, the scanning knob 21 comprises a first scanning knob notch 69*a* and a second scanning knob notch 69*b*, as shown in FIG. 21B. In some embodiments, the first scanning knob notch 69*a* is configured to receive the first retention clip spring 67*a* and the second retention clip spring 67*b*. In some embodiments, the first retention clip 43*a* comprises a first indentation that is configured to receive the first retention clip spring 67*a*. Similarly, in some embodiments, the second retention clip 43*b* comprises a second indentation that is configured to receive the second retention clip spring 67*b*. Thus, in some embodiments, the first retention clip spring 67*a* is positioned between the scanning knob and the first retention clip 43*a* and the second retention clip spring 67*b* is positioned between the scanning knob 21 and the second retention clip 43*b*, as illustrated in FIG. 21B. In some embodiments, the first retention clip 43*a* and the second retention clip spring 67*b* have a compressed state and an uncompressed state. In some embodiments, the first retention clip 43*a* and the second retention clip spring 67*b* are in a biased, uncompressed position or in an unbiased, compressed position.

In some embodiments, the first retention clip spring 67*a* and the second retention clip 67*b* serve as a locking mechanism of the scanning knob 21. FIG. 21C illustrates the scanning knob 21 in a locked state or position. In some embodiments, the first foot 63*a* is inserted into the first ledge 65*a* and the second foot 63*b* is inserted into the second ledge 65*b* when the scanning knob 21 is in a locked position (i.e., when the scanning knob 21 is attached to the tactile sensing device 2100), as shown in FIG. 21C. In some embodiments, the user pinches the first retention clip 43*a* and the second retention clip 43*b* in order to disengage the first foot 63*a* from the first ledge 65*a* and the second foot 63*b* from the second ledge 65*b*. FIG. 21B illustrates the unlocked state of the scanning knob 21. In some embodiments, when the scanning knob 21 is in the unlocked state, the first retention clip spring 67*a* is in an unbiased, compressed position, which causes the first foot 63*a* to point laterally away and disengage from the first ledge 65*a*. Similarly, in some embodiments, when the scanning knob 21 is in the unlocked state, the second retention clip spring 67*b* is in an unbiased, compressed position, which causes the second foot 63*b* to point laterally away and disengage from the second ledge 65*b*.

FIG. 21B illustrates the slider tactile sensing device 2100 comprising a scanhead subassembly 23 that is in a non-depressed state. On the other hand, FIG. 21C shows the slider tactile sensing device 2100 comprising a scanhead subassembly 23 that is in a depressed state. In other words, FIG. 21C shows the scanhead subassembly 23 at a lower position or depth along the X-axis compared to the initial position or depth along the X-axis of the scanhead subassembly 23 that is shown in FIG. 21B. In some embodiments, the scanhead subassembly 23 comprises a first spring 71*a* and a second spring 71*b*. In some embodiments, the scanhead subassembly 23 comprises an indentation located distally from and underneath the first ledge 65*a*, that is configured to receive the first spring 71*a*. Similarly, in some embodiments, the scanhead subassembly 23 comprises a first indentation located distally from and underneath the second ledge 65*b*, that is configured to receive the second spring 71*b*. In some embodiments, the first spring 71*a* is located distally from and underneath the first ledge 65*a*. In some embodiments, the second spring 71*b* is located distally from and underneath the second ledge 65*b*. In some embodiments, the first spring 71*a* is positioned within the first indentation of the scanhead subassembly 23. In some embodiments, the second spring 71b is positioned within the second indentation of the scanhead subassembly 23.

In some embodiments, the user applies a force on or presses down on the scanning knob 21 in order to depress the scanhead subassembly 23. In some embodiments, the user applies a force or presses down on the scanning knob 21 in order to change the position of the scanhead subassembly 23 to a lower position or depth. In some embodiments, the first spring 71a and the second spring 71b change from a biased, uncompressed position to an unbiased, compressed position when the user applies a force on or presses down on the scanning knob 21. FIG. 21B illustrates the first spring 71a and the second spring 71b in a biased, uncompressed position. Meanwhile, FIG. 21C illustrates the first spring 71a and the second spring 71b in an unbiased, compressed position.

In some embodiments, the first spring 71a and the second spring 71b are located directly below the first ledge 65a and the second ledge 65b, respectively, when they are in an unbiased, compressed position (i.e., when the user applies a force on or presses down on the scanning knob 21), as shown in FIG. 21C. In some embodiments, the slider tactile sensing device 2100 comprises a third ledge 65c and a fourth ledge 65d. In some embodiments, the third ledge 65c is located distally away and below the first ledge 65a, as shown in FIG. 21C. In some embodiments, the fourth ledge 65d is located distally away and below the second ledge 65b, as shown in FIG. 21C. In some embodiments, the first spring 71a is located in between the first ledge 65a and the third ledge 65c when the first spring 71a is in an unbiased, compressed position (i.e., when the user applies a force on or presses down on the scanning knob 21). In some embodiments, the second spring 71b is located in between the second ledge 65b and the fourth ledge 65d when the second spring 71b is in an unbiased, compressed position (i.e., when the user applies a force on or presses down on the scanning knob 21).

In alternative embodiments, not illustrated in the figures, the first spring 71a and the second spring 71b are located directly within the third ledge 65c and the fourth ledge 65d, respectively, when they are in an unbiased, compressed position. In other words, in alternative embodiments, the first spring 71a and the second spring 71b are displaced into the third ledge 65c and the fourth ledge 65d, respectively, when the user applies a force on or presses down on the scanning knob 21. In some embodiments, the first spring 71a and the second spring 71b are located in a more proximal position (with respect to the user) than the third ledge 65c and the fourth ledge 65d, respectively, when they are in an unbiased, compressed position (i.e., when the user applies a force on or presses down on the scanning knob 21), as shown in FIG. 21C.

FIG. 21C illustrates a depth 73 (along the X-axis) of the scanhead subassembly. In some embodiments, the user controls the depth 73 of the scanhead subassembly 23 along the X-axis by varying the amount of force that she or he applies to the scanning knob 21. In some embodiments, the first spring 71a and the second spring 71b determine a maximum depth 73 (along the X-axis) of the scanhead subassembly 23. In some embodiments, the maximum depth 73 (along the X-axis) of the scanhead subassembly 23 occurs when the first spring 71a and the second spring 71b are at a fully unbiased, compressed position. In some embodiments, the depth 73 of the scanhead subassembly ranges from about 0 centimeters (cm) to about 10 cm. In some embodiments, the depth 73 of the scanhead subassembly ranges from at least about 0 cm. In some embodiments, the depth 73 of the scanhead subassembly ranges from at most about 10 cm. In some embodiments, the depth 73 of the scanhead subassembly ranges from about 0 cm to about 1 cm, about 0 cm to about 2 cm, about 0 cm to about 3 cm, about 0 cm to about 4 cm, about 0 cm to about 5 cm, about 0 cm to about 6 cm, about 0 cm to about 7 cm, about 0 cm to about 8 cm, about 0 cm to about 9 cm, about 0 cm to about 10 cm, about 1 cm to about 2 cm, about 1 cm to about 3 cm, about 1 cm to about 4 cm, about 1 cm to about 5 cm, about 1 cm to about 6 cm, about 1 cm to about 7 cm, about 1 cm to about 8 cm, about 1 cm to about 9 cm, about 1 cm to about 10 cm, about 2 cm to about 3 cm, about 2 cm to about 4 cm, about 2 cm to about 5 cm, about 2 cm to about 6 cm, about 2 cm to about 7 cm, about 2 cm to about 8 cm, about 2 cm to about 9 cm, about 2 cm to about 10 cm, about 3 cm to about 4 cm, about 3 cm to about 5 cm, about 3 cm to about 6 cm, about 3 cm to about 7 cm, about 3 cm to about 8 cm, about 3 cm to about 9 cm, about 3 cm to about 10 cm, about 4 cm to about 5 cm, about 4 cm to about 6 cm, about 4 cm to about 7 cm, about 4 cm to about 8 cm, about 4 cm to about 9 cm, about 4 cm to about 10 cm, about 5 cm to about 6 cm, about 5 cm to about 7 cm, about 5 cm to about 8 cm, about 5 cm to about 9 cm, about 5 cm to about 10 cm, about 6 cm to about 7 cm, about 6 cm to about 8 cm, about 6 cm to about 9 cm, about 6 cm to about 10 cm, about 7 cm to about 8 cm, about 7 cm to about 9 cm, about 7 cm to about 10 cm, about 8 cm to about 9 cm, about 8 cm to about 10 cm, or about 9 cm to about 10 cm. In some embodiments, the depth 73 of the scanhead subassembly ranges from about 0 cm, about 1 cm, about 2 cm, about 3 cm, about 4 cm, about 5 cm, about 6 cm, about 7 cm, about 8 cm, about 9 cm, or about 10 cm. Alternatively, in other embodiments not illustrated in the drawings, the scanning head 21 has a second locking mechanism to lock the scanning knob 21 at various depths along the X-axis. For example, in some embodiments, the user pinches the first retention clip 43a and the second retention clip 43b and disengages the first foot 63a and the second foot 63b, the user is able to depress the entire scanhead subassembly 23 along the X-axis by pressing down on the scanning knob 21 while maintaining both retention clips pinched. In some embodiments, the user further locks the scanhead subassembly 23 in a depressed state (i.e., at a determined depth) by releasing the first retention clip 43a and the second retention clip 43b and allowing the first foot 63a to insert into a third ledge (not shown in the figures) and allowing the second foot 63b to insert into a fourth ledge (not shown in the figures). In some embodiments, the scanhead assembly 23 comprises two or more ledges that enable the user to lock the scanhead assembly 23 at a predetermined depth. In some embodiments, the scanhead assembly 23 comprises about 4, 6, 8, 10, 12, 14, 16, 18, 20, 22, 24, 26, 28, 30, or more ledges.

Figure 22A:
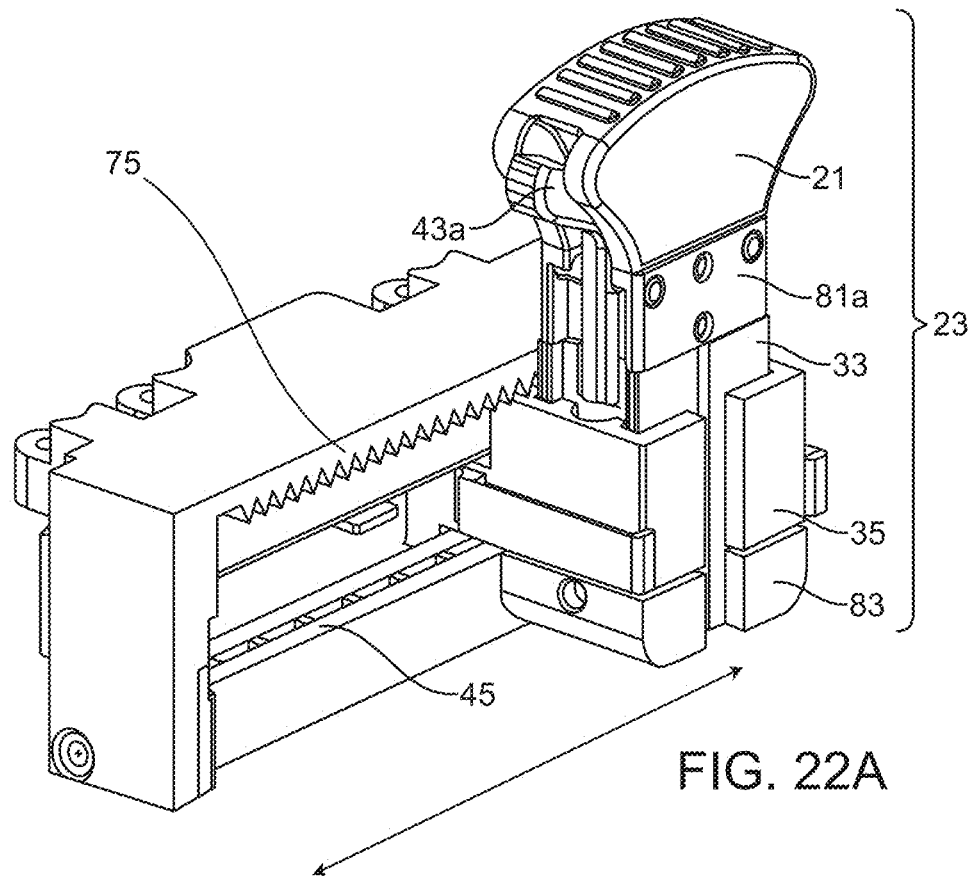
FIGS. 22A-C show an embodiment slider tactile sensing device scanhead subassembly 23 including a scanning track 45 and locking rack and release button or scanning knob retention clip.
Figure 22B:
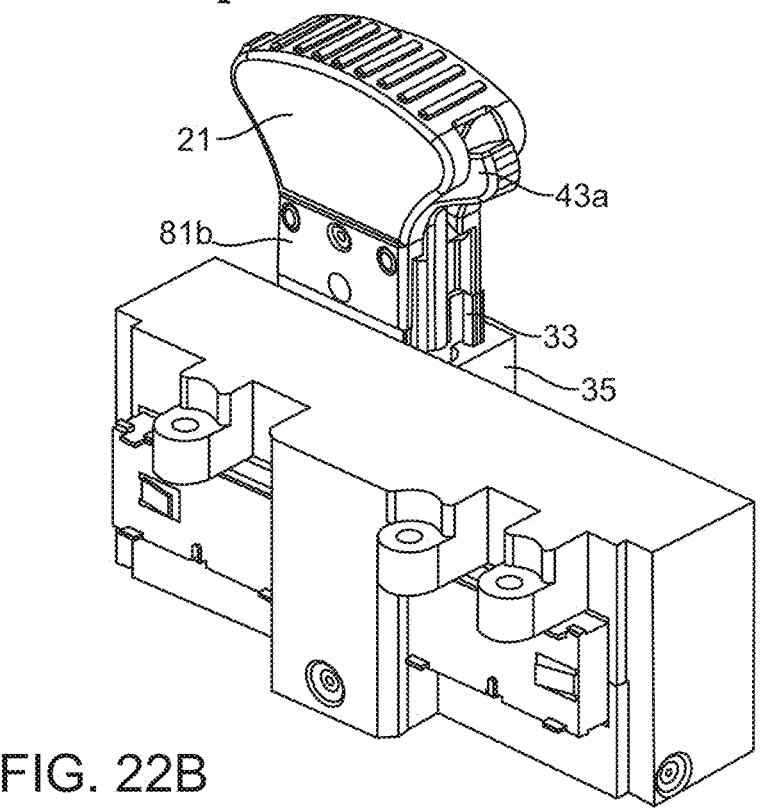
Figure 22C:
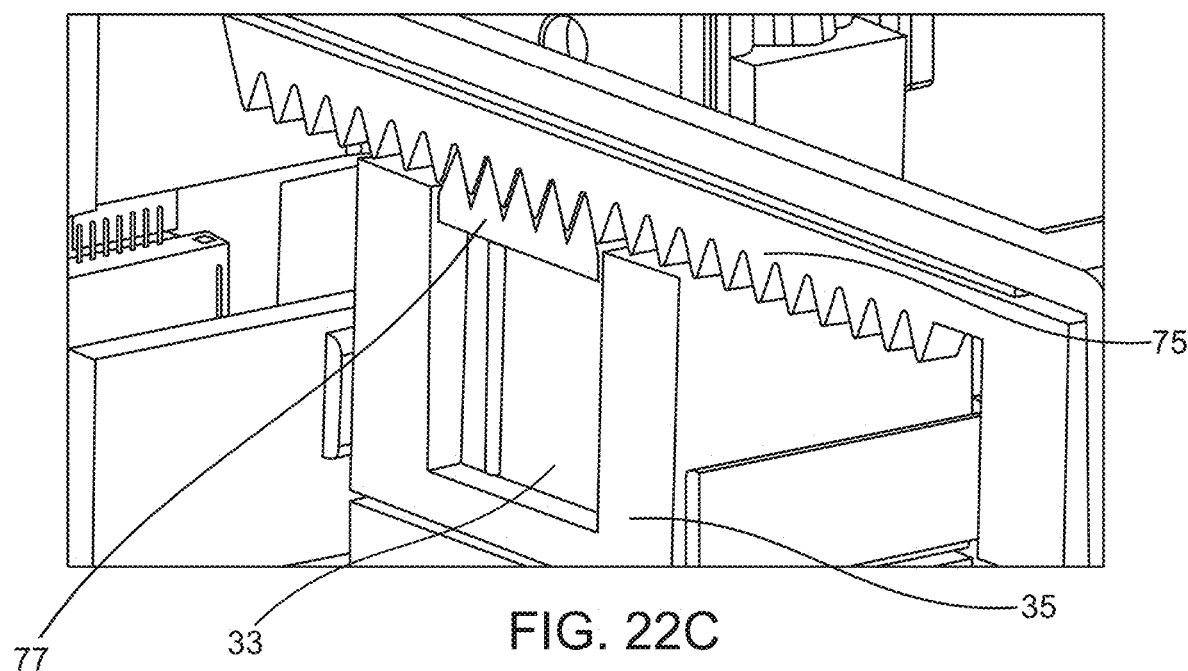

FIGS. 22A-C show how the scanhead subassembly 23 attaches to the slider tactile sensing device 2100. FIG. 22A illustrates an isometric view of the scanhead subassembly 23. In some embodiments, the scanhead subassembly 23 comprises a scanhead 33, a scanning knob 21, and a carriage 35. In some embodiments, the slider tactile sensing device 2100 comprises a scanning track 45 and a locking rack 75. In some embodiments, the slider design comprises a scanning track 45. In some embodiments, the scanning track 45 is part of the main housing frame 19. In some embodiments the scanning track 45 is a removable part that is assembled with the main housing frame 19. In some embodiments, the scanning track 45 comprises a track 45 that is configured to translate the scanhead 33 along the skin surface of the patient. In some embodiments, the scanning track 45 is configured to translate the scanhead 33 along the direction of the arrows shown in FIG. 22A. In some embodiments, the scanning track 45 is configured to receive the carriage 35. In some embodiments, the carriage 35 sits on the scanning track 45. In some embodiments, the carriage 35 glides over the scanning track 45. In some embodiments, the carriage 35 snaps onto the scanning track 45. In some embodiments, the scanning track 45 comprises grooves that allow a scanhead to be locked into place after an insertion site is identified. In some embodiments, the subassembly comprises a locking rack 75 and a release button (not shown in the figures).

In some embodiments, the scanning track 45 allows for about 2.75 inches to about 3 inches of scanhead travel. In some embodiments, the length of the scanning track is based on the distance between the top and bottom of consecutive spinous processes. In some embodiments, the scanning track 45 allows for a scanhead travel distance of about 1 cm to about 10 cm. In some embodiments, the scanning track 45 allows for a scanhead travel distance of at least about 1 cm. In some embodiments, the scanning track 45 allows for a scanhead travel distance of at most about 10 cm. In some embodiments, the scanning track 45 allows for a scanhead travel distance of about 1 cm to about 2 cm, about 1 cm to about 3 cm, about 1 cm to about 4 cm, about 1 cm to about 5 cm, about 1 cm to about 6 cm, about 1 cm to about 7 cm, about 1 cm to about 8 cm, about 1 cm to about 9 cm, about 1 cm to about 10 cm, about 2 cm to about 3 cm, about 2 cm to about 4 cm, about 2 cm to about 5 cm, about 2 cm to about 6 cm, about 2 cm to about 7 cm, about 2 cm to about 8 cm, about 2 cm to about 9 cm, about 2 cm to about 10 cm, about 3 cm to about 4 cm, about 3 cm to about 5 cm, about 3 cm to about 6 cm, about 3 cm to about 7 cm, about 3 cm to about 8 cm, about 3 cm to about 9 cm, about 3 cm to about 10 cm, about 4 cm to about 5 cm, about 4 cm to about 6 cm, about 4 cm to about 7 cm, about 4 cm to about 8 cm, about 4 cm to about 9 cm, about 4 cm to about 10 cm, about 5 cm to about 6 cm, about 5 cm to about 7 cm, about 5 cm to about 8 cm, about 5 cm to about 9 cm, about 5 cm to about 10 cm, about 6 cm to about 7 cm, about 6 cm to about 8 cm, about 6 cm to about 9 cm, about 6 cm to about 10 cm, about 7 cm to about 8 cm, about 7 cm to about 9 cm, about 7 cm to about 10 cm, about 8 cm to about 9 cm, about 8 cm to about 10 cm, or about 9 cm to about 10 cm. In some embodiments, the scanning track 45 allows for a scanhead travel distance of about 1 cm, about 2 cm, about 3 cm, about 4 cm, about 5 cm, about 6 cm, about 7 cm, about 8 cm, about 9 cm, or about 10 cm.

FIG. 22B shows a posterior view of the scanhead subassembly 23 while being attached to the main housing frame 19 of the slider tactile sensing device 2100. Furthermore, FIG. 22C is a cutaway illustration of this same posterior view that further shows the locking mechanism between the scanhead subassembly 23 and the main housing frame 19 of the slider tactile sensing device 2100. In some embodiments, the scanhead 33 comprises a locking insert 77. In some embodiments, the locking insert 77 comprises a sawtooth edge. In some embodiments, the sawtooth edge of the locking insert 77 projects downwards. In some embodiments, the locking insert 77 is protrudes from the posterior side of the scanhead 33. In some embodiments, the locking insert 77 is configured to couple with the locking rack 75. In some embodiments, the locking rack 75 comprises a sawtooth edge. In some embodiments, the locking rack 75 is a sawtooth rack. In some embodiments, the sawtooth edge of the locking rack 75 projects upwards. In some embodiments, the locking insert 77 and the locking rack 75 comprise sawtooth projections that have a same pitch. In some embodiments, the locking insert 77 and the locking rack 75 are configured to lock in place when coupled.

In some embodiments, the locking insert 77 and the locking rack 75 serve as a locking mechanism for the scanhead subassembly 23. In some embodiments, the locking insert 77 and the locking rack 75 lock the carriage in place when the teeth from the locking insert 77 engage with the teeth of the locking rack 75. In some embodiments, in order to translate the scanhead 33 along the scanning track 45, the user depresses, pushes down on, or applies a downward force onto the scanhead subassembly 23 that is enough to disengage the locking insert 77 from the locking rack 75. In some embodiments, when the locking insert 77 and the locking rack 75 are engaged, the scanhead 33 cannot be translated along the scanning track 45. In some embodiments, the user locks the scanhead 33 in place by releasing (i.e., stops pushing down on or applying a downward force to) the scanhead subassembly 23 to its initial position (i.e., a depth of 0 cm), thereby causing the teeth of the locking insert 77 to engage or mate with the teeth of the locking rack 75. In some embodiments, the translation of the scanhead 33 is automated and controlled by the computing device of the slider tactile sensing device 2100.

Figure 23A:
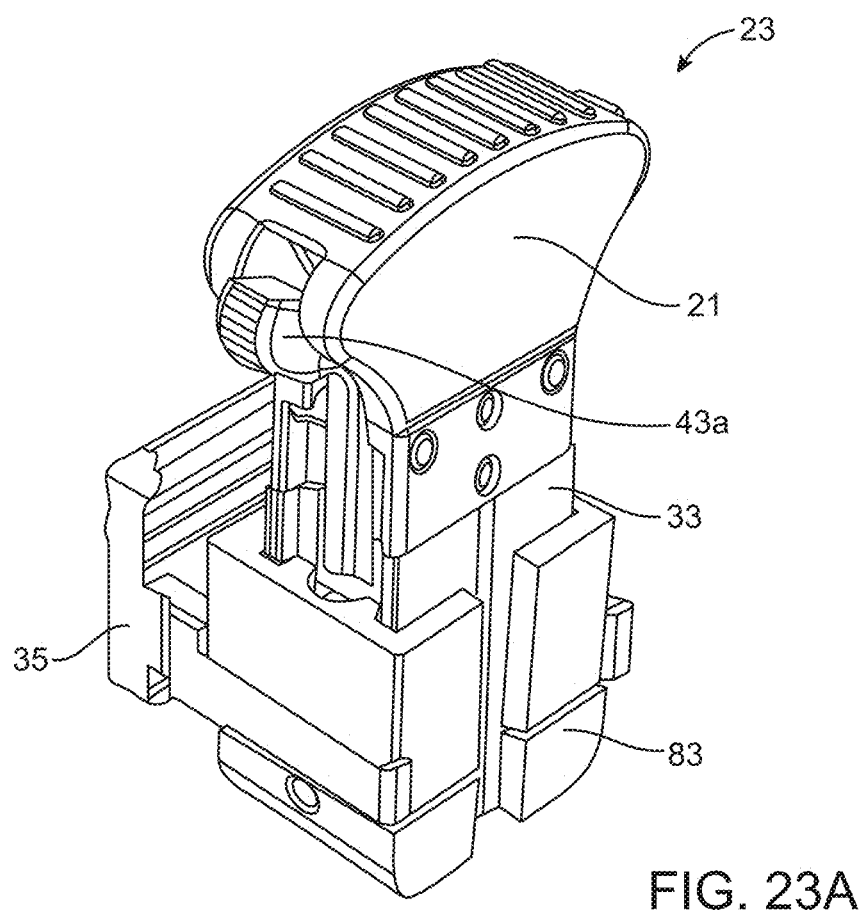
FIGS. 23A-B show assembled and assembly view embodiment of a carriage and scanning knob including two scanning knob retention clips of an embodiment slider tactile sensing device.
Figure 23B:
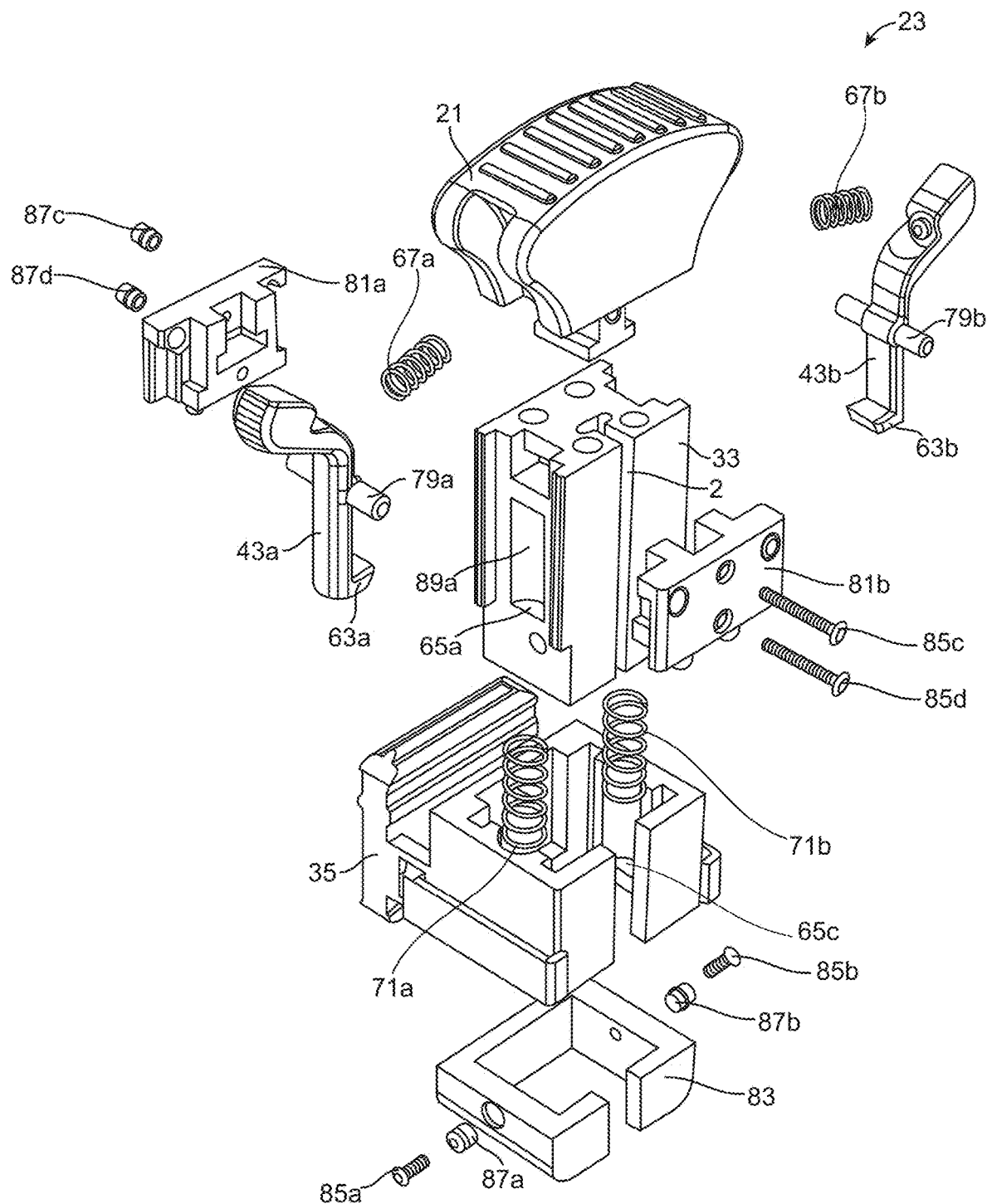

FIGS. 23A-B show an assembled and exploded view of the scanning scanhead subassembly 23, respectively. In some embodiments, the scanhead subassembly 23 comprises a scanning knob 21, scanhead 33, and a carriage 35.

In some embodiments, the scanning knob 21 comprises a first retention clip 43*a* and a second retention clip 43*b*. In some embodiments, the scanning knob 21 enables the user to translate the scanhead 33 along the scanning track 45. In some embodiments, the scanning knob 21 comprises the first retention clip 43*a* and the second retention clip 43*b*. In some embodiments, the scanning knob 21 comprises the first retention clip spring 67*a* and the second retention clip spring 67*b*. In some embodiments, the first retention clip spring 67*a* and the second retention clip spring 67*b* are placed in between the scanning knob 21 and first retention clip 43*a* and the second retention clip 43*b*, respectively, under some tension. In some embodiments, the first retention clip 43*a* comprises a first pin 79*a*, as shown in FIG. 23B. In some embodiments, the second retention clip 43*b* comprises a second pin 79*b*, as shown in FIG. 23B. In some embodiments, the first pin 79*a* is anchored into a first cavity 89*a* of the scanhead 33. In some embodiments, the first foot 63*a* rests on the first ledge 65*a* that is found within the first cavity 89*a*. In some embodiments, the second foot 63*b* rests on the second ledge 65*b* that is found within the second cavity (not shown in FIG. 23B). In some embodiments, the first pin 79*a* is anchored into a second cavity (not shown in FIG. 23B) of the scanhead 33. In some embodiments, the first retention clip 43*a* pivots on the first pin 79*a* and compresses the first retention clip spring 67*a*. In some embodiments, the second retention clip 43*b* pivots on the second pin 79*b* and compresses the second retention clip spring 67*b*.

In some embodiments, the first retention clip 43*a* and the second retention clip 43*b* are further held in place by use of a first plate 81*a* and a second plate 81*b*. In some embodiments, the first plate 81 is secured to a posterior side of the scanhead subassembly 23, as shown in FIG. 23B. In some embodiments, the first plate 81*a* is fastened to the second plate 81*b* via a third bolt 85*c*, a fourth bolt 85*d*, a third nut 87*c*, and a fourth nut 87*d*. In some embodiments, the third bolt 85*c* traverses the anterior surface of the second plate 81*b* and the first plate 81*a* and is furthered fastened by the third nut 87*c*, which is placed and secured on the end of the third bolt 85*c* that protrudes from the first plate 81*a*. In some embodiments, the fourth bolt 85*d* traverses the anterior surface of the second plate 81*b* and the first plate 81*a* and is furthered fastened by the fourth nut 87*d*, which is placed and secured on the end of the fourth bolt 85*d* that protrudes from the first plate 81*a*.

In some embodiments the first plate 81*a* and the second plate 81*b* sit on or attach to the top surface of the scanhead 33, as shown in FIGS. 22A-B. In some embodiments, the scanhead 33 is placed and/or fits within the inner frame of the carriage 35. In other words, in some embodiments, the carriage 35 wraps around the scanhead 33. In some embodiments, the scanhead 33 comprises a third ledge 65*c* and a fourth ledge (not shown in FIG. 23B). In some embodiments, the first spring 71*a* and the second spring 71*b* are located within the carriage 35. In some embodiments, the distal end of the first spring 71*a* sits on the fourth ledge (not shown in FIG. 23B) of the carriage 35, and the distal end of the second spring 71*a* sits on the third ledge 65*c* of the carriage 35. In some embodiments, the proximal end of the first spring 71*a* and the second spring 71*b* contact the distal surface of the scanhead 33. Thus, in some embodiments, the first spring 71*a* and the second spring 71*b* are located in between the scanhead 33 and the carriage 35.

In some embodiments, the distal surface of the scanhead 33 comprises the sensor array. In some embodiments, the scanhead 33 comprises a base 83. In some embodiments, the base 83 secures the distal end of the scanhead 33. In some embodiments, the base 83 wraps around the distal end of the scanhead 33, as shown in FIG. 22A. In some embodiments, the base 83 is fastened to the scanhead 33 via a first bolt 85*a*, a second bolt 85*b*, a first nut 87*a*, and a second nut 87*b*. In some embodiments, the first bolt 85*a* traverses the lateral surface of the base 83 and is furthered fastened by the first nut 87*a*, which is placed and secured on the end of the first bolt 85*a* that protrudes from the base 83, once the bolt is inserted through the base 83. Similarly, in some embodiments, the second bolt 85*b* traverses the lateral surface of the base 83 that is directly opposite to the lateral surface in which the first bolt 85*a* was inserted. In some embodiments, the second bolt 85*b* is furthered fastened by the second nut 87*b*, which is placed and secured on the end of the second bolt 85*b* that protrudes from the base 83, once the bolt is inserted through the base 83.

Scanhead

In some embodiments, the slider design comprises a scanhead 33. In some embodiments, the scanhead 33 is mated to the carriage 35 and moved along the scanning track 45. In some embodiments, the scanhead is depressed relative to the carriage in order to better displace tissue and facilitate imaging. In some embodiments, a first spring and a second spring are strategically placed on the interior, anterior, and posterior edges of the scanhead, between the scanhead and the carriage. In some embodiments, the springs facilitate a range of about 3 centimeters (cm) of scanhead depression into the tissue. In some embodiments, the scanhead is depressed by applying downward pressure to the top of the scanhead. In some embodiments, the scanhead is moved along the scanning track by applying anterior or posterior pressure to the scanhead. In some embodiments, the scanhead is a rolling scanhead, which is rotated to travel the full length of the track. In some embodiments, the bottom surface of the scanhead serves as a platform for a sensor array, as described supra. In some embodiments, the sensor array has 11 rows and 9 columns of sensels, with 1.9 mm spacing. In some embodiments, the sensor array has 12 rows and 8 columns of sensels, with 1.9 mm spacing. In some embodiments, the bottom surface of the scanhead is curved. In some embodiments, the bottom surface of the scanhead has a curvature with a radius of about 75 mm opposite that of the vertebrae. In some embodiments, the bottom surface of the scanhead is about 20×16 mm. In some embodiments, the bottom surface of the scanhead is about 30 mm×21 mm. In some embodiments, the anterior and posterior edges of the scanhead are rounded to allow the scanhead to traverse more smoothly along the skin surface. In some embodiments, the anterior and posterior edges of the bottom of the scanhead are filleted with a diameter of about 8 mm, to allow the scanhead to traverse more smoothly along the skin surface. In some embodiments, edge softeners with fillets of about 10 mm in diameter are connected to the anterior and posterior edges of the bottom surface of the scanhead. In some embodiments, the sensor array is mounted to the bottom surface of the scanhead via an adhesive. In some embodiments, the tails of the sensor are tucked into clips on the side of the carriage. In some embodiments, the tails of the sensor are aligned with registration holes on the interior or exterior anterior and posterior faces of the scanhead.

In some embodiments, the scanhead 33 comprises a needle guide 2, as described supra. In some embodiments, the needle guide is inside of the scanhead. In some embodiments, the needle guide is attached to the scanhead once a target tissue location is identified. In some embodiments, the bottom surface of the needle guide 2 serves as a platform for a sensor array, as described supra. In some embodiments, the bottom surface of the needle guide serves as the distal opening of the needle guide, and is aligned with the slot in the sensor array. In some embodiments, the proximal opening of the needle guide is always exposed. In some embodiments, the needle guide is exposed by removing a top surface from the scanhead. In some embodiments, once the target tissue location is identified, the needle guide is exposed by rotating the scanhead. In some embodiments, once the target tissue location is identified, the scanhead and mounted sensor array are removed to expose the needle guide. In some embodiments, a release mechanism exists that enables the device to be pulled away from the needle after insertion.

In some embodiments, the needle guide, as described supra, is located outside of the scanhead. In some embodiments, the sensor array mounted to the bottom of the surface does not require a slot, as it is not mounted directly beneath the needle guide. In some embodiments, the needle guide is located anterior or posterior to the scanhead. In some embodiments, the needle guide is laterally offset from the scanhead during scanning. In some embodiments, the needle guide is fixed to the carriage. In some embodiments, the needle guide is fixed to the scanhead. In some embodiments, the needle guide is attachable. In some embodiments, a cut exists on the interior of the frame to accommodate the needle guide and allow the scanhead to complete its travel along the scanning track. In some embodiments, the proximal opening of the needle is always exposed. In some embodiments, once a target tissue location is identified, the scanhead and carriage are manually moved along the scanning track until the needle guide aligns with the target tissue location. In some embodiments, once a target tissue location is identified, the scanhead and carriage are automatically moved along the sliding track until the needle guide aligns with the target tissue location. In some embodiments, once the target tissue location is identified, the scanhead is rotated to allow the needle guide to be aligned over the target tissue location. In some embodiments, once a target tissue location is identified, the scanhead and carriage are removed, and the needle guide is attached to the device so as to align with the target tissue location. In some embodiments, the device is detached from the needle guide before insertion. In some embodiments, a release mechanism exists that enables the device to be pulled away from the needle after insertion. In some embodiments, the needle is inserted at a location that is anterior to the scanhead 33. In some embodiments, the needle guide 2 is located on a surface (e.g., an anterior surface or a posterior surface) of the scanhead 33 rather than through the center of the scanhead 33. In some embodiments, the needle is inserted at a location that is posterior to the scanhead 33. In some embodiments, the needle is not inserted through the scanhead 33. In other words, in some embodiments, the scanhead 33 does not comprise a needle guide 2 traversing the center of the scanhead 33. In some embodiments, the scanhead 33 does not comprise the needle guide 2. For example, in some embodiments, the needle guide 2 is reversibly attached to the scanhead 33. In some embodiments, the needle guide is not located through the center of the scanhead 33. In some embodiments, the scanhead does not comprise a slot 38.

Scanning Knob

Figure 24A:
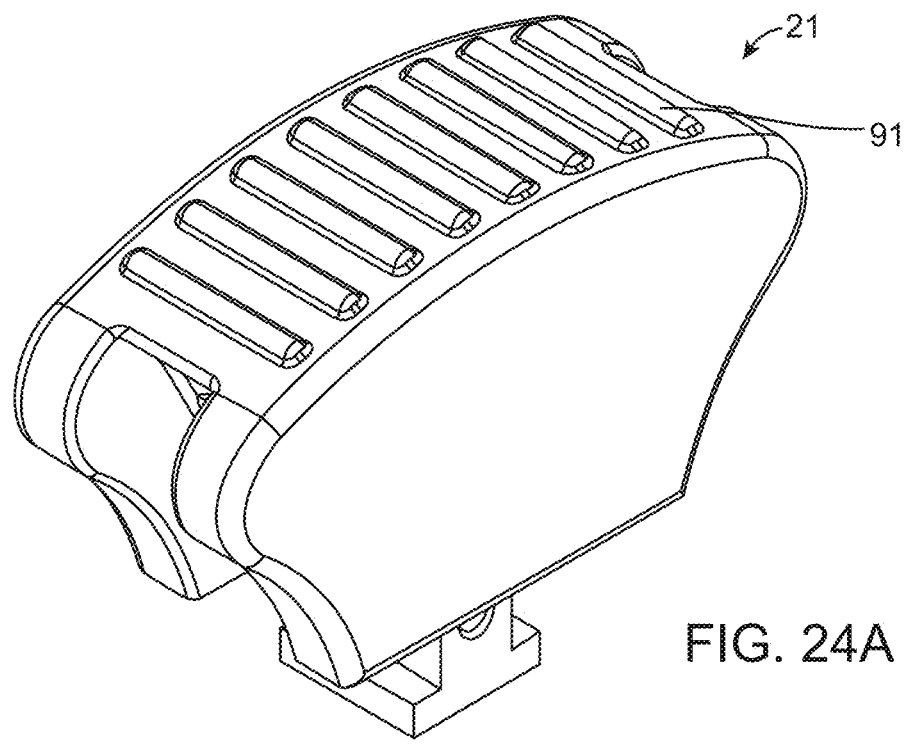
FIGS. 24A-C show embodiment scanning knobs for the tactile sensing device.
Figure 24B:
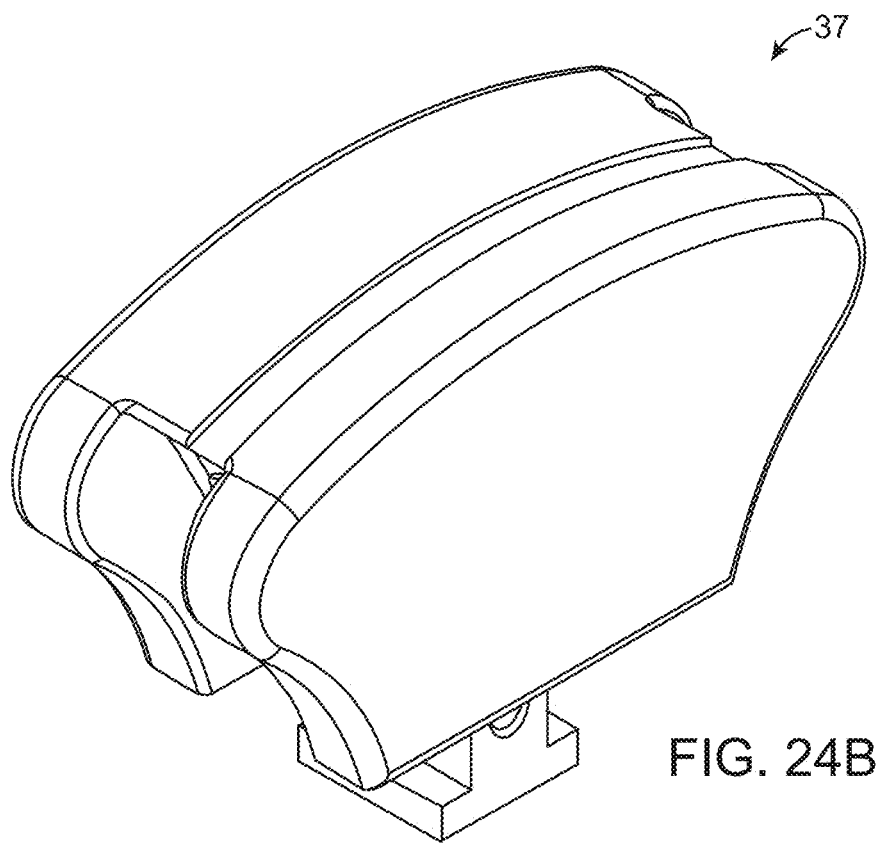
Figure 24C:
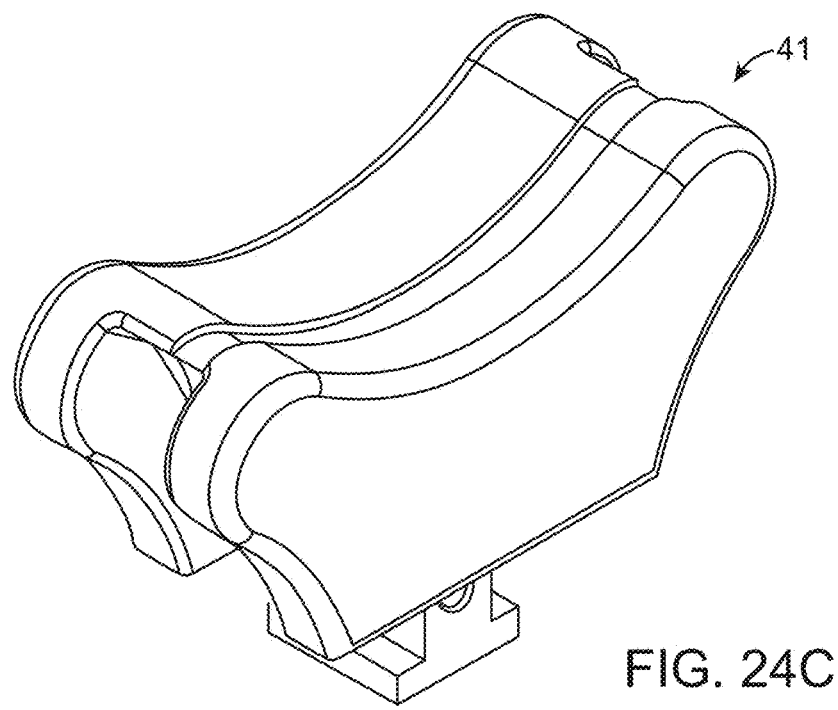

In some embodiments, the slider design comprises a scanning knob 21. In some embodiments, the scanning knob is removable. In some embodiments, the scanning knob is fixed. FIGS. 24A-C show embodiment scanning knobs for the tactile sensing device. In some embodiments, the scanning knob is part of the scanhead. In some assemblies, the scanning knob 21 is attached to the top surface of the scanhead. In some embodiments, the scanning knob 21 comprises ribs 91, as shown in FIG. 24A. In some embodiments, the scanning knob 21 does not comprise ribs. In some embodiments, the scanning knob is a convex scanning knob 37, as shown in FIG. 24B. In some embodiments, the convex scanning knob 37 is a scanning knob comprising a proximal surface (with respect to the user) that is curved like the exterior of a circle and/or a sphere. In some embodiments, the convex scanning knob 37 comprises ribs. In some embodiments, the convex scanning knob 37 does not comprise ribs. In some embodiments, the scanning knob is a concave scanning knob 41, as shown in FIG. 24C. In some embodiments, the concave scanning knob 41 is a knob that comprises a proximal surface (with respect to the user) that curves inward like the interior of a circle and/or a sphere. In some embodiments, the concave scanning knob 37 comprises ribs. In some embodiments, the concave scanning knob 37 does not comprise ribs. In some embodiments, the scanning knob 21 is used to move the scanhead and carriage along the scanning track 45. In some embodiments, the scanning knob is used to move the scanhead proximally and distally (i.e. toward and away from the patient, respectively) relative to the carriage. In some embodiments, the travel of the scanhead 33 along the scanning track, and proximal and distal movement are controlled by the same mechanism. In some embodiments, the travel of the scanhead 33 along the track and the travel of the scanhead 33 relative to the carriage are controlled by independent mechanisms. In some embodiments, movement relative to the carriage prevents movement along the track. In some embodiments a pintle is used to lock the position of the carriage and scanhead during proximal and distal movement of the scanhead. In some embodiments, the scanning knob comprises a button that is configured to release the scanhead from its locked position relative to the carriage. In some embodiments, the scanning knob comprises a button that is configured to release the carriage from its locked position along the track. In some embodiments, an indicator exists to alert to locking of the scanhead in its position along the track or relative to the carriage. In some embodiments, movement of the scanhead is automated. In some embodiments, movement of the scanhead is non-automated and controlled by a user. In some embodiments, movement of the scanhead is controlled by a user via buttons. In some embodiments, movement in the proximal and distal direction is controlled by a mechanism located at the top of the scanning knob. In some embodiments, movement along the scanning track is controlled by a mechanism located on the side of the scanning knob. In some embodiments, movement along the scanning track is controlled by a user via push buttons. In some embodiments, the scanning knob is pushed proximally and distally to allow for travel relative to the carriage. In some embodiments, the scanning knob is pushed anteriorly and posteriorly to allow for travel along the scanning track. In some embodiments, the scanning knob has a rotary dial that is rotated to move the carriage along the scanning track 45. In some embodiments, the scanning knob has a rotary dial that is rotated to move the scanhead proximally and distally relative to the carriage. In some embodiments, the scanhead is moved relative to the carriage via a mechanical actuator. In some embodiments, the scanhead is automatically moved relative to the carriage to a level dictated by patient characteristics, such as body mass index (BMI). In some embodiments, the tactile sensing device comprises a mechanism that locks movement along the track and relative to the carriage. In some embodiments, partial images of captured areas are displayed while the scanning cycle is being completed. In some embodiments, areas currently being acquired are highlighted for clarity. In some embodiments, the scanning process of the slider workflow is most similar to the manual palpation-landmarking process. In some embodiments, the scanning knob is removed to expose a needle guide. In some embodiments, the scanning knob comprises at least one scanning knob retention clip 43a or 43b to secure it to the scanhead 33, as shown in FIGS. 23A and 23B. In some embodiments, scanning knob retention clips are metal or plastic clips that may include living springs or hinges. In some embodiments, scanning knob retention clips are secured to the scanhead. In some embodiments, scanning knob retention clips are pinched to disengage the scanning knob. In some embodiments, at least one button is included to detach the scanning knob. In some embodiments, the carriage 35 is fixed upon disengagement of the scanning knob.

Carriage

In some embodiments, the carriage 35 is reversibly secured around one or more sides of the scanhead 33. In some embodiments, the carriage 35 interacts with the locking rack 75 thereby causing the scanhead subassembly 23 to lock in place. In some embodiments, the carriage 35 contacts the scanning track 45, thereby enabling the scanhead 33 to be translated along the scanning track 45. In some embodiments, the carriage 35 is inserted into the scanning track 45 and used to traverse a scanhead 33 along the spine. In some embodiments, the carriage is magnetically mated to the track. In some embodiments, mating of the carriage 35 with the scanning track 45 is further bolstered through the use of pre-compressed springs. In some embodiments, silicone or other materials are used on the sliding surface between the carriage 35 and scanning track 45 to provide friction and support mating.

In some embodiments, the slider design comprises a position sensor (not shown in the figures). In some embodiments, the position sensor tracks the position of the carriage 35 relative to the scanning track 45. In some embodiments, the position sensor is a linear or multi-turn rotary potentiometer. In some embodiments the position sensor is a magnetic linear encoder, such as, but not limited to a Hall-effect sensor. In some embodiments, the position sensor is a potentiometer, with a wiper contact connected to a linear or rotational shaft, which forms an adjustable voltage divider relative to two end connections, and outputs a resistance proportional to wiper position along the shaft. In some embodiments, a reference voltage is applied across the fixed end connections, and the output voltage is taken from the wiper contact as it moves along the shaft. In some embodiments, the output voltage is inputted to the PCBA in the UI module 1.

In some embodiments, the tactile sensing device comprises a computer program that converts the output voltage to a relative wiper position. In some embodiments the position sensor is a slide potentiometer, which is integrated into the frame parallel to the scanning track 45, with the wiper inserted into a cut in the scanhead 33, such that the output voltage is proportional to the position of the scanhead 33 during scanning. In some embodiments, the calculated position is displayed or reflected in the real-time pressure map 6. In some embodiments, the position sensor is a linear potentiometer with a separate wiper attached to the scanhead 33. In some embodiments, the position sensor is a multi-turn rotary potentiometer. In some embodiments, the position sensor is a magnetic linear encoder, with one or more Hall-effect sensors in the frame. In some embodiments, the position sensor is an optical linear encoder. In some embodiments, the position sensor is a time-of-flight sensor.

Figure 25A:
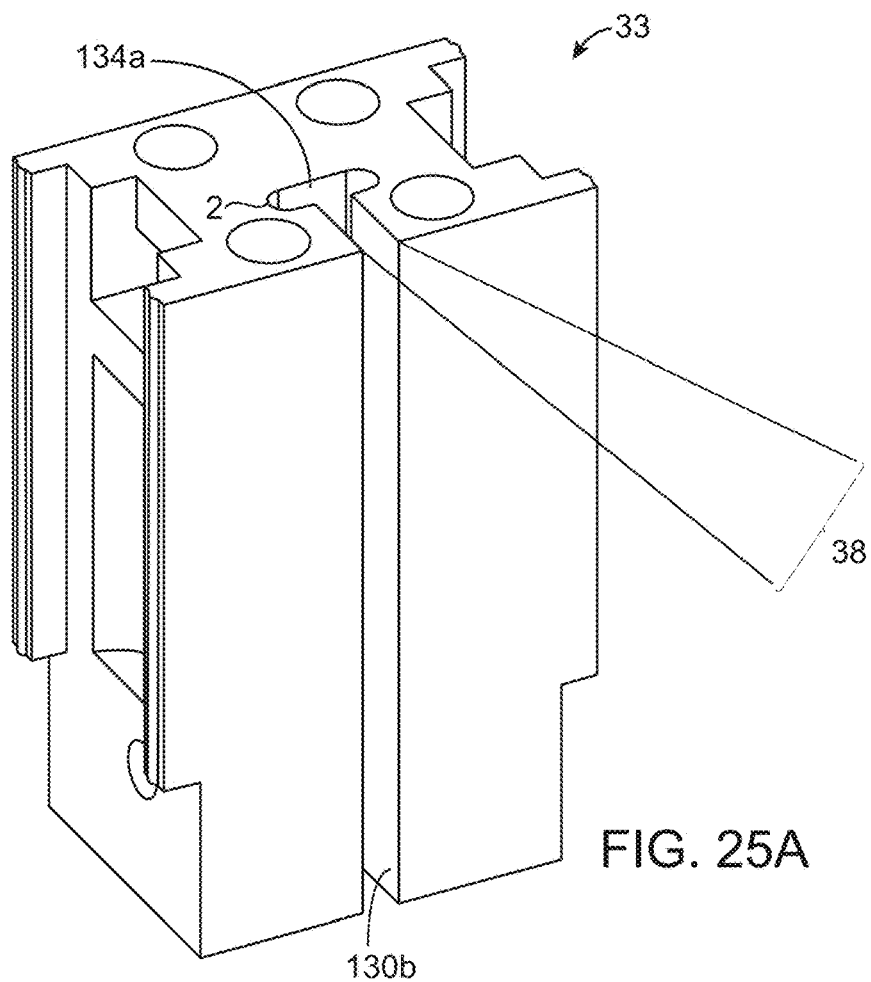
FIGS. 25A-B show embodiment scanhead including a needle track having a proximal needle track opening that tapers to the distal needle track opening.
Figure 25B:
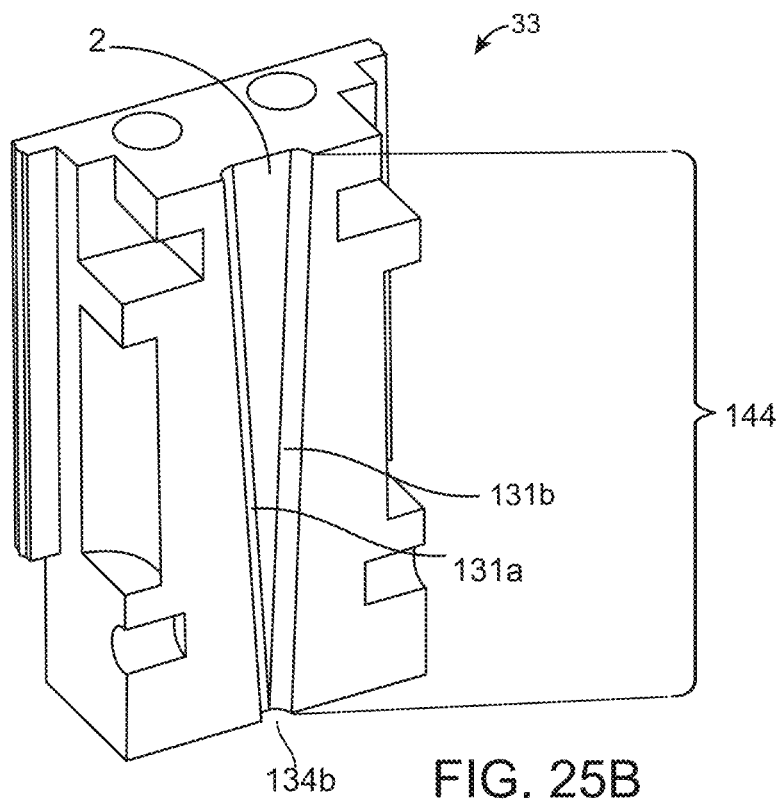

FIGS. 25A-B show an embodiment scanhead 33 comprising a needle guide 2 having a proximal opening 134*a* that tapers to the distal opening 134*b*; FIG. 25B shows the scanhead 33 of FIG. 25A cut away through the needle guide 2. In some embodiments, the scanhead 33 comprises a slot 38, as shown in FIG. 25A. In some embodiments, the slot 38 comprises a first slot wall 130*a* (not shown in FIG. 25A) and a second slot wall 130*b* (shown in FIG. 25A). In some embodiments, the slot 38 provides the user with lateral access to the needle guide 2, as described elsewhere herein in other embodiments. In some embodiments, the needle guide 2 comprises a first needle guide wall 131*a* and a second needle guide wall 131*b*, as shown in FIG. 25B. In some embodiments, the first needle guide wall 131*a* and a second needle guide wall 131*b* connect and form the track 144 of the needle guide 2. In some embodiments, the needle guide is reversibly attached to the tactile sensing device. In some embodiments, the needle comprises a notch.

Figure 26A:
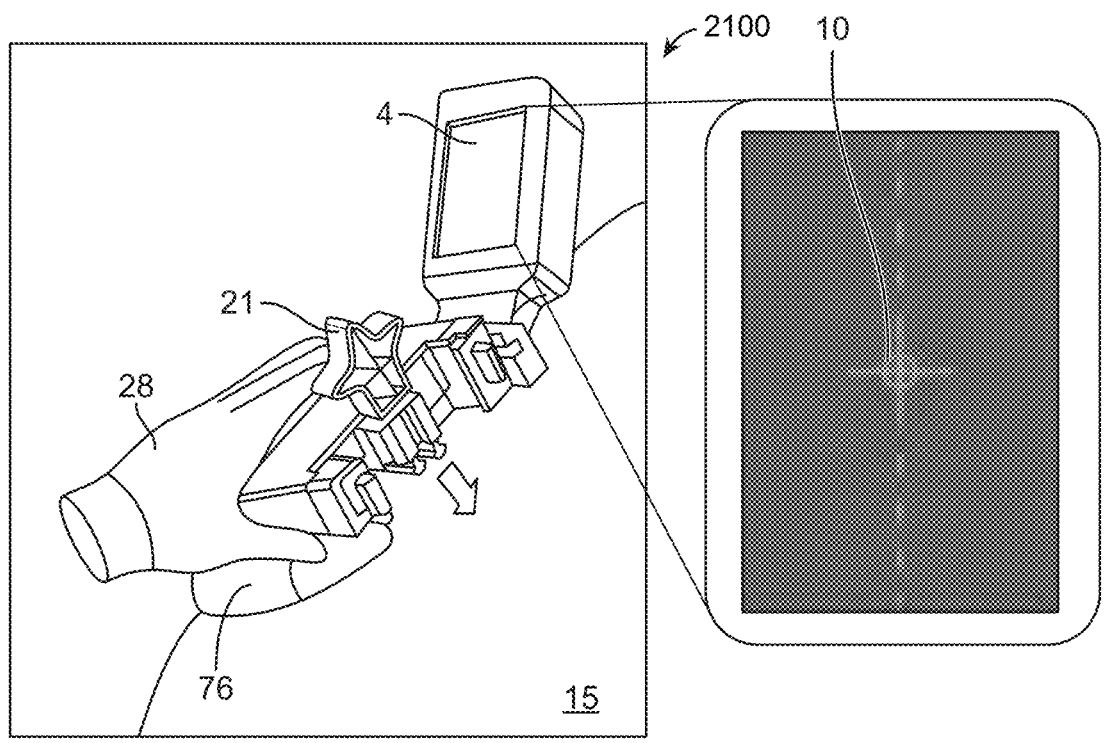
FIGS. 26A-D show the workflow of how a user utilizes the tactile sensing device comprising the slider design when imaging a target tissue location of a patient.
Figure 26B:
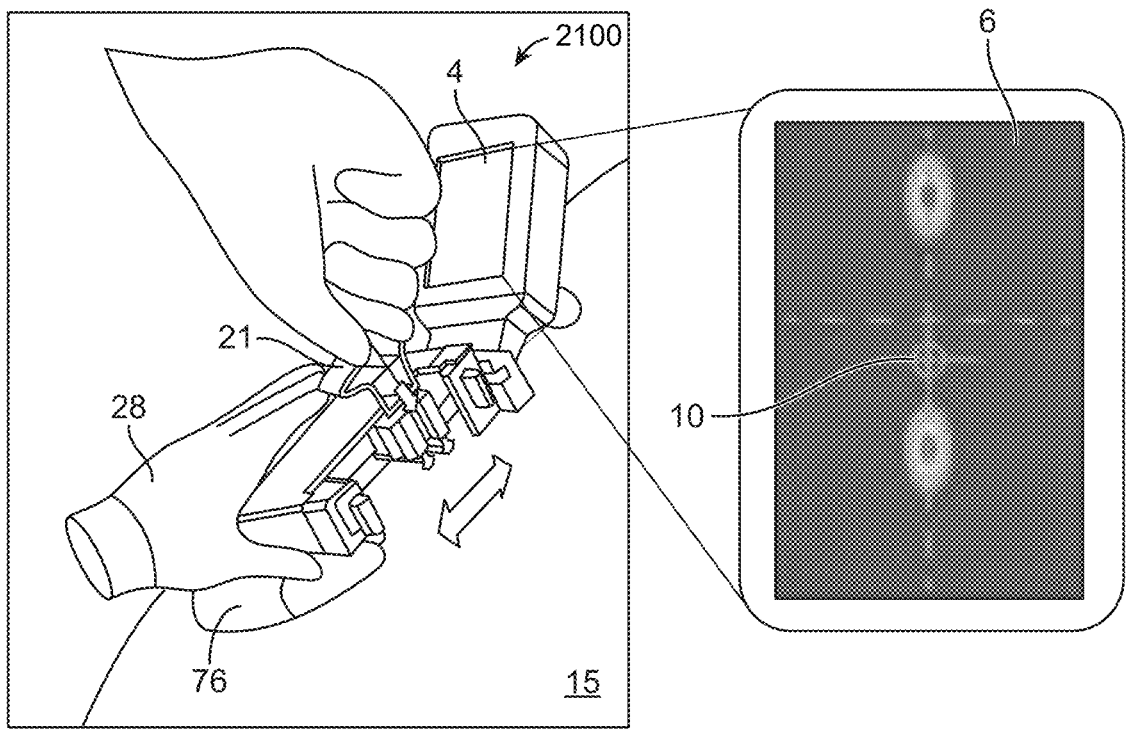

FIGS. 26A-D show the workflow of how a user utilizes the tactile sensing device 2900 comprising the slider design when imaging a target tissue location of a patient. In some embodiments, the tactile sensing device comprising a slider design comprises a reusable UI module, a sleeve, and a reusable charging station, as described supra. In some embodiments, the tactile sensing device comprises a UI module 1 and a scanning knob 21 that are reversibly coupled to the main housing frame 19. In some embodiments, the user inserts the scanning knob 21 into the main housing frame 19 (i.e., into the scanhead 33). Next, in some embodiments, the user visually locates the general area of the target tissue location (e.g., spinous processes). Next, in some embodiments, the user places the tactile sensing device on the skin surface of the patient, ensuring the device is perpendicular to the target tissue location (e.g., the spine), as shown in FIG. 26A. FIG. 26B shows the user 28 applying a constant downward pressure on the scanning knob 21, through the sensor array, and onto the skin surface of the patient. In some embodiments, the user 28 translates the scanning knob 21 up and down over the skin surface of the patient (e.g., over the spinous processes of the patient).

Figure 26C:
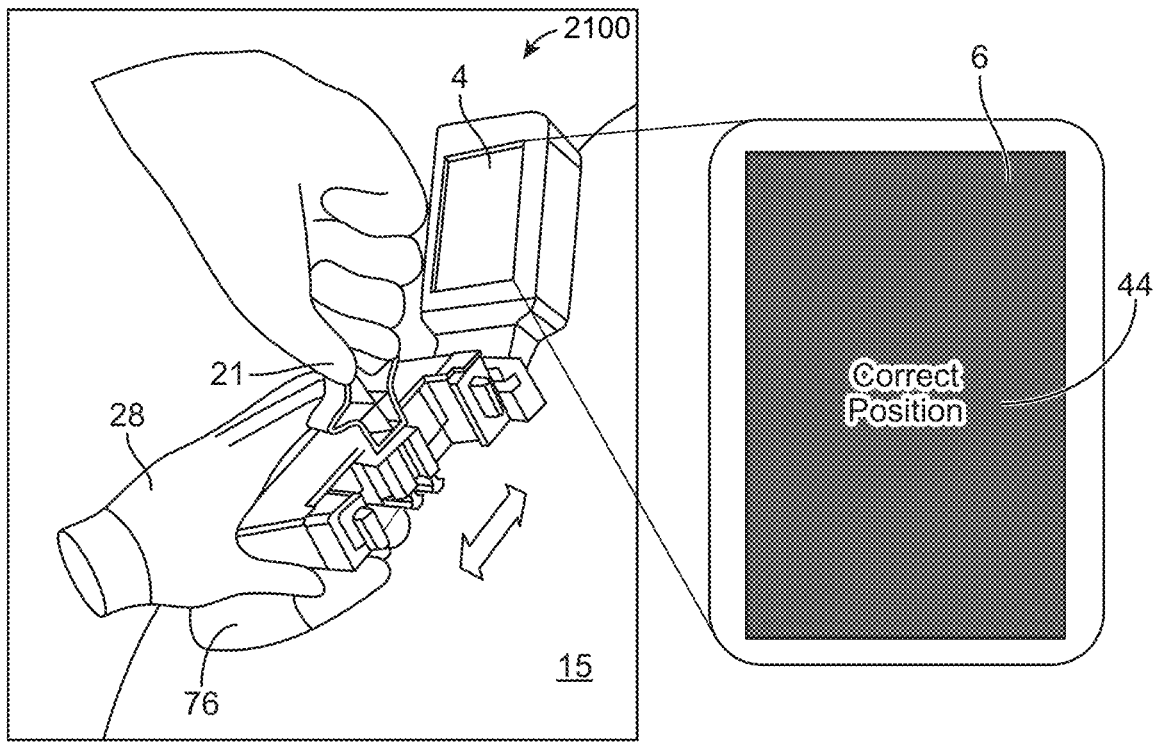
Figure 26D:
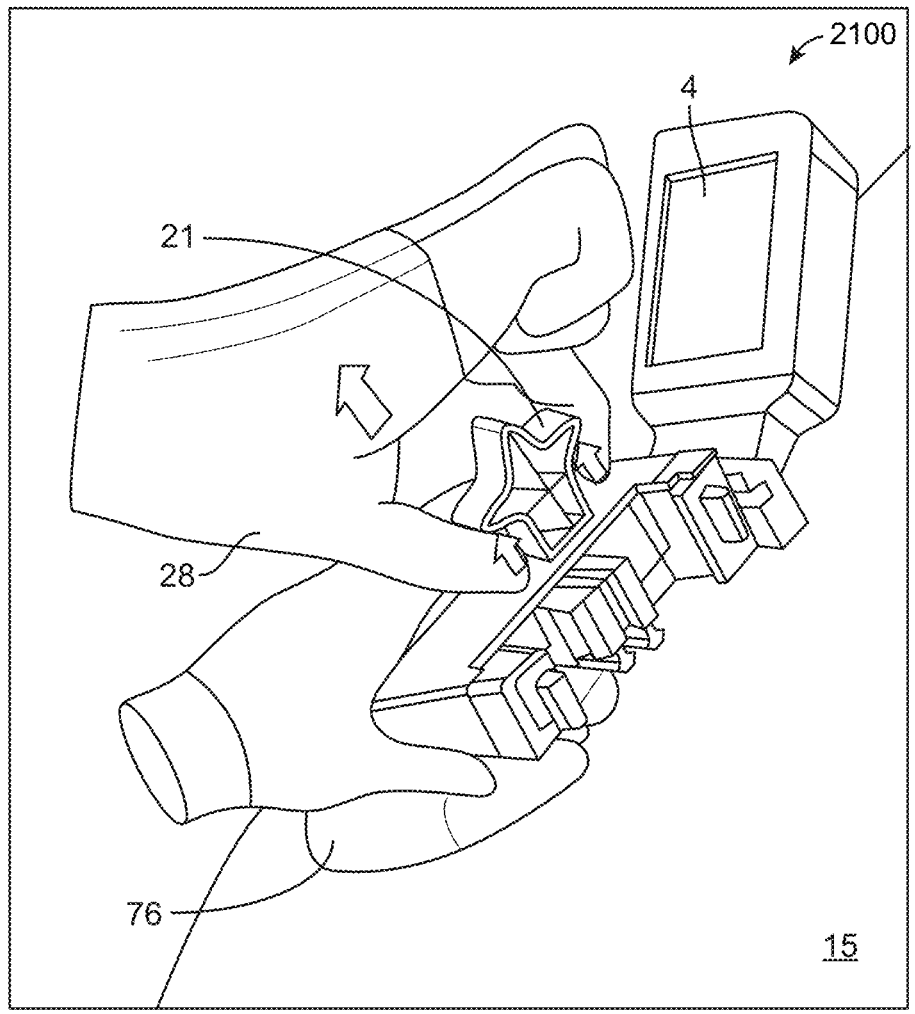

In some embodiments, once the complete image of the target tissue location is acquired, the tactile sensing device prompts the user when the needle guide is at correct location, as shown in FIG. 26C. In some embodiments, upon correct alignment of the needle guide, the user 28 detaches the scanning knob 21 by pulling it up in order to release it from the main housing frame 19, as shown in FIG. 26D. In some embodiments, the scanning knob is detached by pinching at least two clips that releases the knob from the main housing frame 19. In some embodiments, the user locks the scanhead 33 in place by releasing the scanning knob from the main housing frame 19. In some embodiments, releasing the scanning knob from the main housing frame 19 exposes the needle guide. Next, in some embodiments, the user proceeds to insert the needle into the needle guide. In some embodiments, the tactile sensing device comprises a needle retention clip configured to keep the needle and device in place.

Kits

In some embodiments, a tactile sensing device kit comprises a disposable needle; sleeve; subassembly comprising a main housing frame 19 and scanning track 45; and subassembly comprising a scanning knob, carriage, and scanhead. In some embodiments, a tactile sensing device kit comprises a disposable needle; sleeve; power grip handle; and subassembly comprising a main housing frame 19 and curved sensor applicator. In some embodiments, the tactile sensing device kit consists of sterilized and disposable components. In some embodiments, the tactile sensing device kit is packaged in a pre-sealed sterilized bag or blister tray. In some embodiments, the UI module is part of a reusable main housing frame 19 and is not part of the tactile sensing device kit. In some embodiments reusable tactile sensing device components are hygienically cleaned.

Historical and Real Time Image Visualization

In some embodiments, the tactile sensing device comprises a computing device. In some embodiments, the computing device comprises a computer program. In some embodiments, the computer program is, for example, software, including computer algorithms, computer codes, and/or programs, which manages the device's hardware and provides services for execution of instructions such as real-time imaging. In some embodiments, the tactile sensing device comprises a computer algorithm to build up an image from at least two images. In some embodiments, the algorithm takes as an input the type of tactile sensing device being used. In some embodiments, the algorithm automatically determines the type of tactile sensing device being used. In some embodiments, the algorithm automatically selects image-display steps depending on the type of tactile sensing device being used. In some embodiments, the algorithm adjusts drive voltage based on a header in an equilibration file. In some embodiments, imaging is initiated by pressing a touchscreen or physical button. In some embodiments, imaging is automatically initiated when the device is pressed against a skin surface. In some embodiments, the algorithm drives the sensor array and captures sensor data for the current time. In some embodiments, the algorithm applies a Gaussian filter to current data. In some embodiments, the algorithm determines the active area of the current data. In some embodiments, the active area of the current data is determined by obtaining an ordered list of data rows, ignoring rows below a cutoff, and determining the indices of the largest contiguous region of rows above a cutoff. In some embodiments, the active area of the current data is automatically determined based on known scanhead size and current scanhead position. In some embodiments, current scanhead position is determined from a position sensor, such as a potentiometer. In some embodiments, a polynomial approximation of the current data is used in order to apply a flat-field correction to remove artifacts. In some embodiments, the current data are scaled between 0 and 1 by dividing by the sum of the current data and mapping to the scale of displayed data for the previous time. In some embodiments, current displayed data is determined by finding the maximum for each pixel when comparing the current data to the previous displayed data. In some embodiments, the current displayed data is the cumulative sum of previously displayed data. In some embodiments, the current displayed data is then saved as the previous displayed data. In some embodiments, the current displayed data is displayed to the screen of the tactile sensing device. In some embodiments, an imaging cycle is completed when the full sensor array area has been rocked against the target tissue location. In some embodiments, an imaging cycle is completed when a scanhead has been translated along the full length of a scanning track 45. In some embodiments, the active area is highlighted on the display using rectangular or circular patches. In some embodiments, the algorithm displays a line corresponding to the midline. In some embodiments, the algorithm displays a crosshair corresponding to the location of the needle relative to the current display data. In some embodiments, the display screen displays an arrow indicating the direction in which the tactile sensing device should be moved to localize the target tissue location. In some embodiments, the algorithm takes as inputs a patient identifier, patient weight, and patient height. In some embodiments, the algorithm can change screen brightness based on brightness input from a touchscreen or physical button. In some embodiments, the algorithm can change the colormap based on input from a touchscreen or physical button. In some embodiments, the algorithm takes as an input a sensitivity factor. In some embodiments, the sensitivity factor is selected using a touchscreen or physical button, or a dial. In some embodiments, the sensitivity factor is used to rescale the colormap of currently displayed data. In some embodiments the sensitivity factor is used to adjust the drive voltage. In some embodiments, the sensitivity factor is used as the cutoff in determining the active area of current data. In some embodiments, sensitivity is automatically adjusted based on patient BMI, as inputted or calculated from height and weight. In some embodiments, the algorithm displays a splash screen before imaging is initiated. In some embodiments the user can press a touchscreen or physical button to access a menu of input items. In some embodiments, the user can scroll through menu items using touchscreen or physical buttons or a dial. In some embodiments, the algorithm contains steps for equilibration and calibration of the sensor array. In some embodiments, the user can remove high points that show up in current displayed data during application of no force by pressing a touchscreen or physical tare button. In some embodiments, the algorithm automatically removes high points during zero-force application. In some embodiments, the user can refresh the current displayed data by pressing a touchscreen or physical refresh button. In some embodiments, the algorithm can detect if the device is aligned with the midline. In some embodiments the algorithm uses position sensors, such as an accelerometer, to detect if the device is aligned with the midline. In some embodiments, the algorithm can alert the user to off-midline imaging. In some embodiments, the algorithm can automatically refresh the currently displayed data if it corresponds to off-midline imaging. In some embodiments, the algorithm can detect if the tactile sensing device has changed orientation or been moved laterally during an imaging cycle. In some embodiments the algorithm can detect device movement using a position sensor, such as a potentiometer, or a magnetic or optical sensor. In some embodiments, the algorithm can alert the user to device movement during an imaging cycle. In some embodiments, the algorithm can automatically refresh currently displayed data if it detects incorrect device reorientation or movement.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

Example 1: Diagnostic Spinal Puncture Using a Tactile Sensing Device

A health care worker performing a spinal puncture on an obese subject places the tactile sensing device on the lumbar region of the subject. A pressure map, viewed as a heat map by the health care worker, appears on the display screen 4 of the tactile sensing device 100. The heat map indicates bone structures, in this case spinous processes of the lumbar vertebrae, by representing these in red color base and indicates non-bone structures by representing these in a blue color base. The tactile sensing device simultaneously computes a needle projection and displays it on the pressure map in real time as the health care worker advances a needle into the subject. The health care worker adjusts the tactile sensing device's needle guide angle to a cephalad angle degree between 9° and 15°. After identifying a gap between two of the lumbar vertebrae, for example L2 and L3, the health care worker inserts a spinal needle into the tactile sensing device's needle guide. The health care worker uses the needle guide and the needle projection (adjusted in real time) and heat map (shown in real time) on the screen to simultaneously guide the needle into the subarachnoid space. The health care worker then collects the cerebrospinal fluid (CSF). Once all CSF samples are collected, the health care worker uses the tactile sensing device's 100 electronic pressure sensor, which automatically displays the CSF pressure on the display screen in real time, to measure and record the subject's intracranial pressure.

Example 2: Epidural Administration of a Therapeutic Using a Tactile Sensing Device A health care worker performing an epidural administration of an anesthetic on a pregnant patient to places the tactile sensing device on the lumbar region of the pregnant patient. A pressure map, viewed in real time as a heat map by the health care worker, appears on the display screen of the tactile sensing device. The heat map indicates bone structures, in this case, spinous processes of the lumbar vertebrae, by representing these in a darker hue and indicates non-bone structures by representing these in a lighter hue. The tactile sensing device simultaneously computes a projected subcutaneous needle location in real time and displays it on the pressure map. The health care worker adjusts the tactile sensing device's needle guide track angle to a cephalad angle degree between 0° and 15°. After identifying a gap between two of the lumbar vertebrae, for example L2 and L3, the health care worker inserts a spinal needle into the tactile sensing device's needle guide from the proximal opening of the needle guide toward the distal opening of the needle guide, which is closest to the patient, aligning the needle in a track of the needle guide. In the epidural case, the health care worker optionally attaches a loss-of-resistance syringe to the needle hub, to better detect epidural-space entry before or after placement of the needle into the needle guide. The health care worker uses the projected subcutaneous needle location, the original needle insertion site, and the heat map, both shown in real time and continuously adjusting their output (i.e. voltage data and needle location), displayed on the display screen to guide the needle into the epidural space and inject the anesthetic. The device is removed by the health care worker prior to removing the needle from the patient by moving the device such that the needle tracks along the slot of the device, which slot connects to the needle guide.

Example 3: Epidural Administration of a Therapeutic Using a Tactile Sensing Device Having a Notch A health care worker performing an epidural administration of an anesthetic on a pregnant patient to places the tactile sensing device on the lumbar region of the pregnant patient. A pressure map, viewed in real time as a heat map by the health care worker, appears on the display screen of the tactile sensing device. The heat map indicates bone structures, in this case, spinous processes of the lumbar vertebrae, by representing these in a darker hue and indicates non-bone structures by representing these in a lighter hue. The tactile sensing device simultaneously computes a projected subcutaneous needle location in real time and displays it on the pressure map. The health care worker adjusts the tactile sensing device's needle guide track angle to a cephalad angle degree between 0° and 15°. After identifying a gap between two of the lumbar vertebrae, for example L2 and L3, the health care worker inserts a spinal needle into the notch of a tactile sensing device's needle guide, aligning the needle in a track of the needle guide. In the epidural case, the health care worker optionally attaches a loss-of-resistance syringe to the needle hub, to better detect epidural-space entry before or after placement of the needle into the needle guide. The health care worker uses the projected subcutaneous needle location, the original needle insertion site, and the heat map, both shown in real time and continuously adjusting their output (i.e. voltage data and needle location), displayed on the display screen to guide the needle into the epidural space and inject the anesthetic. The device is removed by the health care worker prior to removing the needle from the patient by moving the device such that the needle overcomes the lip of the notch and thereafter tracks along the slot of the device.

What is claimed is:

1. A tactile sensing device, comprising a scanhead sub-assembly comprising:
   a scanhead comprising a sensor array, the sensor array comprising: a first sensor comprising a first surface, a second sensor comprising a second surface, wherein the first sensor is configured to output a first voltage signal in response to a first change in a first pressure applied to the first surface, and the second sensor is configured to output a second voltage signal in response to a second change in a second pressure applied to the second surface; and
   a needle guide comprising a proximal opening and a distal opening, and a needle guide track therebetween, and
   a frame to which the scanhead sub-assembly is moveably coupled,
   wherein the scanhead comprises an undepressed position and a depressed position, the depressed position being distal to the frame as compared to the undepressed position.

2. The tactile sensing device of claim 1, wherein the scanhead sub-assembly further comprises a biasing element that biases the scanhead in the undepressed position.

3. The tactile sensing device of claim 2, wherein the biasing element is a spring.

4. The tactile sensing device of claim 1, wherein the scanhead sub-assembly further comprises a lock configured to lock a position of the scanhead or the needle guide relative to the frame.

5. The tactile sensing device of claim 4, wherein the lock is a pintle locking mechanism or a sawtooth locking mechanism.

6. The tactile sensing device of claim 1, wherein the scanhead sub-assembly further comprises a lock configured to lock a position of the scanhead or the needle guide relative to a length of the frame when the scanhead is in the depressed position.

7. The tactile sensing device of claim 1, wherein the scanhead sub-assembly further comprises a scanning knob, wherein the scanning knob is attached to the scanhead and configured to enable a user to move the scanhead.

8. The tactile sensing device of claim 1, wherein the scanhead or the needle guide is configured to be translated along a length of the frame.

9. The tactile sensing device of claim 1, wherein the tactile sensing device further comprises a position sensor configured to track the position of the scanhead or the needle guide relative to the frame.

10. The tactile sensing device of claim 1, wherein the needle guide is configured to receive the needle or a marking tool.

11. The tactile sensing device of claim 1, wherein the needle guide further comprises a securing mechanism configured to accommodate a plurality of needle gauges.

12. The tactile sensing device of claim 1, wherein the needle guide is angled at a treatment angle that is fixed.

13. The tactile sensing device of claim 1, wherein the needle guide is angled at a treatment angle that is adjustable.

14. The tactile sensing device of claim 1, wherein the needle guide is reversibly attached to the scanhead.

15. The tactile sensing device of claim 1, wherein the needle guide has a slot that is that enables the tactile sensing device to be pulled away from the needle.

16. The tactile sensing device of claim 15, wherein the needle guide further comprises a gate engageable by a user, the gate preventing the needle from sliding out of the slot or the needle guide track when the gate is engaged.

17. The tactile sensing device of claim 1, wherein the scanhead sub-assembly further comprises a carriage configured to receive the scanhead.

18. The tactile sensing device of claim 17, wherein the scanhead is configured to be depressed relative to the carriage.

19. The tactile sensing device of claim 1, wherein the sensor array is adhered to a posterior surface of the scanhead.

20. A tactile sensing system comprising:
- a tactile sensing device, comprising
    - a scanhead sub-assembly comprising:
        - a scanhead comprising a sensor array comprising: a first sensor comprising a first surface, a second sensor comprising a second surface, wherein the first sensor is configured to output a first voltage signal in response to a first change in a first pressure applied to the first surface, and the second sensor is configured to output a second voltage signal in response to a second change in a second pressure applied to the second surface; and
        - a needle guide comprising a proximal opening and a distal opening, and a needle guide track therebetween, and
    - a frame to which the scanhead sub-assembly is moveably coupled, wherein the scanhead comprises an undepressed position and a depressed position, the depressed position being distal to the frame as compared to the undepressed position;
- a fluid pressure sensor; and
- a display operatively coupled to the sensor array configured to display a pressure map representing a tissue location in an individual based upon the first voltage signal and the second voltage signal from the sensor array.

* * * * *